US008987419B2

(12) United States Patent  
Barghorn et al.

(10) Patent No.: US 8,987,419 B2
(45) Date of Patent: Mar. 24, 2015

(54) AMYLOID-BETA BINDING PROTEINS

(75) Inventors: Stefan Barghorn, Mannheim (DE); Heinz Hillen, Hassloch (DE); Andreas Striebinger, Speyer (DE); Simone Giaisi, Edingen-Neckarhaus (DE); Ulrich Ebert, Mannheim (DE); Lorenzo Benatuil, Northborough, MA (US)

(73) Assignees: AbbVie Deutschland GmbH & Co. KG, Wiesbaden (DE); AbbVie Inc., North Chicago, IL (US)

( * ) Notice: Subject to any disclaimer, the term of this patent is extended or adjusted under 35 U.S.C. 154(b) by 0 days.

(21) Appl. No.: 13/085,891

(22) Filed: Apr. 13, 2011

(65) Prior Publication Data

US 2011/0256138 A1  Oct. 20, 2011

Related U.S. Application Data

(60) Provisional application No. 61/446,624, filed on Feb. 25, 2011, provisional application No. 61/373,825, filed on Aug. 14, 2010, provisional application No. 61/324,386, filed on Apr. 15, 2010.

(51) Int. Cl.
*C12P 21/08* (2006.01)
*C07K 16/00* (2006.01)
*C07K 16/18* (2006.01)
*C07K 14/47* (2006.01)

(52) U.S. Cl.
CPC .............. *C07K 16/18* (2013.01); *C07K 14/4711* (2013.01); *C07K 2317/24* (2013.01); *C07K 2317/92* (2013.01)
USPC ..................................... 530/387.3; 530/388.1

(58) Field of Classification Search
None
See application file for complete search history.

(56) References Cited

U.S. PATENT DOCUMENTS

| | | | |
|---|---|---|---|
| 4,399,216 A | 8/1983 | Axel et al. |
| 4,510,245 A | 4/1985 | Cousens et al. |
| 4,526,039 A | 7/1985 | Ceccon et al. |
| 4,582,788 A | 4/1986 | Erlich |
| 4,634,665 A | 1/1987 | Axel et al. |
| 4,666,829 A | 5/1987 | Glenner et al. |
| 4,683,194 A | 7/1987 | Saiki et al. |
| 4,683,202 A | 7/1987 | Mullis |
| 4,816,397 A | 3/1989 | Boss et al. |
| 4,816,567 A | 3/1989 | Cabilly et al. |
| 4,880,078 A | 11/1989 | Inoue et al. |
| 4,946,778 A | 8/1990 | Ladner et al. |
| 4,968,615 A | 11/1990 | Koszinowski et al. |
| 4,980,286 A | 12/1990 | Morgan et al. |
| 5,107,065 A | 4/1992 | Shewmaker et al. |
| 5,128,326 A | 7/1992 | Balazs et al. |
| 5,134,062 A | 7/1992 | Blass |
| 5,168,062 A | 12/1992 | Stinski |
| 5,179,017 A | 1/1993 | Axel et al. |
| 5,218,100 A | 6/1993 | Muller-Hill et al. |
| 5,223,409 A | 6/1993 | Ladner et al. |
| 5,225,539 A | 7/1993 | Winter |
| 5,231,000 A | 7/1993 | Majocha et al. |
| 5,231,020 A | 7/1993 | Jorgensen et al. |
| 5,231,170 A | 7/1993 | Averback |
| 5,234,814 A | 8/1993 | Card et al. |
| 5,258,498 A | 11/1993 | Huston et al. |
| 5,262,332 A | 11/1993 | Selkoe |
| 5,290,540 A | 3/1994 | Prince et al. |
| 5,403,484 A | 4/1995 | Ladner et al. |
| 5,427,908 A | 6/1995 | Dower et al. |
| 5,441,870 A | 8/1995 | Seubert et al. |
| 5,455,169 A | 10/1995 | Mullan |
| 5,516,637 A | 5/1996 | Huang et al. |
| 5,530,101 A | 6/1996 | Queen et al. |
| 5,538,845 A | 7/1996 | Knops et al. |
| 5,545,806 A | 8/1996 | Lonberg et al. |
| 5,565,332 A | 10/1996 | Hoogenboom et al. |
| 5,565,352 A | 10/1996 | Hochstrasser et al. |
| 5,567,720 A | 10/1996 | Averback |
| 5,569,825 A | 10/1996 | Lonberg et al. |
| 5,571,698 A | 11/1996 | Ladner et al. |
| 5,580,717 A | 12/1996 | Dower et al. |
| 5,585,089 A | 12/1996 | Queen et al. |
| 5,593,846 A | 1/1997 | Schenk et al. |
| 5,605,811 A | 2/1997 | Seubert et al. |
| 5,624,821 A | 4/1997 | Winter et al. |
| 5,625,126 A | 4/1997 | Lonberg et al. |
| 5,627,052 A | 5/1997 | Schrader |
| 5,633,425 A | 5/1997 | Lonberg et al. |
| 5,648,260 A | 7/1997 | Winter et al. |
| 5,658,727 A | 8/1997 | Barbas et al. |
| 5,661,016 A | 8/1997 | Lonberg et al. |

(Continued)

FOREIGN PATENT DOCUMENTS

| | | |
|---|---|---|
| AU | 2007200047 | 1/2007 |
| CA | 2541522 | 9/2007 |

(Continued)

OTHER PUBLICATIONS

Paul, Fundamental Immunology, 3rd Edition, 1993, pp. 292-295.*
Rudikoff et al., Proc. Natl. Acad. Sci. USA, 79(6):1979-1983, Mar. 1982.*
Colman, Research in Immunology, 145:33-36, 1994.*
Bendig, Methods: A Companion to Methods in Enzymology, 1995; 8:83-93.*
Citron, Nature Reviews Drug Discovery, 2010:9:387-398.*
McPherson., Eur. J. Biochem. 1990, 189:1-23.*
Kundrot et al. Cell. Mol. Life Sci. 2004, 61: 525-536.*
Benevenuti et al., Nature Protocols, 2007, 2(7):1633-1651.*
Aisen, P.S. et al., "The development of anti-amyloid etherapy for Alzheimer's disease: from secretase modulators to polymerisation inhibitors," CNS Drugs (2005) 19(12):989-996.

(Continued)

Primary Examiner — Hong Sang
(74) Attorney, Agent, or Firm — Lisa V. Mueller; Michael Best & Friedrich LLP

(57) ABSTRACT

The present invention relates to amyloid-beta (Aβ) binding proteins. Antibodies of the invention have high affinity to Aβ(20-42) globulomer or any Aβ form that comprises the globulomer epitope. Method of making and method of using the antibodies of the invention are also provided.

11 Claims, 12 Drawing Sheets

(56) References Cited

U.S. PATENT DOCUMENTS

| | | |
|---|---|---|
| 5,665,355 A | 9/1997 | Primi |
| 5,679,377 A | 10/1997 | Bernstein et al. |
| 5,679,531 A | 10/1997 | Konig |
| 5,693,753 A | 12/1997 | Konig |
| 5,693,762 A | 12/1997 | Queen et al. |
| 5,698,426 A | 12/1997 | Huse |
| 5,705,330 A | 1/1998 | Shah et al. |
| 5,705,401 A | 1/1998 | Masters et al. |
| 5,714,350 A | 2/1998 | Co et al. |
| 5,714,352 A | 2/1998 | Jakobovits |
| 5,721,130 A | 2/1998 | Seubert et al. |
| 5,723,323 A | 3/1998 | Kauffman et al. |
| 5,733,743 A | 3/1998 | Johnson et al. |
| 5,750,349 A | 5/1998 | Suzuki et al. |
| 5,750,753 A | 5/1998 | Kimae et al. |
| 5,763,192 A | 6/1998 | Kauffman et al. |
| 5,766,846 A | 6/1998 | Schlossmacher et al. |
| 5,766,886 A | 6/1998 | Studnicka et al. |
| 5,770,429 A | 6/1998 | Lonberg et al. |
| 5,780,225 A | 7/1998 | Wigler et al. |
| 5,786,180 A | 7/1998 | Konig |
| 5,807,715 A | 9/1998 | Morrison et al. |
| 5,814,318 A | 9/1998 | Lonberg et al. |
| 5,814,476 A | 9/1998 | Kauffman et al. |
| 5,817,483 A | 10/1998 | Kauffman et al. |
| 5,821,047 A | 10/1998 | Garrard et al. |
| 5,824,514 A | 10/1998 | Kauffman et al. |
| 5,837,500 A | 11/1998 | Ladner et al. |
| 5,855,913 A | 1/1999 | Hanes et al. |
| 5,874,064 A | 2/1999 | Edwards et al. |
| 5,877,397 A | 3/1999 | Lonberg et al. |
| 5,879,909 A | 3/1999 | Perl |
| 5,882,644 A | 3/1999 | Chang et al. |
| 5,885,793 A | 3/1999 | Griffiths et al. |
| 5,912,015 A | 6/1999 | Bernstein et al. |
| 5,912,120 A | 6/1999 | Goldstein et al. |
| 5,916,597 A | 6/1999 | Lee et al. |
| 5,916,771 A | 6/1999 | Hori et al. |
| 5,934,272 A | 8/1999 | Lloyd et al. |
| 5,939,598 A | 8/1999 | Kucherlapati et al. |
| 5,955,285 A | 9/1999 | Averback |
| 5,955,317 A | 9/1999 | Suzuki et al. |
| 5,969,108 A | 10/1999 | McCafferty et al. |
| 5,976,862 A | 11/1999 | Kauffman et al. |
| 5,985,309 A | 11/1999 | Edwards et al. |
| 5,985,320 A | 11/1999 | Edwards et al. |
| 5,985,615 A | 11/1999 | Jakobovits et al. |
| 5,989,463 A | 11/1999 | Tracy et al. |
| 5,998,209 A | 12/1999 | Jokobovits et al. |
| 6,010,913 A | 1/2000 | Vandermeeren et al. |
| 6,018,024 A | 1/2000 | Seubert et al. |
| 6,019,968 A | 2/2000 | Platz et al. |
| 6,075,181 A | 6/2000 | Kucherlapati et al. |
| 6,091,001 A | 7/2000 | Jakobovits et al. |
| 6,114,133 A | 9/2000 | Seubert et al. |
| 6,114,598 A | 9/2000 | Kucherlapati et al. |
| 6,130,364 A | 10/2000 | Jakobovits et al. |
| 6,180,370 B1 | 1/2001 | Queen et al. |
| 6,204,023 B1 | 3/2001 | Robinson et al. |
| 6,218,506 B1 | 4/2001 | Krafft et al. |
| 6,284,221 B1 | 9/2001 | Schenk et al. |
| 6,287,793 B1 | 9/2001 | Schenk et al. |
| 6,294,171 B2 | 9/2001 | McMichael |
| 6,309,892 B1 | 10/2001 | Averback |
| 6,323,218 B1 | 11/2001 | Bush et al. |
| 6,333,034 B1 | 12/2001 | Gupta-Bansal et al. |
| 6,350,861 B1 | 2/2002 | Co et al. |
| 6,387,674 B1 | 5/2002 | Trasciatti et al. |
| 6,582,945 B1 | 6/2003 | Raso |
| 6,610,493 B1 | 8/2003 | Citron et al. |
| 6,660,843 B1 | 12/2003 | Feige et al. |
| 6,664,442 B2 | 12/2003 | McConlogue et al. |
| 6,699,658 B1 | 3/2004 | Wittrup et al. |
| 6,710,226 B1 | 3/2004 | Schenk |
| 6,713,450 B2 | 3/2004 | Frangione et al. |
| 6,743,427 B1 | 6/2004 | Schenk |
| 6,750,324 B1 | 6/2004 | Schenk |
| 6,761,888 B1 | 7/2004 | Schenk |
| 6,785,434 B2 | 8/2004 | Castoldi et al. |
| 6,787,138 B1 | 9/2004 | Schenk |
| 6,787,139 B1 | 9/2004 | Schenk |
| 6,787,140 B1 | 9/2004 | Schenk |
| 6,787,143 B1 | 9/2004 | Schenk |
| 6,787,144 B1 | 9/2004 | Schenk |
| 6,787,523 B1 | 9/2004 | Schenk |
| 6,787,637 B1 | 9/2004 | Schenk |
| 6,815,175 B2 | 11/2004 | Weksler |
| 6,849,416 B2 | 2/2005 | Wiltfang et al. |
| 6,866,849 B2 | 3/2005 | Schenk |
| 6,866,850 B2 | 3/2005 | Schenk |
| 6,872,554 B2 | 3/2005 | Raso |
| 6,875,434 B1 | 4/2005 | Schenk |
| 6,905,686 B1 | 6/2005 | Schenk |
| 6,913,745 B1 | 7/2005 | Schenk |
| 6,919,075 B1 | 7/2005 | Solomon et al. |
| 6,972,127 B2 | 12/2005 | Schenk |
| 6,982,084 B2 | 1/2006 | Schenk |
| 7,014,855 B2 | 3/2006 | Schenk |
| 7,022,500 B1 | 4/2006 | Queen et al. |
| 7,045,531 B1 | 5/2006 | Bush et al. |
| 7,060,270 B2 | 6/2006 | Nicolau et al. |
| 7,067,133 B2 | 6/2006 | Nicolau |
| 7,094,884 B2 | 8/2006 | Scholz et al. |
| 7,122,374 B1 | 10/2006 | Saido et al. |
| 7,135,181 B2 | 11/2006 | Jensen et al. |
| 7,169,389 B2 | 1/2007 | Di Padova et al. |
| 7,179,463 B2 | 2/2007 | Lannfelt et al. |
| 7,179,606 B2 | 2/2007 | Jackowski et al. |
| 7,179,892 B2 | 2/2007 | Basi et al. |
| 7,186,881 B2 | 3/2007 | Games et al. |
| 7,189,703 B2 | 3/2007 | Balin et al. |
| 7,189,819 B2 | 3/2007 | Basi et al. |
| 7,195,761 B2 | 3/2007 | Holtzman et al. |
| 7,195,881 B2 | 3/2007 | Geffard |
| 7,196,163 B2 | 3/2007 | Hazuda et al. |
| 7,226,730 B1 | 6/2007 | De La et al. |
| 7,238,488 B2 | 7/2007 | Maresh et al. |
| 7,238,788 B2 | 7/2007 | Lee |
| 7,247,301 B2 | 7/2007 | Van De et al. |
| 7,256,273 B2 | 8/2007 | Basi et al. |
| 7,270,818 B2 | 9/2007 | Averback |
| 7,279,165 B2 | 10/2007 | Bachmann et al. |
| 7,318,923 B2 | 1/2008 | Tsurushita et al. |
| 7,320,790 B2 | 1/2008 | Hinton et al. |
| 7,320,793 B2 | 1/2008 | Renner et al. |
| 7,335,491 B2 | 2/2008 | Drapeau et al. |
| 7,339,035 B2 | 3/2008 | Yanagisawa et al. |
| 7,342,091 B2 | 3/2008 | Kapurniotu et al. |
| 7,371,365 B2 | 5/2008 | Poduslo et al. |
| 7,375,190 B2 | 5/2008 | Cheng et al. |
| 7,413,884 B2 | 8/2008 | Raso |
| 7,427,342 B2 | 9/2008 | Barber |
| 7,625,560 B2 | 12/2009 | Basi et al. |
| 7,772,375 B2 | 8/2010 | Greferath et al. |
| 7,892,544 B2 | 2/2011 | Pfeifer et al. |
| 7,902,328 B2 | 3/2011 | Hillen et al. |
| 2001/0029293 A1 | 10/2001 | Gallatin et al. |
| 2002/0009445 A1 | 1/2002 | Du et al. |
| 2002/0015941 A1 | 2/2002 | Kim et al. |
| 2002/0086014 A1 | 7/2002 | Korman et al. |
| 2002/0086847 A1 | 7/2002 | Chain |
| 2002/0094335 A1 | 7/2002 | Chalifour et al. |
| 2002/0132758 A1 | 9/2002 | Shell et al. |
| 2002/0137134 A1 | 9/2002 | Gerngross |
| 2002/0162129 A1 | 10/2002 | Lannfelt et al. |
| 2002/0182644 A1 | 12/2002 | Diamandis |
| 2002/0182660 A1 | 12/2002 | Fong |
| 2002/0188106 A1 | 12/2002 | Mandelkow et al. |
| 2002/0197258 A1 | 12/2002 | Ghanbari et al. |
| 2003/0065141 A1 | 4/2003 | Carter et al. |
| 2003/0068316 A1 | 4/2003 | Klein et al. |
| 2003/0073655 A1 | 4/2003 | Chain |
| 2003/0077278 A1 | 4/2003 | Gallatin et al. |
| 2003/0077757 A1 | 4/2003 | Andrews |

(56) References Cited

U.S. PATENT DOCUMENTS

| | | |
|---|---|---|
| 2003/0086938 A1 | 5/2003 | Jensen et al. |
| 2003/0100011 A1 | 5/2003 | Jackowski et al. |
| 2003/0100058 A1 | 5/2003 | Roschke et al. |
| 2003/0108551 A1 | 6/2003 | Nicolau et al. |
| 2003/0114510 A1 | 6/2003 | Ingram et al. |
| 2003/0147882 A1 | 8/2003 | Solomon et al. |
| 2003/0148356 A1 | 8/2003 | Cruts et al. |
| 2003/0157117 A1 | 8/2003 | Rasmussen et al. |
| 2003/0180722 A1 | 9/2003 | Godbole et al. |
| 2003/0185826 A1 | 10/2003 | Tobinick |
| 2003/0185827 A1 | 10/2003 | Rodriguez et al. |
| 2003/0186333 A1 | 10/2003 | Loring et al. |
| 2003/0186374 A1 | 10/2003 | Hufton et al. |
| 2003/0190689 A1 | 10/2003 | Crosby et al. |
| 2003/0194403 A1 | 10/2003 | van de Winkel et al. |
| 2003/0195347 A1 | 10/2003 | Baker et al. |
| 2003/0228307 A1 | 12/2003 | Ramakrishnan et al. |
| 2003/0229907 A1 | 12/2003 | Hsiao et al. |
| 2003/0232758 A1 | 12/2003 | St. George-Hyslop et al. |
| 2004/0013647 A1 | 1/2004 | Solomon et al. |
| 2004/0013680 A1 | 1/2004 | Bush et al. |
| 2004/0018590 A1 | 1/2004 | Gerngross et al. |
| 2004/0043418 A1 | 3/2004 | Holtzman et al. |
| 2004/0053371 A1 | 3/2004 | Maresh et al. |
| 2004/0058414 A1 | 3/2004 | Queen et al. |
| 2004/0081657 A1 | 4/2004 | Schenk |
| 2004/0116337 A1 | 6/2004 | Kapumiotu et al. |
| 2004/0127471 A1 | 7/2004 | Reisberg |
| 2004/0138296 A1 | 7/2004 | Robertson et al. |
| 2004/0142872 A1 | 7/2004 | Podusio et al. |
| 2004/0146512 A1 | 7/2004 | Rosenthal et al. |
| 2004/0157267 A1 | 8/2004 | Huang |
| 2004/0157779 A1 | 8/2004 | Schenk |
| 2004/0166119 A1 | 8/2004 | Schenk |
| 2004/0170641 A1 | 9/2004 | Schenk |
| 2004/0175394 A1 | 9/2004 | Schenk |
| 2004/0185039 A1 | 9/2004 | Kohler et al. |
| 2004/0191264 A1 | 9/2004 | Nielsen et al. |
| 2004/0192898 A1 | 9/2004 | Jia et al. |
| 2004/0213800 A1 | 10/2004 | Seubert et al. |
| 2004/0223912 A1 | 11/2004 | Montalto et al. |
| 2004/0223970 A1 | 11/2004 | Afar et al. |
| 2004/0228865 A1 | 11/2004 | Schenk |
| 2004/0241164 A1 | 12/2004 | Bales et al. |
| 2004/0242845 A1 | 12/2004 | Nicolau et al. |
| 2004/0248197 A1 | 12/2004 | Holtzman et al. |
| 2004/0265308 A1 | 12/2004 | Schenk |
| 2004/0265919 A1 | 12/2004 | Vanderstichele et al. |
| 2005/0009110 A1 | 1/2005 | Chang |
| 2005/0014821 A1 | 1/2005 | Tsai et al. |
| 2005/0019330 A1 | 1/2005 | Schenk |
| 2005/0019343 A1 | 1/2005 | Schenk |
| 2005/0031651 A1 | 2/2005 | Gervais et al. |
| 2005/0037026 A1 | 2/2005 | Schenk |
| 2005/0042664 A1 | 2/2005 | Wu et al. |
| 2005/0048584 A1 | 3/2005 | Lamping et al. |
| 2005/0053614 A1 | 3/2005 | Schenk |
| 2005/0057813 A1 | 3/2005 | Hasei et al. |
| 2005/0059591 A1 | 3/2005 | Schenk et al. |
| 2005/0059802 A1 | 3/2005 | Schenk et al. |
| 2005/0090439 A1 | 4/2005 | Chalifour et al. |
| 2005/0112543 A1 | 5/2005 | Bush et al. |
| 2005/0118651 A1 | 6/2005 | Basi et al. |
| 2005/0123544 A1 | 6/2005 | Schenk et al. |
| 2005/0124016 A1 | 6/2005 | LaDu et al. |
| 2005/0129691 A1 | 6/2005 | Gerlai |
| 2005/0129695 A1 | 6/2005 | Mercken et al. |
| 2005/0142131 A1 | 6/2005 | Hinton et al. |
| 2005/0142132 A1 | 6/2005 | Schenk et al. |
| 2005/0147613 A1 | 7/2005 | Raso |
| 2005/0153381 A1 | 7/2005 | Marusich et al. |
| 2005/0163744 A1 | 7/2005 | Rasmussen et al. |
| 2005/0163788 A1 | 7/2005 | Schenk |
| 2005/0169925 A1 | 8/2005 | Bardroff et al. |
| 2005/0175626 A1 | 8/2005 | Delacourte et al. |
| 2005/0249725 A1 | 11/2005 | Schenk et al. |
| 2005/0249727 A1 | 11/2005 | Schenk |
| 2005/0255122 A1 | 11/2005 | Schenk |
| 2005/0272025 A1 | 12/2005 | Suo et al. |
| 2006/0008458 A1 | 1/2006 | Solomon |
| 2006/0029603 A1 | 2/2006 | Ellis et al. |
| 2006/0029611 A1 | 2/2006 | Schenk |
| 2006/0034858 A1 | 2/2006 | Schenk |
| 2006/0039906 A1 | 2/2006 | Holtzman et al. |
| 2006/0057646 A1 | 3/2006 | Wiltfang et al. |
| 2006/0057701 A1 | 3/2006 | Rosenthal et al. |
| 2006/0057702 A1 | 3/2006 | Rosenthal et al. |
| 2006/0062786 A1 | 3/2006 | Salcedo et al. |
| 2006/0073149 A1 | 4/2006 | Bales et al. |
| 2006/0099211 A1 | 5/2006 | Monthe et al. |
| 2006/0104968 A1 | 5/2006 | Bookbinder et al. |
| 2006/0105394 A1 | 5/2006 | Pomara |
| 2006/0110388 A1 | 5/2006 | Davies et al. |
| 2006/0111301 A1 | 5/2006 | Mattner |
| 2006/0127954 A1 | 6/2006 | Mercken et al. |
| 2006/0141541 A1 | 6/2006 | McIntyre |
| 2006/0160161 A1 | 7/2006 | Pavliakova et al. |
| 2006/0165682 A1 | 7/2006 | Basi et al. |
| 2006/0166275 A1 | 7/2006 | Krafft et al. |
| 2006/0166311 A1 | 7/2006 | Okochi et al. |
| 2006/0188505 A1 | 8/2006 | Skurkovich et al. |
| 2006/0193850 A1 | 8/2006 | Warne et al. |
| 2006/0198851 A1 | 9/2006 | Basi et al. |
| 2006/0228349 A1 | 10/2006 | Acton et al. |
| 2006/0234947 A1 | 10/2006 | Gazit |
| 2006/0240007 A1 | 10/2006 | Sanders |
| 2006/0241038 A1 | 10/2006 | Watanabe et al. |
| 2006/0246075 A1 | 11/2006 | Mercken et al. |
| 2006/0257420 A1 | 11/2006 | Zimmerman |
| 2006/0257882 A1 | 11/2006 | Shimkets et al. |
| 2006/0280733 A1 | 12/2006 | Kayed et al. |
| 2006/0292152 A1 | 12/2006 | Rosenthal et al. |
| 2007/0009931 A1 | 1/2007 | Kirsch |
| 2007/0010435 A1 | 1/2007 | Frangione et al. |
| 2007/0010657 A1 | 1/2007 | Klocke et al. |
| 2007/0015217 A1 | 1/2007 | Durham et al. |
| 2007/0015218 A1 | 1/2007 | Cao et al. |
| 2007/0021345 A1 | 1/2007 | Gazit |
| 2007/0031416 A1 | 2/2007 | Shoji et al. |
| 2007/0036789 A1 | 2/2007 | Chung |
| 2007/0036794 A1 | 2/2007 | Devaux |
| 2007/0042424 A1 | 2/2007 | Ebinuma et al. |
| 2007/0048312 A1 | 3/2007 | Klein et al. |
| 2007/0071675 A1 | 3/2007 | Wu et al. |
| 2007/0072307 A1 | 3/2007 | Godavarti et al. |
| 2007/0081998 A1 | 4/2007 | Kinney et al. |
| 2007/0082350 A1 | 4/2007 | Landfield et al. |
| 2007/0086994 A1 | 4/2007 | Wallach et al. |
| 2007/0098721 A1 | 5/2007 | Hillen et al. |
| 2007/0105092 A1 | 5/2007 | Paul et al. |
| 2007/0110750 A1 | 5/2007 | Glabe et al. |
| 2007/0111252 A1 | 5/2007 | Suzuki et al. |
| 2007/0122405 A1 | 5/2007 | Roschke et al. |
| 2007/0128191 A1 | 6/2007 | Barrio |
| 2007/0134247 A9 | 6/2007 | Solomon |
| 2007/0135337 A2 | 6/2007 | Chalifour et al. |
| 2007/0140966 A1 | 6/2007 | Chang et al. |
| 2007/0148167 A1 | 6/2007 | Strohl |
| 2007/0160616 A1 | 7/2007 | Rosenthal et al. |
| 2007/0167522 A1 | 7/2007 | Imawaka et al. |
| 2007/0190046 A1 | 8/2007 | DeMaattos et al. |
| 2007/0196367 A1 | 8/2007 | Dinu |
| 2007/0213512 A1 | 9/2007 | Krafft et al. |
| 2007/0218069 A1 | 9/2007 | Gordon et al. |
| 2007/0218499 A1 | 9/2007 | Lambert et al. |
| 2007/0231331 A1 | 10/2007 | Dewji et al. |
| 2007/0248606 A1 | 10/2007 | Lannfelt et al. |
| 2007/0264276 A1 | 11/2007 | Chalifour et al. |
| 2007/0280953 A1 | 12/2007 | Rosenberg et al. |
| 2007/0292410 A1 | 12/2007 | Cashman et al. |
| 2007/0292895 A1 | 12/2007 | Shi et al. |
| 2008/0009467 A1 | 1/2008 | Henderson |
| 2008/0014194 A1 | 1/2008 | Schenk et al. |
| 2008/0025988 A1 | 1/2008 | Yamaguchi et al. |

(56) References Cited

U.S. PATENT DOCUMENTS

| | | |
|---|---|---|
| 2008/0029911 A1 | 2/2008 | Jeon et al. |
| 2008/0044356 A1 | 2/2008 | Lesne et al. |
| 2008/0044406 A1 | 2/2008 | Johnson-Wood et al. |
| 2008/0051690 A1 | 2/2008 | Mattner et al. |
| 2008/0057053 A1 | 3/2008 | Stolen |
| 2008/0057593 A1 | 3/2008 | Vanderstichele et al. |
| 2008/0058276 A1 | 3/2008 | Lu et al. |
| 2008/0058330 A1 | 3/2008 | Paris et al. |
| 2008/0089885 A1 | 4/2008 | Smith et al. |
| 2008/0096818 A1 | 4/2008 | Schenk et al. |
| 2008/0107601 A1 | 5/2008 | Lauwereys et al. |
| 2008/0107649 A1 | 5/2008 | Zurbriggen |
| 2008/0113444 A1 | 5/2008 | Pray |
| 2008/0131422 A1 | 6/2008 | Sugimura et al. |
| 2008/0199879 A1 | 8/2008 | Takayama et al. |
| 2008/0220449 A1 | 9/2008 | Vasan et al. |
| 2008/0292639 A1 | 11/2008 | Shen et al. |
| 2008/0299111 A1 | 12/2008 | Delacourte et al. |
| 2009/0018084 A1 | 1/2009 | Krafft et al. |
| 2009/0023159 A1 | 1/2009 | Mendez |
| 2009/0035295 A1 | 2/2009 | Hillen et al. |
| 2009/0035307 A1 | 2/2009 | Barghorn et al. |
| 2009/0074775 A1 | 3/2009 | Holtzman et al. |
| 2009/0155246 A1 | 6/2009 | Gellerfors et al. |
| 2009/0156471 A1 | 6/2009 | Gazit et al. |
| 2009/0162362 A1 | 6/2009 | Sarasa |
| 2009/0162878 A1 | 6/2009 | Kim et al. |
| 2009/0175847 A1 | 7/2009 | Hillen |
| 2009/0191190 A1 | 7/2009 | Barghorn |
| 2009/0214515 A1 | 8/2009 | Holzman et al. |
| 2009/0232801 A1 | 9/2009 | Hillen |
| 2009/0238831 A1 | 9/2009 | Hillen et al. |
| 2010/0173828 A1 | 7/2010 | Hillen |
| 2010/0209346 A1 | 8/2010 | Hillen et al. |
| 2011/0092445 A1 | 4/2011 | Barghorn |
| 2011/0212109 A1 | 9/2011 | Barghorn |
| 2011/0256138 A1 | 10/2011 | Barghorn |
| 2011/0287005 A1 | 11/2011 | Hillen |
| 2012/0034166 A1 | 2/2012 | Hillen |

FOREIGN PATENT DOCUMENTS

| | | |
|---|---|---|
| CN | 1396183 | 2/2003 |
| CN | 1446581 | 10/2003 |
| CN | 1673369 | 9/2005 |
| CN | 1721437 | 1/2006 |
| CN | 1803842 | 7/2006 |
| CN | 101058608 | 10/2007 |
| CN | 101084909 | 12/2007 |
| CN | 101152576 | 4/2008 |
| DE | 19902550 | 7/2000 |
| DE | 10055703 | 5/2002 |
| DE | 10303974 | 8/2004 |
| DE | 102004039326 | 2/2006 |
| EP | 0045665 | 2/1982 |
| EP | 0050424 | 9/1985 |
| EP | 0285159 | 10/1988 |
| EP | 0341491 | 11/1989 |
| EP | 0084796 | 5/1990 |
| EP | 0391714 | 10/1990 |
| EP | 0411974 | 2/1991 |
| EP | 0415801 | 3/1991 |
| EP | 0237362 | 3/1992 |
| EP | 0201184 | 12/1992 |
| EP | 0229246 | 8/1993 |
| EP | 0368684 | 3/1994 |
| EP | 0239400 | 8/1994 |
| EP | 0613007 | 8/1994 |
| EP | 0623675 | 11/1994 |
| EP | 0557270 | 5/1995 |
| EP | 0519598 | 6/1995 |
| EP | 0440619 | 1/1996 |
| EP | 0304013 | 6/1996 |
| EP | 0589877 | 11/1996 |
| EP | 0436597 | 4/1997 |
| EP | 0258017 | 6/1997 |
| EP | 0783104 | 7/1997 |
| EP | 0444856 | 9/1997 |
| EP | 0816492 | 1/1998 |
| EP | 0592127 | 4/1998 |
| EP | 0274826 | 8/1998 |
| EP | 0527839 | 12/1998 |
| EP | 1038958 | 9/2000 |
| EP | 1094080 | 4/2001 |
| EP | 1130032 | 11/2001 |
| EP | 1172378 | 1/2002 |
| EP | 1176195 | 1/2002 |
| EP | 0877939 | 6/2002 |
| EP | 0683234 | 5/2003 |
| EP | 1308461 | 5/2003 |
| EP | 1408333 | 4/2004 |
| EP | 1420032 | 5/2004 |
| EP | 1270592 | 9/2004 |
| EP | 1467212 | 10/2004 |
| EP | 0592106 | 11/2004 |
| EP | 1200470 | 11/2004 |
| EP | 0519596 | 2/2005 |
| EP | 1538163 | 6/2005 |
| EP | 1632242 | 3/2006 |
| EP | 1092767 | 10/2006 |
| EP | 1717250 | 11/2006 |
| EP | 0998495 | 12/2006 |
| EP | 1731913 | 12/2006 |
| EP | 1049712 | 1/2007 |
| EP | 1741783 | 1/2007 |
| EP | 1346041 | 2/2007 |
| EP | 1752472 | 2/2007 |
| EP | 1592476 | 4/2007 |
| EP | 0970203 | 5/2007 |
| EP | 1787998 | 5/2007 |
| EP | 0948536 | 6/2007 |
| EP | 1160256 | 6/2007 |
| EP | 1379546 | 6/2007 |
| EP | 1792991 | 6/2007 |
| EP | 1842859 | 10/2007 |
| EP | 1861422 | 12/2007 |
| EP | 1878751 | 1/2008 |
| EP | 1434053 | 3/2008 |
| EP | 1521831 | 4/2008 |
| EP | 1778837 | 4/2008 |
| EP | 1911765 | 4/2008 |
| EP | 1781644 | 5/2008 |
| EP | 0911398 | 6/2008 |
| EP | 1976877 | 10/2008 |
| EP | 2009445 | 12/2008 |
| EP | 1623719 | 1/2009 |
| EP | 1681566 | 8/2009 |
| EP | 1766396 | 8/2010 |
| EP | 1720909 | 11/2011 |
| FR | 2740454 | 4/1997 |
| FR | 2741881 | 6/1997 |
| GB | 1495159 | 12/1977 |
| GB | 2371303 | 7/2002 |
| GR | 1005016 | 10/2005 |
| JP | 63240797 | 10/1988 |
| JP | 4252195 | 9/1992 |
| JP | 4320694 | 11/1992 |
| JP | 7209295 | 8/1995 |
| JP | 7209296 | 8/1995 |
| JP | 07238096 | 9/1995 |
| JP | 7309900 | 11/1995 |
| JP | 8245700 | 9/1996 |
| JP | 9067397 | 3/1997 |
| JP | 10075781 | 3/1998 |
| JP | 10210982 | 8/1998 |
| JP | 2000050885 | 2/2000 |
| JP | 2000354487 | 12/2000 |
| JP | 2001231578 | 8/2001 |
| JP | 2002040023 | 2/2002 |
| JP | 2002253252 | 9/2002 |
| JP | 2004107260 | 4/2004 |
| JP | 2005185281 | 7/2005 |
| JP | 2006166879 | 6/2006 |

(56) References Cited

FOREIGN PATENT DOCUMENTS

| | | |
|---|---|---|
| JP | 2006213621 | 8/2006 |
| JP | 2006265189 | 10/2006 |
| JP | 2007077103 | 3/2007 |
| JP | 2007300856 | 11/2007 |
| JP | 2007319127 | 12/2007 |
| JP | 2008096311 | 4/2008 |
| KR | 100806914 | 2/2008 |
| WO | WO 88/03951 | 6/1988 |
| WO | WO 89/06689 | 7/1989 |
| WO | WO 89/07657 | 8/1989 |
| WO | WO 90/02809 | 3/1990 |
| WO | WO 90/05144 | 5/1990 |
| WO | WO 90/12870 | 11/1990 |
| WO | WO 90/14424 | 11/1990 |
| WO | WO 90/14430 | 11/1990 |
| WO | WO 90/14443 | 11/1990 |
| WO | WO 91/05548 | 5/1991 |
| WO | WO 91/09967 | 7/1991 |
| WO | WO 91/10737 | 7/1991 |
| WO | WO 91/10741 | 7/1991 |
| WO | WO 91/17271 | 11/1991 |
| WO | WO 92/01047 | 1/1992 |
| WO | WO 92/02551 | 2/1992 |
| WO | WO 92/00969 | 6/1992 |
| WO | WO 92/09690 | 6/1992 |
| WO | WO 92/11018 | 7/1992 |
| WO | WO 92/15679 | 9/1992 |
| WO | WO 92/18619 | 10/1992 |
| WO | WO 92/19244 | 11/1992 |
| WO | WO 92/20791 | 11/1992 |
| WO | WO 92/22324 | 12/1992 |
| WO | WO 93/01288 | 1/1993 |
| WO | WO 93/08302 | 4/1993 |
| WO | WO 93/11236 | 10/1993 |
| WO | WO 94/02602 | 3/1994 |
| WO | WO 94/17197 | 8/1994 |
| WO | WO 95/07707 | 3/1995 |
| WO | WO 95/11311 | 4/1995 |
| WO | WO 95/11994 | 5/1995 |
| WO | WO 95/15982 | 6/1995 |
| WO | WO 95/16787 | 6/1995 |
| WO | WO 95/20401 | 8/1995 |
| WO | WO 96/20218 | 7/1996 |
| WO | WO 96/20698 | 7/1996 |
| WO | WO 96/28187 | 9/1996 |
| WO | WO 96/33735 | 10/1996 |
| WO | WO 96/34096 | 10/1996 |
| WO | WO 96/39512 | 12/1996 |
| WO | WO 96/40731 | 12/1996 |
| WO | WO 97/08320 | 3/1997 |
| WO | WO 97/10505 | 3/1997 |
| WO | WO 97/18476 | 5/1997 |
| WO | WO 97/29131 | 8/1997 |
| WO | WO 97/32572 | 9/1997 |
| WO | WO 97/44013 | 11/1997 |
| WO | WO 97/46678 | 12/1997 |
| WO | WO 98/05350 | 2/1998 |
| WO | WO 98/07850 | 2/1998 |
| WO | WO 98/13490 | 4/1998 |
| WO | WO 98/16654 | 4/1998 |
| WO | WO 98/22120 | 5/1998 |
| WO | WO 98/24893 | 6/1998 |
| WO | WO 98/28445 | 7/1998 |
| WO | WO 98/31346 | 7/1998 |
| WO | WO 98/31700 | 7/1998 |
| WO | WO 98/33815 | 8/1998 |
| WO | WO 98/41201 | 9/1998 |
| WO | WO 98/47343 | 10/1998 |
| WO | WO 98/49286 | 11/1998 |
| WO | WO 98/50433 | 11/1998 |
| WO | WO 98/51793 | 11/1998 |
| WO | WO 99/05175 | 2/1999 |
| WO | WO 99/09150 | 2/1999 |
| WO | WO 99/12870 | 3/1999 |
| WO | WO 99/13908 | 3/1999 |
| WO | WO 99/15154 | 4/1999 |
| WO | WO 99/20253 | 4/1999 |
| WO | WO 99/22024 | 5/1999 |
| WO | WO 99/25044 | 5/1999 |
| WO | WO 99/27944 | 6/1999 |
| WO | WO 99/27949 | 6/1999 |
| WO | WO 99/33815 | 7/1999 |
| WO | WO 99/36569 | 7/1999 |
| WO | WO 99/40909 | 8/1999 |
| WO | WO 99/45031 | 9/1999 |
| WO | WO 99/45962 | 9/1999 |
| WO | WO 99/53049 | 10/1999 |
| WO | WO 99/58157 | 11/1999 |
| WO | WO 99/58564 | 11/1999 |
| WO | WO 99/59571 | 11/1999 |
| WO | WO 99/62505 | 12/1999 |
| WO | WO 99/66903 | 12/1999 |
| WO | WO 00/09560 | 2/2000 |
| WO | WO 00/17345 | 3/2000 |
| WO | WO 00/18805 | 4/2000 |
| WO | WO 00/29446 | 5/2000 |
| WO | WO 00/32805 | 6/2000 |
| WO | WO 00/35939 | 6/2000 |
| WO | WO 00/37504 | 6/2000 |
| WO | WO 00/56772 | 9/2000 |
| WO | WO 00/58344 | 10/2000 |
| WO | WO 00/72870 | 12/2000 |
| WO | WO 00/72876 | 12/2000 |
| WO | WO 00/72880 | 12/2000 |
| WO | WO 00/75328 | 12/2000 |
| WO | WO 00/77178 | 12/2000 |
| WO | WO 00/78807 | 12/2000 |
| WO | WO 01/10900 | 2/2001 |
| WO | WO 01/16364 | 3/2001 |
| WO | WO 01/18169 | 3/2001 |
| WO | WO 01/32712 | 5/2001 |
| WO | WO 01/39796 | 6/2001 |
| WO | WO 01/42306 | 6/2001 |
| WO | WO 01/62284 | 8/2001 |
| WO | WO 01/62801 | 8/2001 |
| WO | WO 01/68860 | 9/2001 |
| WO | WO 01/83519 | 11/2001 |
| WO | WO 01/83525 | 11/2001 |
| WO | WO 01/85093 | 11/2001 |
| WO | WO 01/90182 | 11/2001 |
| WO | WO 01/98361 | 12/2001 |
| WO | WO 02/00245 | 1/2002 |
| WO | WO 02/03911 | 1/2002 |
| WO | WO 02/21141 | 3/2002 |
| WO | WO 02/30980 | 4/2002 |
| WO | WO 02/34777 | 5/2002 |
| WO | WO 02/36614 | 5/2002 |
| WO | 02/46237 | 6/2002 |
| WO | WO 02/055552 | 7/2002 |
| WO | WO 02/059155 | 8/2002 |
| WO | WO 02/062851 | 8/2002 |
| WO | WO 02/074240 | 9/2002 |
| WO | WO 02/081505 | 10/2002 |
| WO | WO 02/085922 | 10/2002 |
| WO | WO 02/088306 | 11/2002 |
| WO | WO 02/088307 | 11/2002 |
| WO | WO 02/094870 | 11/2002 |
| WO | WO 02/094985 | 11/2002 |
| WO | WO 02/096350 | 12/2002 |
| WO | WO 02/096937 | 12/2002 |
| WO | WO 03/000714 | 1/2003 |
| WO | WO 03/008626 | 1/2003 |
| WO | WO 03/014162 | 2/2003 |
| WO | WO 03/014329 | 2/2003 |
| WO | WO 03/015617 | 2/2003 |
| WO | WO 03/015691 | 2/2003 |
| WO | WO 03/015812 | 2/2003 |
| WO | WO 03/016466 | 2/2003 |
| WO | WO 03/016467 | 2/2003 |
| WO | WO 03/020212 | 3/2003 |
| WO | WO 03/028668 | 4/2003 |
| WO | WO 03/031475 | 4/2003 |
| WO | WO 03/035835 | 5/2003 |
| WO | WO 03/039467 | 5/2003 |

(56) References Cited

FOREIGN PATENT DOCUMENTS

| | | |
|---|---|---|
| WO | WO 03/045128 | 6/2003 |
| WO | WO 03/046012 | 6/2003 |
| WO | WO 03/047499 | 6/2003 |
| WO | WO 03/051374 | 6/2003 |
| WO | WO 03/070760 | 8/2003 |
| WO | WO 03/074081 | 8/2003 |
| WO | WO 03/074004 | 9/2003 |
| WO | WO 03/074569 | 9/2003 |
| WO | WO 03/076455 | 9/2003 |
| WO | WO 03/077858 | 9/2003 |
| WO | WO 03/080672 | 10/2003 |
| WO | WO 03/089460 | 10/2003 |
| WO | WO 03/090772 | 11/2003 |
| WO | WO 03/091734 | 11/2003 |
| WO | WO 03/095429 | 11/2003 |
| WO | WO 03/100419 | 12/2003 |
| WO | WO 03/104437 | 12/2003 |
| WO | WO 03/105658 | 12/2003 |
| WO | WO 04/001422 | 12/2003 |
| WO | WO 2004/003019 | 1/2004 |
| WO | WO 2004/003563 | 1/2004 |
| WO | WO 2004/006861 | 1/2004 |
| WO | WO 2004/009776 | 1/2004 |
| WO | WO 2004/011674 | 2/2004 |
| WO | WO 2004/011943 | 2/2004 |
| WO | WO 2004/013172 | 2/2004 |
| WO | WO 2004/014296 | 2/2004 |
| WO | WO 2004/014367 | 2/2004 |
| WO | WO 2004/016282 | 2/2004 |
| WO | WO 2004/016655 | 2/2004 |
| WO | WO 2004/018997 | 3/2004 |
| WO | WO 2004/019045 | 3/2004 |
| WO | WO 2004/024090 | 3/2004 |
| WO | WO 2004/029093 | 4/2004 |
| WO | WO 2004/029630 | 4/2004 |
| WO | WO 2004/031241 | 4/2004 |
| WO | WO 2004/031400 | 4/2004 |
| WO | WO 2004/032868 | 4/2004 |
| WO | WO 2004/033397 | 4/2004 |
| WO | WO 2004/038411 | 5/2004 |
| WO | WO 2004/041067 | 5/2004 |
| WO | WO 2004/043989 | 5/2004 |
| WO | WO 2004/044204 | 5/2004 |
| WO | WO 2004/045525 | 6/2004 |
| WO | WO 2004/050707 | 6/2004 |
| WO | WO 2004/050850 | 6/2004 |
| WO | WO 2004/050876 | 6/2004 |
| WO | WO 2004/056318 | 7/2004 |
| WO | WO 2004/058239 | 7/2004 |
| WO | WO 2004/058258 | 7/2004 |
| WO | WO 2004/058820 | 7/2004 |
| WO | WO 2004/062556 | 7/2004 |
| WO | WO 2004/065419 | 8/2004 |
| WO | WO 2004/065569 | 8/2004 |
| WO | WO 2004/067561 | 8/2004 |
| WO | WO 2004/068931 | 8/2004 |
| WO | WO 2004/069182 | 8/2004 |
| WO | WO 2004/071408 | 8/2004 |
| WO | WO 2004/072286 | 8/2004 |
| WO | WO 2004/074837 | 9/2004 |
| WO | WO 2004/078140 | 9/2004 |
| WO | WO 2004/085712 | 10/2004 |
| WO | WO 2004/087733 | 10/2004 |
| WO | WO 2004/087735 | 10/2004 |
| WO | WO 2004/090544 | 10/2004 |
| WO | WO 2004/095031 | 11/2004 |
| WO | WO 2004/098631 | 11/2004 |
| WO | WO 2004/104597 | 12/2004 |
| WO | WO 2004/108895 | 12/2004 |
| WO | WO 2004/111250 | 12/2004 |
| WO | WO 2005/000897 | 1/2005 |
| WO | WO 2005/005638 | 1/2005 |
| WO | WO 2005/011599 | 2/2005 |
| WO | WO 2005/012330 | 2/2005 |
| WO | WO 2005/014618 | 2/2005 |
| WO | WO 2005/016236 | 2/2005 |
| WO | WO 2005/018424 | 3/2005 |
| WO | WO 2005/018536 | 3/2005 |
| WO | WO 2005/025516 | 3/2005 |
| WO | WO 2005/025592 | 3/2005 |
| WO | WO 2005/025616 | 3/2005 |
| WO | WO 2005/026360 | 3/2005 |
| WO | WO 2005/027965 | 3/2005 |
| WO | WO 2005/028511 | 3/2005 |
| WO | WO 2005/033142 | 4/2005 |
| WO | WO 2005/033145 | 4/2005 |
| WO | WO 2005/037209 | 4/2005 |
| WO | WO 2005/041650 | 5/2005 |
| WO | WO 2005/044306 | 5/2005 |
| WO | WO 2005/046605 | 5/2005 |
| WO | WO 2005/047484 | 5/2005 |
| WO | WO 2005/047860 | 5/2005 |
| WO | WO 2005/051998 | 6/2005 |
| WO | WO 2005/052002 | 6/2005 |
| WO | WO 2005/053604 | 6/2005 |
| WO | WO 2005/058815 | 6/2005 |
| WO | WO 2005/058940 | 6/2005 |
| WO | WO 2005/120571 | 7/2005 |
| WO | WO 2005/070965 | 8/2005 |
| WO | WO 2005/072777 | 8/2005 |
| WO | WO 2005/080986 | 9/2005 |
| WO | WO 2005/081872 | 9/2005 |
| WO | WO 2005/090971 | 9/2005 |
| WO | WO 2005/095457 | 10/2005 |
| WO | WO 2005/096730 | 10/2005 |
| WO | WO 2005/100584 | 10/2005 |
| WO | WO 2005/105841 | 11/2005 |
| WO | WO 2005/105847 | 11/2005 |
| WO | WO 2005/105998 | 11/2005 |
| WO | WO 2005/108378 | 11/2005 |
| WO | WO 2005/110056 | 11/2005 |
| WO | WO 2005/123775 | 12/2005 |
| WO | WO 2005/123776 | 12/2005 |
| WO | WO 2006/005588 | 1/2006 |
| WO | WO 2006/005707 | 1/2006 |
| WO | WO 2006/014478 | 2/2006 |
| WO | WO 2006/014638 | 2/2006 |
| WO | WO 2006/015976 | 2/2006 |
| WO | WO 2006/016644 | 2/2006 |
| WO | WO 2006/033688 | 3/2006 |
| WO | WO 2006/036291 | 4/2006 |
| WO | WO 2006/037604 | 4/2006 |
| WO | WO 2006/038729 | 4/2006 |
| WO | WO 2006/039327 | 4/2006 |
| WO | WO 2006/039470 | 4/2006 |
| WO | WO 2006/040153 | 4/2006 |
| WO | WO 2006/041934 | 4/2006 |
| WO | WO 2005/040212 | 5/2006 |
| WO | WO 2006/047254 | 5/2006 |
| WO | WO 2006/047670 | 5/2006 |
| WO | WO 2006/050041 | 5/2006 |
| WO | WO 2006/050667 | 5/2006 |
| WO | WO 2006/052924 | 5/2006 |
| WO | WO 2006/053428 | 5/2006 |
| WO | WO 2006/055178 | 5/2006 |
| WO | WO 2006/066049 | 6/2006 |
| WO | WO 2006/066089 | 6/2006 |
| WO | WO 2006/066118 | 6/2006 |
| WO | WO 2006/066171 | 6/2006 |
| WO | WO 2006/066233 | 6/2006 |
| WO | WO 2006/067792 | 6/2006 |
| WO | WO 2006/069081 | 6/2006 |
| WO | WO 2006/069202 | 6/2006 |
| WO | WO 2006/081171 | 8/2006 |
| WO | WO 2006/083533 | 8/2006 |
| WO | WO 2006/083689 | 8/2006 |
| WO | WO 2006/087550 | 8/2006 |
| WO | WO 2006/094192 | 9/2006 |
| WO | WO 2006/094724 | 9/2006 |
| WO | WO 2006/095041 | 9/2006 |
| WO | WO 2006/096529 | 9/2006 |
| WO | WO 2006/096653 | 9/2006 |
| WO | WO 2006/099543 | 9/2006 |
| WO | WO 2006/100679 | 9/2006 |

(56) References Cited

FOREIGN PATENT DOCUMENTS

| | | |
|---|---|---|
| WO | WO 2006/103116 | 10/2006 |
| WO | WO 2006/110748 | 10/2006 |
| WO | WO 2006/116369 | 11/2006 |
| WO | WO 2006/118959 | 11/2006 |
| WO | WO 2006/119449 | 11/2006 |
| WO | WO 2006/121656 | 11/2006 |
| WO | WO 2006/125830 | 11/2006 |
| WO | WO 2006/128163 | 11/2006 |
| WO | WO 2006/133164 | 12/2006 |
| WO | WO 2006/137354 | 12/2006 |
| WO | WO 2007/005358 | 1/2007 |
| WO | WO 2007/005359 | 1/2007 |
| WO | WO 2007/008547 | 1/2007 |
| WO | WO 2007/011639 | 1/2007 |
| WO | WO 2007/011834 | 1/2007 |
| WO | WO 2007/017686 | 2/2007 |
| WO | WO 2007/019620 | 2/2007 |
| WO | WO 2007/021886 | 2/2007 |
| WO | WO 2007/022416 | 2/2007 |
| WO | WO 2007/040437 | 4/2007 |
| WO | WO 2007/042261 | 4/2007 |
| WO | WO 2007/047967 | 4/2007 |
| WO | WO 2007/047995 | 4/2007 |
| WO | WO 2007/050359 | 5/2007 |
| WO | WO 2007/053661 | 5/2007 |
| WO | WO 2007/059135 | 5/2007 |
| WO | WO 2007/059203 | 5/2007 |
| WO | WO 2007/062088 | 5/2007 |
| WO | WO 2007/062852 | 6/2007 |
| WO | WO 2007/064917 | 6/2007 |
| WO | WO 2007/064919 | 6/2007 |
| WO | WO 2007/064972 | 6/2007 |
| WO | WO 2007/067512 | 6/2007 |
| WO | WO 2007/068411 | 6/2007 |
| WO | WO 2007/068429 | 6/2007 |
| WO | WO 2007/082572 | 7/2007 |
| WO | WO 2007/068412 | 8/2007 |
| WO | WO 2007/088399 | 8/2007 |
| WO | WO 2007/088712 | 8/2007 |
| WO | WO 2007/090872 | 8/2007 |
| WO | WO 2007/092861 | 8/2007 |
| WO | WO 2007/096076 | 8/2007 |
| WO | WO 2007/097251 | 8/2007 |
| WO | WO 2007/098417 | 8/2007 |
| WO | WO 2007/103788 | 9/2007 |
| WO | WO 2007/106617 | 9/2007 |
| WO | WO 2007/108756 | 9/2007 |
| WO | WO 2007/109107 | 9/2007 |
| WO | WO 2007/109749 | 9/2007 |
| WO | WO 2007/112288 | 10/2007 |
| WO | WO 2007/113172 | 10/2007 |
| WO | WO 2007/118984 | 10/2007 |
| WO | WO 2007/119685 | 10/2007 |
| WO | WO 2007/123345 | 11/2007 |
| WO | WO 2007/125351 | 11/2007 |
| WO | WO 2007/127393 | 11/2007 |
| WO | WO 2007/127448 | 11/2007 |
| WO | WO 2007/129457 | 11/2007 |
| WO | WO 2007/144198 | 12/2007 |
| WO | WO 2007/149032 | 12/2007 |
| WO | WO 2008/002893 | 1/2008 |
| WO | WO 2008/008939 | 1/2008 |
| WO | WO 2008/011348 | 1/2008 |
| WO | WO 2008/012101 | 1/2008 |
| WO | WO 2008/015384 | 2/2008 |
| WO | WO 2008/021296 | 2/2008 |
| WO | WO 2008/022349 | 2/2008 |
| WO | WO 2008/027526 | 3/2008 |
| WO | WO 2008/028939 | 3/2008 |
| WO | WO 2008/030251 | 3/2008 |
| WO | WO 2008/030973 | 3/2008 |
| WO | WO 2008/031911 | 3/2008 |
| WO | WO 2008/045962 | 4/2008 |
| WO | WO 2008/047111 | 4/2008 |
| WO | WO 2008/051017 | 5/2008 |
| WO | WO 2008/051326 | 5/2008 |
| WO | WO 2008/057240 | 5/2008 |
| WO | WO 2008/060364 | 5/2008 |
| WO | WO 2008/061795 | 5/2008 |
| WO | WO 2008/064244 | 5/2008 |
| WO | WO 2008/067464 | 6/2008 |
| WO | WO 2008/070229 | 6/2008 |
| WO | WO 2008/071394 | 6/2008 |
| WO | WO 2008/084402 | 7/2008 |
| WO | WO 2008/104385 | 9/2008 |
| WO | WO 2008/104386 | 9/2008 |
| WO | WO 2008/107677 | 9/2008 |
| WO | WO 2008/110885 | 9/2008 |
| WO | WO 2008/122441 | 10/2008 |
| WO | WO 2008/124940 | 10/2008 |
| WO | WO 2008/129023 | 10/2008 |
| WO | WO 2008/130449 | 10/2008 |
| WO | WO 2008/131298 | 10/2008 |
| WO | WO 2008/134034 | 11/2008 |
| WO | WO 2008/143708 | 11/2008 |
| WO | WO 2008/150467 | 11/2008 |
| WO | WO 2008/150946 | 12/2008 |
| WO | WO 2008/150949 | 12/2008 |
| WO | WO 2008/156621 | 12/2008 |
| WO | WO 2008/156622 | 12/2008 |
| WO | WO 2009/008890 | 1/2009 |
| WO | WO 2009/008891 | 1/2009 |
| WO | WO 2009/009768 | 1/2009 |
| WO | WO 2009/044160 | 4/2009 |
| WO | WO 2009/048537 | 4/2009 |
| WO | WO 2009/048538 | 4/2009 |
| WO | WO 2009/048539 | 4/2009 |
| WO | WO 2010/097012 | 9/2010 |

OTHER PUBLICATIONS

Albert, S.E. et al., "Time-dependent induction of protective anti-influenza immune responses in human peripheral blood lymphocyte/SCID mice," J. Immunol. (1997) 153(3):1393-1403.

Almquist, R.G. et al., "Synthesis and biological activity of a ketomethylene analogue of a tripeptide inhibitor of angiotensin converting enzyme," J. Med. Chem. (1980) 23:1392-1398.

Altschul, S.F. et la., "Gapped BLAST and PSI_BLAST: a new generation of protein database search programs," Nucl. Acids Res. (1997) 25(17):3389-3402.

Ames, R.S. et al., "Conversion of murine Fabs isolated from a combinatorial phage display library to full length immunoglobulins," J. Immunol. Meth. (1995) 184:177-186.

Arai, K. et al., "An ELISA to determine the biodistribution of human monoclonal antibody in tumor-xenografted SCID mice," J. Immunol. Meth. (1998) 217:79-85.

Ardaillou, R., "An Ang II antagonist improves the Alzheimer's disease of the mouse," Medecine/Sciences (2008) 24(1):41.

Arispe, N. et al., "Alzheimer disease amyloid beta protein forms calcium channels in bilayer membranes: blockage by tromethamine and aluminum," Proc. Natl. Acad. Sci. (1993) 90:567-571.

Armstrong, J. et al., "Familial Alzheimer disease associated with A713T mutation in APP," Neurosci. Letters (2004) 370;241-243.

Asakura, K. et al., "Alpha-eudesmol, a P/Q-type Ca2+ channel blocker, inhibits neurogenic vasodilatation and extravasation following electrical stimulation of trigeminal gangion," Brain Res. (2000) 873:94-101, abstract.

Asakura, K. et al., "P/Q-type Ca2+ channel blocker game-agatoxin IVA protects against brain injury after focal ischemia in rats," Brain Res. (1997) 776:140-145, abstract.

Askanas, V. et al., "Inclusion-body myositis: a myodegenerative conformational disorder associated with Abeta, protein misfolding, and proteasome inhibition," Neurology (2006) 66(2) Supp 1:S39-48.

Askanas, V. et al., "Molecular pathology and pathogenesis of inclusion-body myositis," Microscopy Res. Technique (2005) 67:114-120.

Askanas, V. et al., "Proposed pathogenetic cascade of inclusion-body myositis: importance of amyloid-beta, misfolded proteins, predisposing genes, and aging," Curr. Opin. Rheumatol. (2003) 15(6):737-744.

(56) References Cited

OTHER PUBLICATIONS

Atherton et al., "The fluorenylmethoxycarbonyl amino protecting group," The Peptides: Analysis, Synthesis, Biology (1987) 9:1-38, Academic Press.

Ausubel, et al., Current Protocols in Molecular Biology (1993) Table of Contents.

Ausubel, F. et al., Short Protocols in molecular biology, 3rd Edition (1995), Table of Contents.

Ausubel, F.M. et al., Current Protocols in Molecular Biology (1989). Author Guidelines, Journal of Neurochemistry, Version 13, Jun. 2012, 14 pages.

Auvynet, C. et al., "Structural requirements for antimicrobial versus chemoattractant activities for dermaseptin S9," FEBS J. (2008) 275:4134-4151.

Awasthi et al., "Amyloid-beta causes apoptosis of newronal cells via caspase cascade, which can be prevented by amyloid-beta-derived short peptides," Exp. Neurology (2005) 196(2):282-289.

Azzazy, H.M.E. et al., "Phage display technology: clinical applications and recent innovations," Clin. Biochem. (2002) 35:425-445.

Babcook, J.S. et al., "A novel strategy for generating monoclonal antibodies from single, isolated lymphocytes producing antibodies of defined specificities," Proc. Natl. Acad. Sci. (1996) 93:7843-7848.

Bagriantsev, S. et al., "Modulation of Abeta SUB 42 low-n oligomerization using a novel yeast reporter system," BMC Biol. (2006) 4:32, 12 pages.

Banker, G.A. et al., "Rat hippocampal neurons in dispersed cell culture," Brain Res. (1977) 126(3):397-425.

Barany, G. et al., "Solid-phase peptide synthesis," in The Peptides: Analysis, Synthesis, Biology, (1980), Academic Press, Gross editor, vol. 2, p. 1-284.

Barbas, III, C.F. et al., "Assembly of combinatorial antibody libraries on phage surfaces: the gene III site," proc. Natl. Acad. Sci. USA (1991) 88:7978-7982.

Barghorn, S. et al., "Globular amyloid beta-peptide 1-42 oligomer—a homogeneous and stable neuropathological protein in Alzheimer's disease," J. Neurochem. (2005) 95(1):834-847.

Barghorn, S. et al., "Abeta-oligomer selective antibody A-887755 exhibits a favorable profile for Alzheimer's disease immunotherapy compared to Abeta-peptide unselective antibodies," Alzheimer's & Dementia: The Journal of the Alzheimer's & Association (2009) 5(4):P424.

Barrow, C.J. et al., "Solution conformations and aggregational properties of synthetic amyloid beta-peptides of Alzheimer's disease. Analysis of circular dichroism spectra," J. Mol. Biol. (1992) 225(4):1075-1093.

Bartolini, M. et al., "Insight into the kinetic of amyloid beta (1-42) peptide self-aggregation: elucidation of inhibitors' mechanism of action," Chembiochem. (2007) 8(17):2152-61.

Bateman, D. et al., "Specific binding of Alzheimer amyloid peptides to the cell surface implicates the presence of a membrane receptor," Neurobiol. of Aging (2004) 9th International Conf. on Alzheimers Disease and Related Disorders, Philadelphia, PA, Jul. 17-22, 2004.

Bateman, R.J. et al., "Human amyloid-beta synthesis and clearance rates as measured in cerebrospinal fluid in vivo," Nature Med. (2006) 12(7):856-861.

Bates, K.A. et al., "Clearance mechanisms of Alzheimer's amyloid-Beta peptide: implications for therapeutic design and diagnostic tests," Mol. Psych. (2009) 14(5):469-486.

Bayer, T.A. et al., "Review on the APP/PS1K1 mouse model: intraneuronal A beta accumulation triggers axonopathy, neuron loss and working memory impairment," Genes Brain Behav. (2008) 7:6-11.

Bedzyk, W.D. et al., "Active site structure and antigen binding properties of idiotypically cross-reactive anti-fluorescein monoclonal antibodies," J. Biol. Chem. (1990) 265(1):133-138.

Bell, K.A. et al., MAPK recruitment by beta-amyloid in organotypid hippocampal slice cultures depends on physical state and exposure time, J. Neurochem. (2004) 91(2):349-361.

Belokon, Y.N. et al., "Improved procedures for the synthesis of (S)-2-[N-(N'-benzyl-prolyl)amino]benzophenoe (BPB) and Ni(II) complexes of Schiff's bases derived from BPB and amino acids," Tetrahedron: Asymmetry (1998) 9:4249-4252.

Bennett et al., "Immunization therapy for Alzheimer disease?" Neurology (2005) 64:10-12.

Berman, D.E. et al., "Oligomeric amyloid-beta peptide disrupts phosphatidylinositol-4,5-bisphosphate metabolism," Nat. Neurosci. (2008) 11(5):547-554.

Bernstein, S.L. et al., "Amyloid beta-protein: monomer structure and early aggregation states of Abeta42 and its pro SUP 19 alloform," J. Am. Chem. Soc. (2005) 127(7):2075-2084.

Bernstein, S.L. et al., "Amyloid-beta protein oligomerization and the importance of tetramers and dodecamers in the aetiology of Alzheimer's disease," Nature Chem. (2009) 1:326-331.

Better, M. et al., "Escherichia coli secretion of an active chimeric antibody fragment," Science (1988) 240:1041-1043.

Bezprozvanny, I. et al., "Neuronal calcium mishandling and the pathogenesis of Alzheimer's disease," Trends Neurosci. (2008) 31(9):454-463.

Bharadwaj, P. e al., "A new method to measure cellular toxicity of non-fibrillar and fibrillar Alzheimer's Abeta using yeast," J. Alzheimer's Disease (2008) 13(2):147-150.

Bhaskar, K. et al., "The P13K-Akt-mTOR pathway regulates a oligomer induced neuronal cell cycle events," Mol. Neurodegeneration (2009) 4:1.

Bieniarz, C. et al., "Extended length heterobifunctional coupling agents for protein conjugations," Bioconjug. Chem. (1996) 7(1):88-95.

Bird, R.E. et al., "Single-chain antigen-binding proteins," Science (1988) 242:423-426.

Birren, B. et al., Genome Analysis—A Laboratory Manual, vols. 1 & 2, Table of Contents (1998).

Bitan, G. et al., "A molecular switch in amyloid assembly: met35 and amyloid beta-protein oligomerization," J. Am. Chem. Soc. (2003) 125:15359-15365.

Bitan, G. et al., "Amyloid beta-protein (Abeta) assembly: Abeta40 and Abeta42 oligomerize through distinct pathways," Proc. Natl. Acad. Sci. USA (2003) 100(1):330-335.

Bitan, G. et al., "Primary-quaternary structure relationships controlling early A beta oligomerizationpeptide revolution: genomics, proteomics and therapeutics," 18th American Peptide Symposium, Boston, MA Jul. 19-23, 2003, 765-767.

Bitan, G. et al., "Towards inhibition of amyloid beta-protein oligomerization," Biopolymers (2005) 80573, 19th American Peptide Symposium, San Diego, CA Jun. 18-23, 2005.

Bobich, J.A. et al., "Incubation of nerve endings with a physiological concentration of Abeta SUB 1-42 activates CaV2.2(N-type)-voltage operated calcium channels and acutely increases glutamate and noradrenaline release," J. Alzheimer's Dis. (2004) 6(3):243-255.

Bocher, W.O. et al., "Antigen-specific B and T cells in human/ouse radiation chimera following immunization in vivo," Immunol. (1999) 96:634-641.

Bombil, F. et al., "A promising model of primaray human immunization in human-scid mouse," Immuolbiol. (1996) 195:360-375.

Boridy, S. et al., "The binding of pullalan modified cholesteryl nanogels to Abeta oligomers and their suppression of cytotoxicity," Biomaterials (2009) 30(29):5583-5591.

Boss, M.A. et al., "Genetically engineered antibodies," Immunol. (1985) 6(1):12-13.

Boutaud, O. et al., "PGH SUB 2-derived levuglandin adducts increase the neurotoxicity of amyloid beta 1-42," J. Neurochem. (2006) 96(4):917-923.

Boutaud, O. et al., "Prostaglandin H2 (PGH2) accelerates formation of amyloid beta1-42 oligomers," J. Neurochem. (2002) 82:1003-1006.

Boyd-Kimball, D. et al., "Neurotoxicity and oxidative stress in D1M-substituted Alzheimer's Abeta(1-42): relevance to N-terminal methionine chemistry in small model peptides," Peptides (2005) 26:665-673.

Bravo, R. et al., "Sulfated polysaccharides promote the assembly of amyloid beta 1-42 peptide into stable fibrils of reduced cytotocity," J. Biol. Chem. (2008) 283:32471-32483.

Brettschneider, S. et al., "Decreased serum amyloid Beta1-42 autoantibody levels in Alzheimer's disease, determined by a newly

(56) References Cited

OTHER PUBLICATIONS developed immuno-precipitation assay with radiolabeled amyloid beta1-42 peptide," Biol. Psychiatry (2005) 57:813-816.
Brinkley, M.A., "A survey of methods for preparing protein conjugates with dyes, haptens and crosslinking reagents," Bioconjugate Chem. (1992) 3:2-13.
Brinkman, U. et al., "Phage display of disulfide-stabilized FV fragments," J. Immunol. Meth. (1995) 182:41-50.
Britschgi, M. et al., "Neuroprotective natural antibodies to assemblies of amyloidogenic peptides decrease with normal aging and advancing Alzheimer's disease," Proc. Natl. Acad. Sci. USA (2009) 106(29):12145-12150.
Brorson et al., "Mutational analysis of avidity and fine specificity of anti-levan antibodies," J. Immunol. (1999) 163:6694-6701.
Brown, J.P. et al., "Protein antigens of normal and malignant human cells identified by immunoprecipitation with monoclonal antibodies," J. Biol. Chem. (1980) 255(11):4980-4983.
Brown, J.P. et al., "Structural characterization of human melanoma-associated antigen p97 with monoclonal antibodies," J. Immunol. (1981) 127(2):539-546.
Brummell et al., "Probing the combining site of an anti-carbohydrate antibody by saturation-mutagenesis: role of the heavy-chain CDR3 residues," Biochem. (1993) 32:1180-1187.
Brunger et al., "Crystallography and NMR system: a new software suite for macromolecular structure determination," Acta Crystallogr. (1998) D54(Pt5):905-921.
Brutlag, D. "Computational Molecular Biology—Multiple Sequence Alignment," (2007).
Buchwald, H. et al., "Long-term continuous intravenous heparin administration by an implantable infusion pump in ambulatory patients with recurrent venous thrombosis," Surgery (1980) 88:507-516.
Buraei, Z. et al., "Roscovitine differentially affects CaV2 and Kv channels by binding to the open state," Neuropharmacology (2007) 52:883-894.
Burks et al., "In vitro scanning saturation mutagenesis of an antibody binding pocket," Proc. Natl. Acad. Sci. USA (1997) 94:412-417.
Burton, D.R. et al., "Human antibodies from combinatorial libraries," Adv. In Immunol. (1994) 57:191-208.
Butler, D. et al., "Cellular responses to protein accumulation involve autophagy and lysosomal enzyme activation," Rejuvenation Res. (2005) 8(4):227-237.
Carlsson, J. et al., "Protein thiolation and reversible protein-protein conjugation. N-succinimidyl 3-(2-pyridyldithio) propionate, a new heterobifunctional reagent," Biochem. J. (1978) 173(3):723-737.
Carter, D.A. et al., "More missense in amyloid gene," Nat. Genet. (1992) 2:255-256.
Carter, P. et al., "Humanization of an anti-p185HER2 antibody for human cancer therapy," Proc. Natl. Acad.Sci. (1992) 89:4285-4289.
Casset et al., "A peptide mimetic of an anti-CD4 monoclonal antibody by rational design," Biochem. Biophys. Res. Comm. (2003) 307:198-205.
Catterall, W.A. et al., "International Union of Pharmacology. XLVIII. Nomenclature and structure-function relationships of voltage-gated calcium channels," Pharm. Rev. (2005) 57(4):411-425.
Cecchini, C. et al., "Increased susceptibility to amyloid toxicity in familial Alzheimer's fibroblasts," Neurobiol. Aging (2007) 28(6):863-876.
Cecchini, M. et al., "A molecular dynamics approach to the structural characterization of amyloid aggregation," J. Mol. Biol. (2006) 357(4):1306-1321.
Chacon, M.A. et al., "Frizzled-1 is involved in he neuroprotective effect of Wnt3a against Abeta oligomers," J. Cell. Physiol. (2008) 217(1):215-227.
Chaiken, I.M., "Semisynthetic peptides and proteins," CRC Crit. Rev. Biochem. (1981) 11(3):255-301.
Chamat, S. et al., "Human monoclonal antibodies isolated from spontaneous Epstein-Barr virus-transformed tumors of Hu-SPL-SCID mice and specific for fusion protein display broad neutralizing activity toward respiratory syncytial virus," J. Infect. Dis. (1999) 180:268-277.
Chander, H. et al., "Binding of trypsin to fibrililar amyloid beta-protein," Brain Res. (2006) 1082(1):173-181.
Chang, L. et al., "Femtomole immunodetection of synthetic and endogenous amyloid-beta oligomers and its application to Alzheimer's disease drug candidate screening," J. Mol. Neurosci. (2003) 20(3):305-313.
Chanki, H. et al., "Ex situ atomic force microscopy analysis of beta-amyloid self-assembly and deposition on a synthetic template," Langmuir (2006) 16(22):6977-6985.
Chen et al., "Selection and analysis of an optimized anti-VEGF antibody: crystal structure of an affinity-matured Fab in complex with antigen," J. Mol. Biol. (1999) 293:865-881.
Chen, K. et al., "Cooperation between NOD2 and toll-like receptor 2 ligands in the up-regulation of mouse mFPR2, a G-protein-coupled Aalpha SUB 42 peptide receptor, in microglial cells," J. Leukocyte Biol. (2008) 83(6):1467-1475.
Chen, Y-R. et al., "Distinct early folding and aggregation properties of Alzheimer amyloid-beta peptides A beta 40 and A beta 42—stable trimer or tetramer formation by A beta 42," J. Biol. Chem. (2006) 281:24414-24422.
Chiang, H-C. et al., "Distinctive roles of different beta-amyloid 42 aggregates in modulation of synaptic functions," FASEB Journal (2009) 23(6):1969-1977.
Chiang, P.K. et al., "The many faces of amyloid beta in Alzheimer's disease," Curr. Mol. Med. (2008) 8(6):580-584.
Chiarini, A. et al., "Calcium-sensing receptor (CaSR) in human brain's pathophysiology: roles in late-onset Alzheimer's disease (LOAD)," Curr. Pharma. Biotech. (2009) 10(3):317-326.
Choo-Smith, LP et al., "The interaction between Alzheimer amyloid beta (1-40) peptide and ganglioside Gmi-containing membranes," FEBS Lett. (1997) 402:95-98.
Chothia, C. et al., "Canonical structures for the hypervariable regions of immunoglobulins," J. Mol. Biol. (1987) 196:901-917.
Chothia, C. et al., "Conformations of immunoglobulin hypervariable regions," Nature (1989) 342:877-883.
Chothia, C. et al., "Structural repertoire of the human VH segments," J. Mol. Biol. (1992) 227:799-817.
Chrisey, L. et al., "Covalent attachment of synthetic DNA to self-assembled monolayer films," Nucl. Acids. Res. (1996) 24(15):3031-3039.
Christensen, D.D., "Changing the course of Alzheimer's disease: anti-amyloid disease-modifying treatments on the horizon," Primary Care Companion J. Clin. Psych. (2007) 9(1):32-41.
Chromy et al., "Oligomer/conformation-dependent Abeta antibodies," Abstracts of the Annual Meeting of the Society for Neuroscience (2000) 26(1-2):4.
Chromy, B. et al., "Self-assembly of a beta 1-42 into globular neurotoxins," Biochem. (2003) 42(17):12749-12760.
Chromy, B.A. et al., "Stability of small oligomers of Abeta1-42( ADDLs)," Society for Neuroscience Abstracts (1999) Abstract No. 252129, 29th Annual Meeting of the Society for Neuroscience, Miami Beach, FL, Oct. 23-28, 1999.
Chung, H. et al., "Degradation of beta-amyloid peptide by microglia," Society for Neuroscience Abstracts (2000) 26 Abstract No. 858.10, 30th Annual Meeting of the Society of Neuroscience, New Orleans, LA, Nov. 4-9, 2000.
Ciccotosto, G.B. et al., "Methionine oxidation: implications for the mechanism of toxicity of the beta-amyloid peptide from Alzheimer's disease," Lett. Peptide Sci. (2003) 10(5-6):413-417.
Clackson, T. et al., "Making antibody fragments using phage display libraries," Nature (1991) 352:624-628.
Clark, M.S., Plant Molecular Biology—A Laboratory Manual, Table of Contents (1997).
Cleary, J.P. et al., "Cognitive effects of oligomeric and fibril Abeta in rats," Soc. for Neuroscience Abstract Viewer and Itinerary Planner (2002) Abstract No. 882.2, 32nd Annual meeting of the Society for Neuroscience, Orlando, FL, Nov. 2-7, 2002.
Cleek, R.L. et al., "Biodegradable polymeric carriers for a bFGF antibody for cardiovascular application," Proc. Intl. Symp. Control. Re. Bioact. Mater. (1997) 24:853-854.

(56) References Cited

OTHER PUBLICATIONS

Co, M.S. et al., "Genetically engineered deglycosylation of the variable domain increases the affinity of an anti-Cd33 monoclonal antibody," Molec. Immunol (1993) 30(15):1361-1367.
Cole, G.M. et al., "Alzheimer's amyloid story finds its star," Trends Mol. Med. (2006) 12(9):395-396.
Cole, G.M. et al., "Cat and mouse," Neuron (2006) 51(6):671-672.
Cole, G.M. et al., "Docosahexaenoic acid protecs from amyloid and dendritic pathology in an Alzheimer's disease mouse model," Nutrition and Health (2006) 18(3):249-259.
Cole, M.S. et al., "Human IgG2 variants of chimmeric anti-CD3 are nonmitogenic to T cells," J. Immunol. (1997) 159(7):3613-3621.
Colombo, R. et al., "CE can identify small molecules that selectively target soluble oligomers of amyloid beta protein and display antifibrillogenic activity," Electrophoresis (2009) 30(8):1418-1429.
Costantini, C. et al., "The expression of p75 neurotrophin receptor protects against the neurotoxicity of soluble oligomers of beta-amyloid," Exp. Cell Res. (2005) 311(1):126-134.
Craft, J.M. et al., "Enhanced susceptibility of S-100B transgenic mice to neuroinflammation and neuronal dysfunction induced by intracerebroventricular infusion of human beta-amyloid," Glia (2005) 51(3):209-216.
Crouch, P.J. et al., "Soluble oligomeric amyloid beta 1-42 specifically inhibits cytochrome c oxidase of human mitochondria," Mitochondrial Medicine (2004) 4:71-72.
Crouse, N.R. et al., "Oligomeric amyloid-beta(1-42) induces THP-1 human monocyte adhesion and maturation," Brain Res. (2009) 1254:109-119.
Dahlgren, K.N. et al., "Oligomeric and fibrillar species of amyloid-beta peptides differentially affect neuronal viability," J. Biol. Chem. (2002) 277(35):32046-32053.
Das, U. et al., "Interface peptide of Alzheimer's amyloid beta: application in purification," Biochem. Biophys. Res. Commun. (2007) 362(2):538-542.
Dasilva, K.A. et al., "Reduced oligomeric and vascular amyloid-beta following immunization of TgCRND8 mice with an Alzheimer's DNA vaccine," Vaccine (2009) 27136-1376.
De Felice, F.G. et al., "Alzheimer's disease-type neuronal tau hyperphosphorylation induced by Abeta oligomers," Neurobiol. Aging (2008) 29(9):1334-1347.
De Pascalis, R. et al., "Grafting of 'abbreviated' complementarity-determining regions containing specificity-determining residues essential for ligand contact to engineer a less immunogenic humanized monoclonal antibody," J. Immunol. (2002) 169:3076-3084.
Dealmeida, E.R.P. et al., "Transgenic expression of two marker genes under the control of an *Arabidopsis* rbcS promoter: sequences encoding the Rubisco transit peptide increase expression levels," Mol Gen. Genet. (1989) 218:78-86.
deChaves, P.E. et al., "Lipid rafts in amyloid beta endocytosis and amyloid beta-induced apoptosis," J. Neurochem. (2009) 110(2):146, S20-23.
DeMattos et al., "P4-358 in vitro and in vivo characterization of beta-amyloid antibodies binding to cerebral amyloid angiopathy (CAA) and the selective exacerbation of CAA-associated microhemorrhage," Neurobiol. Aging (2004) 25(S2):S577.
DeMattos, R.B. et al., "Peripheral anti-Abeta antibody alters CNS and plasma Abeta clearance and decreases brain Abeta burden in a mouse model of Alzheimer's disease," Proc. Natl. Acad. Sci. USA (2001) 98(15):8850-8855.
Demeester, N. et al., "Comparison of the aggregation properties, secondary structure and apoptotic effects of wild-type, Flemish and Dutch N-terminally truncated amyloid beta peptides," Euro. J. Neurosci. (2001) 13(11):2015-2024.
Demuro, A. et al., "Calcium dysregulation and membrane disruption as a ubiquitous neurotoxic mechanism of soluble amyloid oligomers," J. Biol. Chem. (2005) 280(17):17294-17300.
Denkewalter et al., "Fortschritte der arzneimittelforschung progress in drug research progres des recehrches pharmaceutiques," (1996) 10:224-285.

Dewachter, I. et al., "Neuronal deficiency of presenillin 1 inhibits amyloid plaque formation and corrects hippocampal long-term potentiation but not a cognitive defect of amyloid precursor protein [V717I] transgenic mice," J. Neurosci. (2002) 22(9):3445-3453.
Dickson, D.W. et al., "Correlations of synaptic and pathological markers with cognition of the elderly," Neurobiol. Aging (1995) 16(3):285-304.
Dillen, K. et al., "A two decade contribution of molecular cell biology to the centennial of Alzheimer's disease: are we progressing toward therapy?" Int. Rev. Cytol. (2006) 254:215-300.
Dingledine, R. et al., Brain slices, Plenum Press (1984) Table of Contents.
Donnet et al., "Plasma treatment effect on the surface energy of carbon and carbon fibers," Carbon (1986) 24(6):757-770.
Du, Y. et al., "Reduced levels of amyloid beta-peptide antibody in Alzheimer disease," Neurology (2001) 57:801-805.
Dufner, P. et al., "Harnessing phage and ribosome display for antibody optimisation," Trends Biotech. (2006) 24(11):523-529.
During, M.J. et al., "Controlled release of dopamine from a polymeric brain implant: in vivo characterization," Ann. Neurol. (1989) 25:351-356.
Durocher, Y. et al., "High-level and high-throughput recombinant protein prouction by transient transfection of suspension-growing human 293-EBNA1 cells," Nucl. Acid. Res. (2002) 30(2):e9-11.
Eckenhoff, R.G. et al., "Anesthetics and neurodegenerative disorders: a molecular basis for concern?" Anesthesiology Abstracts of Scientific Papers Annual Meeting, 2003, Abstract No. A-848, 2003 Annual Meeting of the American Society of Anesthesiologists, San Francisco, CA, Oct. 11-15, 2003.
Eckert, A. et al., "Oligomeric and fibrillar species of beta-amyloid (A beta 42) both impair mitochondrial function in P301L tau transgenic mice," J. Mol. Med. (2008) 86(11):1255-67.
Eisenberg et al., "Analysis of membrane and surface protein sequences with the hydrophobic moment plot," J. Mol. Biol. (1984) 179(1):125-142.
Englund, H. et al., Oligomerization partially explains the lowering of A beta 42 in Alzheimer's disease cerebrospinal fluid, Neurodegenerative Dis. (2009) 6:139-147.
Eren, R. et al., "Human monoclonal antibodies specific to hepatitis B virus generated in a human/mouse radiation chimera: the Trimera system," Immunol. (1998) 93:154-161.
Esteras-Chopo, A. et al., "New strategy for the generation of specific D-peptide amyloid inhibitors," J. Mol. Biol. (2008) 377:1372-1381.
Evans et al., "Design of a nonpeptidal ligands for a peptide receptor: cholecystokinin antagonists," J. Med. Chem. (1987) 30:1229.
Evans, C.G. et al., "Heat shock proteins 70 and 90 inhibit early stages of amyloid beta-(1-42) aggregation in vitro," J. Biol. Chem. (2006) 281:33182-33191.
Evans, N.A. et al., "Abeta SUB 1-42 reduces synapse number and inhibits neurite outgrowth in primary cortical and hippocampal neurons: a quantitative analysis," J. Neurosci. Methods (2008) 175(1):96-103.
Evin, G., "Gamma-secretase modulators: hopes and setbacks for the future of Alzheimer's treatment," Expert Rev. Neurother. (2008) 8(11):1611-1613.
Fauchere, "Elements for the rational design of peptide drugs," Adv. Drug Res. (1986) 15:29-69.
Feld, M. et al., "Effect on memory of acute administration of naturally secreted fibrils and synthetic amyloid-beta peptides in an invertebrate model," Neurobiol. Learn. Mem. (2008) 89(4):407-418.
Ferrao-Gonzales, A et al., "Controlling beta-amyloid oligomerization by the use of naphthalene sulfonates: trapping low molecular weight oligomeric species," J. Biol. Chem. (2005) 280(41):34747-34754.
Fishwild, D.M. et al., "High-avidity human IgGx monoclonal antibodies from a novel strain of minilocus transgenic mice," Nature Biotech. (1996) 14:845-851.
Flink, M.T. et al., "Ca2+ channels as targets of neurolgoical disease: Lambert-Eaton Syndrome and other Ca2+ channelopathies," J. Bioeng. Biomembr. (2003) 35(6):697-718.
Foote, J. et al., "Antibody framework residues affecting the conformation of the hypervariable loops," J. Mol. Biol. (1992) 224:487-499.

(56) References Cited

OTHER PUBLICATIONS

Forsell, C. et al., "Amyloid precursor protein mutation at codon 713 (Ala→Val) does not cause schizophrenia: non-pathogenic variant found at codon 705 (silent)," Neurosci. Lett. (1995) 184:90-93.
Fradinger, E.A. et al., "C-terminal peptides coassemble into Abeta42 oligomers and protect neurons against Abeta42-induced neurotoxicity," Proc. Natl. Acad. Sci. USA 92008) 105(37):14175-14180.
Fuchs, P. et al., "Targeting recombinant antibodies to the surface of *Escherichia coli*: fusion to a peptidoglycan associated lipoprotein," BioTech. (1991) 9:1369-1372.
Funke, S.A. et al., "Detection of amyloid-beta aggregates in body fluids: a suitable method for early diagnosis of Alzheimer's disease?" Current Alzheimer's Research (2009) 6(3):285-289.
Galfre, G. et al., "Antibodies to major histocompatibility antigens produced by hybrid cell lines," Nature (1977) 266(5602):550-552.
Gallo, M.L. et al., "The human immunoglobulin loci introduced into mice: V(D) and J gene segment usage similar to that of adult humans," Eur. J. Immunol (2000) 30:534-540.
Garrard, L.J. et al., "FAB assembly and enrichment in a monovalent phage display system," BioTech. (1991) 9:1373-1377.
Garzon, D.J. et al., "Oligomeric amyloid decreases basal levels of brain-derived neurotrophic factor (BDNF) mRNA via specific downregulation of BDNF transcripts IV and V in differentiated human neuroblastoma cells," J. Neurosci. (2007) 27(10):2628-2635.
Gavilondo, J.V. et al., "Antibody engineering at the millennium," BioTechniques (2002) 29:128-145.
Gefter, M.L. et al., "A simple method for polyethylene glycol-promoted hybridization of mouse myeloma cells," Somatic Cell Genetics (1997) 3(2):231-236.
Gellermann, G.P. et al., "Abeta-globulomers are formed independently of the fibril pathway," Neurobiol. of Dis. (2008) 30(2):212-220.
Gervais, F. et al., "Targeting soluble Abeta peptide with tramiprosate for the treatment of brain amyloidosis," Neurobiol. Aging (2007) 28(4):537-547.
Ghiso, J. et al., "Systemic catabolism of Alzheimer's Abeta40 and Abeta42," J. Biol. Chem. (2004) 279:45897-45908.
Ghosal, K. et al., "Alzheimer's disease-like pathological features in transgenic mice expressing the APP intracellular domain," Proc. Natl. Acad. Sci. (2009) 106(43):18367-18372.
Giacobini, E. et al., "One hundred years after the discovery of Alzheimer's disease. A turning point for therapy? The multifaceted aspects of Alzheimer's disease: from social to molecular problems," J. Alzheimer's Disease (2007) 12(1):37-52.
Gibbs, M.E. et al., "Rescue of Abeta SUB 1-42-induced memory impairment in day-old chick by facilitation of astrocytic oxidative metabolism: implications for Alzheimer's disease," J. Neurochem. (2009) 109 Suppl. 1:230-236.
Giege, R. et al., "An introduction to the crystallogenesis of biological macromolecules," Crystallization of Nucleic Acids & Proteins, a Practical Approach, 2nd Edition: 1-16 (1999).
Giliberto, L. et al., "Mutant presenilin 1 increases the expression and activity of BACE1," J. Biol. Chem. (2009) 284(14):9027-9038.
Gillies, S.D. et al., "High-level expression of chimeric antibodies using adapted cDNA variable region cassettes," J. Immunol. Meth. (1989) 125:191-202.
Giuffrida, M.L. et al., "A beta(25-35) and its C- and/or N-blocked derivatives: copper driven structural features and neurotoxicity," J. Neursci. Res. (2007) 85:623-633.
Giuffrida, M.L. et al., "Beta-amyloid monomers are neuroprotective," J. Neurosci. (2009) 29(34):10582-10587.
Goeddel, D., "Systems for heterologous gene expression," Meth. in Enzymol. (1990) 185:3-7.
Goldspiel, B.R. et al., "Human gene therapy," Clin. Pharm. (1993) 12:488-505.
Gong, Y. et al., "Abeta-derived diffusible ligands in Alzheimer's disease brain as therapeutic antibody targets," Abstracts of the Annual Meeting of the Society of Neuroscience (2002) 1 page.
Gong, Y., "Alzheimer's disease-affected brain: presence of oligomeric A ligands (ADDLs) suggests a molecular basis for reversible memory loss," Proc. Natl. Acad. Sci. (2003) 100(18):10417-10422.
Gonzalo-Ruiz, A. et al., "Oligomers of beta-amyloid (1-42) peptide induce co-localization of AB and TAU proteins associated with calpain activity," J. Neurochem. (2009) 110:57-58.
Goodson, J.M., "Dental applications" in Medical Applications of Controlled Release, (1984) vol. II, Chapter 6, 115-138.
Gowing, E. et al., "Chemical characterization of A beta 17-42 peptide, a component of diffuse amyloid deposits of Alzheimer disease," J. Biol. Chem. (1994) 269:10987-10988.
Grabarek, Z. et al., "Zero-length crosslinking procedure with the use of active esters," Anal. Biochem. (1990) 185(1):131-135.
Grabowski, T.J. et al., "Novel amyloid precursor protein mutation in an Iowa family with dementia and severe cerebral amyloid angiopathy," Ann. Neurol. (2001) 49(6):697-705.
Grace, S.Y. et al., "Abeta induces oxidative-degradative stress through NADPH oxidase and phopholipase A2," J. Neurochem. (2009) 110222, 22nd Biennial Meeting of the International Society of Neurochemistry, South Korea, Aug. 23-29, 2009.
Gram, H. et al., "In vitro selection and affinity maturation of antibodies from a naïve combinatorial immunoglobulin library," Proc. Natl. Acad. Sci. USA (1992) 89:3576-3580.
Grange, P.De La. et al., "FAST DB: a website resource for the study of the expression regulation of human gene products," Nucl. Acids Res. (2005) 33(13):4276-4284.
Green, L.L. et al., "Antigen-specific human monoclonal antibodies from mice engineered with human Ig heavy and light chain YACs," Nature Genetics (1994) 7(1):13-21.
Green, L.L. et al., "Regulation of B cell development by variable gene complexity in mice reconsituted with human immunoglobulin yeast artificial chromosomes," J. Exp. Med. (1998) 188(3):483-495.
Green, L.L., "Antibody engineering via genetic engineering of the mouse: XenoMouse strains are a vehicle for the facile generation of therapeutic human monoclonal antibodies," J. Immunol. Meth. (1999) 231:11-23.
Griffiths, A.D. et al., "Human anti-self antibodies with high specificity from phage display libraries," The EMBO Journal (1993) 12(2):725-734.
Guo, L. et al., "APOE down regulates pro-inflammatory responses induced by oligomeric Abeta in activated glia," Soc. for Neurosci. Abstract Viewer and Itinerary Planner (2002), Abstract No. 883.12, 32nd Annual meeting of the Society for Neuroscience, Orlando, FL, Nov. 2-7, 2002.
Ha, C. et al., "Ex situ atomic force microscopy analysis of beta-amyloid self-assembly and deposition on a synthetic template," Langmuir (2006) 22:6977-6985.
Ha, C. et al., "Metal ions differntially influence the aggregation and deposition of Alzheimer's beta-amyloid on a solid template," Biochem. (2007) 46(20):6118-6125.
Ha, H.J. et al., "Development of herbal medicine for Alzheimer's disease from RHEI rhizoma," J. Neurochem. (2009) 110114.
Haass, C. et al., "Soluble protein oligomers in neurodegeneration: lessons from the Alzheimer's amyloid beta-peptide," Nat. Rev. Mol. Cell Biol. (2007) 8(2):101-112.
Hachiya, N.S. et al., "Oligomeric Aip2p/Dld2p modifies the protein conformation of both properly folded and misfolded substrates in vitro," Biochem. Biophys. Res. Comm. (2004) 323(1):339-344.
Hagemeyer, C.E. et al., "Single-chain antibodies as diagnostic tools and therapeutic agents," Thromb. Haemost. (2009) 101:1012-1019.
Halladay, M.W. et al., "Synthesis of hydroxyethelene and ketomethylene dipeptide isosteres," Tetrahedron Lett. (1983) 24:4401-4404.
Hann, M.M., "On the double bond isostere of the peptide bond: preparation of an enkephalin analogue," J. Chem. Soc. Perkin Transactions (1982) 1:307-314.
Harding, F.A. et al., "Class switching in human immunoglobulin transgenic mice," Ann. N.Y. Acad. Sci. (1995) 764:536-546.
Hardy, J. et al., "The amyloid hypothesis of Alzheimer's disease: progress and problems on the road to therapeutics," Science (2002) 297:353-356.

(56) References Cited

OTHER PUBLICATIONS

Harris-White, M.E. et al., "Effects of low dose, low MW soluble amyloid oligomers on spatial memory performance," Society for Neurosci. Abstr. Viewer and Itin. Plann. (2003) Abstract No. 240.11, 33rd Annual Meeting of the Society of Neuroscience, Nov. 8-12, 2003, New Orleans.

Hartley, D.M. et al., "Transglutaminase induces protofibril-like amyloid beta-protein assemblies that are protease-resistant and inhibit long-term potentiation," J. Biol. Chem. (2008) 283(24):16790-16800.

Hashida, S. et al., "More useful maleimide compounds for the conjugation of Fab to horseradish peroxidase through thiol groups in the hinge," J. Appl. Biochem. (1984) 6:56-63.

Hashimoto, M. et al., "Role of protein aggregation in mitochondrial dysfunction and neurodegeneration in Alzheimer's and Parkinson's disease," Neuromol. Med. (2003) 4(1-2):21-36.

Hawkins, R.E., "Selection of phage antibodies by binding affinity—imicking affinity maturation," J. Mol. Biol. (1992) 226:889-896.

Hay, B.N. et al., "Bacteriophage cloning and *Escherichia coli* expression of a human IgM fab," Hum. Antibod. Hybridomas (1992) 3:81-85.

Hayes, G.M. et al., "Production of beta-amyloid by primary human foetal mixed brain cell cultures and its modulation by exogenous soluble beta-amyloid," Neurosci. (2002) 113(3):641-646.

Head, E. et al., "A two-year study with fibrillar beta-amyloid (Abeta) immunization in aged canines: effects on cognitive function and brain Abeta," J. Neurosci. (2008) 28(14):3555-3566.

Head, E. et al., "The effffects of immunization with fibrillar or oligomeric Abeta in the brain and CSF of aged canines: a pilot study," Society for Neuroscience Abstract Viewer and Itinerary Planner (2003) Abstract No. 525.24, 33rd Annual Meeting of the Society of Neuroscience, New Orleans, LA, Nov. 8-12, 2003.

Heard, C. et al., "Two neutralizing human anti-RSV antibodies: cloning, expression, and characterization," Molec. Med. (1999) 5:35-45.

Heinitz, K. et al., "Toxicity mediated by soluble oligomers of beta-amyloid(1-42) on cholinergic SN56.B5.G4 cells," J. Neurochem. (2006)98(6):1930-1945.

Helisalmi, S. et al., "Screening for amyloid beta precursor protein codon 665, 670/671 and 717 mutations in Finnish patients with Alzheimer's disease," Neurosci. Left. (1996) 205:68-70.

Herz, U. et al., "The humanized (Hu-PBMC) SCID mouse as an in vivo model for human IgE production and allergic inflammation of the skin," Int. Arch Allergy Immunol. (1997) 113(1-3):150-152.

Hess et al., "Cooperation of glycolytic enzymes," J. Adv. Enzyme Reg. (1968) 7:149-167.

Hieter, P.A. et al., "Evolution of human immunoglobulin kJ region genes," J. Biol. Chem. (1982) 257(3):1516-1522.

Higgins, D.G. et al., "Fast and sensitive multiple sequence alignments on a microcomputer," CABIOS Comm. (1989) 5(2):151-153.

Higuchi, R., "Using PCR to engineer DNA," PCR Technol: Princ. & Appl. for DNA Amplification (1989) 61-70.

Hilbich, C. et al., "Aggregation and secondary structure of synthetic amyloid betaA4 peptides of Alzheimer's disease," J. Mol. Biol. (1991) 218:149-163.

Hillen, H. et al., "Generation and therapeutic efficacy of highly oligomer-specific beta-amyloid antibodies," J. Neurosci. (2010) 30(31):10369-10379.

Hirko, A.C. et al., "Peripheral transgene expression of plasma gelsolin reduces amyloid in transgenic mouse models of Alzheimer's disease," Mol. Ther. (2007) 15(9):1623-9.

Hock, C. et al., "Clinical observations with AN-1792 using TAPIR analyses," Neurodegenerative Dis. (2006) 2(5):273-276.

Holliger, P. et al., ""Diabodies" small bivalent and bispecific antibody fragments," Proc. Natl. Acad. Sci. (1993) 90:6444-6448.

Holm et al., "Functional mapping and single chain construction of the anti-cytokeratin 8 monoclonal antibody TS1," Mol. Immunol. (2007) 44:1075-1084.

Hong, H-S. et al., "Combining the rapid MTT formazan exocytosis assay and the MC65 protection assay led to the discovery of carbozole analogs as small molecule inhibitors of Abeta oligomer-induced cytotoxicity," Brain Res. (2007) 1130(1):223-234.

Hong, H-S. et al., "Inhibition of Alzheimer's amyloid toxocity with a tricyclic pyrone molecule in vitro and in vivo," J. Neurochem. (2009) 108(4):1097-1108.

Hoogenboom, H.R. et al., "Multi-subunit proteins on the surface of silamentous phage: methodologies for displaying antibody (Fab) heavy and light chains," Nucl. Acids Res. (1991) 19(15):4133-4137.

Hoogenboom, H.R. et al., "Natural and designer binding sites made by phage display technology," Immunol. Today (2000) 21(8):371-378.

Hoogenboom, H.R., "Designing and optimizing library selection strategies for generating high-affinity antibodies," Tibtech (1997) 15:62-70.

Hoozemans, J.J.M. et al., "Always around, never the same: pathways of amyloid beta induced neurodegeneration throughout the pathogenic cascade of Alzheimer's disease," Curr. Med. Chem. (2006) 13(22):2599-2605.

Hossain, S. et al., "Mechanism of docosahexaenoic acid-induced inhibition of in vitro Abetal-42 fibrillation and Abetal-42-induced toxicity in SH-S5Y5 cells," J. Neurochem. (2009) 111(2):568-579.

Howard III, M.A. et al., "Intracerebral drug delivery in rats with lesion-induced memory deficits," J. Neurosurg. (1989) 71:105-112.

Howlett, D.R. et al., "The pathology of APP transgenic mice: a model of Alzheimer's disease or simply overexpression of APP?" Histol. Histopathol. (2009) 24(1):83-100.

Hoyer, W. et al., "Stabilization of a beta-hairpin in monomeric Alzheimer's amyloid-beta peptide inhibits amyloid formation," Natl. Acad. Sci. Proc. Natl. Acad. Sci. (2008) 105(13):5099-5104.

Hruby, V.J., "Conformational restrictions of biologically active peptides via amino acid side chain groups," Life Sci. (1982) 31:189-199.

Hsiao et al., "Correlative memory deficits, abeta elevation, and amyloid plaques in transgenic mice," Science (1996) 274(5284):99-102.

Huang, C. et al., "Isoproterenol potentiates synaptic transmission primarily by enhancing presynaptic calcium influx via P- and/or Q-type calcium channels in the rat amygdala," J. Neurosci. (1996) 16(3):1026-1033.

Huang, C.C. et al., "Selective enhancement of P-type calcium currents by isoproterenol in the rat amygdata," J. Neurosci. (1998) 18(6):2276-2282.

Huang, X. et al., "Metal-dependence of Abeta oligomerization," Soc. for Neurosci. Abstract Viewer and Itinerary Planner (2002), Abstract No. 19.1, 32nd Annual meeting of the Society for Neuroscience, Orlando, FL, Nov. 2-7, 2002.

Huse, W.D. et al., "Generation of a large combinatorial library of the immunoglobulin repertoire in phage lambda," Science (1989) 246:1275-1281.

Huston, J.S. et al., "Protein engineering of antibody binding sites: recovery of specific activity in all anti-digoxin single-chain Fv analogue produced in *Escherichia coli*," PNAS (1988) 85:5879-5883.

Huston, J.S. et al., "Protein engineering of single-chain Fv analogs and fusion proteins," Meth. in Enzymol. (1991) 203:46-88.

Hutchins, W.A. et al., "Human immune response to a peptide mimic of neisseria meningitis serogroup C in hu-PBMC-SCID mice," Hybridoma (1999) 18(2):121-129.

Hyman et al., "Autoantibodies to Amyloid-beta and Alzheimer's disease," Ann. Neurol. (2001) 49:808-810.

Iijima, K. et al., "A beta 42 mutants with different aggregation profiles induce distinct pathologies in *Drosophila*," PLoS One (2008) 3 Article No. E1703.

Ilan, E. et al., "The hepatitis B virus-trimera mouse: a model for human HBV infection and evaluation of anti-HBV therapeutic agents," Hepatology (1999) 29:553-562.

Ingelbrect, I.L.W. et al., "Different 3' end regions strongly influence the level of gene expression in plant cells," The Plant Cell (1989) 1:671-780.

Jang et al., "The structural basis for DNA binding by an anti-DNA autoantibody," Molec. Immunol. (1998) 35:1207-1217.

Janssen, J.C. et al., "Early onset familial Alzheimer's disease: mutation frequency in 31 families," Neurology (2003) 60(2):235-239.

(56) References Cited

OTHER PUBLICATIONS

Jefferis, R., "Glycosylation of recombinant antibody therapeutics," Biotechnol. Prog. (2005) 21:11-16.
Jennings-White, C. et al., "Synthesis of ketomethylene analogogs of dipeptides," Tetrahedr. Lett. (1982) 23(25):2533-2534.
Jensen, M.T. et al., "Lifelong immunization with human beta-amyloid (1-42) protects Alzheimer's transgenic mice against cognitive impairment throughout aging," Neurosci. (2005) 130:667-684.
Jiang, S. et al., "Recent progress of synthetic studies to peptide and peptidomimetic cyclization," Curr. Org. Chem. (2008) 12(17):1502-1542.
Joerchel, S. et al., "Oligomeric beta-amyloid(1-42) induces the expression of Alzheimer disease-relevant proteins in cholinergic SN56.B5.G4 cells as revealed by proteomic analysis," Int. J. Developm. Neurosci. (2008) 26(3-4):301-308.
Johansson, A.S. et al., "Attenuated amyloid-beta aggregation and neurotoxicity owing to methionine oxidation," NeuroReport (2007) 18(6):559-563.
Johansson, A.S. et al., "Dramatic changes in fibrillization rate and oligomer/protofibrillar formation of beta-amyloid peptide with oxidized methionine: implications for novel therapeutic approaches in Alzheimer's disease," Soc. for Neurosci. Abstract Viewer and Itinerary Planner (2002), Abstract No. 123.8, 32nd Annual meeting of the Society for Neuroscience, Orlando, FL, Nov. 2-7, 2002.
Johansson, A-S. et al., "Docosahexaenoic acid stabilizes soluble amyloid-beta protofibrils and sustains amyloid-beta-induced neurotoxicity in vitro," FEBS J. (2007) 274(14):990-1000.
Johansson, A-S. et al., "Physiochemical characterization of the Alzheimer's disease-related peptides Abeta1-42Arctic and Abeta1-42wt," FEBS Journal (2006) 273(12):2618-2630.
Johnsson, B. et al., "Comparison of methods for immobilozation to carboxymethyl dextran sensor surfaces by analysis of the specific activity of monoclonal antibodies," J. Mol. Rec. (1995) 8:125-131.
Johnsson, B. et al, "Immobilizataion of progeins to a carboxymethyldextran-modified gold surface for biospecific interaction analysis in surface plasmon resonance sensors," Anal. Biochem. (1991) 198:268-277.
Joliot, A. et al., "Antennapedia homeobox peptide regulates neural morphogenesis," Proc. Natl. Acad. Sci. USA (1991) 88:1864-1868.
Jones, C.T. et al., "Mutation in codon 713 of the beta-amyloid precursor protein gene presenting with schizophrenia," Nat. Genet. (1992) 1(4):306-309.
Jones, J.D.G. et al., "High level expression of introduced chimaeric genes in regenerated transformed plants," EMBO J. (1985) 4(10):2411-2418.
Jonsson, U. et al., "Introducing a biosensor based technology for real-time biospecific interaction analysis," Ann. Biol. Clin. (1993) 51:19-26.
Jonsson, U. et al., "Real-time biospecific interaction analysis using surface plasmon resonance and a sensor chip technology," BioTechniques (1991) 11(5):620-627.
Jungbauer, L.M. et al., "Preparation of fluorescently-labeled amyloid-beta peptide assemblies: the effect of luorophore conjugation on structure and function," J. Mol. Recogn. (2009) 22(5):403-413.
Kabat, E.A. et al., "Attempts to locate complementarity-determining residues in the variable positions of light and heavy chains," Ann. NY Acad. Sci. (1971) 190:382-391.
Kabat, E.A. et al., Sequences of Proteins of Immunological Interest, 5th Edition, NIH Publ. #91-3242 (1981), Table of Contents.
Kaiser et al., "Peptide and protein synthesis by segment synthesis-condensation," Science (1989) 243:187.
Kakio, A. et al., "Interactions of amyloid beta-protein with various gangliosides in raft-like membranes: importance of GM1 ganglioside-bound form as an endogenous seed fr Alzheimer amyloid," Biochem. (2002) 41:7385-7390.
Kamino, K. et al., "Linkage and mutational analysis of familial Alzheimer disease kindreds for the APP gene region," Am. J. Hum. Genet. (1992) 51(5):998-1014.
Kanemitsu, H. et al., "Human neprilysin is capable of degrading amyloid beta peptide not only in the monomeric form but also the pathologica oligomeric form," Neursci. Lett. (2003) 350:113-116.
Kaufman, R.J. et al., "Amplification and expression of sequences contrasfected with a modular dihydrofolate reductase complementary DNA gene," Mol. Biol. (1982) 159:601-621.
Kawarabayashi, T. et al., "Age-dependent changes in brain, CSF, and plasma amyloid beta protein in the Tg2576 transgenic mouse model of Alzheimer's disease," J. Neurosci. (2001) 21(3):372-381.
Kawarabayashi, T. et al., "Dimeric amyloid beta protein rapidly accumulates in lipid rafts followed by apolipoprotein E and phosphorylated Tau accumulation in the Tg2576 mouse model of Alzheimer's disease," J. Neurosci. (2004) 24(15):3801-3809.
Kayed, R. et al., "Common structure of soluble amyloid oligomers implies common mechanism of pathogenesis," Science (2003) 300(18):486-489.
Kellermann, S-A. et al., "Antibody discovery: the use of transgenic mice to generate human monoclonal antibodies for therapeutics," Curr. Opin. in Biotechnol. (2002) 13:593-597.
Kenneth, R.H. in Monoclonal Antibodies: A New Dimension in Biological Analyses, Plenum Publishing Corp. New York, New York (1980).
Kent, S.B.H., "Chemical synthesis of peptides and proteins," Ann. Rev. Biochem. (1988) 57:957-989.
Keowkase, R. et al., "Mechanism of CNS drugs and their combinations for Alzheimer's disease," Central Nervous System Agents in Medicinal Chemistry (2008) 8(4):241-248.
Kettleborough, C.A. et al., "Isolation of tumor cell-specific single-chain Fv from immunized mice using phage-antibody libraries and the re-construction of whole antibodies from these antibody fragments," Eur. J. Immunol. (1994) 24:952-958.
Kim, N.D. et al., "Putative therapeutic agents for the learning and memory deficits of people with Down syndrome," Bioorg. Med. Chem. Lett. (2006) 16(14):3772-3776.
Kim, Y.S. et al., "Biological tuning of synthetic tactics in solid-phase synthesis: application to Abeta(1-42)" J. Org. Chem. (2004) 69(22):7776-7778.
Kipriyanov, S.M. et al., "Recombinant single-chain Fv fragments carrying C-terminal cysteine residues: production of bivalent and biotinylated miniantibodies," Mol. Immun. (1994) 31(14):1047-1058.
Kipriyanov, S.M. et al., "Single-chain antibody streptavidin fusions: tetrameric bifunctional scFv-complexes with biotin binding activity and enhanced affinity to antigen," Hum. Antibod. Hybridomas (1995) 6(3):93-101.
Kirkitadze, M.d. et al., "Identification and characterization of key kinetic intermediates in amyloid B-protein fibrillogenesis," J. Mol. Biol. (2001) 312:1103-1119.
Kitamura, Y. et al., "Stress proteins and regulation of microglial amyloid-beta phagocytosis," Folia Pharmacologica Japonica (2004) 124(6):407-413.
Kitchin, K. et al., "Cloning, expression, and purification of an anti-desipramine single chain antibody in NS/0 myeloma cells," J. Pharm. Sci. (1995) 84(10):1184-1189.
Klafki, H-W. et al., "Electrophoretic separation of beta-A4 peptides (1-40) and 1-42)," Anal. Biochem. (1996) 237:24-29.
Klein, W., "A beta toxicity in Alzheimers disease; globular oligomers (ADDLs) as new vaccine and drug targets," Neurochem. Intl. (2002) 41(5):345-352.
Klyubin, I. et al., "Amyloid beta-protein (abeta) bearing the arctic mutation is a more potent inhibitor of LTP than wild type Abeta," Society for Neuroscience Abstract Viewer and Itinerary Planner (2003), 2003Abstract No. 904.13, 33rd Annual Meeting of the Society of Neuroscience, New Orleans, LA, Nov. 8-12, 2003.
Knappik, A. et al., "Fully synthetic human combinatorial antibody libraries (hUCAL) based on modular consensus frameworks and CDRs randomized with trinucleotides," J. Mol. Biol. (2000) 296:57-86.
Knowles, J.K. et al., "The p75 neurotrophin receptor promotes amyloid-beta(1-42)-induced neuritic dystrophy in vitro and in vivo," J. Neurosci. (2009) 29:10627-10637.

(56) References Cited

OTHER PUBLICATIONS

Kobayashi et al., "Tryptophan H33 plays an important role in Pyrimidine (6-4) pyrimidone photo product binding by a high-affinity antibody," Protein Eng. (1999) 12:879-884.

Koh, S-H. et al., "Amyloid-beta-induced neurotoxicity is reduced by inhibition of glycogen synthase kinase-3," Brain Res. (2008) 1188:254-262.

Kohler, "Continuous cultues of fused cells secreting antibody of predefined specificity," Nature (1975) 256:495-497.

Kokubo, H. et al., "Oligomeric proteins ultrastructurally localize to cell processes, especially to axon terminals with higher density, but not to lipid rafts in Tg2576 mouse brain," Brain Res. (2005) 1045(1-2):224-228.

Kontermann, Antibody Engineering, Springer-Verlag, Berlin, Table of Contents (2001).

Kooistra, J. et al., "A new function of human htra2 as an amyloid-beta oligomerization inhibitor," J. Alzheimer's Disease (2009) 17(2):281-294.

Kortekaas, P. et al., "Development of HVA and LVA calcium currents in pyramidal CA1 neurons in the hippocampus of the rat," Dev. Brain Res. (1997) 101(1-2):139-147.

Kranenburg, O. et al., "beta-Amyloid (Abeta) cuases detachment of N1E-115 neuroblastoma cells by acting as a scaffold for cell-associated plasminogen activity," Mol. Cell. Neurosci. (2005) 28(3):496-508.

Kriegler, M., Gene Transfer and Expression—A Laboratory Manual (1990) Table of Contents.

Kumar et al., "Molecular cloning and expression of the Fabs of human autoantibodies in *Escherichia coli*," J. Biol. Chem. (2000) 275:35129-35136.

Kumar, A. et al., "Neuropathology and therapeutic management of Alzheimer's disease—an update," Drugs of the Future (2008) 33(5):433-446.

Kumar-Singh, S. et al., "Dense-core senile plaques in the Flemish variant of Alzheimer's disease are vasocentric," Am. J. Pathol. (2002) 161(2):507-520.

Kuo, Y-M. et al., "Water-soluble Abeta (N-40, N-42) oligomers in normal and Alzheimer disease brains," J. Biol. Chem. (1996) 271(8):4077-4081.

Kwon, Y.E. et al., "Synthesis, in vitro assay, and molecular modeling of new piperidine derivatives having dual inhibitory potency against acetylcholinesterase and Abeta SUB 1-42 aggregation for Alzheimer's disease therapeutics," Bioorg. Med. Chem. (2007) 15(20):6596-6607.

Lacor et al., "Synaptic targeting by Alzheimer's-related amyloid beta oligomers," J. Neurosci. (2004) 24:10191-10200.

Laemmli, U.K. et al., "Cleavage of structural proteins during the assembly of the head of bacteriophage T4," Nature (1970) 227:680-685.

Lahiri, D.K. et al., "Lethal weapon: amyloid beta-peptide, role in the oxidative stress and neurodegeneration of Alzheimer's disease," Neurobiol Aging (2004) 25(5):581-587.

Lam, a.R. et al., "Effects of the Arctic (E22-G) mutation on amyloid beta-protein folding: discrete molecular dynamics study," J. Amer. Chem. Soc. (2008) 130(51):17413-22.

Lam, X.M. et al., "Microencapsulation of recombinant humanized monoclonal antibody for local delivery," Proceedings Intl. Symp. Control. Rel. Bioact. Mater. (1997) 24:759-760.

Lambert, M.P. et al., "Diffusible, nonfibrillar ligands derived from A Beta1-42 are potent central nervous system neurotoxins," Proc. Natl. Acad. Sci. (1998) 95:6448-6453.

Lambert, M.P. et al., "Monoclonal antibodies that target pathological assemblies of A beta," J. Neurochem. (2007) 100(1):23-35.

Lambert, M.P. et al., Vaccination with soluble AB oilgerm generates toxicity-neutralizing antibodies, J. Neurochem. (2001) 79(3):595-605.

Langer & Peppas, Editors, Journal of Macromolec. Sci. (1983) 23:61-127.

Langer, R., New methods of drug delivery, Science (1990) 249:1527-1533.

Lanni, C. et al., "Studies and screening of molecules interacting with beta amyloid and other amyloidogenic proteins," Society for Neuroscience Abstract Viewer and Itinerary Planner (2003) Abstract No. 841.1, 33rd Annual Meeting of the Society of Neuroscience, New Orleans, LA, Nov. 8-12, 2003.

Lashuel, H.A. et al., "Amyloid pores from pathogenic mutations," Nature (2002) 418(6895):291.

Lau, T-L. et al., "Cholesterol and clioquinol modulation of A beta(1-42) interaction with phospholipid bilayers and metals," Biochimica et biophysica acta (2007)1768(12):3135-44.

Lauren, J. et al., "Cellular prion protein mediates impairment of synaptic plasticity by amyloid-beta oligomers," Nature (2009) 457(7233):1128-1132.

Lazo, N.D. et al., "On the nucleation of amyloid beta-protein monomer folding," Protein Sci. (2005) 14(6):1581-15196.

Leader, K.A. et al., "Antibody responses to the blood group antigen D in SCID mice reconstituted with human blood mononuclear cells," Immunology (1992) 76:229-234.

Lecanu, L. et al., "Caprospinol: moving from a neuroactive steroid to a neurotropic drug," Exp. Opin. Invest. Drugs (2009) 18(3):265-276.

Lee, C-C. et al., "Insulin rescues amyloid beta-induced impairment of hippocampal long-term potentiation," Neurobiol. Aging (2009) 30(3):377-387.

Lee, D.H.S., et al., "Differential physiologic responses of alpha7 nicotinic acetylcholine receptors to beta-amyloid SUB 1-40 and beta-amyloid SUB 10-42," J. Neurobiol. (2003) 55(1):25-30.

Lee, E.B. et al., "Secretion and intracellular generation of truncated Abeta in beta-site amyloid-beta precursor protein-cleaving enzyme expressing human neurons," J. Biol Chem. (2003) 278(7):4458-4466.

Lee, E.B. et al., "Targeting amyloid-beta peptide (Abeta) oligomers by passive immunization with a conformation-selective monoclonal antibody improves learning and memory in Abeta precursor protein (APP) transgenic mice," J. Biol. Chem. (2006) 281(7):4292-4299.

Lee, H-K. et al., "The insulin/Akt signaling pathway is targeted by intracellular beta-amyloid," Mol. Biol. Cell (2009) 20(5):1533-1544.

Lee, T.Y. et al., "Artificial proteases toward catalytic drugs for amyloid diseases," Pure and Applied Chem. (2009) 81:255-262.

Lemere, C.A. et al., "Amyloid-beta immunotherapy for the prevention and treatment of Alzheimer disease: lessons from mice, monkeys, and humans," Rejuvenation Res. (2006) 9(1):77-84.

Lemere, C.A. et al., "Developing novel immunogens for a safe and effective Alzheimer's disease vaccineNeurotherapy: Progress in Restorative Neuroscience and Neurology," Progress in Brain Research (2009) 175:83-93.

Lerner, E.A., "How to make a hybridoma," The Yale Journal of Biology and Medicine (1981) 54(5):387-402.

Leveille, F. et al., "Influence des formes oligomeriques du peptide amyloide beta 1-42 sur la viabilite neuronale," Revue Neurologique (2007) 163(11)-2:4523.

Levine, H. et al., "Alzheimer's .beta.-peptide oligomer formation at physiologic concentrations," Anal. Biochem. (2004) 335:81-90.

Levitt, M., "Molecular dynamics of native protein," J. Mol. Biol. (1983) 168:595-620.

Levy et al., "Inhibition of calcification of bioprosthetic heart valves by local controlled-release diphosphonate," Science (1985) 228:190-192.

Lewis, H. et al., "Quantification of Alzheimer pathology in ageing and dementia: age-related accumulation of amyloid-beta(42) peptide in vascular dementia," Neuropath. Appl. Neurobiol. (2006) 32(2):103-118.

Li, H. et al., "SAR and mechanistic studies of tetrapeptide inhibitors of A beta 42-induced neurotoxicity," Biopolymers (2009) 92(4):P077.

Liao, Y.J. et al., "Anti-Ca2+ channel antibody attenuates Ca2+ currents and mimics cerebellar ataxia in vio," Proc. Natl. Acad. Sci. USA (2008) 105(7):2705-2710.

Liirs, T. et al., "3D structure of Alzheimer's amyloid-beta (1-42) fibrils," Proc. Natl. Acad. Sci. (2005) 102(48):17342-17347.

Lindberg, C. et al., "Beta-amyloid protein structure determines the nature of cytokine release from rat microglia," J. Mol. Neurosci. (2005) 271-12.

(56) References Cited

OTHER PUBLICATIONS

Little, M. et al., "Of mice and men: hybridoma and recombinant antibodies," Immun. Today (2000) 21(8):364-370.
Liu, M. et al., "Progress in soluble Abeta oligomers in Alzheimer's disease and drugs targeting Abeta oligomers," Chinese Pharmacological Bulletin (2008) 24(12):1554-1557.
Liu, Q. et al., "A novel nicotinic acetylcholine receptor subtype in basal forebrain cholinergic neurons with high sensitivity to amyloid peptides," J. Neurosci. (2009) 29(4):918-929.
Liu, R. et al., "Residues 17-20 and 35-35 of beta-amyloid play critical roles in aggregation," J. Neurosci Res. (2004) 75(2):162-171.
Liu, R. et al., "Trehalose differentially inhibits aggregation and neurotoxicity of beta-amyloid 40 and 42," Neurobiol. Dis. (2005) 20(1):74-81.
Lonberg, N. et al., "Antigen-specific human antibodies from mice comprising four distinct genetic modifications," Nature (1994) 368:856-859.
Lonberg, N. et al., "Human antibodies from transgenic mice," Intern. Rev. Immunol. (1995) 13:65-92.
Lue, L-F et al., "Soluble amyloid beta peptide concentration as a predictor of synaptic change in Alzheimer's disease," Am. J. Path. (1999) 155(3):853-862.
Lunn, M.P.T. et al., "High-affinity anti-ganglioside IgG antibodies raised in complex ganglioside knockout mice: reexamination of FDIa immunolocalization," J. Neurochem. (2000) 75:404-412.
Ma, Q.L. et al., "p21-activated kinase-aberrant activation and translocation in Alzheimer's disease pathogenesis," J. Biol. Chem. (2008) 283(20):14132-14143.
Macao, B. et al., "Recombinant amyloid beta-peptide production by coexpression with an affibody ligand," BMC Biotechnology (2008) 8:82.
MacCallum, R. M. et al., "Antibody-antigen interactions: contact analysis and binding site topography," J. Mol. Biol. (1996) 262:732-745.
Maccioni, R.B. et al., "What have we learned from the tau hypothesis? Current hypothesis and research milestones in Alzheimer's disease current hypotheses and research milestones in Alzheimer's disease," International Summitt Meeting on Current Hypotheses on Alzheimer Disease, Renaca, Chile, Nov. 22-25, 2007.
Macquitty, J.M. et al., "GenPharm's knockout mice," Science (1992) 257:1188.
Mader, C. et al., "Interaction of the crystalline bacterial cell surface layer protein SbsB and the secondary cell wall polymer of *Geobacillus stearothermophilus* PV72 assessed by real-time surface plasmon resonance biosensor technology," J. Bacteriol. (2004).
Madrigal, J.L.M. et al., "Neuroprotective actions of noradrenaline: effects of glutathione synthesis and activation of peroxisome proliferator activated receptor delta," J. Neurochem. (2007) 103(5):2092-101.
Maier, M. et al., "Short amyloid-beta immunogens reduce cerebral in an Alzheimer's disease mouse model in the absence of an Amyloid-beta-specific cellular immune response," J. Neurosci. (2006) 26(18):4717-4728.
Maliga, P. et al., Methods in Plant Molecular Biology—A Laboratory Manual, Table of Contents (1995).
Mandal, P.K. et al., "Alzheimer's disease: halothane induces Abeta peptide to oligomeric form—solution NMR studies," Neurochem. Res. (2006) 31(7):883-890.
Manelli, A.M. et al., "A beta 42 neurotoxicity in primary co-cultures: effect of apoE isoform and A beta conformation," Neurobiol. of Aging (2007) 281139-1147.
Manelli, A.M. et al., "ApoE and Abeta1-42 interactions," J. Mol. Neurosci. (2004) 23235-246.
Manelli, A.M. et al., "Glial activation by oligomeric versus fibrillar Abetal-42," Soc. for Neurosci. Abstract Viewer and Itinerary Planner (2002), Abstract No. 193.9, 32nd Annual meeting of the Society for Neuroscience, Orlando, FL, Nov. 2-7, 2002.
Marachalonis, J.J. et al., "Evolutionary factors in the emergence of the combinatorial germline antibody repertoire," Adv. Exp. Med. Biol. (2001) 484:13-30.
Maria, T.J. et al., "Upregulation of p21(Cip1) in activated glial cells," Glia (2009) 57524-534.
Mariette, X., "Nucleotidic sequence analysis of the variable domains of four human monoclonal IgM with an antibody activity to myelin-associated glycoprotein," Eur. J. Immunol. (1993) 23:846-851.
Marlow, L. et al., "APH1, PEN2 and Nicastrin increase Abeta levels and gamma-secretase activity," Biochem. Biophys. Res. Comm. (2005) 305(3):502-509.
Masliah, E. et al., "Progress in the development of new treatments for combined Alzheimer's and Parkinson's diseases," Drug Development Res. (2002) 56282-292.
Masman, MF. Et al., "In silico study of full-length amyloid beta 1-42 tri- and penta-oligomers in solution," J. Phys. Chem. B. (2009) 113:11710-11719.
Masters, C.L. et al., "Amyloid plaque core portein in Alzheimer disease and Down syndrome," Proc. Natl. Acad. Sci. USA (1985) 82:4245-4249.
Mastrangelo, I.A. et al., "High-resolution atomic force microscopy of soluble A.beta.42 oligomers," J. Mol. Biol. (2006) 358:106-119.
Masuda, Y. et al., "Identification of physiological and toxic conformations in Abeta42 aggregates," Chem Bio Chem. (2009) 10(2):287-295.
Mathura, V.S. et al., "Model of Alzheimer's disease amyloid-beta peptide based on a RNA binding protien," Biochem. Biophys. Res. Comm. (2005) 332(2):585-592.
Mattson et al., "A practical approach to crosslinking," Mol. Biol. Reports (1993) 17:167-183.
Mattson, M.P., "Pathways towards and away from Alzheimer's disease," Nature (2004) 430:631-639.
Mattson, M.P., "Pathways towards and away from Alzheimer's disease," Nature (2004) 431(7004):107.
Maurer, M.H. et al., "The proteome of neural stem cells from adult rat hippocampus," Proteome Sci. (2003) 1(1):4.
May, K., "Buying a new immnoassay system?" BioTechnology—TIBTECH (1993) 11:272-273.
McCafferty, J. et al., "Phage antibodies: filamentous phage displaying antibody variable domains," Nature (1990) 348:552-554.
McLaurin, J. et al., "Inositol steroisomers stabilize an oligomeric aggregate of Alzheimer amyloid beta peptide and inhibit Abeta-induced toxicity," J. Biol. Chem. (2000) 27518495-18502.
McLaurin, J. et al., "Review modulating factors in amyloid-beta fibril formation," J. Structural Biol. (2000) 130(2-3):259-270.
McLean, C.A. et al., "Soluble pool of Abeta amyloid as a determinant of severity of neurodegeneration in Alzheimer's disease," Am. Neurol. Assoc. (1999) 46:860-866.
Meijer et al., "Biochemical and cellular effects of roscovitine, a potent and selective inhibitor of the cyclindependent kinases cdc2, cdk2 and cdk5," Eur. J. Biochem. (1997) 243(1-2):527-536.
Meli, G. et al., "Direct in vivo intracellular selection of conformation-sensitive antibody domains targeting Alzheimer's amyloid-beta oligomers," J. Mol. Biol. (2009) 287(3):584-606.
Mendez, M.J. et al., "Functional transplant of megabase human immunoglobulin loci recapitulates human antibody response in mice," Nat. Genet. (1997) 15(2):146-156.
Merrifield, B., "Solid phase synthesis," Science (1986) 232:342.
Merrifield, J., "The total synthesis of an enzyme with ribonuclease A activity," J. Am. Chem. Soc. (1969) 91:501-502.
Miller, Y. et al., "Polymorphism of Alzheimer's A beta(17-42) (p3) oligomers: the importance of the turn location and its conformation," Biophys. J. (2009) 971168-1177.
Minkeviciene, R. et al., "Amyloid beta-induced neuronal hyperexcitability triggers progressive epilepsy," J. Neurosci. (2009) 29(11):3453-3462.
Mizushima, S. et al., "pEF-BOX, a powerful mammalian expression vector," Nucl. Acids Res. (1990) 18(17):5322.
Moechars et al., "Early phenotypic changes in transgenic mice that overexpress different mutants of amyloid precursor protein in brain," J. Biol. Chem. (1999) 274(10):6483-6492.
Moir et al., "Autoantibodies to redox-modified oligomeric Abeta are attenuated in the plasma of Alzheimer's disease patients," J. Biol. Chem. (2005) 280:17458-17463.

(56) References Cited

OTHER PUBLICATIONS

Monien, B.H. et al., "A novel approach to Alzheimer's disease therapy: inhibition of A beta 42 oligomerization by C-terminal A beta 42 fragments," J. Peptide Sci. (2006) 12147.

Morgan, R.a. et al., "Human gene therapy," Ann. Rev. Biochem. (1993) 62:191-217.

Morgan, T.E. et al., "Abeta-derived diffusible ligands (ADDLs): Clusterin (apo J), congo red binding and toxicity," Society for Neuroscience Abstracts (1999) Abstract No. 252130, 29th Annual Meeting of the Society for Neuroscience, Miami Beach, FL, Oct. 23-28, 1999.

Morley, J.S., "Modulation of the action of regulatory peptides by structural modification," TIPS (1980) 463-468.

Morrison, S.L. et al., "Chimeric human antibody molecules: mouse antigen-binding domains with human constant region domains," Proc. Natl. Acad. Sci. (1984) 81:6851-6855.

Morrison, S.L., "Transfectomas provide novel chimeric antibodies," Science (1986) 229:1202-1207.

Mueller, W. et al., "Apolipoprotein E isoforms increase intracellular Ca2+ differentially through an omega-agatoxin IVA-sensitive Ca2+ channel," Brain Pathology (1998) 8(4):641-653.

Mullan et al., "A locus for familial early-onset Alzheimer's disease on the long arm of chromosome 14, proximal to the alpha1-amtichymotrypain gene," Nature Genet. (1992) 2:340-342.

Mullan, M. et al., "A pathogenic mutation for probable Alzheimer's disease in the APP gene at the N-terminus of beta-amyloid," Nat. Genet. (1992) 1(5):345-347.

Muller, W. et al., "Impaired Ca-signling in astroycytes from the Ts16 mouse model of Down syndrome," Neurosci. Lett. (1997) 223(2):81-84.

Mulligan, R.C., "The basic science of gene therapy," Science (1993) 260:926-932.

Mullis, K. et al., "Specific enzymatic amplification of DNA in vitro: the polymerase chain reaction," Cold Spring Harbor Symp. Quant. Biol. (1986) 51:263-273.

Munter, L.-M. et al., "GxxxG motifs within the amyloid precursor protein transmembrane sequence are critical for the etiology of Abeta42," EMBO J. (2007) 26(6):1702-1712.

Murphy, W.J. et al., "CD40 stimulation promotes human dsecondary immunoglobulin responses in HuPBL-SCID chimeras," Clin. Immunol. (1999) 90(1):22-27.

Murphy, W.J. et al., "The huPBL-SCID mouse as a means to examine human immune functionin vivo," Immunol. (1996) 8:233-241.

Murray, M.M. et al., "Amyloid beta protein: a beta 40 inhibits A beta 42 oligomerization," J. Am. Chem. Soc. (2009) 131:6316-6317.

Myagkova, M.A. et al., "Autoantibodies to beta-amyloid and neurotransmitters in patients with Alzheimer's disease and senile dementia of the Alzheimer type," Bulletin of Exp. Biol. Med. (2001) 2:127-129.

Nagele, R.G. et al., "Contribution of glial cells to the development of amyloid plaques in Alzheimer's disease," Neurobiol of Aging (2004) 25(5):663-674.

Naslund, J. et al., "Relative abundance of Alzheimer Abeta amyloid peptide variants in Alzheimer disease and normal aging," Proc. Natl. Acad. Sci. (1994) 91:8378-8382.

Nath et al., "Autoantibodies to amyloid B-peptide (AB) are increased in Alzheimer's disease patients and AB antibodies can enhance AB neurotoxicity," Neuromol. Med. (2003) 3:29-39.

Needleman, S.B. et al., "A general method applicable to the search for similarities in the amino acid sequence of two proteins," J. Mol. Biol. (1970) 48:443-453.

Nerelius, C. et al., "Alpha-Helix targeting reduces amyloid-beta peptide toxicity," Proc. Natl. Acad. Sci. USA (2009) 106(23):9191-9196.

Neuberger, M.S. et al., "Recombinant antibodies possessing novel effector functions," Nature (1984) 312:604-608.

Nguyen, H. et al., "Production of human monoclonal antibodies in SCID mouse," Microbiol. Immunol. (1997) 41(12):901-907.

Nicholas, M.R. et al., "Different amyloid-ent amyloid-beta aggregation states induced monocyte differentiation or activation," J. Neurochem. (2009) 10867, 40th Annual Meeting of the American Society for Neurochemistry, Charleston, South Carolina, Mar. 7-11, 2009.

Nielsen, H.M. et al., "Preferential uptake of amyloid beta 1-42 oligomers by primary human astrocytes in vitro: influence of SAP and C1q," Mol. Immunol. (2009) 262860, 12th European Meeting on Complement in Human Disease, Hungary, Sep. 5-8, 2009.

Nilges, M. et al., "Determination of three-dimensional structures of proteins from interproton distance data by hybrid distance geometry-dynamical simulated annealing calculations," FEBS Lett. (1989) 229(2):317-324.

Nimmrich, V. et al., "Amyloid beta oligomers (A beta(1-42) globulomer) suppress spontaneous synaptic activity by inhibition of P/Q-type calcium currents," J. Neurosci. (2008) 28(4):788-797.

Nimmrich, V. et al., "Is Alzheimer's disease a result of presynaptic failure?—Synaptic dysfunctions induced by oligomeric p-amyloid," Rev. Neurosci. (2009) 20(1):1-12.

Ning, S. et al., "Intratumoral radioimmunotherapy of a human colon cancer xenograft using a sustained-release gel," Radiotherapy & Oncology (1996) 39:179-189.

Nomura, I. et al., "Mechanism of impairment of long-term potentiation by amyloid beta is independent of NMDA receptors or voltage-dependent calcium channels in hippocampal CA1 pyramidal neurons," Neurosci. Lett. (2005) 391(1-2):1-6.

Oi, V.T. et al., "Chimeric antibodies," BioTechniques (1985) 4(3):214-215.

Okamuro et al., The Biochemistry of Plants—A comprehensive Treatise, V. 15, 1-82 (1989).

Ono, K. et al., "Effects of grape seed-derived polyphenols on amyloid beta-protein self-assembly and cytotoxicity," J. Biol. Chem. (2008) 283(47):32176-32187.

Opazo, C. et al., "Metalloenzyme-like activity of Alzheimer's disease beta-amyloid: Cu-dependent catalytic conversion of dopamine, cholesterol, and biological reducing agents to neurotoxic H SUB 2O SUB 2," J. Biol. Chem. (2002) 277(43):40302-40308.

Orgogozo et al., "Subacute meningoencephalitis in a subset of patients with AD after Abeta42 immunization," Neurology (2003) 61:46-54.

Origlia, N. et al., "Abeta-dependent inhibition of LTP in different intracortical circuits of the visual cortex: the role of RAGE," J. Alzheimer's Disease (2009) 17(1):59-68.

Otto, M. et al., "Neurochemical approaches of cerebrospinal fluid diagnostics in neurogenerative diseases," Methods (2008) 44(4):289-298.

Padlan et al., "Structure of an antibody-antigen complex: crystal structure of the HyHEL-10 Fab-lysozyme complex," Proc. Natl. Acad. Sci USA (1989) 86:5938-5942.

Padlan, E.A. et al., "Identification of specificity-determining residues in antibodies," FASEB (1995) 9:133-139.

Padlan, E.A., "A possible procedure for recucing the immunogenicity of antibody variable domains while preserving their ligand-binding properties," Molec. Immunol. (1991) 28(4/5):489-498.

Palmer, J. et al., "Endothelin-converting enzyme-2 is increased in Alzheimer's disease and up-regulated by Abeta," Am. J. Path. (2009) 175(1):262-270.

Pan, X.D. et al., "Tripchlorolide protects neuronal cells from microglia-mediated beta-amyloid neurotoxicity through inhibiting NF-kappa B and JNK signaling," GLIA (2009) 57:1227-1238.

Pan, X-D. et al., "Effect of inflammatory responses in microglia induced by oligomeric beta-amyloid SUB 1-42 on neuronal cells," Acta Anatomica Sinica (2008) 39(6):804-809.

Partis, M.D. et al., "Crosslinking of proteins by omega-maleimido alkanoyl N-hydroxysuccinimide esters," J. Protein Chem. (1983) 2:263-277.

Pastor, M.T. et al., "Amyloid toxicity is independent of polypeptide sequence, length and chirality," J. Mol. Biol. (2008) 375:695-707.

Peacock, M.L. et al., "Novel amyloid precursor protein gene mutation (codon 665Asp) in a patient with late-onset Alzheimer's disease," Ann. Neurol. (1994) 35(4):432-438.

Peacock, M.L. et al., "Novel polymorphism in the A4 region of the amyloid precursor protein gene in a patient without Alzheimer's disease," Neurol. (1993) 43(6):1254-1256.

(56) References Cited

OTHER PUBLICATIONS

Pearson, W.R. et al., "Improved tools for biological sequence comparison," PNAS (1988) 85:2444-2448.
Pellicano, M. et al., "The sea urchin embryo: a mdoel to study Alzheimer's beta amyloid induced toxicity," Archives of Biochem. Biophys. (2009) 483:120-126.
Perouansky, M., "Liaisons dangereuses? General anaesthetics and long-term toxicity in the CNS," Eur. J. Anaesthesiol. (2007) 24(2):107-115.
Persic, L. et al., "An integrated vector system for the eukaryotic expression of antibodies or their fragments after selection from phage display libraries," Gene (1997) 187:9-18.
Petrushina, I., "Alzheimer's disease peptide epitope vaccine reduces insoluble but not soluble/oligomeric Abeta species in amyloid precursor protein transgenic mice," J. Neurosci. (2007) 27(46):12721-12731.
Pfeifer, M. et al., "Cerebral hemorrhage after passitve anti-Abeta immunotherapy," Science (2002) 298:1379.
Phu, M-J et al., "Fluorescence resonance energy transfer analysis of apolipoprotein e C-terminal domain and amyloid beta peptide (1-42) interaction," J. Neurosci. Res. (2005) 80(6):877-886.
Pike, C.J. et al., "Structure—activity analyses of B-amyloid peptides: contributions of the B25-35 region to aggregation and neurotoxicity," J. Neurochem. (1995) 64(1):253-265.
Plant, LD. Et al., "The production of amyloid beta peptide is a critical requirement for the viablility of central neurons," J. Neurosci. (2003) 23(13):5531-5535.
Podlisny, M.B. et al., "Aggreagation of secreted amyloid beta-protein into sodium dodecyl sufate-stable oligomers in cell culture," J. Biol. Chem. (1995) 270(16):9564-9570.
Poljak, R.J., "Production and structure of diabodies," Structure (1994) 2:1121-1123.
Portelius, E. et al., "Targeted proteomics in Alzheimer's disease: focus on amyloid-beta," Exp. Rev. Proteomics (2008) 5(2):225-237.
Portolano, S. et al., "High affinity, thyroid-specific human autoantibodies displayed on the surface of filamentous phage use V genes similar to other autoantibodies," J. Immunol. (1993) 151(5):L2839-2851.
Presta, LG. et al., "Humanization of an antibody directed against IgE," J. Immunol. (1993) 151(5):2623-2632.
Putney, P.W., Calcium Signaling, CRC Press Inc. (2005).
Puzzo, D. et al., "Picomolar amyloid-beta positively modulates synaptic plasticity and memory in hippocampus," J. Neurosci. (2008) 28:14537-14545.
Qian, J. et al., "Presynaptic Ca2+ channels and neurotransmitter release at the terminal of a mouse cortical neuron," J. Neurosci. (2001) 21(11):3721-3728.
Qiu, W. et al., "Convenient, large-scale asymmetric synthesis of eriantiomerically pure trans-cinnamylglycine and -alpha-alamine," Tetrahedron (2000) 56:2577-2582.
Qiu, W.Q. et al., "Degradation of amyloid beta-protein by a metalloprotease secreted by microglia and other neural and non-neural cells," J. Biol. Chem. (1997) 272(10):6641-6646.
Qiu, W.Q. et al., "Insulin-degrading enzyme regulates extracellular levels of amyloid beta-protein by degradation," J. Biol. Chem. (1998) 273(49):32730-32738.
Qiu, W., "Facile synthesis of hydrocarbon-stapled peptides," Anaspec poster at 20th American Peptide Society Annual Meeting (2008).
Racke, M.M. et al., "Exacerbation of cerebral amyloid angiopathy-associated microhemmorrhage in amyloid precursor protein transgenic mice by immunotherapy is dependent on antibody recognition of deposited forms of amyloid beta," J. Neurosci. (2005) 25(3):629-636.
Rahimi, F. et al., "Photo-induced cross-linking of unmodified proteins (PICUP) applied to amyloidogenic peptides," J. Visualized Exp. (2009) 23.
Rahimi, F. et al., "Structure-function relationships of pre-fibrillar protein assemblies in Alzheimer's disease and related disorders," Curr. Alzheimer Res. (2008) 5(3):319-341.
Rambaldi, D.C. et al., "In vitro amyloid A beta(1-42) peptide aggregation monitoring by asymmetrical flow field-flow fractionation with multi-angle light scattering detection," Anal. Bioanal. Chem. (2009) 394:2145-2149.
Rangachari, V. et al., "Amyloid beta(1-42) rapidly forms protofibrils and oligomers by distinct pathways in low concentrations of sodium dodecylsulfatet," Biochem. (2007) 46:12451-12462.
Rangachari, V. et al., "Rationally designed dehydroalanine (Delta Ala)-containing peptides inhibit amyloid-beta (A beta) peptide aggregation," Biopolymers (2009) 91:456-465.
Rangachari, V. et al., "Secondary structure and interfacial aggregation of Amyloid beta(1-40) on sodium dodecyl sulfate micelles," Biochem. (2006) 45:8639-8648.
Ravault, S. et al., "Fusogenic Alzheimer's peptide fragment Abeta (29-42) in interaction with lipid bilayers: secondary structure, dynamics, and specific interaction with phosphatidyl ethanolamine polar heads as revealed by solid-state NMR," Protein Sci. (2005) 14(5):1181-1189.
Ravetch, J.V. et al., "Structure of the human immunoglobulin μ locus: characterization of embryonic and rearranged J and D genes," Cell (1981) 27:583-591.
Reisner, Y. et al., "The trimera mouse: generating human monoclonal antibodies and an animal model for human diseases," Trends in Biotech. (1998) 16:242-246.
Remington: The Science and Practice of Pharmacy, Mack Publishing (1995) 19th Edition: Table of Contents.
Resende, R. et al., "ER stress is involved in Abeta-induced GSK-3 beta activation and tau phosphorylation," J. Neurosci. Res. (2008) 86(9):2091-2099.
Resende, R. et al., "Neurotoxic effect of oligomeric and fibrillar species of amyloid-beta peptide 1-42: involvement of endoplasmic reticulum calcium release in oligomer-induced cell death," Neurosci. (2008) 155(3):725-737.
Riechman, L. et al., "Reshaping human antibodies for therapy," Nature (1988) 332:323-327.
Robert, R. et al., "Engineered antibody intervention strategies for Alzheimer's disease and related dementias by targeting amyloid and toxic oligomers," Protein Engineering, Design and Selection (2009) 22(3):199-208.
Roberts, R.W. et al., "RNA-peptide fusions for the in vitro selection of peptides and proteins," Proc. Natl. Acad. Sci. USA (1997) 94:12297-12302.
Robinson, J.R. et al., Sustained and Controlled Release Drug Delivery Systems, (1978) Table of Contents.
Roes, J. et al., "Mouse anti-mouse IgD monoclonal antibodies generated in IgD-deficient mice," J. Immunol. Meth. (1995) 183:231-237.
Roguska, M.A. et al., "Humanization of murine monclonal antibodies through variable domain resurfacing," Proc. Natl. Acad. Sci. (1994) 91:969-973.
Roher, A.A. et al., "Oligomerization and fibril assembly of the amyloid-beta protein," Biochimica et Biophysica Acta (2000) 1502(1):31-43.
Roher, A.E. et al., "Morphology and toxicity of Abeta-(1-42) dimer derived from neuritic and vascular amyloid deposits of Alzheimer's disease," J. Biol. Chem. (1996) 271(34):20631-20635.
Ronicke, R. et al., Abeta mediated diminution of MTT reduction—an artefact or single cell culture? PLoS ONE (2008) 3(9) e3236.
Rossi, G. et al., "A family with Alzheimer disease and strokes associated with A713T mutation of the APP gene," Neurology (2004) 63(5):910-912.
Rouillard, J-M et al., "Gene2Oligo: oligonucleotide design for in vitro gene synthesis," Nucl. Acids. Res. (2004) 32:W176-180.
Russo, C. et al., "Presenilin-1 mutatiosn in Alzheimer's disease," Nature (2000) 405:531-532.
Sabella, S. et al., "Capillary electrophoresis studies on the aggregation process of beta-amyloid 1-42 and 1-40 peptides," Electrophoresis (2004) 25:3186-3194.
Saido, T.C. et al., "Dominant and differential deposition of distinct beta-amyloid peptide species, AbetaN3 in senile plaques," Neuron (1995) 14:457-486.
Sakmann, B. et al., "Single-channel recording" in Antibodies, 2nd edition, Springer, Table of Contents (1995).

(56) References Cited

OTHER PUBLICATIONS

Salomon, A.R. et al., "Nicotine inhibits amyloid formation by the beta-peptide," Biochem. (1996) 35(42):13568-78.

Sambamurti, K. et al., "A partial failure of membrane protein turnover may cause Alzheimer's disease: a new hypothesis," Curr. Alzheimer Res. (2006) 3:81-90.

Sambrook, J. et al., Molecular Cloning—A Laboratory Manual, 2nd Edition (1989) Table of Contents 17.2-17.9.

Samoszuk, M.K. et al., "A peroxide-generating immunoconjugate directed to eosinophil peroxidase is cytotoxic to Hodgkin's disease cells in vitro," Antibody, Immunoconjugates and Radiopharmaceuticals (1989) 2:37-45.

Sandberg, A. et al., "Stabilization of neurotoxic Alzheimer amyloid-beta oligomers by protein engineering," Proc. Natl. Acad. Sci. (2010) 107(35):15595-15600.

Sankaranarayanan, S., "Genetically modified mice models for Alzheimer's disease," Curr. Top. Med. Chem. (2006) 6(6):609-627.

Santos, A.N. et al., "A method for the detection of amyloid-beta SUB 1-40, amyloid-beta SUB 1-42 and amyloid-beta oligomers in blood using magnetic beads in combination with flow cytometry and its application in the diagnostics of Alzheimer's disease," J. Alzheimer's Dis. (2008) 14(2):127-131.

Sanz-Blasco, S. et al., "Mitochondrial Ca2+ overload underlies a beta oligomers neurotoxicity providing an unexpected mechanism of neuroprotection by NSAIDs," PloS One (2008) 3 Article No. e2718.

Sato, J. et al., "Design of peptides that form amyloid-like fibrils capturing amyloid beta 1-42 peptides," Chemistry A Eur. J. (2007) 13:7745-7752.

Sato, N. et al., "Development of new screening system for Alzheimer disease, in vitro Abeta sink assay, to identify the dissocation of soluble Abeta from fibrils," Neurobiol. Dis. (2006) 22(3):487-495.

Saudek, C.D. et al., "A preliminary trail of the programmable implantable medication system for insulin delivery," New Engl. J. Med. (1989) 321(9):574-579.

Sawai, H. et al., "Direct production of the fab fragment derived from the sperm immobilizing antibody using polymerase chain reaction and cDNA expression vectors," Amer. J. Reproduc. Immunol. (1995) 34:26-34.

Schafmeister et al., "An all-hydrocarbon cross-linking system for enhancing the helicity and metabolilc stability of peptides," J. Am. Chem. Soc. (2000) 122:5891-5892.

Schenk et al., "Current progress in beta-amyloid immunotherapy," Curr. Opin. Immun. (2004) 16:599-606.

Schenk, D., "Amyloid-beta immunotherapy for Alzheimer's disease: the end of the beginning," Nature (2002) 3:824-828.

Schilling, S. et al., "On the seeding and oligomerization of pGlu-amyloid peptides (in vitro)," Biochem. (2006) 45(41):12393-12399.

Scholtzova, H. et al., "Induction fo toll-like receptor 9 signaling as a method for ameliorating Alzheimer's disease-related pathology," J. Neurosci. (2009) 291846-1854.

Schott, J.M. et al., "New developments in mild cognitive impairment and Alzheimer's disease," Curr. Opin. Neurol. (2006) 19(6):552-558.

Schuck, P., "Size distribution analysis of macromolecules by sedimentation velocity ultracentrifugation and Lamm equation modeling," Biophys. J. (2000) 78:1606-1619.

Sciaretta et al., "Abeta40-Lactam (D23/K28) models a conformation highly favorable for nucleation of amyloid," Biochem. (2005) 44:6003-6014.

Sefton, M.V., "Implantable pumps," Critical Reviews in Biomedical Engineering (1987) 14(3):201-240.

Selenica, M.L. et al., "Cystatin C reduces the in vitro formation of soluble Abeta1-42 oligomers and protofibrils," Scan. J. Clin. Lab. Invest. (2007) 67(2):179-190.

Selkoe, D.J., "Alzheimer's disease: genes, proteins and therapy," Physiol. Reviews, American Physiological Society (2001) 81(2):741-766.

Selkoe, D.J., Clearing the brain's amyloid cobwebs, Neuron (2001) 32:177-180.

Sergeant, N. et al., "Truncated beta-amyloid peptide species in pre-clinical Alzheimer's disease as new targets for the vaccination approach," J. Neurochem. (2003) 85:1581-1591.

Shapiro, .S. et al., "DNA target motifs of somatic mutagenesis in antibody genes," Crit. Rev. in Immunol. (2002) 22(3):183-200.

Shields, R.L. et al., "Lack of fucose on human IgG1 N-linked oligosaccharide improves binding to human FcγRIII and antibody-dependent cellular toxiciy," J. Biol. Chem. (2002) 277(30):26733-26740.

Shimizu, E. et al., "Il-4-induced selective clearance of oligomeric beta-amyloid peptide(1-42) by rat primary type 2 microglia," J. Immun. (2008) 181(9):6503-6513.

Shu, L. et al., "Secretion of a single-gene-encoded immunoglobulin from myeloma cells," Proc. Natl. Acad. Sci.(1993) 90:7995-7999.

Shughrue et al., "Anti=ADDL antibodies differentially block oligomer binding to hippocampal neurons," Neurobiol. Aging (2010) 31:189-202.

Sikorski, P. et al., "Structure and texture of fibrous crystals formed by Alzheimer's abeta(11-25) peptide fragment," Structure (London) (2003) 11(8):915-926.

Sims, M.J. et al., "A humanized CD18 antibody can block function without cell destruction," J. Immunol. (1993) 151(4):2296-2308.

Sinz, A., "Chemical cross-linking and mass spectrometry for mapping three-dimensional structures of proteins and protein complexes," J. Mass Spectrom. (2003) 38:1225-1237.

Sjogren, M. et al., "Cholesterol and Alzheimer's disease—is there a relation?," Mechanisms of Aging and Development (2006) 127:138-147.

Sjogren, M. et al., "The link between cholesterol and Alzheimer's disease," World J. Biol. Psych. (2005) 6(2):85-97.

Skerra, A. et al., "Assembly of a functional immunoglobulin F fragment in *Escherichia coli*," Science (1988) 240:1038-1040.

Smith, D.P. et al., "Concentration dependent Cu SUP 2+ induced aggregation and dityrosine formation of the Alzheimer's disease amyloid-betapeptide," Biochem. (2007) 46(10):2881-2891.

Smith, N.W. et al., "Amphotericin B interactions with soluble oligomers of amyloid A beta 1-42 peptide," Bioorg. Med. Chem. (2009) 17:2366-2370.

Smith, T.F. et al., "Comparison of biosequences," Adv. in Applied Math (1981) 2:482-489.

Smith-Gill et al., "Contributions of immunoglobulin heavy and light chains to antibody specificity for lysozyme and two haptens," J. Immunol. (1987) 139:4135-4144.

Smithson, S.L. et al., "Molecular analysis of the heavy chain of antibodies that recognize the capsular polysaccharide of *Neisseria meningitides* in hu-PBMC reconstituted SCID mice and in the immunized human donor," Molec. Immunol. (1999) 36:113-124.

Smolen, V.F. et al., editors, Controlled Drug Bioavailability (1984) 1:Table of Contents.

Solorzano-Vargas, R.S. et al., "Epitope mapping and neuroprotective properties of a human single chain FV antibody that binds an internal epitope of amyloid-beta 1-42," Molecular Immunol. (2008) 45(4):881-886.

Sondag, C.M. et al., "Beta amyloid oligomers and fibrils stimulate differential activation of primary microglia," J. Neuroinflamm. (2009) 6 article No. 1.

Song et al., Biochem. Biophys. Res. Comm. (2000) 268:390-394.

Song, Y.K. et al., "Antibody mediated lung targeting of long-circulating emulsions," PDA J. of Pharm. Sci Tech. (1995) 50:372-397.

Soos, K. et al., "An improved synthesis of beta-amyloid peptides for in vitro and in vivo experiments," J. Peptide Science (2004) 10:136.

Sorensen, K. et al., "ApoE counteracts the impairment of mitochondrial activity induced by oligomeric A beta 1-42," Eur. J. Neurol. (2008) 15:45.

Spatola, A.F. et al., "Structure-activity relationships of enkephalins containing serially replaced thiomethylene amide bond surrogates," Life Sci. (1986) 38:1243-1249.

Spatola, A.F. et al., In Chemistry and Biochemistry of Amino Acids, Peptides and Proteins, B. Weinstein editor, Marcel Dekker, New York (1983) vol. VII, 267-357.

Spencer, B. et al., "Novel strategies for Alzheimer's disease treatment," Exp. Opin. Biol. Ther. (2007) 7(12): 1853-1867.

(56) References Cited

OTHER PUBLICATIONS

Stan, R.V., "Multiple PV1 dimers reside in the same stomatal or fesestral diaphragm," Am. J. Physiol. Heart Circ. Physiol. (2004) 286(4):H1347-1353.
Standridge, J.B., "Vicious cycles within the neuropathophysiologic mechanisms of Alzheimer's disease," Curr. Alzheimer Res. (2006) 3(2):95-107.
Staros et al., "Enhancement by N-hydroxysulfosuccinimide of water-soluble carbodilimide-mediated coupling reactions," Anal. Biochem. (1986) 156(1):220-222.
Stewart, J.M. et al., Solid-Phase Peptide Synthesis, 2nd Edition, Pierce Chemical Company (1984) Table of Contents.
Stine, W. et al., "In vitro characterization of conditions for amyloid-beta peptide oligomerization and fibrillogenesis," J. Biol. Chem. (2003) 278(13):11612-11622.
Stine, W.B. et al., "Antibodies specific for toxic Abeta oligomers," Abst. Viewer/Itinerary Planner, Soc. of Neurosci. (2003) 1.
Studnicka, G.M. et al., "Human-engineered monoclonal antibodies retain full specific binding activity by preserving non-CDR complementarity-modulating residues," Protein Eng. (1994) 7(6):805-814.
Suram, A. et al., "A new evidence for DNA nicking property of amyloid beta-peptide (1-42): relevance of Alzheimer's disease," Archives of Biochem. Biophys. (2007) 463(2):245-252.
Tabaton, M. et al., "Role of water-soluble amyloid-beta in the pathogenesis of Alzheimer's disease: role of amyloid-beta in Alzheimer's disease," Int. J. Exp. Path. (2005) 3(85):139-145.
Tabaton, M., "Coffee 'breaks' Alzheimer's disease," J. Alzheimer's Disease (2009) 17/3:699-700.
Taguchi, J. et al., "Different expresison of calreticulin and immunoglobulin binding protein in Alzheimer's disease brain," Acta Neuropathologica (2000) 100(2):153-160.
Takano, K., "Amyloid beta conformation in aqueous environment," Curr. Alzheimer Res. (2008) 5(6):540-547.
Takata, K. et al., "High mobility group box protein-1 enhances amyloid-beta neurotoxicity," J. Pharm. Sci. (2006) 100154P, 79th Annual Meeting of the Japanese Pharmacological Society, Yokohama, Japan, Mar. 8-10, 2006.
Takata, K. et al., "Possible involvement of small oligomers of amyloid-beta peptides in 15-deoxyDELTA12, 14 prostaglandin J2-sensitive microglial activation," J. Pharm. Sci. (2003) 91:330-333.
Takeda, S.I. et al., "Construction of chimaeric processed immunoglobulin genes containing mouse variable and human constant region sequences," Nature (1985) 314:452-454.
Tamagno, E. et al., "The various aggregation states of beta-amyloid 1-42 mediate different effects on oxidative stress, neurodegeneration, and BACE-1 expression," Free Radic. Biol. Med. (2006) 41(2):202-212.
Tamura, M. et al., "Structural correleates of an anticarcinoma antibody: identification of specificity-determining residues (SDRs) and development of a minimally immunogenic antibody variant by retention of SDRs only," J. Immunol. (2000) 164(3):1432-1441.
Taniguchi, A. et al., "'Click peptide': pH-triggered in situ production and aggregation of monomer Abeta1-42," Chembiochem. (2009) 10(4);710-715.
Taniuchi, M. et al., "Induction of nerve growth factor receptor in Schwann cells after axotomy," Proc. Natl. Acad. Sci. (1986) 83:4094-4098.
Tanzi, R., "Alzheimer research forum discussion: gain or loss of function—time to shake up assumptions on gamma-secretase in Alzheimer disease? Commentary," J. Alzheimer's Dis. (2007) 11(3):409.
Tanzi, R.E., "Novel therapeutics for Alzheimer's disease," Neurotherapeutics (2008) 5(3):377-380.
Tarozzi, A. et al., "Cyanidin 3-O-glucopyranoside protects and rescues SH-Sy5Y cells against amyloid-beta peptide-induced toxicity," Neuroreport (2008) 19(15):1483-1486.
Taylor, L.D. et al., "A transgenic mouse that expresses a diversity of human sequence heavy and light chain immunoglobulins," Nucl. Acids. Rse. (1992) 20(23):6287-6295.
Teplow, D.B. et al., "Effects of structural modifications in a beta on its oligomer size distribution," Soc. for Neurosci. Abstract Viewer and Itinerary Planner (2002), Abstract No. 19.6, 32nd Annual meeting of the Society for Neuroscience, Orlando, FL, Nov. 2-7, 2002.
Terry, R.D. et al., "Physical basis of cognitive alterations in Alzheimer's disease: synapse loss is the major correlate of cognitive impairment," Am. Neurol. Assoc. (1991) 572-580.
Terryberry, J.W. et al., "Autoantibodies in neurodegenerative diseases: antigen-specific frequencies and intrathecal analysis," Neurobiology of Aging (1998) 19(3):205-216.
Tew, D.J. et al., "Stabilization of neurotoxic soluble beta-sheet-rich conformations of the Alzheimer's disease amyloid-beta peptide," Biophys. J. (2008) 974752-2766.
Thal, D.R. et al., "Fleecy amyloid deposits in the internal layers of the human entorhinal cortex are comprised of N-terminal truncated fragments of A13," J. Neuropath. Exp. Neurol. (1999) 58:210-216.
Tijssen, P., editor, "Hybridization with nucleic acid probes—Part II: Probe labeling and hybridzation techniques," Laboratory Techniques in Biochemistry and Molecular Biology, (1993) 24:iii-vi, 269-613, table of contents.
Tolstoshev, P., "Gene therapy, concentps, current trials and future directions," Ann. Rev. Pharmacol. Toxicol. (1993) 32:573-596.
Tomaselli, S. et al., "The alpha-to-beta conformational transition of Alzheimer's Abeta-(1-42) peptide in aqueous media is reversible: a step by step conformational analysis suggests the location of beta conformation seeding," ChemBioChem. (2006) 7(2):257-267.
Tomidokoro, Y. et al., "Familial Danish dementia: co-existence of Danish and Alzheimer amyloid subunits (Adan and Abeta) in the absence of compact plaques," J. Biol. Chem. (2005) 280(44):36883-36894.
Tomidokoro, Y. et al., "Familial Danish dementia: the relationship of two different amyloids (Adan/Abeta) deposited in the brain," Society for Neuroscience Abstract Viewer and Itinerary Planner (2002) 2002Abstract No. 328.9, 32nd Annual Meeting of the Society of Neuroscience, Orlando, FL, Nov. 2-7, 2002.
Tomiyama, T. et al., "A new amyloid beta variant favoring oligomerization in Alzheimer's-type dementia," Ann. Neurol. (2008) 63(3):377-387.
Tsubuki, S. et al., "Dutch, Flemish, Italian and Arctic mutations of APP and resistance of Abeta to physiologically relevant proteolytic degradation," Lancet (2003) 361(9373):1957-1958.
Turner, R. et al., "The potential exploitation of plant viral translational enhancers in biotechnology for increased gene expression," Mol. Biotech. (1995) 3:225-236.
Tusell, J.M. et al., "upregulation of p21Cip1 in activated glial cells," Glia (2009) 57(5):524-534.
Ueki et al., "Solid phase synthesis and biological activities of (Arg8)-vasopressin methylenedithioether," Bioorg. Med. Chem. Lett. (1999) 9:1767-1772.
Umana, P. et al., "Engineered glycoforms of an antieuro-blastoma IgG1 with optimized antibody-dependent cellular cytotoxic activity," Nature Biotech. (1999) 17:176-180.
Urbanc, B. et al., "Computer simulations of Alzheimer's amyloid beta-protein folding and assembly," Curr. Alzheimer Res. (2006) 3(5):493-504.
Urbanc, B. et al., "In silico study of amyloid beta-protein folding and oligomerization," Proc. Natl. Acad. Sci. USA (2004) 101:17345-17350.
Urbanc, B. et al., "Molecular dynamics simulation of amyloid beta dimer formation," Biophys. J. (2004) 87(4):2310-2321.
Urlaub et al., "Isolation of Chinese hamster cell mutants deficient in dihydrofolate reductase activity," Proc. Natl. Acad. Sci. (1980) 77:4216-4220.
Uto, L. et al., "Determination of urinary Tamm-Horsfall protein by ELISA using a maleimide method for enzyme-antibody conjugation," J. Immunol. Methods (1991) 138:87-94.
Vajdos et al., J. Mol. Biol. (2002) 320(2):415-428.
Valincius, G. et al., "Soluble amyloid beta-oligomers affect dielectric membrane properties by bilayer insertion and domain formation: implications for cell toxicity," Biophys. J. (2008) 95(10):4845-4851.
Van Broeck, B. et al., "Current insights into molecular mechanisms of Alzheimer disease and their implications for therapeutic approaches," Neurdegenerative Dis. (2007) 4(5):349-365.

(56) References Cited

OTHER PUBLICATIONS

Van Broeckhoven et al., "Amyloid beta protein precursor gene and hereditary cerebral hemorrhage with amyloidosis (Dutch)" Science (1990) 248(4959):1120-1122.
Vattemi, G. et al., "Amyloid-beta42 is preferentially accumulated in muscle fibers of patients with sporadic inclusion-body myositis," Acta Neuropathol. (2009) 117(5):569-574.
Veber, D.F. et al., "The design of metabolically-stable peptide analogs," TINS (1985) 392-396.
Verhoeven, M. et al., "Engineering of antibodies," Bioessays (1988) 8(2):74-78.
Vestergaard, M. et al., "Detection of Alzheimer's amyloid beta aggregation by capturing molecular trails of individual assemblies," Biochem. Biophys. Res. Comm. (2008) 377(2):725-728.
Vickers, "A vaccine against Alzheimer's disease," Drugs Aging (2002) 19:487-494.
Viola, K.L. et al., "Add1s bind selectively to nerve cell surfaces in receptor-like puncta," Soc. for Neurosci. Abstract Viewer and Itinerary Planner (2002), Abstract No. 91.9, 32nd Annual meeting of the Society for Neuroscience, Orlando, FL, Nov. 2-7, 2002.
Viola, K.L. et al., "Immunolocalization of oligomeric Abeta42 bindnig to primary mouse hippocampal cells and B103 rat neuroblastoma cells," Society for Neuroscience Abstracts (1999), 29th Annual Meeting of the Society for Neuroscience, Miami Beach, FL, Oct. 23-28, 1999.
Wahlstrom, A. et al., "Secondary structure conversions of Alzheimer's A beta(1-40) peptide induced by membrane-mmimicking detergents," FEBS J. (2008) 275:5117-5128.
Wakutani, Y. et al., "Novel amyloid precursor protein gene missense mutation (D678N) in probable familial Alzheimer's disease," J. Neurol. Neurosurg. Psychiatry (2004) 75(7):1039-1042.
Walensky et al., "Activation of apoptosis in vivo by a hydrocarbon-stapled BH3 helix," Science (2004) 305:1466-1470.
Wallick, S.C. et al., "Glycosylation of a V(H) residue of a monoclonal antibody against alpha-1-6) dextran increases its affinity for antigen," J. Exp. Med. (1988) 168:1099-1109.
Wang, H. et al, "Soluble oligomers of Abeta(1-42) impair LTP in rat hippocampal dentate gyms," Society for Neuroscience Abstracts (2000) Abstract No. 663.18, 30th Annual Meeting of the Society of Neuroscience, New Orleans, LA, Nov. 4-9, 2000.
Wang, H. et al., "Direct and selective elimination of specific prions and amyloids by 4,5-dianilinophthalimide and analogs," Proc. Natl. Acad. Sci. USA (2008) 105:7159-7164.
Wang, H.W. et al., "Differential effect of Abeta1-42 conformation and apoE isoform on LTP," Society for Neurosci. Abstracts (2001) 752.18, 31st Annual meeting of the Society for Neurosci., San Diego, CA, Nov. 10-15, 2001.
Wang, H-W. et al., "Soluble oligomers of beta amyloid (1-42) inhibito long-term potentiation but not long-term depression in rat dentate gyms," Brain Res. (2002) 924(2):133-140.
Wang, J. et al., "Development and characterization of a TAPIR-like mouse monoclonal antibody to amyloid-beta," J. Alzheimer's Disease (2008) 14(2):161-173.
Wang, R. et la., "The profile of soluble amyloid beta protein in cultured cell medicine . . . " J. Biol. Chem. (1996) 271(50):31894-31902.
Wang, Z. et al., "Per-6-substituted-per-6-deoxy beta-cyclodextrins inhibit the formation of beta-amyloid peptide derived soluble oligomers," J. Med. Chem. (2004) 47:3329-3333.
Ward, E.S. et al., "Binding activities of a repetoire of single immunoglobulin varialbe domains secreted from *Escherichia coli*," Nature (1989) 341:544-546.
Weggen, S. et al., "Evidence that nonsteroidal anti-inflammatory drugs decrease amyloid beta-42 production by direct moculation of γ-secretase activity," J. Biol. Chem. (2003) 276(34):31831-31837.
Weksler et al., "Patients with Alzheimer disease have lower levels of serum anti-amyloid peptide antibodies than healthy elderly individuals," Gerontology (2002) 37:943-948.

Wels, B. et al., "Synthesis of a novel potent cyclic peptide MC4-ligand by ring-closing metathesis," Bioorg. Med. Chem. (2005) 13:4221-4227.
Wermuth, C.G. et al., "Glossary of terms used in medicinal chemistry," Pure and Applied Chem. (1998) 70:1129-1143.
Westlind-Danielsson, A. et la., "Spontaneous in vitro formation of supramolecular beta-amyloid structures, 'betaamy balls' by beta-amyloid 1-40 peptide," Biochem. (2001) 40(49):14736-43.
White, J.A. et al., "Differential effects of oligomeric and fibrillar amyloid-beta 1-42 on astrocyte-mediated inflammation," Neurbiol. of Disease (2005) 18(3):459-465.
Wilcock et al., "Passive immunotherapy against Abeta in aged APP-transgenic mice reverses cognitive deficits and depletes parenchymal amyloid deposits in spite of increased vascular amyloid and microhemorrhage," J. Neuroinflammation (2004) 1(24):1-11.
Wilcock, D.M. et al., "Intracranially administered anti-A-beta antobodies reduce beta-amyloid depsoition by mechanisms both independent of and associated with microglial activation," J. Neurosci. (2003) 23(9):3745-3751.
Williamson, M.P. et al., "Binding of amyloid beta-peptide to ganglioside micelles is dependent on histidine-13," Biochem. J. (2006) 397:483-490.
Wilson, D.M. et al., "Free fatty acids stimulate the polymerization of tau and amyloid beta peptides in vitro evidence for a common effector in pathogenesis in Alzheimer's disease," Am. J. Path. (1997) 150(6):2181-2195.
Wiltfang, J. et al., "Highly conserved and disease-specific patterns of carboxyterminally truncated A-beta peptides 1-37/38/39 in addition to 1-40/42 in Alzheimer's disease and in patients with chronic neuroinflammation," J. Neurochem. (2002) 81:481-495.
Windisch, M. et al., "The role of alpha-synuclein in neurodegenerative diseases: a potential target for new treatment strategies," Neuro-Degenerative Diseases (2008) 5(3-4):218-221.
Winnacker, E-L., From Genes to Clones: Introduction to Gene Technology (1987) Table of Contents.
Wong, P.T. et al., "Amyloid-beta membrane binding and permeabilization are distinct processes influenced separately by membrane charge and fluidity," J. Mol. Biol. (2009) 286(1):81-96.
Woodhouse, A. et al., "Vaccination strategies for Alzheimer's disease: a new hope?" Drugs Aging (2007) 24(2):107-119.
Wright, A. et al., "Antibody variable region glycosylation: position effects on antigen binding and carbohydrate structure," EMBO J. (1991) 10(10):2717-2723.
Wu et al., "Humanization of a murine monoclonal antibody by simultaneous optimization of framework and CDR residues," J. Mol. Biol. (1999) 294:151-162.
Wu, C. et al., "The structure of Abeta42 C-terminal fragments probed by a combined experimental and theoretical study," J. Mol. Biol. (2009) 287(2):492-501.
Wu, G.Y. et al., "Delivery systems for gene therapy," Biotherapy (1991) 3:87-95.
Wu, G.Y. et al., "Receptor-mediated in vitro ene transformation by a soluble DNA carrier system," J. Biol. Chem. (1987) 262:4429-4432.
Wurth, C. et al., "Mutations that reduce aggregation of the Alzheimer's Abeta42 peptide: an unbiased search for the sequence determinants of Abeta amyloidogenesis," J. Mol. Biol. (2002) 319(5):1279-1290.
Xia, W. et al., "A specific enzyme-linked immunosorbent assay for measuring beta-amyloid protein oligomers in human plasma and brain tissue of patients with Alzheimer disease," Archives of Neurology (2009) 66190-199.
Xia, W. et al., "Enhanced production and oligomerization fo the 42-residue amyloid beta-protein by Chinese hamster ovary cells stably expressing mutant presenilins," J. Biol. Chem. (1997) 272(12):7977-7982.
Xu, X. et al., "Gamma-secretase catalyzes sequential cleavages of the A beta PP transmembrane domain," J. Alzheimer's Disease (2009) 16:211-224.
Yamamoto, N. et al., "Environment- and mutation-dependent aggregation behavior of Alzheimer amyloid beta-protein," J. Neurochem. (2004) 90:62-69.

(56) References Cited

OTHER PUBLICATIONS

Yamin, G. et al., "Amyloid beta-protein assembly as a therapeutic target of Alzheimer's disease," Curr. Pharm. Design (2008) 14:3231-3246.
Yamin, G. et al., "NMDA receptor-dependent signaling pathways that underlie amyloid beta-protein disruption of LTP in the hippocampus," J. Neuroscience Res. (2009) 87(8):1729-1736.
Yan, Y. et al., "Protection mechanisms against Abeta42 aggregation," Curr. Alzheimer Res. (2008) 5(6):548-554.
Yan, Z. et al., "Roscovitine: a novel regulator of P/Q-type calcium channels and transmitter release in central neurons," J. Physiol. (2002) 540(3):761-770.
Yang, M. et al., "Amyloid beta-protein monomer folding: free-energy surfaces reveal alloform-specific differences," J. Mol. Biol. (2008) 384(2):450-464.
Yang, X.D. et al., "Fully human anti-interleukin-8 monoclonal antibodies: potential therapeutics for the treatment of inflammatory disease status," J. Leukocyte Biol. (1999) 66:401-410.
Yeh, M.Y. et al., "A cell-surface antigen which is present in the ganglioside fraction and shared by human melanomas," Int. J. Cancer (1982) 29:269-275.
Yeh, M.Y. et al., "Cell surface antigens of human melanoma identified by monoclonal antibody," Proc. Natl. Acad. Sci. USA (1979) 76(6):2927-2931.
Yoshinari, K. et al., "Differential effects of immunosuppressants and antibiotics on human monoclonal antibody production is SCID mouse ascites by five heterohybridomas," Hybridoma (1998) 17(1):41-45.
Yoshitake et al., "Mild and efficient conjugation of rabbit Fab and horseradish peroxide using a maleimide compound and its use for enzyme immunoassay," J. Biochem. (1982) 92:1413-1424.
Young, K.F. et al., "Oligomeric amyloid-beta 1-42 activates extracellular signal regulated kinases ERK1 and ERK2 of the mitogen activated protein kinase pathway in SH-SY5YCELLS," Neurobiol of Aging (2004) 25:S150.
Youssef, I. et al., "N-truncated amyloid-beta oligomers induce learning impairment and neuronal apoptosis," Neurobiol of Aging (2008) 29:1319-1333.
Yu, L. et al., "Structural characterization of a soluble amyloid beta-peptide oligomer," Biochem. (2009) 48:1870-1877.
Yun, S. et al., "Role of electrostatic interactions in amyloid beta-protein (Abeta) oligomer formation: a discrete molecular dynamics study," Biophys. J. (2007) 92(11):4064-4077.
Yun, S.H. et al., "Amyloid-beta 1-42 reduces neuronal excitability I nmouse dentate gyrus," Neurosci. Lett. (2006) 403:162-165.
Zameer, A. et al., "Anti-oligomeric abeta single-chain variable domain antibody blocks abeta-induced toxicity against human neuroblastoma cells," J. Mol. Biol. (2008) 384(4):917-928.
Zarandi, M. et al., "Synthesis of Abeta[1-42] and its derivatives with improved efficiency," J. Peptide Sci. (2007) 13(2):94-99.
Zhao, J-H. et al., "Molecular dynamics simulations to investigate the aggregation behaviors of the Abeta(17-42) oligomers," J. Biomol. Struct. Dyn. (2009) 26(4):481-490.
Zhao, W. et al., "Identification of antihypertensive drugs which inhibit amyloid-beta protein oligomerization," J. Alzheimer's Dis. (2009) 16(1):49-57.
Zheng, J. et al., "Annular structures as intermediates in fibril formation of Alzheimer Abeta17-42," J. Phys. Chem. (2008) 112(22):6856-6865.
Zhu, D. et la., "Phospholipases A2 mediate amyloid-beta peptide-induced mitochondrial dysfunction," J. Neurosci. (2006) 26(43):11111-11119.
Zlokovic, B.V., "Clearing amyloid through the blood-brain barrier," J. neurochem. (2004) 89(40:807-811.
Zou, K et al., "A novel function of monomeric amyloid beta-protein serving as an antioxidant molecule against metal-induced oxidative damage," J. Neurosci. (2002) 22:4833-4841.
Zou, K. et al., "Amyloid beta-protein (Abeta)1-40 protects neurons from damage induced by Abeta1-42 in culture and in rat brain," J. Neurochem. (2003) 87(3):609-619.
European Patent Office Search Report for Application No. 09180982 dated May 31, 2010 (4 pages).
Notice of Opposition for European Application No. 06707413/Patent No. 1861422 dated Nov. 24, 2010.
Supplemental European Patent Office Search Report for Application No. 07864914 dated Apr. 28, 2010 (5 pages).
Supplemental European Search Report from European Patent Publication No. 2303920 dated Sep. 26, 2011.
European Patent Office Action for Application No. 087160818 dated Dec. 22, 2011 (6 pages).
European Patent Office Action for Application No. 101783942 dated Mar. 2, 2012 (4 pages).
European Patent Office Action for Application No. 101783942 dated Aug. 22, 2012 (4 pages).
International Preliminary Report on Patentability and Written Opinion for Application No. PCT/EP2004/000927 dated Aug. 5, 2005 (11 pages).
International Preliminary Report on Patentability and Written Opinion for Application No. PCT/EP2006/011530 dated Jun. 3, 2008 (11 pages).
International Preliminary Report on Patentability and Written Opinion for Application No. PCT/EP2008/001548 dated Sep. 1, 2008 (11 pages).
International Preliminary Report on Patentability and Written Opinion for Application No. PCT/IB2009/006636 dated Jan. 25, 2011 (7 pages).
International Preliminary Report on Patentability and Written Opinion for Application No. PCT/US2006/046043 dated Jun. 30, 2008 (32 pages).
International Preliminary Report on Patentability and Written Opinion for Application No. PCT/US2006/046148 dated Jun. 3, 2008 (8 pages).
International Preliminary Report on Patentability and Written Opinion for Application No. PCT/US2007/085932 dated Jun. 3, 2009 (5 pages).
International Preliminary Report on Patentability and Written Opinion for Application No. PCT/US2008/065199 dated Dec. 1, 2009 (10 pages).
International Preliminary Report on Patentability and Written Opinion for Application No. PCT/US2008/065205 dated Dec. 1, 2009 (6 pages).
International Preliminary Report on Patentability and Written Opinion for Application No. PCT/US2009/051721 dated Jan. 25, 2011 (7 pages).
International Search Report for Application No. PCT/EP2004/000927 dated Jun. 14, 2004 (4 pages).
International Search Report for Application No. PCT/EP2008/001548 dated Jul. 4, 2008 (3 pages).
International Search Report for Application No. PCT/EP2008/001549 mailed on Dec. 23, 2008 (6 pages).
International Search Report for Application No. PCT/IB2009/006636 dated Jan. 22, 2010 (6 pages).
International Search Report for Application No. PCT/PCT/EP2006/011530 dated Jun. 6, 2007 (7 pages).
International Search Report for Application No. PCT/US2006/046043 dated Jun. 21, 2008 (16 pages).
International Search Report for Application No. PCT/US2006/046148 dated Jun. 19, 2007 (5 pages).
International Search Report for Application No. PCT/US2007/085932 dated Spetember 22, 2008 (3 pages).
International Search Report for Application No. PCT/US2008/065199 dated Sep. 26, 2008 (4 pages).
International Search Report for Application No. PCT/US2008/065205 dated Oct. 31, 2008 (3 pages).
International Search Report for Application No. PCT/US2009/051721 mailed on Mar. 16, 2010 (6 pages).
International Search Report for Application No. PCT/US2011/047622 dated Jan. 2, 2012 (6 pages).
Written Opinion for Application No. PCT/US2011/047622 dated Jan. 2, 2012 (8 pages).
United States Patent Office Action for U.S. Appl. No. 11/574,844 dated Feb. 10, 2011 (11 pages).

(56) References Cited

OTHER PUBLICATIONS

United States Patent Office Action for U.S. Appl. No. 11/574,847 dated Jul. 14, 2011 (22 pages).
United States Patent Office Action for U.S. Appl. No. 11/574,876 dated Jan. 23, 2012 (17 pages).
United States Patent Office Action for U.S. Appl. No. 11/574,876 dated Nov. 15, 2012 (9 pages).
United States Patent Office Action for U.S. Appl. No. 11/885,362 dated Jul. 22, 2010 (10 pages).
United States Patent Office Action for U.S. Appl. No. 11/885,362 dated Mar. 29, 2011 (8 pages).
United States Patent Office Action for U.S. Appl. No. 11/945,124 dated Mar. 3, 2010 (15 pages).
United States Patent Office Action for U.S. Appl. No. 11/945,124 dated Oct. 14, 2010 (8 pages).
United States Patent Office Action for U.S. Appl. No. 12/509,315 dated Jun. 6, 2012 (10 pages).
United States Patent Office Action for U.S. Appl. No. 12/509,325 dated Jun. 6, 2012 (14 pages).
United States Patent Office Action for U.S. Appl. No. 12/529,467 dated Dec. 6, 2011 (24 pages).
United States Patent Office Action for U.S. Appl. No. 12/529,467 dated May 24, 2012 (19 pages).
United States Patent Office Action for U.S. Appl. No. 13/102,713 dated Apr. 19, 2012 (20 pages).
United States Patent Office Action for U.S. Appl. No. 13/102,713 dated Oct. 1, 2012 (14 pages).
United States Patent Office Action for U.S. Appl. No. 13/188,034 dated Jan. 3, 2012 (35 pages).
United States Patent Office Action for U.S. Appl. No. 13/188,034 dated Sep. 11, 2012 (18 pages).
United States Patent Office Action for U.S. Appl. No. 13/195,533 dated Nov. 13, 2012 (23 pages).
United States Patent Office Notice of Allowance for U.S. Appl. No. 11/574,844 dated Aug. 11, 2011 (14 pages).
United States Patent Office Notice of Allowance for U.S. Appl. No. 11/574,844 dated May 9, 2012 (8 pages).
United States Patent Office Notice of Allowance for U.S. Appl. No. 11/574,847 dated Feb. 10, 2012 (12 pages).
United States Patent Office Notice of Allowance for U.S. Appl. No. 11/574,847 dated Oct. 4, 2012 (8 pages).
United States Patent Office Notice of Allowance for U.S. Appl. No. 11/945,124 dated Apr. 4, 2011 (8 pages).
United States Patent Office Notice of Allowance for U.S. Appl. No. 11/945,124 dated Mar. 5, 2012 (7 pages).
United States Patent Office Notice of Allowance for U.S. Appl. No. 11/945,124 dated Oct. 9, 2012 (7 pages).
Co-pending U.S. Appl. No. 13/893,780, filed May 14, 2013.
Co-pending U.S. Appl. No. 13/862,865, filed Apr. 15, 2013.
United States Patent Office Action for U.S. Appl. No. 13/195,533 dated Jul. 11, 2013 (21 pages).
United States Patent Office Action for U.S. Appl. No. 11/885,362 dated Sep. 26, 2013 (11 pages).
United States Patent Office Notice of Allowance for U.S. Appl. No. 11/574,876 dated Sep. 30, 2013 (11 pages).
U.S. Patent Office Notice of Allowance for U.S. Appl. No. 13/102,713 dated Mar. 14, 2014 (9 pages).
Acha-Orbea et al., "Anti-T-cell receptor V beta antibodies in autoimmunity," Immunol Ser. (1993) 59:193-202.
Anderson et al., "Characterization of beta amyloid assemblies in drusen: the deposits associated with aging and age-related macular degeneration," Experimental Eye Research (2004) 78:243-256.
Bard et al., "Epitope and isotype specificities of antibodies to beta-amyloid peptide for protection against Alzheimer's disease-like neuropathology," Proc. Natl. Acad. Sci. (2003) 100(4):2023-2028.
Bard et al., "Peripherally administered antibodies against amyloid bipeptide enter the central nervous system and reduce pathology in a mouse model of Alzheimer disease," Nature Med. (2000) 6:916-919.

Brown, M. et al., "Tolerance to single, but not multiple, amino acid replacements in antibody V-H CDR2: a means of minimizing B cell wastage from somatic hypermutation?" J. Immunol. (1996) 156(9):3285-3291.
Campbell et al., "General properties and applications of monoclonal antibodies," Elsevier Science Publishers B.V. (1984) pp. 1-32.
Celli et al., "Origin and pathogenesis of antiphospholipid antibodies," Braz. J. Med. Biol. Res. (1998) 31(6):723-732.
Database EMBL, "Mouse immunoglobulin rearranged kappa-chain V-region V105 gene from, C.AL20-TEPC-105 myeloma, exons 1 and 2," Jul. 16, 1988, Database Accession No. M12183.
Database EMBL, "*Mus musculus* F5.20G3 low-affinity anti-phosphorylcholine IgG antibody mRNA, partial cds," Feb. 8, 1999, Database Accession No. AF044238.
Database Geneseq, "Anti-human Fas monoclonal antibody CH11 light chain cDNA," retrieved from EBI Accession No. GSN:AAV66736, Jan. 18, 1999, Database Accession No. AAV66736.
Database Geneseq, "Mouse DNA encoding antibody 3D8 heavy chain variable region," Apr. 22, 2003, Database Accession No. ABX16569.
Database Geneseq, "Mouse monoclonal antibody 4785 heavy chain SEQ ID 38", retrieved from EBI Accession No. GSP:ADX39137, 2005) Database Accession No. ADX39137.
Database Geneseq., Humanized monoclonal antibody H74785-2 heavy chain, retrieved from EBI accession No. GSP:ADX39139, 2005, Database Accession No. ADX39139.
Database Geneseq., "Humanized monoclonal antibody Hu4785-2 partial protein," retrieved from EBI Accession No. GSP:ADX39104 (2005) Database Accession No. ADX39104.
Database Geneseq., "Humanized monoclonal antibody Hu4785-2 VH region," retrieved from EBI accession No. GSP:ADX39143 (2005), Database Accession No. ADX39143.
Database Geneseq., "Mouse monoclonal antibody 4785 heavy chain SEQ ID 1," retrieved from EBI Accession No. GSP:ADX39100 (2005) Database Accession No. ADX39100.
Database NCBI Protein dated Apr. 11, 1996, Accession No. AAA96779.
Database NCBI Protein dated Mar. 23, 2002, Accession No. AAA92933.
Database NCBI Protein, dated Mar. 23, 2002, Accession No. AAL92941.
Database NCBL Protein, dated Aug. 30, 1993, Accession No. AAA38584.
David et al., A significant reduction in the incidence of collagen induced arthritis in mice treated with anti-TCRV-beta antibodies, J. Cell Biochem. (1991) 179.
DeGiorgi et al., "Induction of foetal lethality in AKR offspring after repeated inoculations into AKR females of anti-TCR/V beta 6 monoclonal antibody," Res. Immunol. (1993) 144(4):245-255.
DeGiorgi et al., "Murine hybridomas secreting monoclonal antibodies reacting with Misa antigens," Exp. Clin. Immunogenet. (1993) 10(4):219-223.
Ding et al., "Targeting age-related macular degeneration with Alzheimer's disease based immunotherapies: anti-amyloid-beta antibody attenuates pathologies in an age-related macular degeneration mouse model," Vision Research, Pergamon Press, Oxford, GB (2007) 48(3):339-345.
Dorronsoro et al., "Peripheral and dual binding site inhibitors of acetylcholinesterase as neurodegenerative disease-modifying agents," Exp. Opin. Ther. Pat. (2003) 13(11):1725-1732.
Frenkel et al., "Modulation of Alzheimer's beta-amyloid neurotoxicity by site-directed single-chain antibody," J. Neuroimmunol. (2000) 106(1-2):23-31.
Fujimoro et al., "Production and characterization of monoclonal antibodies specific to multi-ubiquitin chains of polyubiquitinated proteins," FEBS (1994) 349:173-180.
Fujimoro et al., "Production of antipolyubiquitin monoclonal antibodies and their use for characterization and isolation of polyubiquitinated proteins," Meth. Enzymol. (2005) 399:75-86.
Fukuchi et al., "Amelioration of amyloid load by anti-Abeta single-chain antibody in Alzheimer mouse model," Biochem. Biophys. Res. Commun. (2006) 344(1):79-86.

(56) References Cited

OTHER PUBLICATIONS

Guo et al., "Targeting amyloid-beta in glaucoma treatment," Proc. Natl. Acad. Sci. USA (2007) 104(33):13444-13449.
Hicke, "Protein regulation by monoubiquitin," Nat. Rev. (2001) 2:196-201.
Kim et al., "Development of conformation-specific antibodies for neutralization of beta-amyloid oligomers," Neurobiol. Aging (2004) 25(1):S145, P1-175 Abstract.
Kisilevsky et al., "Arresting amyloidosis in vivo using small-molecule anionic sulphonates or sulphates: implications for Alzheimer's disease," Nat. Med. (1995) 1(2):143-148.
Kisilevsky, "Anti-amyloid drugs potential in the treatment of diseases associated with aging," Drugs Aging (1996) 8(2):75-83.
Langdon et al., "Germline sequences of VH7183 gene family members in C57BL/6 mice demonstrate natural selection of particular sequences during recent evolution," Immunogen (2000) 51:241-245.
Lee et al., "Molecular cloning of agonistic and antagonistic monoclonal antibodies against human 4-IBB," Eur. J. Immunogenet. (2002) 29(5):449-452.
LeVine, H, III., "4,4'-dianilino-1,1"-binaphthy1-5'-disulfonate (bis-ANS) reports on non-beta-sheet conformers of Alzheimer's peptide beta (1-40), Arch Biochem. Biophys. (2002) 404:106-115.
Liu, et al., "Single chain variable fragments against beta-amyloid (Abeta) can inhibit Abeta aggregation and prevent Abeta-induced neurotoxicity," Biochem. (2004) 43:6959-6967.
Lund et al., "Oligosaccharide-protein interactions in IgG can modulate recognition by Fc-gamma receptors," FASEB J. (1995) 9(1):115-119.
McKinnon et al., "Caspase activation and amyloid precursor protein cleavage in rat ocular hypertension," Investigative Ophthalmology & Visual Science (2002) 43(4):1077-1087.
McLaurin et al., "Therapeutically effective antibodies against amyloid-beta peptide target amyloid-beta residues 4-10 and inhibit cytotoxicity and fibrillogenesis," Nat. Med. (2002) 8(11):1263-1269.
Moretto et al., "Conformation-sensitive antibodies against Alzheimer amyloid-beta by immunization with a thioredoxin-constrained B-cell epitope peptide," J. Biol. Chem. (2007) 282(15):11436-11445.
Nemes et al., "Cross-linking of obiquitin, HSP27, parkin, and alpha-synuclein by gamma-glutamyl-ε-lysine bonds in Alzheimer's neurofibrillary tangles," FASEB J. (2004) 18:1135-1137.
Nicolau et al., "A liposome-based therapetuci vaccine against beta-amyloid plaques on the pancreas of transgenic NORBA mice," Proc. Natl. Acad. Sci. USA (2002) 99(4):2332-2337.
Rzepecki et al., "Prevention of Alzheimer's disease-associated Abeta aggregation by rationally designed non-peptide beta-sheet ligands," J. Biol. Chem. (2004) 279(46):47497-47505.
Schable et al., "Characteristics of the immunoglobulin V kappa genes, pseudogenes, relics and orphons in the mouse genome," Eur. J. Immunol. (1999) 29:2082-2086.
Schenk et al., "Immunization with amyloid-beta attenuates Alzheimer' disease-like pathology in the PDAPP mouse," Nature (1999) 400:173-177.

Solomon et al., "Disaggregation of Alzheimer beta-amyloid by site-directed mAb," Proc. Natl. Acad. Sci. USA (1997) 94:4109-4112.
Solomon et al., "Monoclonal antibodies inhibit in vitro fibrillar aggregation fo the Alzheimer beta-amyloid peptide," Proc. Natl. Acad. Sci. USA (1996) 93:452-455.
Tenno et al., "Structural basis for distinct roles of Lys63- and Lys48-linked polyubiquitin chains," Genes to Cells (1994) 9:865-875.
Van Gool et al., "Concentrations of amyloid-beta protein in cerebrospinal fluid increase with age in patients free from neurodegenerative disease," Neurosci Lett. (1994) 172(1-2):122-124.
Weaver-Feldhaus et al., "Yeast mating for combinatorial Fab library generation and surface display," FEBS Lett. (2004) 564(2):24-34.
Chen, C., "Beta-amyloid increases dendritic Ca2+ influx by inhibiting the A-type K+ current in hippocampal CA1 pyramidal neurons," Biochem. Biophys. Res. Comm. (2005) 338:1913-1919.
Jeon, D. et al., "Impaired long-term memory and long-term potentiation in N-type Ca2+ channel-deficient mice," Genes, Brain Behavior (2007) 6:375-388.
Lipscombe, D. et al., "Functional diversity in neuronal voltage-gated calcium channels by alternative splicing of Cav. alpha1," Mol. Neurobiol. (2002) 26(1):21-44.
Rovira, C. et al., "Abeta(25-35) and Abeta(1-40) act on different calcium channels in CA1 hippocampal neurons," Biochem. Biophys. Res. Comm. (2002) 296;1317-1321.
Shankar, G.M. et al., "Natural oligomers of the Alzheimer amyloid-beta protein induce reversible synapse loss by modulating an NMDA-type glutamate receptor-dependent signaling pathway," J. Neurosci. (2007) 27(11):2866-2875.
Ye, C.P. et al., "Protofibrils of amyloid beta-protein inhibit specific K+ currents in neocortical cultures," Neurobiol. Disease (2003) 13:177-190.
United States Patent Office Action for U.S. Appl. No. 12/529,467 dated Feb. 14, 2014 (17 pages).
United States Patent Office Action for U.S. Appl. No. 13/195,533 dated Feb. 24, 2014 (9 pages).
United States Patent Office Notice of Allowance for U.S. Appl. No. 12/529,467 dated Jul. 9, 2014.
United States Patent Office Notice of Allowance for U.S. Appl. No. 13/102,713 dated Jun. 24, 2014.
Ma, B. et al., "Polymorphic C-terminal-sheet interactions determine the formation of fibril or amyloid-derived diffusible ligand-like globulomer for the Alzheimer A42 dodecamer," J. Biol. Chem. (2010) 285(47):37102-37110.
European Patent Office Action for Application No. 10179297 dated Jul. 21, 2014 (9 pages).
European Patent Office Action for Application No. 10179281 dated Jul. 21, 2014 (11 pages).
European Patent Office Action for Application No. 10179255 dated Jul. 21, 2014 (11 pages).
European Patent Office Action for Application No. 11715837 dated Oct. 10, 2014 (4 pages).

\* cited by examiner

FIGURE 1

SEQ ID NO:1

DVVMTQX$^7$PLSLPVTX$^{15}$GQPASISCKSSQSLLDIDGKTYLNWX$^{41}$X$^{42}$QX$^{44}$PGQSPX$^{50}$R
LIYLVSKLDSGVPDRFSGSGSGTDFTLKISRVEAEDVGVYYCWQGTHFPYTFGQGTK
LEIKR

SEQ ID NO:2

EVQLVESGGGLX$^{12}$QPGGSLRLSCAX$^{24}$SGFTX$^{29}$SSYGVHWVRQAPGKGLEWX$^{48}$X$^{49}$VI
WRGGRIDYNAAFMSRX$^{67}$TISX$^{71}$DNSKX$^{76}$TX$^{78}$YLQMNSLRAEDTAVYYCARNSDVW
GQGTTVTVSS

SEQ ID NO:3

X$^1$VQLQESGPGLVKPSETLSLTCTVSGX$^{27}$SX$^{29}$SSYGVHWX$^{37}$RQPPGKGLEWX$^{48}$GVI
WRGGRIDYNAAFMSRX$^{67}$TISX$^{71}$DTSKX$^{76}$QX$^{78}$SLKLSSVTAADTAVYYCARNSDVW
GQGTTVTVSS

SEQ ID NO:4

EVQLVESGGGLIQPGGSLRLSCAASGFTVS<u>SYGVH</u>WVRQAPGKGLEWVS<u>VIWRGGR
IDYNAAFMS</u>RFTISRDNSKNTLYLQMNSLRAEDTAVYYCAR<u>NSDV</u>WGQGTTVTVSS

FIGURE 5

SEQ ID NO:5

EVQLVESGGGLVQPGGSLRLSCAASGFTVS<u>SYGVH</u>WVRQAPGKGLEWVS<u>VIWRGG
RIDYNAAFMS</u>RFTISRDNSKNTLYLQMNSLRAEDTAVYYCAR<u>NSDV</u>WGQGTTVTVS
S

FIGURE 6

SEQ ID NO:6

EVQLVESGGGLVQPGGSLRLSCAVSGFTLS<u>SYGVH</u>WVRQAPGKGLEWLG<u>VIWRGG
RIDYNAAFMS</u>RLTISKDNSKSTVYLQMNSLRAEDTAVYYCAR<u>NSDV</u>WGQGTTVTVS
S

FIGURE 7

SEQ ID NO:7

EVQLVESGGGLIQPGGSLRLSCAASGFTLS<u>SYGVH</u>WVRQAPGKGLEWVS<u>VIWRGGR
IDYNAAFMS</u>RFTISKDNSKNTLYLQMNSLRAEDTAVYYCAR<u>NSDV</u>WGQGTTVTVSS

FIGURE 8

SEQ ID NO:8

QVQLQESGPGLVKPSETLSLTCTVSGGSIS<u>SYGVH</u>WIRQPPGKGLEWIG<u>VIWRGGRID
YNAAFMS</u>RVTISVDTSKNQFSLKLSSVTAADTAVYYCAR<u>NSDV</u>WGQGTTVTVSS

FIGURE 9

SEQ ID NO:9

5   EVQLQESGPGLVKPSETLSLTCTVSGGSIS<u>SYGVH</u>WIRQPPGKGLEWIG<u>VIWRGGRID</u>
    <u>YNAAFMS</u>RVTISVDTSKNQFSLKLSSVTAADTAVYYCAR<u>NSDV</u>WGQGTTVTVSS

FIGURE 10

SEQ ID NO:10

10  EVQLQESGPGLVKPSETLSLTCTVSGFSLS<u>SYGVH</u>WVRQPPGKGLEWLG<u>VIWRGGRI</u>
    <u>DYNAAFMS</u>RLTISKDTSKSQVSLKLSSVTAADTAVYYCAR<u>NSDV</u>WGQGTTVTVSS

FIGURE 11

SEQ ID NO:11

15  EVQLQESGPGLVKPSETLSLTCTVSGFSLS<u>SYGVH</u>WIRQPPGKGLEWIG<u>VIWRGGRID</u>
    <u>YNAAFMS</u>RVTISKDTSKNQFSLKLSSVTAADTAVYYCAR<u>NSDV</u>WGQGTTVTVSS

FIGURE 12

SEQ ID NO:12

20  DVVMTQSPLSLPVTLGQPASISC<u>KSSQSLLDIDGKTYLN</u>WFQQRPGQSPRRLIY<u>LVSK</u>
    <u>LDS</u>GVPDRFSGSGSGTDFTLKISRVEAEDVGVYYC<u>WQGTHFPYT</u>FGQGTKLEIKR

FIGURE 13

SEQ ID NO:13

25  DVVMTQTPLSLPVTPGQPASISC<u>KSSQSLLDIDGKTYLN</u>WFLQKPGQSPQRLIY<u>LVSK</u>
    <u>LDS</u>GVPDRFSGSGSGTDFTLKISRVEAEDVGVYYC<u>WQGTHFPYT</u>FGQGTKLEIKR

FIGURE 14

SEQ ID NO:14

DVVMTQTPLSLPVTPGQPASISC<u>KSSQSLLDIDGKTYLN</u>WLLQKPGQSPQRLIY<u>LVSK
LDS</u>GVPDRFSGSGSGTDFTLKISRVEAEDVGVYYC<u>WQGTHFPYT</u>FGQGTKLEIKR

FIGURE 15

SEQ ID NO:15

DVVMTQTPLSLPVTLGQPASISC<u>KSSQSLLDIDGKTYLN</u>WLLQRPGQSPRRLIY<u>LVSK
LDS</u>GVPDRFSGSGSGTDFTLKISRVEAEDVGVYYC<u>WQGTHFPYT</u>FGQGTKLEIKR

FIGURE 16

SEQ ID NO:16

DVVMTQTPLSLPVTLGQPASISC<u>KSSQSLLDIDGKTYLN</u>WFLQKPGQSPRRLIY<u>LVSK
LDS</u>GVPDRFSGSGSGTDFTLKISRVEAEDVGVYYC<u>WQGTHFPYT</u>FGQGTKLEIKR

FIGURE 17

| SEQ ID NO: | | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 |
|---|---|---|---|---|---|---|---|---|---|---|---|---|---|---|---|---|---|---|---|---|---|---|---|---|---|---|---|---|---|---|---|---|---|---|---|
| 23 | m4D10_VH | Q | V | Q | L | K | Q | S | G | P | S | L | I | Q | P | S | Q | S | L | S | I | T | C | T | V | S | G | F | S | L | T | S | Y | G | V |
| 4 | 4D10hum_VH.1z | E | V | Q | L | V | E | S | G | G | G | L | I | Q | P | G | G | S | L | R | L | S | C | A | A | S | G | F | T | V | S | S | Y | G | V |
| 5 | 4D10hum_VH.1 | E | V | Q | L | V | E | S | G | G | G | L | V | Q | P | G | G | S | L | R | L | S | C | A | A | S | G | F | T | V | S | S | Y | G | V |
| 6 | 4D10hum_VH.1a | E | V | Q | L | V | E | S | G | G | G | L | V | Q | P | G | G | S | L | R | L | S | C | A | V | S | G | F | T | L | S | S | Y | G | V |
| 7 | 4D10hum_VH.1b | E | V | Q | L | V | E | S | G | G | G | L | I | Q | P | G | G | S | L | R | L | S | C | A | A | S | G | F | T | L | S | S | Y | G | V |
| 2 | 4D10hum_VH3 consensus | E | V | Q | L | V | E | S | G | G | G | L | X | Q | P | G | G | S | L | R | L | S | C | A | X | S | G | F | T | X | S | S | Y | G | V |

| SEQ ID NO: | 35 | 36 | 37 | 38 | 39 | 40 | 41 | 42 | 43 | 44 | 45 | 46 | 47 | 48 | 49 | 50 | 51 | 52 | 53 | 54 | 55 | 56 | 57 | 58 | 59 | 60 | 61 | 62 | 63 | 64 | 65 | 66 | 67 | 68 | 69 | 70 | 71 | 72 | 73 |
|---|---|---|---|---|---|---|---|---|---|---|---|---|---|---|---|---|---|---|---|---|---|---|---|---|---|---|---|---|---|---|---|---|---|---|---|---|---|---|---|
| 23 | H | W | V | R | Q | S | P | G | K | G | L | E | W | L | G | V | I | W | R | G | G | R | I | D | Y | N | A | A | F | M | S | R | L | S | I | T | K | D | N |
| 4 | H | W | V | R | Q | A | P | G | K | G | L | E | W | V | S | V | I | W | R | G | G | R | I | D | Y | N | A | A | F | M | S | R | F | T | I | S | R | D | N |
| 5 | H | W | V | R | Q | A | P | G | K | G | L | E | W | V | S | V | I | W | R | G | G | R | I | D | Y | N | A | A | F | M | S | R | F | T | I | S | R | D | N |
| 6 | H | W | V | R | Q | A | P | G | K | G | L | E | W | L | G | V | I | W | R | G | G | R | I | D | Y | N | A | A | F | M | S | R | L | T | I | S | K | D | N |
| 7 | H | W | V | R | Q | A | P | G | K | G | L | E | W | V | S | V | I | W | R | G | G | R | I | D | Y | N | A | A | F | M | S | R | F | T | I | S | K | D | N |
| 2 | H | W | V | R | Q | A | P | G | K | G | L | E | W | X | X | V | I | W | R | G | G | R | I | D | Y | N | A | A | F | M | S | R | X | T | I | S | X | D | N |

| SEQ ID NO: | 74 | 75 | 76 | 77 | 78 | 79 | 80 | 81 | 82 | 83 | 84 | 85 | 86 | 87 | 88 | 89 | 90 | 91 | 92 | 93 | 94 | 95 | 96 | 97 | 98 | 99 | 100 | 101 | 102 | 103 | 104 | 105 | 106 | 107 | 108 | 109 | 110 | 111 | 112 |
|---|---|---|---|---|---|---|---|---|---|---|---|---|---|---|---|---|---|---|---|---|---|---|---|---|---|---|---|---|---|---|---|---|---|---|---|---|---|---|---|
| 23 | S | K | S | Q | V | F | F | K | M | N | S | L | Q | A | D | D | T | A | I | Y | Y | C | A | R | N | S | D | V | W | G | T | G | T | T | V | T | V | S | S |
| 4 | S | K | N | T | L | Y | L | Q | M | N | S | L | R | A | E | D | T | A | V | Y | Y | C | A | R | N | S | D | V | W | G | Q | G | T | T | V | T | V | S | S |
| 5 | S | K | N | T | L | Y | L | Q | M | N | S | L | R | A | E | D | T | A | V | Y | Y | C | A | R | N | S | D | V | W | G | Q | G | T | T | V | T | V | S | S |
| 6 | S | K | S | T | V | Y | L | Q | M | N | S | L | R | A | E | D | T | A | V | Y | Y | C | A | R | N | S | D | V | W | G | Q | G | T | T | V | T | V | S | S |
| 7 | S | K | N | T | L | Y | L | Q | M | N | S | L | R | A | E | D | T | A | V | Y | Y | C | A | R | N | S | D | V | W | G | Q | G | T | T | V | T | V | S | S |
| 2 | S | K | X | T | X | Y | L | Q | M | N | S | L | R | A | E | D | T | A | V | Y | Y | C | A | R | N | S | D | V | W | G | Q | G | T | T | V | T | V | S | S |

FIGURE 18

| SEQ ID NO: | | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 |
|---|---|---|---|---|---|---|---|---|---|---|---|---|---|---|---|---|---|---|---|---|---|---|---|---|---|---|---|---|---|---|---|---|---|---|---|
| 23 | m4D10_VH | Q | V | Q | L | K | Q | S | G | P | S | L | I | Q | P | S | Q | S | L | S | I | T | C | T | V | S | G | F | S | L | T | S | Y | G | V |
| 8 | 4D10hum_VH.2z | Q | V | Q | L | Q | E | S | G | P | G | L | V | K | P | S | E | T | L | S | L | T | C | T | V | S | G | G | S | I | S | S | Y | G | V |
| 9 | 4D10hum_VH.2 | E | V | Q | L | Q | E | S | G | P | G | L | V | K | P | S | E | T | L | S | L | T | C | T | V | S | G | G | S | I | S | S | Y | G | V |
| 10 | 4D10hum_VH.2a | E | V | Q | L | Q | E | S | G | P | G | L | V | K | P | S | E | T | L | S | L | T | C | T | V | S | G | F | S | L | S | S | Y | G | V |
| 11 | 4D10hum_VH.2b | E | V | Q | L | Q | E | S | G | P | G | L | V | K | P | S | E | T | L | S | L | T | C | T | V | S | G | F | S | L | S | S | Y | G | V |
| 3 | 4D10hum_VH4 consensus | X | V | Q | L | Q | E | S | G | P | G | L | V | K | P | S | E | T | L | S | L | T | C | T | V | S | G | X | S | X | S | S | Y | G | V |

| SEQ ID NO: | 35 | 36 | 37 | 38 | 39 | 40 | 41 | 42 | 43 | 44 | 45 | 46 | 47 | 48 | 49 | 50 | 51 | 52 | 53 | 54 | 55 | 56 | 57 | 58 | 59 | 60 | 61 | 62 | 63 | 64 | 65 | 66 | 67 | 68 | 69 | 70 | 71 | 72 | 73 |
|---|---|---|---|---|---|---|---|---|---|---|---|---|---|---|---|---|---|---|---|---|---|---|---|---|---|---|---|---|---|---|---|---|---|---|---|---|---|---|---|
| 23 | H | W | V | R | Q | S | P | G | K | G | L | E | W | L | G | V | I | W | R | G | G | R | I | D | Y | N | A | A | F | M | S | R | L | S | I | T | K | D | N |
| 8 | H | W | I | R | Q | P | P | G | K | G | L | E | W | I | G | V | I | W | R | G | G | R | I | D | Y | N | A | A | F | M | S | R | V | T | I | S | V | D | T |
| 9 | H | W | I | R | Q | P | P | G | K | G | L | E | W | I | G | V | I | W | R | G | G | R | I | D | Y | N | A | A | F | M | S | R | V | T | I | S | V | D | T |
| 10 | H | W | V | R | Q | P | P | G | K | G | L | E | W | L | G | V | I | W | R | G | G | R | I | D | Y | N | A | A | F | M | S | R | L | T | I | S | K | D | T |
| 11 | H | W | I | R | Q | P | P | G | K | G | L | E | W | I | G | V | I | W | R | G | G | R | I | D | Y | N | A | A | F | M | S | R | V | T | I | S | K | D | T |
| 3 | H | W | X | R | Q | P | P | G | K | G | L | E | W | X | G | V | I | W | R | G | G | R | I | D | Y | N | A | A | F | M | S | R | X | T | I | S | X | D | T |

| SEQ ID NO: | 74 | 75 | 76 | 77 | 78 | 79 | 80 | 81 | 82 | 83 | 84 | 85 | 86 | 87 | 88 | 89 | 90 | 91 | 92 | 93 | 94 | 95 | 96 | 97 | 98 | 99 | 100 | 101 | 102 | 103 | 104 | 105 | 106 | 107 | 108 | 109 | 110 | 111 | 112 |
|---|---|---|---|---|---|---|---|---|---|---|---|---|---|---|---|---|---|---|---|---|---|---|---|---|---|---|---|---|---|---|---|---|---|---|---|---|---|---|---|
| 23 | S | K | S | Q | V | F | F | K | M | N | S | L | Q | A | D | D | T | A | I | Y | Y | C | A | R | N | S | D | V | W | G | T | G | T | T | V | T | V | S | S |
| 8 | S | K | N | Q | F | S | L | K | L | S | S | V | T | A | A | D | T | A | V | Y | Y | C | A | R | N | S | D | V | W | G | Q | G | T | T | V | T | V | S | S |
| 9 | S | K | N | Q | F | S | L | K | L | S | S | V | T | A | A | D | T | A | V | Y | Y | C | A | R | N | S | D | V | W | G | Q | G | T | T | V | T | V | S | S |
| 10 | S | K | S | Q | V | S | L | K | L | S | S | V | T | A | A | D | T | A | V | Y | Y | C | A | R | N | S | D | V | W | G | Q | G | T | T | V | T | V | S | S |
| 11 | S | K | N | Q | F | S | L | K | L | S | S | V | T | A | A | D | T | A | V | Y | Y | C | A | R | N | S | D | V | W | G | Q | G | T | T | V | T | V | S | S |
| 3 | S | K | X | Q | X | S | L | K | L | S | S | V | T | A | A | D | T | A | V | Y | Y | C | A | R | N | S | D | V | W | G | Q | G | T | T | V | T | V | S | S |

FIGURE 19

| SEQ ID NO: | | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 |
|---|---|---|---|---|---|---|---|---|---|---|---|---|---|---|---|---|---|---|---|---|---|---|---|---|---|---|---|---|---|---|---|---|---|---|---|
| 24 | m4D10_VL | D | V | V | M | T | Q | T | P | L | T | L | S | V | T | I | G | Q | P | A | S | I | S | C | K | S | S | Q | S | L | L | D | I | D | G |
| 12 | 4D10hum_Vκ.1z | D | V | V | M | T | Q | S | P | L | S | L | P | V | T | L | G | Q | P | A | S | I | S | C | K | S | S | Q | S | L | L | D | I | D | G |
| 13 | 4D10hum_Vκ.1 | D | V | V | M | T | Q | T | P | L | S | L | P | V | T | P | G | Q | P | A | S | I | S | C | K | S | S | Q | S | L | L | D | I | D | G |
| 14 | 4D10hum_Vκ.1a | D | V | V | M | T | Q | T | P | L | S | L | P | V | T | P | G | Q | P | A | S | I | S | C | K | S | S | Q | S | L | L | D | I | D | G |
| 15 | 4D10hum_Vκ.1b | D | V | V | M | T | Q | T | P | L | S | L | P | V | T | L | G | Q | P | A | S | I | S | C | K | S | S | Q | S | L | L | D | I | D | G |
| 16 | 4D10hum_Vκ.1c | D | V | V | M | T | Q | T | P | L | S | L | P | V | T | L | G | Q | P | A | S | I | S | C | K | S | S | Q | S | L | L | D | I | D | G |
| 1 | 4D10hum_Vκ consensus | D | V | V | M | T | Q | X | P | L | S | L | P | V | T | X | G | Q | P | A | S | I | S | C | K | S | S | Q | S | L | L | D | I | D | G |

| SEQ ID NO: | 35 | 36 | 37 | 38 | 39 | 40 | 41 | 42 | 43 | 44 | 45 | 46 | 47 | 48 | 49 | 50 | 51 | 52 | 53 | 54 | 55 | 56 | 57 | 58 | 59 | 60 | 61 | 62 | 63 | 64 | 65 | 66 | 67 | 68 | 69 | 70 | 71 | 72 | 73 |
|---|---|---|---|---|---|---|---|---|---|---|---|---|---|---|---|---|---|---|---|---|---|---|---|---|---|---|---|---|---|---|---|---|---|---|---|---|---|---|---|
| 24 | K | T | Y | L | N | W | L | L | Q | R | P | G | Q | S | P | K | R | L | I | Y | L | V | S | K | L | D | S | G | V | P | D | R | F | T | G | S | G | S | G |
| 12 | K | T | Y | L | N | W | F | Q | Q | R | P | G | Q | S | P | R | R | L | I | Y | L | V | S | K | L | D | S | G | V | P | D | R | F | S | G | S | G | S | G |
| 13 | K | T | Y | L | N | W | F | L | Q | K | P | G | Q | S | P | Q | R | L | I | Y | L | V | S | K | L | D | S | G | V | P | D | R | F | S | G | S | G | S | G |
| 14 | K | T | Y | L | N | W | L | L | Q | K | P | G | Q | S | P | Q | R | L | I | Y | L | V | S | K | L | D | S | G | V | P | D | R | F | S | G | S | G | S | G |
| 15 | K | T | Y | L | N | W | L | L | Q | R | P | G | Q | S | P | R | R | L | I | Y | L | V | S | K | L | D | S | G | V | P | D | R | F | S | G | S | G | S | G |
| 16 | K | T | Y | L | N | W | F | L | Q | K | P | G | Q | S | P | R | R | L | I | Y | L | V | S | K | L | D | S | G | V | P | D | R | F | S | G | S | G | S | G |
| 1 | K | T | Y | L | N | W | X | X | Q | X | P | G | Q | S | P | X | R | L | I | Y | L | V | S | K | L | D | S | G | V | P | D | R | F | S | G | S | G | S | G |

| SEQ ID NO: | 74 | 75 | 76 | 77 | 78 | 79 | 80 | 81 | 82 | 83 | 84 | 85 | 86 | 87 | 88 | 89 | 90 | 91 | 92 | 93 | 94 | 95 | 96 | 97 | 98 | 99 | 100 | 101 | 102 | 103 | 104 | 105 | 106 | 107 | 108 | 109 | 110 | 111 | 112 | 113 |
|---|---|---|---|---|---|---|---|---|---|---|---|---|---|---|---|---|---|---|---|---|---|---|---|---|---|---|---|---|---|---|---|---|---|---|---|---|---|---|---|---|
| 24 | T | D | F | T | L | K | I | S | R | V | E | A | E | D | L | G | V | Y | Y | C | W | Q | G | T | H | F | P | Y | T | F | G | G | G | T | K | L | E | I | K | R |
| 12 | T | D | F | T | L | K | I | S | R | V | E | A | E | D | V | G | V | Y | Y | C | W | Q | G | T | H | F | P | Y | T | F | G | Q | G | T | K | L | E | I | K | R |
| 13 | T | D | F | T | L | K | I | S | R | V | E | A | E | D | V | G | V | Y | Y | C | W | Q | G | T | H | F | P | Y | T | F | G | Q | G | T | K | L | E | I | K | R |
| 14 | T | D | F | T | L | K | I | S | R | V | E | A | E | D | V | G | V | Y | Y | C | W | Q | G | T | H | F | P | Y | T | F | G | Q | G | T | K | L | E | I | K | R |
| 15 | T | D | F | T | L | K | I | S | R | V | E | A | E | D | V | G | V | Y | Y | C | W | Q | G | T | H | F | P | Y | T | F | G | Q | G | T | K | L | E | I | K | R |
| 16 | T | D | F | T | L | K | I | S | R | V | E | A | E | D | V | G | V | Y | Y | C | W | Q | G | T | H | F | P | Y | T | F | G | Q | G | T | K | L | E | I | K | R |
| 1 | T | D | F | T | L | K | I | S | R | V | E | A | E | D | V | G | V | Y | Y | C | W | Q | G | T | H | F | P | Y | T | F | G | Q | G | T | K | L | E | I | K | R |

FIGURE 20
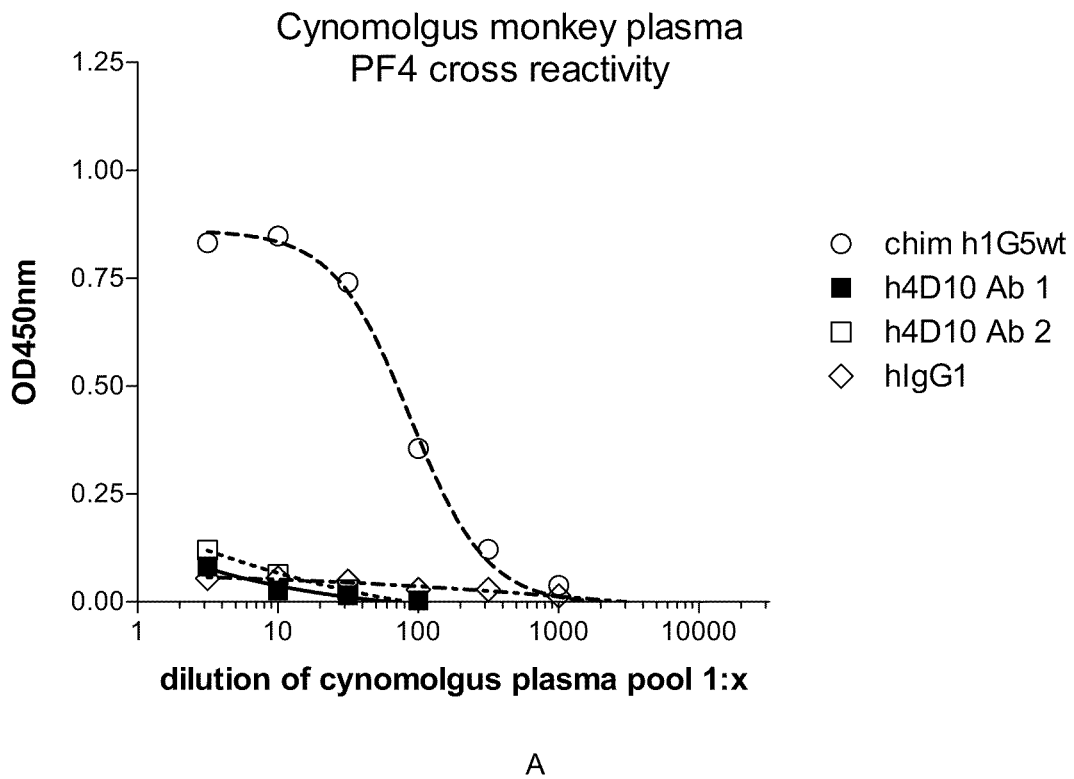
A
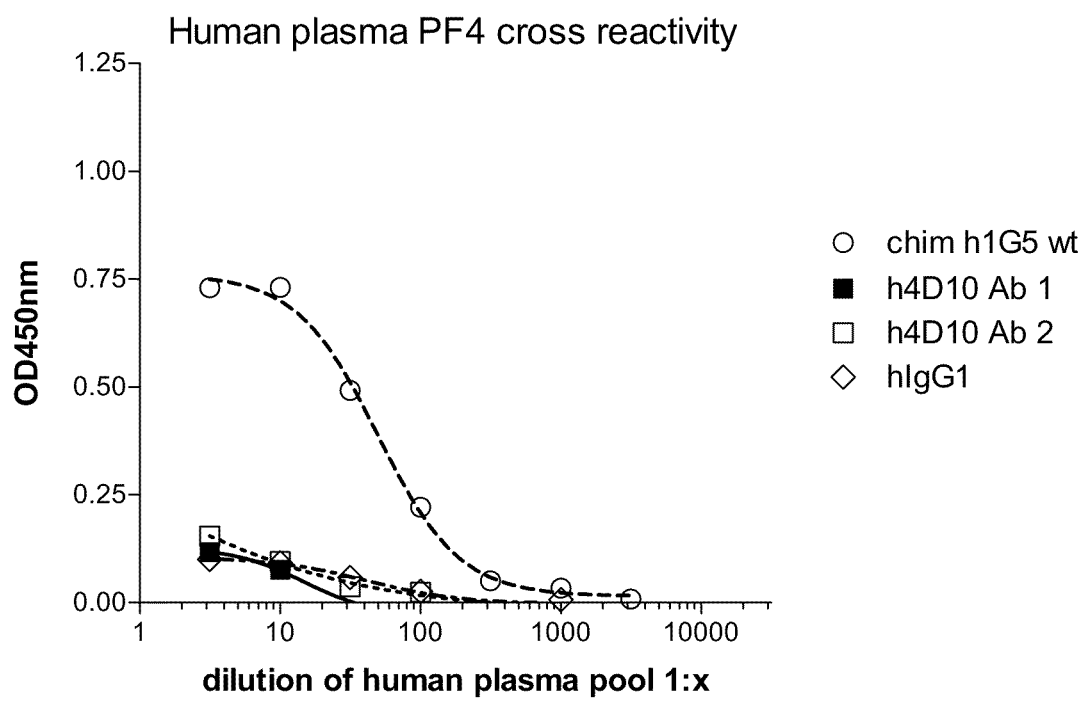
B

FIGURE 21
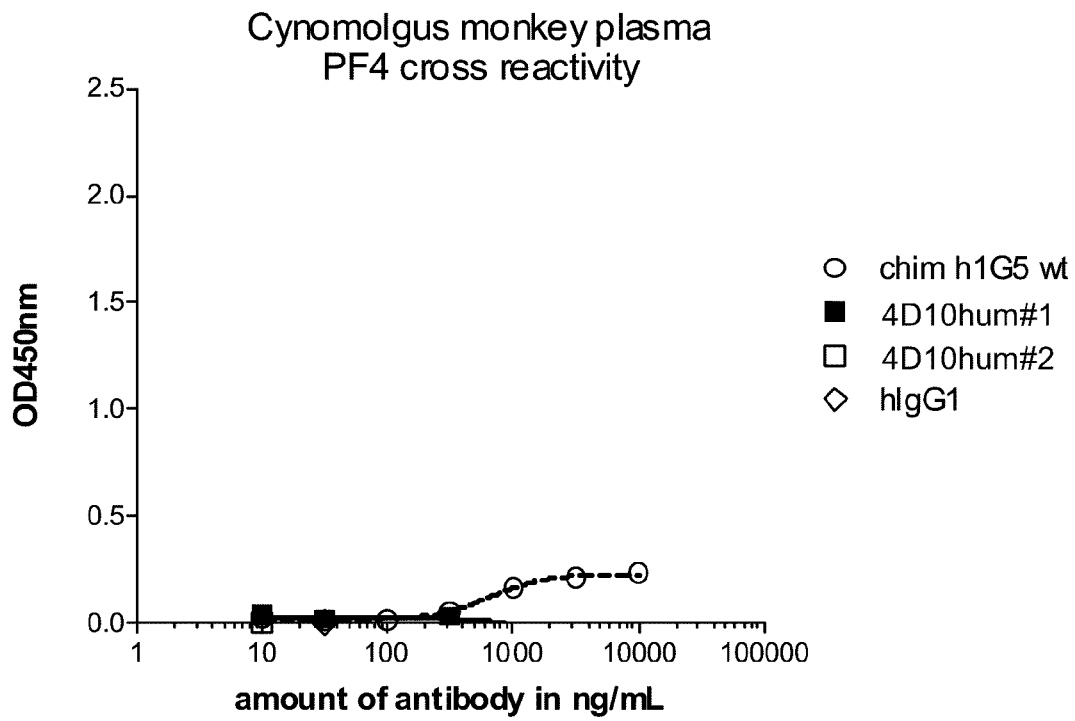
A
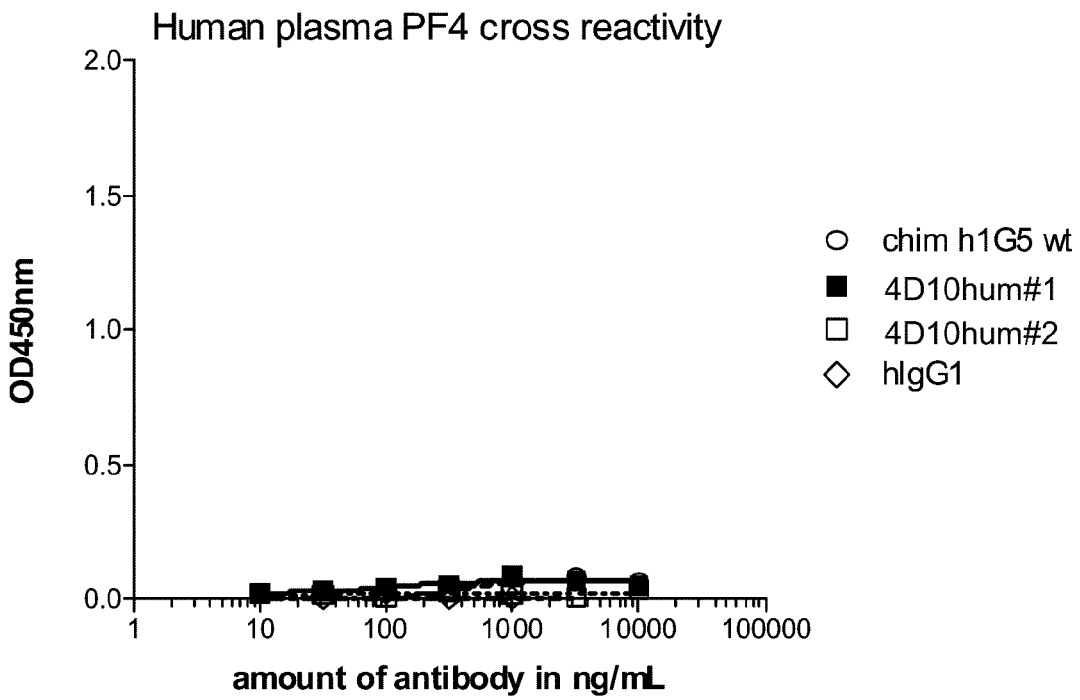
B

FIGURE 22
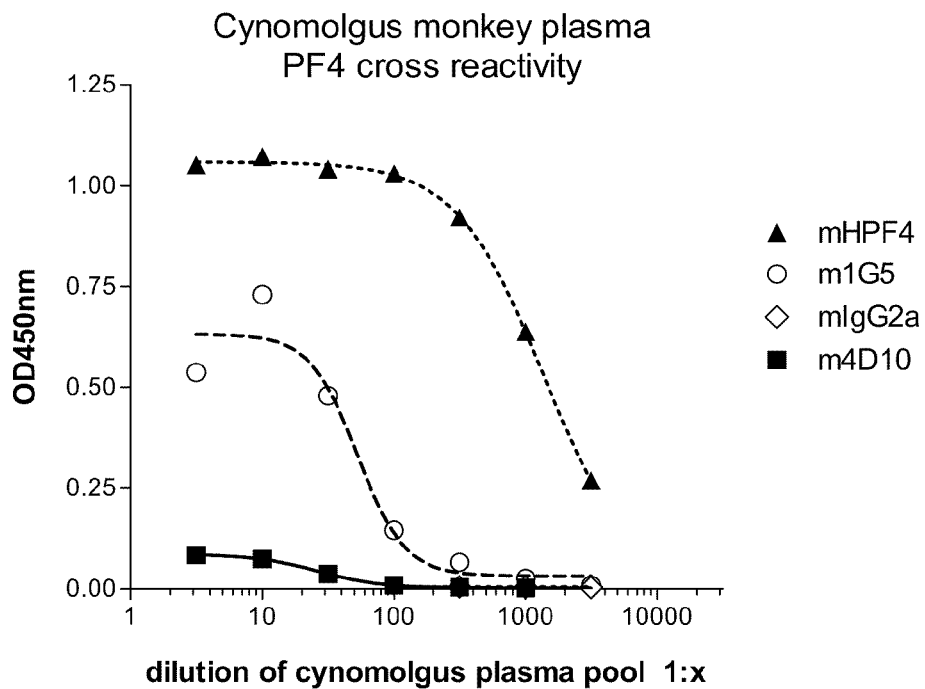
A
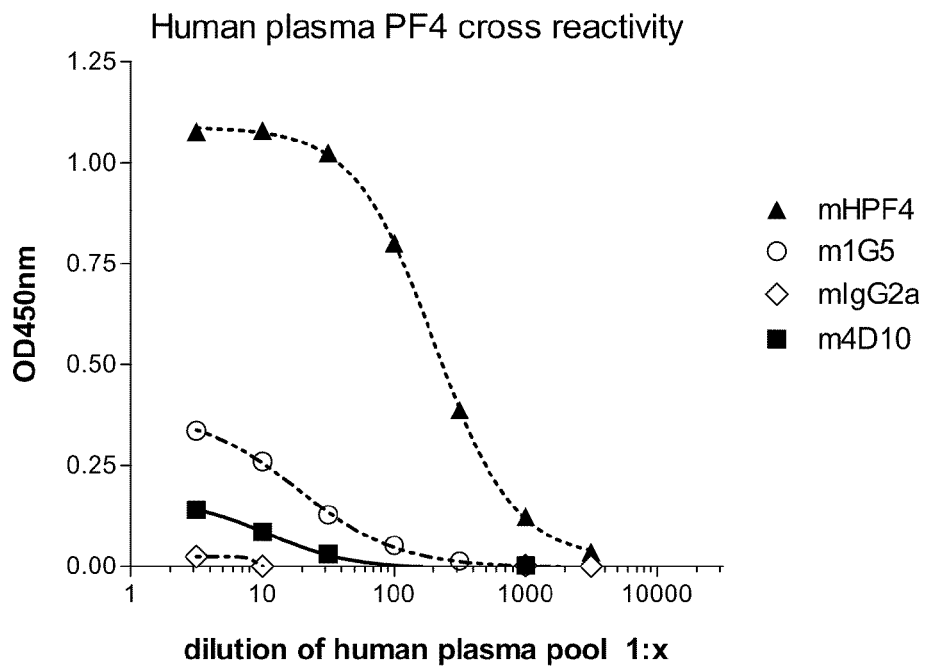
B

FIGURE 23
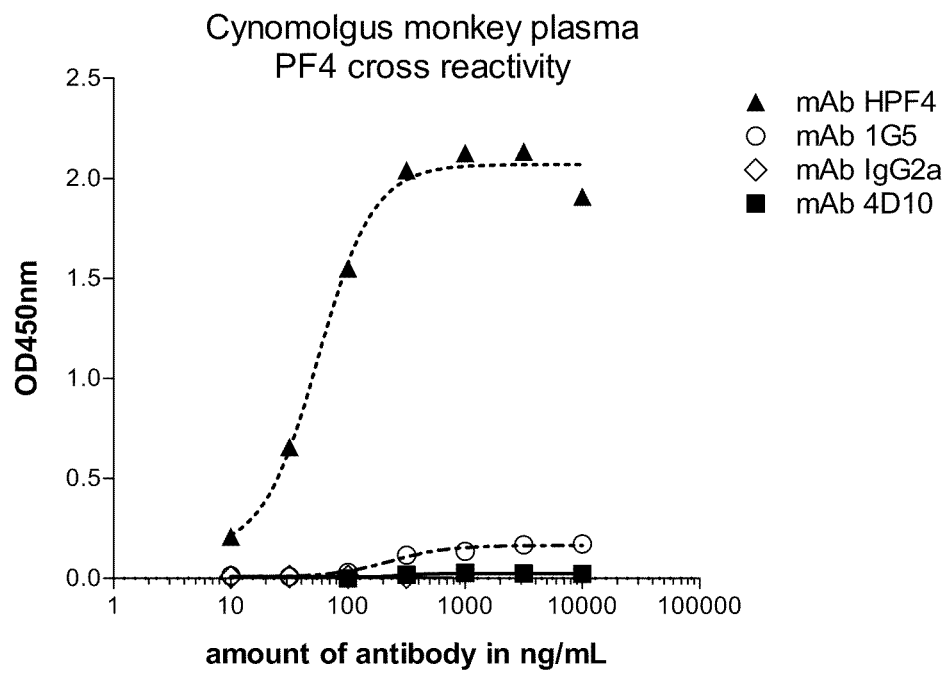
A
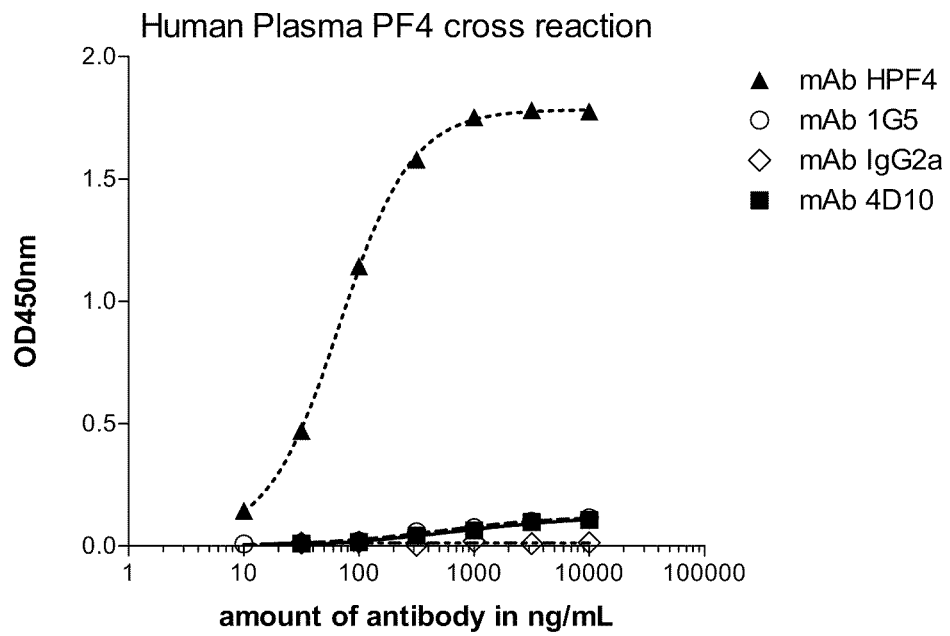
B

FIGURE 24

SEQ ID NO:46

EVQLVESGGGLVQPGGSLRLSCAVSGFTLS<u>SYGVH</u>WVRQAPGKGLEWLG<u>VIWRGG
RIDYNAAFMS</u>RLTISKDNSKSTVYLQMNSLRAEDTAVYYCAR<u>NSD</u>VWGQGTTVTVS
SASTKGPSVFPLAPSSKSTSGGTAALGCLVKDYFPEPVTVSWNSGALTSGVHTFPAVL
QSSGLYSLSSVVTVPSSSLGTQTYICNVNHKPSNTKVDKKVEPKSCDKTHTCPPCPAP
ELLGGPSVFLFPPKPKDTLMISRTPEVTCVVVDVSHEDPEVKFNWYVDGVEVHNAK
TKPREEQYNSTYRVVSVLTVLHQDWLNGKEYKCKVSNKALPAPIEKTISKAKGQPR
EPQVYTLPPSREEMTKNQVSLTCLVKGFYPSDIAVEWESNGQPENNYKTTPPVLDSD
GSFFLYSKLTVDKSRWQQGNVFSCSVMHEALHNHYTQKSLSLSPGK

FIGURE 25

SEQ ID NO:47

EVQLQESGPGLVKPSETLSLTCTVSGFSLS<u>SYGVH</u>WVRQPPGKGLEWLG<u>VIWRGGRI
DYNAAFMS</u>RLTISKDTSKSQVSLKLSSVTAADTAVYYCAR<u>NSD</u>VWGQGTTVTVSSA
STKGPSVFPLAPSSKSTSGGTAALGCLVKDYFPEPVTVSWNSGALTSGVHTFPAVLQS
SGLYSLSSVVTVPSSSLGTQTYICNVNHKPSNTKVDKKVEPKSCDKTHTCPPCPAPEL
LGGPSVFLFPPKPKDTLMISRTPEVTCVVVDVSHEDPEVKFNWYVDGVEVHNAKTK
PREEQYNSTYRVVSVLTVLHQDWLNGKEYKCKVSNKALPAPIEKTISKAKGQPREPQ
VYTLPPSREEMTKNQVSLTCLVKGFYPSDIAVEWESNGQPENNYKTTPPVLDSDGSF
FLYSKLTVDKSRWQQGNVFSCSVMHEALHNHYTQKSLSLSPGK

FIGURE 26

SEQ ID NO:48

DVVMTQTPLSLPVTPGQPASISC<u>KSSQSLLDIDGKTYLN</u>WLLQKPGQSPQRLIY<u>LVSK
LDS</u>GVPDRFSGSGSGTDFTLKISRVEAEDVGVYYC<u>WQGTHFPYT</u>FGQGTKLEIKRTV
AAPSVFIFPPSDEQLKSGTASVVCLLNNFYPREAKVQWKVDNALQSGNSQESVTEQD
SKDSTYSLSSTLTLSKADYEKHKVYACEVTHQGLSSPVTKSFNRGEC

AMYLOID-BETA BINDING PROTEINS

CROSS-REFERENCE TO RELATED APPLICATIONS

This claims priority to U.S. Patent Application No. 61/446,624, filed on Feb. 25, 2011, U.S. Patent Application No. 61/373,825, filed on Aug. 14, 2010, and U.S. Patent Application No. 61/324,386, filed on Apr. 15, 2010, the entire contents of all of which are fully incorporated herein by reference.

FIELD OF THE INVENTION

The present invention relates to amyloid-beta (Aβ) binding proteins, nucleic acids encoding said proteins, methods of producing said proteins, compositions comprising said proteins and the use of said proteins in diagnosis, treatment and prevention of conditions such as amyloidoses, e.g., Alzheimer's disease.

BACKGROUND OF THE INVENTION

Alzheimer's disease (AD) is a neurodegenerative disorder characterized by a progressive loss of cognitive abilities and by characteristic neuropathological features comprising deposits of amyloid beta (Aβ) peptide, neurofibrillary tangles and neuronal loss in several regions of the brain (Hardy and Selkoe, Science 297: 353, 2002; Mattson, Nature 431: 7004, 2004. Cerebral amyloid deposits and cognitive impairments very similar to those observed in Alzheimer's disease are also hallmarks of Down syndrome (trisomy 21), which occurs at a frequency of about 1 in 800 births.

The Aβ peptide arises from the amyloid precursor protein (APP) by proteolytic processing. This processing is effected by the cooperative activity of several proteases named α-, β- and γ-secretase and leads to a number of specific fragments of differing length. The amyloid desposits consist mostly of peptides with a length of 40 or 42 amino acids (Aβ40, Aβ42). This also includes, in addition to human variants, isoforms of the amyloid β(1-42) protein present in organisms other than humans, in particular, other mammals, especially rats. This protein, which tends to polymerize in an aqueous environment, may be present in very different molecular forms. A simple correlation of the deposition of insoluble protein with the occurrence or progression of dementia disorders such as, for example, Alzheimer's disease, has proved to be unconvincing (Terry et al., Ann. Neurol. 30: 572-580, 1991; Dickson et al., Neurobiol. Aging 16: 285-298, 1995). In contrast, the loss of synapses and cognitive perception seems to correlate better with soluble forms of Aβ(1-42) (Lue et al., Am. J. Pathol. 155: 853-862, 1999; McLean et al., Ann. Neurol. 46: 860-866, 1999).

None of the polyclonal and monoclonal antibodies which have been raised in the past against monomeric Aβ(1-42) have proven to produce the desired therapeutic effect without also causing serious side effects in animals and/or humans. For example, passive immunization results from preclinical studies in very old APP23 mice which received a N-terminal directed anti-Aβ(1-42) antibody once weekly for 5 months indicate therapeutically relevant side effects. In particular, these mice showed an increase in number and severity of microhemorrhages compared to saline-treated mice (Pfeifer et al., Science 298: 1379, 2002). A similar increase in hemorrhages was also described for very old (>24 months) Tg2576 and PDAPP mice (Wilcock et al., J Neuroscience 23: 3745-51, 2003; Racke et al., J Neuroscience 25: 629-636, 2005). In both strains, injection of anti-Aβ(1-42) resulted in a significant increase of microhemorrhages.

WO 2004/067561 refers to globular oligomers ("globulomers") of Aβ(1-42) peptide and a process for preparing them. WO 2006/094724 relates to non-diffusible globular Aβ(X-38 ... 43) oligomers wherein X is selected from the group consisting of numbers 1 ... 24. WO 2004/067561 and WO 2006/094724 further describes that limited proteolysis of the globulomers yields truncated versions of said globulomers such as Aβ(20-42) or Aβ(12-42) globulomers. WO 2007/064917 describes the cloning, expression and isolation of recombinant forms of amyloid β peptide (referred to hereafter as N-Met Aβ(1-42)) and globulomeric forms thereof. The data suggest the existence of an amyloid fibril independent pathway of Aβ folding and assembly into Aβ oligomers which display one or more unique epitopes (hereinafter referred to as the globulomer epitopes). Since globulomer epitopes were detected in the brain of AD patients and APP transgenic mice and the globulomer specifically binds to neurons and blocks LTP, the globulomer represents a pathologically relevant Aβ conformer. It has been found that soluble Aβ globulomer exert its detrimental effects essentially by interaction with the P/Q type presynaptic calcium channel, and that inhibitors of this interaction are therefore useful for treatment of amyloidoses such as Alzheimer's disease (WO 2008/104385).

Antibodies which selectively bind to such globulomeric forms of Aβ have been described in WO 2007/064972, WO 2007/062852, WO 2008067464, WO 2008/150946 and WO 2008/150949. For instance, several monoclonal antibodies known from WO 2007/062852 and WO 2008/150949 specifically recognize Aβ(20-42) globulomer.

There exists a tremendous, unmet therapeutic need for the development of biologics such as Aβ binding proteins that prevent or slow down the progression of the disease without inducing negative and potentially lethal effects on the human body. Such a need is particularly evident in view of the increasing longevity of the general population and, with this increase, an associated rise in the number of patients annually diagnosed with Alzheimer's disease or related disorders. Further, such Aβ binding proteins will allow for proper diagnosis of Alzheimer's disease in a patient experiencing symptoms thereof, a diagnosis which can only be confirmed upon autopsy at the present time. Additionally, the Aβ binding proteins will allow for the elucidation of the biological properties of the proteins and other biological factors responsible for this debilitating disease.

SUMMARY OF THE INVENTION

The present invention provides a novel family of Aβ binding proteins (or simply "binding proteins"), CDR grafted antibodies, humanized antibodies, and fragments thereof, capable of binding to soluble Aβ globulomers, for example, Aβ(20-42) globulomer as described herein. It is noted that the binding proteins of the present invention may also be reactive with (i.e. bind to) Aβ forms other than the Aβ globulomers described herein, such Aβ forms may be present in the brain of a patient having an amyloidosis such as Alzheimer's disease. These Aβ forms may or may not be oligomeric or globulomeric. The Aβ forms to which the binding proteins of the present invention bind include any Aβ form that comprises the globulomer epitope with which the murine/mouse monoclonal antibody m4D10 is reactive (hereinafter referred to as "m4D10"). m4D10 and its properties are described in WO 2007/062852, which is incorporated herein by reference. Such Aβ forms are hereinafter referred to as "targeted Aβ forms". Further, the present invention also provides a therapeutic means with which to inhibit the activity of said targeted Aβ forms and provides compositions and methods for treating diseases associated with said targeted Aβ forms, particularly amyloidosis such as Alzheimer's disease.

In one aspect, the invention provides a binding protein comprising: a first amino acid sequence which is at least 90% identical to
SEQ ID NO:2:

EVQLVESGGGLX$^{12}$QPGGSLRLSCAX$^{24}$SGFTX$^{29}$SSYGVHWVRQAPGKG

LEWX$^{48}$X$^{49}$VIWRGGRIDYNAAFMSRX$^{67}$TISX$^{71}$DNSKX$^{76}$TX$^{78}$YLQMNS

LRAEDTAVYYCARNSDVWGQGTTVTVSS, wherein $X^{12}$ is I or V, $X^{24}$ is A or V, $X^{29}$ is V or L, $X^{48}$ is V or L, $X^{49}$ is S or G, $X^{67}$ is F or L, $X^{71}$ is R or K, $X^{76}$ is N or S, and $X^{78}$ is L or V; or
SEQ ID NO:3:

X$^{1}$VQLQESGPGLVKPSETLSLTCTVSGX$^{27}$SX$^{29}$SSYGVHWX$^{37}$RQPPGK

GLEWX$^{48}$GVIWRGGRIDYNAAFMSRX$^{67}$TISX$^{71}$DTSKX$^{76}$QX$^{78}$SLKLSS

VTAADTAVYYCARNSDVWGQGTTVTVSS, wherein $X^{1}$ is Q or E, $X^{27}$ is G or F, $X^{29}$ is I or L, $X^{37}$ is I or V, $X^{48}$ is I or L, $X^{67}$ is V or L, $X^{71}$ is V or K, $X^{76}$ is N or S, and $X^{78}$ is F or V;
and a second amino acid sequence which is at least 90% identical to
SEQ ID NO:1:

DVVMTQX$^{7}$PLSLPVTX$^{15}$GQPASISCKSSQSLLDIDGKTYLNWX$^{41}$X$^{42}$Q

X$^{44}$PGQSPX$^{50}$RLIYLVSKLDSGVPDRFSGSGSGTDFTLKISRVEAEDV

GVYYCWQGTHFPYTFGQGTKLEIKR, wherein $X^{7}$ is S or T, $X^{15}$ is L or P, $X^{41}$ is F or L, $X^{42}$ is Q or L, $X^{44}$ is R or K, and $X^{50}$ is R or Q.

In a further aspect of the invention, the binding protein described above comprises a first amino acid sequence which is at least 90%, 91%, 92%, 93%, 94%, 95%, 96%, 97%, 98%, or 99% identical to an amino acid sequence selected from the group consisting of SEQ ID NO:4, SEQ ID NO:5, SEQ ID NO:6, SEQ ID NO:7, SEQ ID NO:8, SEQ ID NO:9, SEQ ID NO:10, and SEQ ID NO:11. In still a further aspect of the invention, the binding protein described above comprises a first amino acid sequence selected from the group consisting of SEQ ID NO:4, SEQ ID NO:5, SEQ ID NO:6, SEQ ID NO:7, SEQ ID NO:8, SEQ ID NO:9, SEQ ID NO:10, and SEQ ID NO:11.

In another aspect of the invention, the binding protein described above comprises a second amino acid sequence which is at least 90%, 91%, 92%, 93%, 94%, 95%, 96%, 97%, 98%, or 99% identical to an amino acid sequence selected from the group consisting of SEQ ID NO:12, SEQ ID NO:13, SEQ ID NO:14, SEQ ID NO:15, and SEQ ID NO:16. In still another aspect of the invention, the binding protein described above comprises a second amino acid sequence selected from the group consisting of SEQ ID NO:12, SEQ ID NO:13, SEQ ID NO:14, SEQ ID NO:15, and SEQ ID NO:16.

In one aspect of the invention, the binding protein described above comprises a first amino acid sequence which is at least 90%, 91%, 92%, 93%, 94%, 95%, 96%, 97%, 98%, or 99% identical to an amino acid sequence selected from the group consisting of SEQ ID NO:4, SEQ ID NO:5, SEQ ID NO:6, SEQ ID NO:7, SEQ ID NO:8, SEQ ID NO:9, SEQ ID NO:10, and SEQ ID NO:11; and a second amino acid sequence which is at least 90%, 91%, 92%, 93%, 94%, 95%, 96%, 97%, 98%, or 99% identical to an amino acid sequence selected from the group consisting of SEQ ID NO:12, SEQ ID NO:13, SEQ ID NO:14, SEQ ID NO:15, and SEQ ID NO:16. In a further aspect of the invention, the binding protein described above comprises a first amino acid sequence selected from the group consisting of SEQ ID NO:4, SEQ ID NO:5, SEQ ID NO:6, SEQ ID NO:7, SEQ ID NO:8, SEQ ID NO:9, SEQ ID NO:10, and SEQ ID NO:11; and a second amino acid sequence selected from the group consisting of SEQ ID NO:12, SEQ ID NO:13, SEQ ID NO:14, SEQ ID NO:15, and SEQ ID NO:16.

In a particular aspect of the invention, the binding protein described above comprises a first amino acid sequence which is at least 90%, 91%, 92%, 93%, 94%, 95%, 96%, 97%, 98%, or 99% identical to the amino acid sequence set forth in SEQ ID NO:6; and a second amino acid sequence which is at least 90%, 91%, 92%, 93%, 94%, 95%, 96%, 97%, 98%, or 99% identical to an amino acid sequence set forth in SEQ ID NO:14. In a further particular aspect of the invention, the binding protein described above comprises a first amino acid sequence set forth in SEQ ID NO:6; and a second amino acid sequence set forth in SEQ ID NO:14.

In a particular aspect of the invention, the binding protein described above comprises a first amino acid sequence which is at least 90%, 91%, 92%, 93%, 94%, 95%, 96%, 97%, 98%, or 99% identical to the amino acid sequence set forth in SEQ ID NO:10; and a second amino acid sequence which is at least 90%, 91%, 92%, 93%, 94%, 95%, 96%, 97%, 98%, or 99% identical to an amino acid sequence set forth in SEQ ID NO:14. In a further particular aspect of the invention, the binding protein described above comprises a first amino acid sequence set forth in SEQ ID NO:10; and a second amino acid sequence set forth in SEQ ID NO:14.

In one aspect, the binding protein described herein is an antibody. This antibody may be, for example, an immunoglobulin molecule, a disulfide linked Fv, a monoclonal antibody (mab), a single chain Fv (scFv), a chimeric antibody, a single domain antibody, a CDR-grafted antibody, a diabody, a humanized antibody, a multispecific antibody, a Fab, a dual specific antibody, a dual variable domain (DVD) binding molecule, a Fab', a bispecific antibody, a F(ab')$_2$, or a Fv.

When the binding protein described herein is an antibody, it comprises at least one variable heavy chain that corresponds to the first amino acid sequence as defined above, and at least one variable light chain that corresponds to the second amino acid sequence as defined above. For example, an antibody of the invention comprises (i) at least one variable heavy chain comprising an amino acid sequence which is at least 90%, 91%, 92%, 93%, 94%, 95%, 96%, 97%, 98%, 99% or 100% identical to an amino acid sequence selected from the group consisting of SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, and SEQ ID NO:11, and (ii) at least one variable light chain comprising an amino acid sequence which is at least 90%, 91%, 92%, 93%, 94%, 95%, 96%, 97%, 98%, 99% or 100% identical to an amino acid sequence selected from the group consisting of SEQ ID NO:1, SEQ ID NO:12, SEQ ID NO:13, SEQ ID NO:14, SEQ ID NO:15, and SEQ ID NO:16. In a particular aspect of the invention, the antibody of the invention comprises (i) at least one variable heavy chain comprising an amino acid sequence which is at least 90%, 91%, 92%, 93%, 94%, 95%, 96%, 97%, 98%, 99% or 100% identical to an amino acid sequence set forth in SEQ ID NO:6 or SEQ ID NO:10, and (ii) at least one variable light chain comprising an amino acid sequence which is at least 90%, 91%, 92%, 93%, 94%, 95%, 96%, 97%, 98%, 99% or 100% identical to an amino acid sequence set forth in SEQ ID NO:14.

The binding protein described herein may further (in addition to the first and second amino acid sequence) comprise another moiety which may be another amino acid sequence or other chemical moiety. For instance, an antibody of the present invention may comprise a heavy chain immunoglobulin constant domain. Said heavy chain immunoglobulin constant domain may be selected from the group consisting of a human IgM constant domain, a human IgG4 constant domain, a human IgG1 constant domain, a human IgE constant domain, a human IgG2 constant domain, a human IgG3 constant domain, and a human IgA constant domain. In another aspect, the binding protein of the invention further comprises a heavy chain constant region having an amino acid sequence selected from the group consisting of SEQ ID NO:25 and SEQ ID NO:26, additionally a light chain constant region having an amino acid sequence selected from the group consisting of SEQ ID NO:27 and SEQ ID NO:28. In a particular aspect of the invention, the binding protein described herein comprises a variable heavy chain comprising an amino acid sequence set forth in SEQ ID NO:6 or SEQ ID NO:10; a variable light chain comprising an amino acid sequence set forth in SEQ ID NO:14; a heavy chain constant region having an amino acid sequence set forth in SEQ ID NO:25; and a light chain constant region having an amino acid sequence set forth in SEQ ID NO:27. In a further particular aspect of the invention, the binding protein described herein comprises a first amino acid sequence set forth in SEQ ID NO:46 or SEQ ID NO:47, and a second first amino acid sequence set forth in SEQ ID NO:48.

The binding protein, e.g. the antibody, described herein may further comprise a therapeutic agent, an imaging agent, residues capable of facilitating formation of an immunoadhesion molecule and/or another functional molecule (e.g. another peptide or protein). The imaging agent can be a radiolabel including but not limited to $^{3}$H, $^{14}$C, $^{35}$S, $^{90}$Y, $^{99}$Tc, $^{111}$In, $^{125}$I, $^{131}$I, $^{177}$Lu, $^{166}$Ho, and $^{153}$Sm; an enzyme, a fluorescent label, a luminescent label, a bioluminescent label, a magnetic label, or biotin.

The binding protein of the present invention can be glycosylated. According to one aspect of the invention, the glycosylation pattern is a human glycosylation pattern.

In one aspect of the invention, the above-described binding protein binds to an Aβ form that comprises the globulomer epitope with which the murine monoclonal antibody m4D10 is reactive (i.e. a targeted Aβ form). In particular the above-described binding proteins bind to amyloid-beta (20-42) globulomer as described herein.

In one aspect of the invention, the binding protein described herein is capable of modulating a biological function of Aβ(20-42) globulomer. In a further aspect of the invention, the binding protein described herein is capable of neutralizing Aβ(20-42) globulomer activity.

The binding protein of the present invention may exist as a crystal. In one aspect, the crystal is a carrier-free pharmaceutical controlled release crystal. In another aspect, the crystallized binding protein has a greater half life in vivo than its soluble counterpart. In still another aspect, the crystallized binding protein retains biological activity after crystallization.

The present invention also provides an isolated nucleic acid encoding any one of the binding proteins disclosed herein. A further embodiment provides a vector comprising said nucleic acid. Said vector may be selected from the group consisting of pcDNA, pTT (Durocher et al., Nucleic Acids Research 30(2), 2002), pTT3 (pTT with additional multiple cloning site), pEFBOS (Mizushima and Nagata, Nucleic acids Research 18(17), 1990), pBV, pJV, and pBJ.

In another aspect of the invention, a host cell is transformed with the vector disclosed above. According to one embodiment, the host cell is a prokaryotic cell including but not limited to *E. coli*. In a related embodiment, the host cell is a eukaryotic cell selected from the group comprising a protist cell, animal cell, plant cell and fungal cell. The animal cell may be selected from the group consisting of a mammalian cell, an avian cell and an insect cell. According to one aspect of the invention, said mammalian cell is selected from the group comprising CHO and COS, said fungal cell is a yeast cell such as *Saccharomyces cerevisiae*, and said insect cell is an insect Sf9 cell.

Further, the invention provides a method of producing a binding protein as disclosed herein that comprises culturing any one of the host cells disclosed herein in a culture medium under conditions and for a time suitable to produce said binding protein. Another embodiment provides a binding protein of the invention produced according to the method disclosed herein. In another embodiment, the invention provides a binding protein produced according to the method disclosed above.

The invention also provides a pharmaceutical composition comprising a binding protein, e.g. an antibody, as disclosed herein and a pharmaceutically acceptable carrier.

One embodiment of the invention provides a composition for the release of the binding protein described herein wherein the composition comprises a formulation which in turn comprises a crystallized binding protein, e.g. a crystallized antibody, as disclosed above, and an ingredient; and at least one polymeric carrier. In one aspect the polymeric carrier is a polymer selected from one or more of the group consisting of: poly(acrylic acid), poly(cyano-acrylates), poly (amino acids), poly(anhydrides), poly(depsipeptides), poly (esters), poly(lactic acid), poly(lactic-co-glycolic acid) or PLGA, poly(β-hydroxybutyrate), poly(caprolactone), poly (dioxanone); poly(ethylene glycol); poly((hydroxypropyl) methacrylamide), poly((organo)phosphazene), poly(ortho esters), poly(vinyl alcohol), poly(vinylpyrrolidone), maleic anhydride-alkyl vinyl ether copolymers, pluronic polyols, albumin, alginate, cellulose and cellulose derivatives, collagen, fibrin, gelatin, hyaluronic acid, oligosaccharides, glycaminoglycans, sulfated polysaccharides, blends and copolymers thereof. In another aspect the ingredient is selected from the group consisting of: albumin, sucrose, trehalose, lactitol, gelatin, hydroxypropyl-β-cyclodextrin, methoxypolyethylene glycol and polyethylene glycol.

The present invention also relates to a method of inhibiting (i.e. reducing) the activity of Aβ(20-42) globulomer (or any other targeted Aβ form) comprising contacting said targeted Aβ form with binding protein(s) of the invention such that the activity of said targeted Aβ form is inhibited (i.e. reduced). In a particular embodiment, said activity is inhibited in vitro. This method may comprise adding the binding protein of the invention to a sample, e.g. a sample derived from a subject (e.g., whole blood, cerebrospinal fluid, serum, tissue, etc.) or a cell culture which contains or is suspected to contain a targeted Aβ form, in order to inhibit (i.e. reduce) the activity of the Aβ form in the sample. Alternatively, the activity of said targeted Aβ form may be inhibited (i.e. reduced) in a subject in vivo. Thus, the present invention further relates to the binding protein described herein for use in inhibiting (i.e. reducing) the activity of a targeted Aβ form in a subject comprising contacting said Aβ form with binding protein(s) of the invention such that the activity of the Aβ form is inhibited (i.e. reduced).

In a related aspect, the invention provides a method for inhibiting (i.e. reducing) the activity of a targeted Aβ form in a subject suffering from a disease or disorder in which the activity of said Aβ form is detrimental. In one embodiment, said method comprises administering to the subject at least one of the binding proteins disclosed herein such that the activity of a targeted Aβ form in the subject is inhibited (i.e. reduced). Thus, the invention provides the Aβ binding proteins described herein for use in inhibiting (i.e. reducing) a targeted Aβ form in a subject suffering from a disease or disorder as described herein, wherein at least one of the binding proteins disclosed herein is administered to the subject such that the activity of said Aβ form in the subject is inhibited (i.e. reduced).

In a related aspect, the invention provides a method for treating (e.g., curing, suppressing, ameliorating, delaying or preventing the onset of, or preventing recurrence or relapse of) or preventing a disease or disorder selected from the group consisting of Alpha1-antitrypsin-deficiency, C1-inhibitor deficiency angioedema, Antithrombin deficiency thromboembolic disease, Kuru, Creutzfeld-Jacob disease/scrapie, Bovine spongiform encephalopathy, Gerstmann-Straussler-Scheinker disease, Fatal familial insomnia, Huntington's disease, Spinocerebellar ataxia, Machado-Joseph atrophy, Dentato-rubro-pallidoluysian atrophy, Frontotemporal dementia, Sickle cell anemia, Unstable hemoglobin inclusion-body hemolysis, Drug-induced inclusion body hemolysis, Parkinson's disease, Systemic AL amyloidosis, Nodular AL amyloidosis, Systemic AA amyloidosis, Prostatic amyloidosis, Hemodialysis amyloidosis, Hereditary (Icelandic) cerebral angiopathy, Huntington's disease, Familial visceral amyloidosis, Familial visceral polyneuropathy, Familial visceral amyloidosis, Senile systemic amyloidosis, Familial amyloid neurophathy, Familial cardiac amyloidosis, Alzheimer's disease, Down syndrome, Medullary carcinoma thyroid and Type 2 diabetes mellitus (T2DM). In a particular embodiment, said disease or disorder is an amyloidosis such as Alzheimer's disease or Down syndrome. In one embodiment, said method comprising the step of administering any one of the Aβ binding proteins disclosed herein such that treatment is achieved. In another embodiment, the invention provides a method of treating a subject suffering from a disease or disorder disclosed herein comprising the step of administering any one of the Aβ binding proteins disclosed herein, concurrent with or after the administration of one or more additional therapeutic agent(s). Thus, the invention provides the Aβ binding proteins disclosed herein for use in treating a subject suffering from a disease or disorder disclosed herein comprising the step of administering any one of the binding proteins disclosed herein, concurrent with or after the administration of one or more additional therapeutic agent(s). For instance, the additional therapeutic agent is selected from the group of therapeutic agents listed herein.

The binding proteins disclosed herein and the pharmaceutical compositions comprising said binding proteins are administered to a subject by at least one mode selected from parenteral, subcutaneous, intramuscular, intravenous, intraarticular, intrabronchial, intraabdominal, intracapsular, intracartilaginous, intracavitary, intracelial, intracerebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, and transdermal.

In another embodiment, the present invention provides a method for detecting a targeted Aβ form in a sample comprising (i) contacting said sample with binding protein(s) of the invention and (ii) detecting formation of a complex between said binding protein(s) and elements of said sample, wherein formation or increased formation of the complex in the sample relative to a control sample indicates the presence of said Aβ form in the sample. The sample may be a biological sample obtained from a subject which is suspected of having a disease or disorder as disclosed herein (e.g., whole blood, cerebrospinal fluid, serum, tissue, etc.) or a cell culture which contains or is suspected to contain said Aβ form. The control sample does not contain said Aβ form or is obtained from a patient not having a disease as described above. The presence of a complex between said binding protein(s) and elements of a sample obtained from a patient suspected of having Alzheimer's disease indicates a diagnosis of this disease in said patient.

In an alternative embodiment, the detection of the targeted Aβ form may be performed in vivo, e.g. by in vivo imaging in a subject. For this purpose, the binding protein(s) of the invention may be administered to a subject or a control subject under conditions that allow binding of said protein(s) to the targeted Aβ form and detecting formation of a complex between said binding protein(s) and said Aβ form, wherein formation or increased formation of the complex in the subject relative to the control subject indicates the presence of said Aβ form in the subject. The subject may be a subject which is known or suspected to suffer from a disorder or disease in which activity of a targeted Aβ form is detrimental.

BRIEF DESCRIPTION OF THE FIGURES

FIG. 1 illustrates amino acid sequences (SEQ ID NO:1) of the variable light chain of humanized 4D10 antibodies comprising Jκ2 and Vκ A17/2-30 framework regions. All CDR regions are underlined.

FIG. 2 illustrates amino acid sequences (SEQ ID NO:2) of the variable heavy chain of humanized 4D10 antibodies comprising human JH6 (hJH6) and VH3_53 framework regions. All CDR regions are underlined.

FIG. 3 illustrates amino acid sequences (SEQ ID NO:3) of the variable heavy chain of humanized 4D10 antibodies comprising human JH6 and VH4_59 framework regions. All CDR regions are underlined.

FIG. 4 illustrates the amino acid sequence (SEQ ID NO:4) of the variable heavy chain of humanized 4D10 antibodies comprising human JH6 (hJH6) and VH3_53 framework regions. All CDR regions are underlined.

FIG. 5 illustrates the amino acid sequence (SEQ ID NO:5) of the variable heavy chain of humanized 4D10 antibodies comprising human JH6 and VH3_53 framework regions with VH3 consensus change I12V. All CDR regions are underlined.

FIG. 6 illustrates the amino acid sequence (SEQ ID NO:6) of the variable heavy chain of humanized 4D10 antibodies comprising human JH6 and VH3_53 framework regions with VH3 consensus change I12V and framework backmutations A24V, V29L, V48L, S49G, F67L, R71K, N76S and L78V. All CDR regions are underlined.

FIG. 7 illustrates the amino acid sequence (SEQ ID NO:7) of the variable heavy chain of humanized 4D10 antibodies comprising human JH6 and VH3_53 framework regions with framework backmutations V29L and R71K. All CDR regions are underlined.

FIG. 8 illustrates the amino acid sequence (SEQ ID NO:8) of the variable heavy chain of humanized 4D10 antibodies comprising human JH6 and VH4_59 framework regions. All CDR regions are underlined.

FIG. 9 illustrates the amino acid sequence (SEQ ID NO:9) of the variable heavy chain of humanized 4D10 antibodies comprising human JH6 and VH4_59 framework regions with a Q1E change to prevent N-terminal pyroglutamate formation. All CDR regions are underlined.

FIG. 10 illustrates the amino acid sequence (SEQ ID NO:10) of the variable heavy chain of humanized 4D10 antibodies comprising human JH6 and VH4_59 framework regions with a Q1E change to prevent N-terminal pyroglutamate formation, and framework backmutations G27F, I29L, I37V, I48L, V67L, V71K, N76S and F78V. All CDR regions are underlined.

FIG. 11 illustrates the amino acid sequence (SEQ ID NO:11) of the variable heavy chain of humanized 4D10 antibodies comprising human JH6 and VH4_59 framework regions with a Q1E change to prevent N-terminal pyroglutamate formation, and framework backmutations G27F, I29L and V71K. All CDR regions are underlined.

FIG. 12 illustrate the amino acid sequence (SEQ ID NO:12) of the variable light chain of humanized 4D10 antibodies comprising Jκ2 and Vκ A17/2-30 framework regions. All CDR regions are underlined.

FIG. 13 illustrates the amino acid sequence (SEQ ID NO:13) of the variable light chain of humanized 4D10 antibodies comprising Jκ2 and Vκ A17/2-30 framework regions with Vκ2 consensus changes S7T, L15P, Q37L, R39K and R45Q. All CDR regions are underlined.

FIG. 14 illustrates the amino acid sequence (SEQ ID NO:14) of the variable light chain of humanized 4D10 antibodies comprising Jκ2 and Vκ A17/2-30 framework regions with Vκ2 consensus changes S7T, L15P, Q37L, R39K and R45Q, and framework backmutation F36L. All CDR regions are underlined.

FIG. 15 illustrates the amino acid sequence (SEQ ID NO:15) of the variable light chain of humanized 4D10 antibodies comprising Jκ2 and Vκ A17/2-30 framework regions with Vκ2 consensus changes S7T and Q37L. All CDR regions are underlined.

FIG. 16 illustrates the amino acid sequence (SEQ ID NO:16) of the variable light chain of humanized 4D10 antibodies comprising Jκ2 and Vκ A17/2-30 framework regions with Vκ2 consensus changes S7T, Q37L and R39K. All CDR regions are underlined.

FIG. 17 illustrates an amino acid sequence alignment of the variable heavy chains of murine monoclonal antibody 4D10 (m4D19) and humanized 4D10 antibodies (4D10hum) comprising human JH6 (hJH6) and VH3_53 framework regions. All CDR regions are printed in bold letters. X on position 12 is I or V, X on position 24 is A or V, X on position 29 is V or L, X on position 48 is V or L, X on position 49 is S or G, X on position 67 is F or L, X on position 71 is R or K, X on position 76 is N or S, and X on position 78 is L or V.

FIG. 18 illustrates an amino acid sequence alignment of the variable heavy chains of murine monoclonal antibody 4D10 (m4D19) and humanized 4D10 antibodies (4D10hum) comprising human JH6 and VH4_59 framework regions. All CDR regions are printed in bold letters. X on position 1 is Q or E, X on position 27 is G or F, X on position 29 is I or L, X on position 37 is I or V, X on position 48 is I or L, X on position 67 is V or L, X on position 71 is V or K, X on position 76 is N or S, and X on position 78 is F or V.

FIG. 19 illustrates an amino acid sequence alignment of the variable light chains of murine monoclonal antibody 4D10 (m4D19) and humanized 4D10 antibodies (4D10hum) comprising Jκ2 and Vκ A17/2-30 framework regions. All CDR regions are printed in bold letters. X on position 7 is S or T, X on position 15 is L or P, X on position 41 is F or L, X on position 42 is Q or L, X on position 44 is R or K, and X on position 50 is R or Q.

FIGS. 20A and B show platelet factor 4 (PF-4) cross-reaction of humanized monoclonal antibodies 4D10hum#1 and 4D10hum#2, human/mouse chimeric antibody h1G5 (positive control) and human polyclonal antibody hIgG1 (negative control) in (A) Cynomolgus monkey plasma and (B) human plasma, as determined by sandwich-ELISA. Binding of PF-4 to the immobilized antibodies was detected.

FIGS. 21A and B show platelet factor 4 (PF-4) cross-reaction of humanized monoclonal antibodies 4D10hum#1 and 4D10hum#2, human/mouse chimeric antibody h1G5 (positive control) and human polyclonal antibody hIgG1 (negative control) in (A) Cynomolgus monkey plasma and (B) human plasma, as determined by aligned sandwich-ELISA. The antibodies were captured on the plate by immobilized anti-mouse IgG. Binding of PF-4 to the captured antibodies was detected.

FIGS. 22A and B show platelet factor 4 (PF-4) cross-reaction of murine monoclonal antibodies m4D10 and m1G5, anti human PF-4 antibody (positive control) and IgG2a (negative control) in (A) Cynomolgus monkey plasma and (B) human plasma, as determined by sandwich-ELISA. Binding of PF-4 to the immobilized antibodies was detected.

FIGS. 23A and B show platelet factor 4 (PF-4) cross-reaction of murine monoclonal antibodies m4D10 and m1G5, anti human PF-4 antibody (positive control) and IgG2a (negative control) in (A) Cynomolgus monkey plasma and (B) human plasma, as determined by aligned sandwich-ELISA. The antibodies were captured on the plate by immobilized anti-mouse IgG. Binding of PF-4 to the captured antibodies was detected.

FIG. 24 illustrates the amino acid sequence (SEQ ID NO:46) of the heavy chain of a humanized 4D10 antibody comprising human JH6 and VH3_53 framework regions with VH3 consensus change I12V and framework backmutations A24V, V29L, V48L, S49G, F67L, R71K, N76S and L78V; and an Ig gamma-1 constant region. All CDR regions are underlined.

FIG. 25 illustrates the amino acid sequence (SEQ ID NO:47) of the heavy chain of a humanized 4D10 antibody comprising human JH6 and VH4_59 framework regions with a Q1E change to prevent N-terminal pyroglutamate formation, and framework backmutations G27F, I29L, I37V, I48L, V67L, V71K, N76S and F78V; and an Ig gamma-1 constant region. All CDR regions are underlined.

FIG. 26 illustrates the amino acid sequence (SEQ ID NO:48) of the light chain of a humanized 4D10 antibody comprising Jκ2 and Vκ A17/2-30 framework regions with Vκ2 consensus changes S7T, L15P, Q37L, R39K and R45Q, and framework backmutation F36L; and an Ig kappa constant region. All CDR regions are underlined.

DETAILED DESCRIPTION OF THE INVENTION

Unless otherwise defined herein, scientific and technical terms used in connection with the present invention shall have the meanings that are commonly understood by those of ordinary skill in the art. The meaning and scope of the terms should be clear, however, in the event of any latent ambiguity, definitions provided herein take precedent over any dictionary or extrinsic definition. Further, unless otherwise required by context, singular terms shall include pluralities and plural terms shall include the singular. In this application, the use of "or" means "and/or" unless stated otherwise. Furthermore, the use of the term "including", as well as other forms, such as "includes" and "included", is not limiting. Also, terms such as "element" or "component" encompass both elements and components comprising one unit and elements and components that comprise more than one subunit unless specifically stated otherwise.

Generally, nomenclatures used in connection with, and techniques of, cell and tissue culture, molecular biology, immunology, microbiology, genetics, protein and nucleic acid chemistry, and hybridization described herein are those well known and commonly used in the art. The methods and techniques of the present invention are generally performed according to conventional methods well known in the art and as described in various general and more specific references that are cited and discussed throughout the present specification unless otherwise indicated. Enzymatic reactions and purification techniques are performed according to manufacturer's specifications, as commonly accomplished in the art or as described herein. The nomenclatures used in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

The present invention pertains to Aβ binding proteins, particularly anti-Aβ antibodies or an Aβ binding portion thereof, particularly those binding to Aβ(20-42) globulomer. These Aβ binding proteins are capable of discriminating not only other forms of Aβ peptides, particularly monomers and fibrils, but also untruncated forms of Aβ globulomers. Thus, the present invention relates to an Aβ binding protein having a binding affinity to an Aβ(20-42) globulomer that is greater than the binding affinity of this Aβ binding protein to an Aβ(1-42) globulomer.

The term "Aβ(X-Y)" as used herein refers to the amino acid sequence from amino acid position X to amino acid position Y of the human amyloid beta (Aβ) protein including both X and Y, in particular to the amino acid sequence from amino acid position X to amino acid position Y of the amino acid sequence DAEFRHDSGY EVHHQKLVFF AEDVGSNKGA IIGLMVGGVV IAT (SEQ ID NO:29) (corresponding to amino acid positions 1 to 43) or any of its naturally occurring variants, in particular those with at least one mutation selected from the group consisting of A2T, H6R, D7N, A21G ("Flemish"), E22G ("Arctic"), E22Q ("Dutch"), E22K ("Italian"), D23N ("Iowa"), A42T and A42V wherein the numbers are relative to the start of the Aβ peptide, including both position X and position Y or a sequence with up to three additional amino acid substitutions none of which may prevent globulomer formation. According to one aspect, there are no additional amino acid substitutions in the portion from amino acid 12 or X, whichever number is higher, to amino acid 42 or Y, whichever number is lower. According to another aspect, there are no additional amino acid substitutions in the portion from amino acid 20 or X, whichever number is higher, to amino acid 42 or Y, whichever number is lower. According to another aspect, there are no additional amino acid substitutions in the portion from amino acid 20 or X, whichever number is higher, to amino acid 40 or Y, whichever number is lower. An "additional" amino acid substitution herein is any deviation from the canonical sequence that is not found in nature.

More specifically, the term "Aβ(1-42)" as used herein refers to the amino acid sequence from amino acid position 1 to amino acid position 42 of the human Aβ protein including both 1 and 42, in particular to the amino acid sequence DAEFRHDSGY EVHHQKLVFF AEDVGSNKGA IIGLMVGGVV IA (SEQ ID NO:30) or any of its naturally occurring variants, in particular those with at least one mutation selected from the group consisting of A2T, H6R, D7N, A21G ("Flemish"), E22G ("Arctic"), E22Q ("Dutch"), E22K ("Italian"), D23N ("Iowa"), A42T and A42V wherein the numbers are relative to the start of the Aβ peptide, including both 1 and 42 or a sequence with up to three additional amino acid substitutions none of which may prevent globulomer formation. According to one aspect, there are no additional amino acid substitutions in the portion from amino acid 20 to amino acid 42. Likewise, the term "Aβ(1-40)" as used herein refers to the amino acid sequence from amino acid position 1 to amino acid position 40 of the human Aβ protein including both 1 and 40, in particular to the amino acid sequence DAEFRHDSGY EVHHQKLVFF AEDVGSNKGA IIGLMVGGVV (SEQ ID NO:31) or any of its naturally occurring variants, in particular those with at least one mutation selected from the group consisting of A2T, H6R, D7N, A21G ("Flemish"), E22G ("Arctic"), E22Q ("Dutch"), E22K ("Italian"), and D23N ("Iowa") wherein the numbers are relative to the start of the Aβ peptide, including both 1 and 40 or a sequence with up to three additional amino acid substitutions none of which may prevent globulomer formation. According to one aspect, there are no additional amino acid substitutions in the portion from amino acid 20 to amino acid 40.

More specifically, the term "Aβ(12-42)" as used herein refers to the amino acid sequence from amino acid position 12 to amino acid position 42 of the human Aβ protein including both 12 and 42, in particular to the amino acid sequence VHHQKLVFF AEDVGSNKGA IIGLMVGGVV IA (SEQ ID NO:32) or any of its naturally occurring variants, in particular those with at least one mutation selected from the group consisting of A21G ("Flemish"), E22G ("Arctic"), E22Q ("Dutch"), E22K ("Italian"), D23N ("Iowa"), A42T and A42V wherein the numbers are relative to the start of the Aβ peptide, including both 12 and 42 or a sequence with up to three additional amino acid substitutions none of which may prevent globulomer formation. According to one aspect, there are no additional amino acid substitutions in the portion from amino acid 20 to amino acid 42. Likewise, the term "Aβ(20-42)" as used herein refers to the amino acid sequence from amino acid position 20 to amino acid position 42 of the human amyloid β protein including both 20 and 42, in particular to the amino acid sequence F AEDVGSNKGA IIGLMVGGVV IA (SEQ ID NO:33) or any of its naturally occurring variants, in particular those with at least one mutation selected from the group consisting of A21G ("Flemish"), E22G ("Arctic"), E22Q ("Dutch"), E22K ("Italian"), D23N ("Iowa"), A42T and A42V wherein the numbers are relative to the start of the Aβ peptide, including both 20 and 42 or a sequence with up to three additional amino acid substitutions none of which may prevent globulomer formation. According to one aspect, there are any additional amino acid substitutions.

The term "Aβ(X-Y) globulomer" (Aβ(X-Y) globular oligomer) as used herein refers to a soluble, globular, non-covalent association of Aβ(X-Y) peptides as defined above, possessing homogeneity and distinct physical characteristics. According to one aspect, Aβ(X-Y) globulomers are stable, non-fibrillar, oligomeric assemblies of Aβ(X-Y) peptides which are obtainable by incubation with anionic detergents. In contrast to monomer and fibrils, these globulomers are characterized by defined assembly numbers of subunits (e.g. early assembly forms with 4-6 subunits, "oligomers A"; and late assembly forms with 12-14 subunits, "oligomers B"; as described in WO2004/067561). The globulomers have a 3-dimensional globular type structure ("molten globule", see Barghorn et al., J Neurochem 95: 834-847, 2005). They may be further characterized by one or more of the following features:

cleavability of N-terminal amino acids X-23 with promiscuous proteases (such as thermolysin or endoproteinase GluC) yielding truncated forms of globulomers;

non-accessibility of C-terminal amino acids 24-Y with promiscuous proteases and antibodies;

truncated forms of these globulomers maintain the 3-dimensional core structure of said globulomers with a better accessibility of the core epitope Aβ(20-Y) in its globulomer conformation.

According to the invention and in particular for the purpose of assessing the binding affinities of the Aβ binding proteins of the present invention, the term "Aβ(X-Y) globulomer" here refers in particular to a product which is obtainable by a process as described in WO2004/067561, which is incorporated herein by reference. Said process comprises unfolding a natural, recombinant or synthetic Aβ(X-Y) peptide or a derivative thereof; exposing the at least partially unfolded Aβ(X-Y) peptide or derivative thereof to a detergent, reducing the detergent action and continuing incubation.

For the purpose of unfolding the peptide, hydrogen bond-breaking agents such as, for example, hexafluoroisopropanol (HFIP) may be allowed to act on the protein. Times of action of a few minutes, for example about 10 to 60 minutes, are sufficient when the temperature of action is from about 20 to 50° C. and in particular about 35 to 40° C. Subsequent dissolution of the residue evaporated to dryness, e.g. in concentrated form, in suitable organic solvents miscible with aqueous buffers, such as, for example, dimethyl sulfoxide (DMSO), results in a suspension of the at least partially unfolded peptide or derivative thereof, which can be used subsequently. If required, the stock suspension may be stored at low temperature, for example at about 20° C., for an interim period. Alternatively, the peptide or the derivative thereof may be taken up in slightly acidic, e.g. aqueous, solution, for example, an about 10 mM aqueous HCl solution. After an incubation time of usually a few minutes, insoluble components are removed by centrifugation. A few minutes at 10,000 g is expedient. These method steps can be carried out at room temperature, i.e. a temperature in the range from 20 to 30° C. The supernatant obtained after centrifugation contains the Aβ(X-Y) peptide or the derivative thereof and may be stored at low temperature, for example at about −20° C., for an interim period. The following exposure to a detergent relates to the oligomerization of the peptide or the derivative thereof to give an intermediate type of oligomers (in WO 2004/067561 referred to as oligomers A). For this purpose, a detergent is allowed to act on the at least partially unfolded peptide or derivative thereof until sufficient intermediate oligomer has been produced. Preference is given to using ionic detergents, in particular anionic detergents.

According to a particular embodiment, a detergent of the formula (I):

is used, in which the radical R is unbranched or branched alkyl having from 6 to 20, e.g. 10 to 14, carbon atoms or unbranched or branched alkenyl having from 6 to 20, e.g. 10 to 14, carbon atoms, the radical X is an acidic group or salt thereof, with X being selected, e.g., from among —COO-M⁺, —SO₃-M⁺, and especially —OSO₃-M⁺ and M⁺ is a hydrogen cation or an inorganic or organic cation selected from, e.g., alkali metal and alkaline earth metal cations and ammonium cations. Advantageous are detergents of the formula (I), in which R is unbranched alkyl of which alk-1-yl radicals must be mentioned in particular. For example, sodium dodecyl sulfate (SDS), lauric acid, the sodium salt of the detergent lauroylsarcosin (also known as sarkosyl NL-30 or Gardol®) and oleic acid can be used advantageously. The time of detergent action in particular depends on whether (and if yes, to what extent) the peptide or the derivative thereof subjected to oligomerization has unfolded. If, according to the unfolding step, the peptide or derivative thereof has been treated beforehand with a hydrogen bond-breaking agent, i.e. in particular with hexafluoroisopropanol, times of action in the range of a few hours, advantageously from about 1 to 20 and in particular from about 2 to 10 hours, are sufficient when the temperature of action is about 20 to 50° C. and in particular about 35 to 40° C. If a less unfolded or an essentially not unfolded peptide or derivative thereof is the starting point, correspondingly longer times of action are expedient. If the peptide or the derivative thereof has been pretreated, for example, according to the procedure indicated above as an alternative to the HFIP treatment or said peptide or derivative thereof is directly subjected to oligomerization, times of action in the range from about 5 to 30 hours and in particular from about 10 to 20 hours are sufficient when the temperature of action is about 20 to 50° C. and in particular about 35 to 40° C. After incubation, insoluble components are advantageously removed by centrifugation. A few minutes at 10,000 g is expedient. The detergent concentration to be chosen depends on the detergent used. If SDS is used, a concentration in the range from 0.01 to 1% by weight, e.g. from 0.05 to 0.5% by weight, for example of about 0.2% by weight, proves expedient. If lauric acid or oleic acid are used, somewhat higher concentrations are expedient, for example in a range from 0.05 to 2% by weight, e.g. from 0.1 to 0.5% by weight, for example of about 0.5% by weight. The detergent action should take place at a salt concentration approximately in the physiological range. Thus, in particular NaCl concentrations in the range from 50 to 500 mM, e.g. from 100 to 200 mM or at about 140 mM are expedient. The subsequent reduction of the detergent action and continuation of incubation relates to a further oligomerization to give the Aβ(X-Y) globulomer of the invention (in WO2004/067561 referred to as oligomers B). Since the composition obtained from the preceding step regularly contains detergent and a salt concentration in the physiological range it is then expedient to reduce detergent action and also the salt concentration. This may be carried out by reducing the concentration of detergent and salt, for example, by diluting, expediently with water or a buffer of lower salt concentration, for example Tris-HCl, pH 7.3. Dilution factors in the range from about 2 to 10, advantageously in the range from about 3 to 8 and in particular of about 4, have proved suitable. The reduction in detergent action may also be achieved by adding substances which can neutralize said detergent action. Examples of these include substances capable of complexing the detergents, like substances capable of stabilizing cells in the course of purification and extraction measures, for example particular EO/PO block copolymers, in particular the block copolymer under the trade name Pluronic® F 68. Alkoxylated and, in particular, ethoxylated alkyl phenols such as the ethoxylated t-octylphenols of the Triton® X series, in particular Triton® X100, 3-(3-cholamidopropyldimethylammonio)-1-propanesulfonate (CHAPS®) or alkoxylated and, in particular, ethoxylated sorbitan fatty esters such as those of the Tween® series, in particular Tween® 20, in concentration ranges around or above the particular critical micelle concentration, may be equally used. Subsequently, the solution is incubated until sufficient Aβ(X-Y) globulomer of the invention has been produced. Times of action in the range of several hours, e.g. in the range from about 10 to 30 hours or in the range from about 15 to 25 hours, are sufficient when the temperature of action is about 20 to 50° C. and in particular about 35 to 40° C. The solution may then be concentrated and possible residues may be removed by centrifugation. Here too, a few minutes at 10,000 g proves expedient. The supernatant obtained after centrifugation contains an Aβ(X-Y) globulomer of the invention. An Aβ(X-Y) globulomer of the invention can be finally recovered in a manner known per se, e.g. by ultrafiltration, dialysis, precipitation or centrifugation. For example, electrophoretic separation of the Aβ(X-Y) globulomers under denaturing conditions, e.g. by SDS-PAGE, may produce a double band (e.g. with an apparent molecular weight of 38/48 kDa for Aβ(1-42)), and upon glutardialdehyde treatment of the globulomers before separation these two bands can merge into one. Size exclusion chromatography of the globulomers may result in a single peak (e.g. corresponding to a molecular weight of approximately 100 kDa for Aβ(1-42) globulomer or of approximately 60 kDa for glutardialdehyde cross-linked Aβ(1-42) globulomer), respectively. Starting out from Aβ(1-42) peptide, Aβ(12-42) peptide, and Aβ(20-42) peptide said processes are in particular suitable for obtaining Aβ(1-42) globulomers, Aβ(12-42) globulomers, and Aβ(20-42) globulomers.

In a particular embodiment of the invention, Aβ(X-Y) globulomers wherein X is selected from the group consisting of the numbers 2 . . . 24 and Y is as defined above, are those which are obtainable by truncating Aβ(1-Y) globulomers into shorter forms wherein X is selected from the group consisting of the numbers 2 . . . 24, for example with X being 20 or 12, and Y is as defined above, which can be achieved by treatment with appropriate proteases. For instance, an Aβ(20-42) globulomer can be obtained by subjecting an Aβ(1-42) globulomer to thermolysin proteolysis, and an Aβ(12-42) globulomer can be obtained by subjecting an Aβ(1-42) globulomer to endoproteinase GluC proteolysis. When the desired degree of proteolysis is reached, the protease is inactivated in a generally known manner. The resulting globulomers may then be isolated following the procedures already described herein and, if required, processed further by further work-up and purification steps. A detailed description of said processes is disclosed in WO2004/067561, which is incorporated herein by reference.

For the purposes of the present invention, an Aβ(1-42) globulomer is, in particular, the Aβ(1-42) globulomer as described in Example 1a below; an Aβ(20-42) globulomer is in particular the Aβ(20-42) globulomer as described in Example 1b below, and an Aβ(12-42) globulomer is in particular the Aβ(12-42) globulomer as described in Example 1c below. According to one aspect of the invention, the globulomer shows affinity to neuronal cells and/or exhibits neuromodulating effects.

According to another aspect of the invention, the globulomer consists of 11 to 16, e.g. of 12 to 14 Aβ(X-Y) peptides. According to another aspect of the invention, the term "Aβ(X-Y) globulomer" herein refers to a globulomer consisting essentially of Aβ(X-Y) subunits, where for example on average at least 11 of 12 subunits are of the Aβ(X-Y) type, or less than 10% of the globulomers comprise any non-Aβ(X-Y) peptides, or the content of non-Aβ(X-Y) peptides is below the detection threshold. More specifically, the term "Aβ(1-42) globulomer" herein refers to a globulomer consisting essentially of Aβ(1-42) units as defined above; the term "Aβ(12-42) globulomer" herein refers to a globulomer consisting essentially of Aβ(12-42) units as defined above; and the term "Aβ(20-42) globulomer" herein refers to a globulomer consisting essentially of Aβ(20-42) units as defined above.

The term "cross-linked Aβ(X-Y) globulomer" herein refers to a molecule obtainable from an Aβ(X-Y) globulomer as described above by cross-linking, e.g. by chemically cross-linking, aldehyde cross-linking, glutardialdehyde cross-linking, of the constituent units of the globulomer. In another aspect of the invention, a cross-linked globulomer is essentially a globulomer in which the units are at least partially joined by covalent bonds, rather than being held together by non-covalent interactions only. For the purposes of the present invention, a cross-linked Aβ(1-42) globulomer is in particular the cross-linked Aβ(1-42) oligomer as described in Example 1d below.

The term "Aβ(X-Y) globulomer derivative" herein refers in particular to a globulomer that is labelled by being covalently linked to a group that facilitates detection, for example a fluorophore, e.g. fluorescein isothiocyanate, phycoerythrin, *Aequorea victoria* fluorescent protein, Dictyosoma fluorescent protein or any combination or fluorescence-active derivative thereof; a chromophore; a chemoluminophore, e.g. luciferase, in particular *Photinus pyralis* luciferase, *Vibrio fischeri* luciferase, or any combination or chemoluminescence-active derivative thereof; an enzymatically active group, e.g. peroxidase, e.g. horseradish peroxidase, or any enzymatically active derivative thereof; an electron-dense group, e.g. a heavy metal containing group, e.g. a gold containing group; a hapten, e.g. a phenol derived hapten; a strongly antigenic structure, e.g. peptide sequence predicted to be antigenic, e.g. predicted to be antigenic by the algorithm of Kolaskar and Tongaonkar; an aptamer for another molecule; a chelating group, e.g. hexahistidinyl; a natural or nature-derived protein structure mediating further specific protein-protein interactions, e.g. a member of the fos/jun pair; a magnetic group, e.g. a ferromagnetic group; or a radioactive group, e.g. a group comprising 1H, 14C, 32P, 35S or 125I or any combination thereof; or to a globulomer flagged by being covalently or by non-covalent high-affinity interaction linked to a group that facilitates inactivation, sequestration, degradation and/or precipitation, for example flagged with a group that promotes in vivo degradation such as ubiquitin, this flagged oligomer being, e.g., assembled in vivo; or to a globulomer modified by any combination of the above. Such labelling and flagging groups and methods for attaching them to proteins are known in the art. Labelling and/or flagging may be performed before, during or after globulomerisation. In another aspect of the invention, a globulomer derivative is a molecule obtainable from a globulomer by a labelling and/or flagging reaction. Correspondingly, term "Aβ(X-Y) monomer derivative" here refers in particular to an Aβ monomer that is labelled or flagged as described for the globulomer.

In a further aspect of the invention, the binding proteins described herein bind to the Aβ(20-42) globulomer with a high affinity, for instance with a dissociation constant ($K_D$) of at most about $10^{-6}$ M; at most about $10^{-7}$ M; at most about $10^{-8}$ M; at most about $10^{-9}$ M; at most about $10^{-10}$ M; at most about $10^{-11}$ M; at most about $10^{-12}$ M; and at most $10^{-13}$ M. In one aspect the on-rate constant ($k_{on}$) of the binding protein described herein to Aβ(20-42) globulomer is selected from the group consisting of: at least about $10^2$ $M^{-1}s^{-1}$; at least about $10^3$ $M^{-1}s^{-1}$; at least about $10^4$ $M^{-1}s^{-1}$; at least about $10^5$ $M^{-1}s^{-1}$; and at least about $10^6 M^{-1}s^{-1}$; as measured by surface plasmon resonance. In another aspect, the binding proteins have an off-rate constant ($k_{off}$) to Aβ(20-42) globulomer selected from the group consisting of: at most about $10^{-3} s^{-1}$; at most about $10^{-4} s^{-1}$; at most about $10^{-5} s^{-1}$; and at most about $10^{-6} s^{-1}$, as measured by surface plasmon resonance. In a particular aspect of the invention, the binding proteins described herein bind to the Aβ(20-42) globulomer with a dissociation constant from $1\times10^{-9}$ to $1\times10^{-10}$ M. In a further particular aspect of the invention, the on-rate constant ($k_{on}$) of the binding protein described herein to Aβ(20-42) globulomer is from $1\times10^5$ to $1\times10^6 M^{-1}s^{-1}$. In a further particular aspect of the invention, the binding proteins described herein have an off-rate constant ($k_{off}$) to Aβ(20-42) globulomer from $8\times10^{-5}$ to $8\times10^{-4} s^{-1}$.

In another aspect of the invention, the binding affinity of the binding proteins described herein to Aβ(20-42) globulomer is greater than to an Aβ(1-42) globulomer.

The term "greater affinity" herein refers to a degree of interaction where the equilibrium between unbound Aβ binding protein and unbound Aβ globulomer on the one hand and Aβ binding protein-globulomer complex on the other is further in favour of the Aβ binding protein-globulomer complex. Likewise, the term "smaller affinity" here refers to a degree of interaction where the equilibrium between unbound Aβ binding protein and unbound Aβ globulomer on the one hand and Aβ binding protein-globulomer complex on the other is further in favour of the unbound Aβ binding protein and unbound Aβ globulomer. The term "greater affinity" is synonymous with the term "higher affinity" and term "smaller affinity" is synonymous with the term "lower affinity".

In a related aspect of the invention, the binding affinity of the binding proteins described herein to Aβ(20-42) globulomer is at least 2 times (e.g., at least 3 or at least 5 times), at least 10 times (e.g., at least 20 times, at least 30 times or at least 50 times), at least 100 times (e.g., at least 200 times, at least 300 times or at least 500 times), and at least 1,000 times (e.g., at least 2,000 times, at least 3,000 times or at least 5000 times), at least 10,000 times (e.g., at least 20,000 times, at least 30,000 times or at least 50,000 times), or at least 100,000 times greater than the binding affinity of the binding protein to the Aβ(1-42) globulomer.

In still a further aspect of the invention, the binding proteins described herein bind to the Aβ(12-42) globulomer with a relatively high affinity, for instance with a dissociation constant ($K_D$) of at most about $10^{-6}$ M; at most about $10^{-7}$ M; at most about $10^{-8}$ M; at most about $10^{-9}$ M; at most about $10^{-10}$ M; at most about $10^{-11}$ M; at most about $10^{-12}$ M; and at most $10^{-13}$ M. In one aspect the on-rate constant ($k_{on}$) of the binding protein described herein to Aβ(12-42) globulomer is selected from the group consisting of: at least about $10^2 M^{-1}s^{-1}$; at least about $10^3 M^{-1}s^{-1}$; at least about $10^4 M^{-1}s^{-1}$; at least about $10^5 M^{-1}s^{-1}$; and at least about $10^6 M^{-1}s^{-1}$; as measured by surface plasmon resonance. In another aspect, the binding proteins have an off-rate constant ($k_{off}$) to Aβ(12-42) globulomer selected from the group consisting of: at most about $10^{-3} s^{-1}$; at most about $10^{-4} s^{-1}$; at most about $10^{-5} s^{-1}$; and at most about $10^{-6} s^{-1}$, as measured by surface plasmon resonance.

In a related aspect of the invention, the binding affinity of the binding proteins described herein to Aβ(20-42) globulomer is about 1.1 to 3 times greater than the binding affinity of the binding proteins to Aβ(12-42) globulomer.

According to one aspect, the Aβ binding proteins of the present invention bind to at least one Aβ globulomer, as defined above, and have a comparatively smaller affinity for at least one non-globulomer form of Aβ. Aβ binding proteins of the present invention with a comparatively smaller affinity for at least one non-globulomer form of Aβ than for at least one Aβ globulomer include Aβ binding protein with a binding affinity to the Aβ(20-42) globulomer that is greater than to an Aβ(1-42) monomer. According to an alternative or additional aspect of the invention, the binding affinity of the Aβ binding protein to the Aβ(20-42) globulomer is greater than to an Aβ(1-40) monomer. In particular, the affinity of the Aβ binding proteins to the Aβ(20-42) globulomer is greater than its affinity to both the Aβ(1-40) and the Aβ(1-42) monomer.

The term "Aβ(X-Y) monomer" as used herein refers to the isolated form of the Aβ(X-Y) peptide, in particular to a form of the Aβ(X-Y) peptide which is not engaged in essentially non-covalent interactions with other Aβ peptides. Practically, the Aβ(X-Y) monomer is usually provided in the form of an aqueous solution. In a particular embodiment of the invention, the aqueous monomer solution contains 0.05% to 0.2%, e.g. about 0.1% $NH_4OH$. In another particular embodiment of the invention, the aqueous monomer solution contains 0.05% to 0.2%, e.g. about 0.1% NaOH. When used (for instance for determining the binding affinities of the Aβ binding proteins of the present invention), it may be expedient to dilute said solution in an appropriate manner. Further, it is usually expedient to use said solution within 2 hours, in particular within 1 hour, and especially within 30 minutes after its preparation.

More specifically, the term "Aβ(1-40) monomer" here refers to an Aβ(1-40) monomer preparation as described herein, and the term "Aβ(1-42) monomer" here refers to an Aβ(1-42) preparation as described herein.

Expediently, the Aβ binding proteins of the present invention bind to one or both monomers with low affinity, for example with a $K_D$ of $1\times10^{-8}$ M or smaller affinity, e.g. with a $K_D$ of $3\times10^{-8}$ M or smaller affinity, with a $K_D$ of $1\times10^{-7}$ M or smaller affinity, e.g. with a $K_D$ of $3\times10^{-7}$ M or smaller affinity, or with a $K_D$ of $1\times10^{-6}$ M or smaller affinity, e.g. with a $K_D$ of $3\times10^{-5}$ M or smaller affinity, or with a $K_D$ of $1\times10^{-5}$ M or smaller affinity.

According to one aspect of the invention, the binding affinity of the Aβ binding proteins of the present invention to the Aβ(20-42) globulomer is at least 2 times, e.g. at least 3 times or at least 5 times, at least 10 times, e.g. at least 20 times, at least 30 times or at least 50 times, at least 100 times, e.g. at least 200 times, at least 300 times or at least 500 times, at least 1,000 times, e.g. at least 2,000 times, at least 3,000 times or at least 5,000 times, at least 10,000 times, e.g. at least 20,000 times, at least 30,000 or at least 50,000 times, or at least 100,000 times greater than the binding affinity of the Aβ binding proteins to one or both monomers.

Aβ binding proteins of the present invention having a comparatively smaller affinity for at least one non-globulomer form of Aβ than for at least one Aβ globulomer further include Aβ binding proteins having a binding affinity to the Aβ(20-42) globulomer that is greater than to Aβ(1-42) fibrils. According to an alternative or additional aspect of the invention, the binding affinity of the Aβ binding proteins to the Aβ(20-42) globulomer is greater than to Aβ(1-40) fibrils. According to one particular embodiment, the invention relates to Aβ binding proteins having a binding affinity to the Aβ(20-42) globulomer which is greater than their binding affinity to both Aβ(1-40) and Aβ(1-42) fibrils.

The term "fibril" herein refers to a molecular structure that comprises assemblies of non-covalently associated, individual Aβ(X-Y) peptides, which show fibrillary structure in the electron microscope, which bind Congo red and then exhibit birefringence under polarized light and whose X-ray diffraction pattern is a cross-β structure. In another aspect of the invention, a fibril is a molecular structure obtainable by a process that comprises the self-induced polymeric aggregation of a suitable Aβ peptide in the absence of detergents, e.g. in 0.1 M HCl, leading to the formation of aggregates of more than 24 or more than 100 units. This process is well known in the art. Expediently, Aβ(X-Y) fibrils are used in the form of an aqueous solution. In a particular embodiment of the invention, the aqueous fibril solution is made by dissolving the Aβ peptide in 0.1% NH$_4$OH, diluting it 1:4 with 20 mM NaH$_2$PO$_4$, 140 mM NaCl, pH 7.4, followed by readjusting the pH to 7.4, incubating the solution at 37° C. for 20 h, followed by centrifugation at 10,000 g for 10 min and resuspension in 20 mM NaH$_2$PO$_4$, 140 mM NaCl, pH 7.4. The term "Aβ(X-Y) fibril" herein also refers to a fibril comprising Aβ(X-Y) subunits where, e.g., on average, at least 90% of the subunits are of the Aβ(X-Y) type, at least 98% of the subunits are of the Aβ(X-Y) type or the content of non-Aβ(X-Y) peptides is below the detection threshold. More specifically, the term "Aβ(1-42) fibril" herein refers to a Aβ(1-42) fibril preparation as described in Example 3.

Expediently, the Aβ binding proteins of the present invention bind to one or both fibrils with low affinity, for example with a $K_D$ of $1\times10^{-8}$ M or smaller affinity, e.g. with a $K_D$ of $3\times10^{-8}$ M or smaller affinity, with a $K_D$ of $1\times10^{-7}$ M or smaller affinity, e.g. with a $K_D$ of $3\times10^{-7}$ M or smaller affinity, or with a $K_D$ of $1\times10^{-6}$ M or smaller affinity, e.g. with a $K_D$ of $3\times10^{-5}$ M or smaller affinity, or with a $K_D$ of $1\times10^{-5}$ M or smaller affinity.

According to one aspect of the invention, the binding affinity of the Aβ binding proteins of the present invention to the Aβ(20-42) globulomer is at least 2 times, e.g. at least 3 times or at least 5 times, at least 10 times, e.g. at least 20 times, at least 30 times or at least 50 times, at least 100 times, e.g. at least 200 times, at least 300 times or at least 500 times, at least 1,000 times, e.g. at least 2,000 times, at least 3,000 times or at least 5,000 times, at least 10,000 times, e.g. at least 20,000 times, at least 30,000 or at least 50,000 times, or at least 100,000 times greater than the binding affinity of the Aβ binding proteins to one or both fibrils.

According to a particular embodiment, the present invention relates to Aβ binding proteins having a comparatively smaller affinity for both the monomeric and fibrillary forms of Aβ than for at least one Aβ globulomer, in particular Aβ(20-42) globulomer. These Aβ binding proteins sometimes are referred to as globulomer-specific Aβ binding proteins.

The binding proteins of the present invention, e.g. humanized antibody 4D10 (4D10hum), include globulomer-specific binding proteins recognizing predominantly Aβ(20-42) globulomer forms and not standard preparations of Aβ(1-40) monomers, Aβ(1-42) monomers, Aβ-fibrils or sAPP (i.e. soluble Aβ precursor) in contrast to, for example, competitor antibodies such as m266 and 3D6. Such specificity for globulomers is important because specifically targeting the globulomer form of Aβ with humanized 4D10 will: 1) avoid targeting insoluble amyloid deposits, binding to which may account for inflammatory side effects observed during immunizations with insoluble Aβ; 2) spare Aβ monomer and APP that are reported to have precognitive physiological functions (Plan et al., J Neurosci 23: 5531-5535, 2003; and 3) increase the bioavailability of the antibody, as it would not be shaded or inaccessible through extensive binding to insoluble deposits.

PF-4 is a small, 70-amino acid cytokine that belongs to the CXC chemokine family and is also known as chemokine (C-X-C motif) ligand 4 (CXCL4). PF-4 is released from alpha-granules of activated platelets during platelet aggregation, and promotes blood coagulation by moderating the effects of heparin-like molecules. Due to these functions, it is predicted to be involved in wound repair and inflammation (Eismann et al., Blood 76(2): 336-44, 1990). PF-4 is usually found in a complex with proteoglycan and can form complexes with the anticoagulant heparin which is in use as pharmacological treatment of thrombosis. It has a well described pathological function in heparin-induced thrombocytopenia (HIT), an idiosyncratic autoimmune reaction to the administration of the anticoagulant heparin (Warkentin, N. Engl. J. Med. 356(9): 891-3, 2007), wherein the heparin: PF4 complex is the antigen. PF4 autoantibodies have also been found in patients with thrombosis and features resembling HIT but no prior administration of heparin (Warkentin et al., Am. J. Med. 121(7): 632-6, 2008). Heparin-induced thrombocytopenia is characterized by the development of thrombocytopenia (a low platelet count), and in addition HIT predisposes to thrombosis. In view of these functions and involvement of PF-4 in pathological processes it can be concluded that the administration of binding proteins (e.g. antibodies) showing binding (e.g. cross-reactivity) to the PF-4 present in a subject may affect said PF-4 functions and thus result in adverse (side) effects. The degree and nature of such adverse effects may vary depending on parameters such as location and size of the epitope on PF-4, binding strength and nature of the respective binding protein.

According to one aspect of the invention, the binding proteins of the present invention do show no or low binding to platelet factor 4 (PF-4). Said cross-reaction to PF-4 may be evaluated by using standardized in vitro immunoassays such as ELISA, dot blot or BIAcore analyses.

According to a particular embodiment, the cross-reaction to PF-4 of a binding protein defined herein refers to ratio of values for said binding protein and a reference anti-PF-4 antibody obtained by (i) performing a sandwich-ELISA with a ~1:3 dilution series of human or cynomolgus plasma from about 1:3.16 to about 1:3160 (final plasma dilution) (e.g. as described in examples 3.1 and 3.2), (ii) plotting detected signal (y-axis) against log-transformed plasma dilutions (x-axis), and (iii) determining the area under the curve (AUC, or total peak area) from these non-curve fitted data in the measured range (final plasma dilutions from about 1:3.16 to about 1:3160). According to a particular embodiment of the invention, determining the cross-reaction to PF-4 by sandwich-ELISA comprises the following: a certain amount of the binding protein under investigation or the reference anti-PF-4 antibody or, expediently, an appropriate dilution thereof, for instance 100 μl of a 10 μg/ml binding protein or antibody solution in 100 mM sodium hydrogen carbonate, pH 9.6, is used for coating wells of a protein adsorbing microtiter plate; the plate is then washed, blocked, and washed again; then contacted with a ~1:3 dilution series of cynomolgus or human plasma, e.g. human plasma spiked with human PF-4, from about 1:3.16 to about 1:3160 (final plasma dilution) followed by detection of the PF-4 bound to each well, e.g. by means of a primary PF-4 specific antibody, an enzyme-conjugated secondary antibody and a colorimetric reaction.

A "reference anti-PF-4 antibody", as used herein, is an antibody, in particular a monoclonal antibody, that is specifically reactive with PF-4, in particular human (HPF4). Such an antibody is obtainable by providing an antigen comprising human PF-4, for instance human PF-4 having amino acid sequence EAEEDGDLQCLCVKTTSQVRPRHITSLE-VIKAGPHCPTAQUATLKNGRKICLDLQAP LYKKI-IKKLLES (SEQ ID NO:70), exposing an antibody repertoire to said antigen and selecting from said antigen repertoire an antibody which binds specifically to human PF-4. The antibody may optionally be affinity purified using the immunogen (human PF-4). Such reference anti-PF4 antibodies are commercially available, for example, monoclonal anti-HPF4 antibody, Abcam cat. no.: ab49735.

According to another particular embodiment, the cross-reaction to PF-4 of a binding protein defined herein refers to ratio of AUC values for said binding protein and a reference anti-PF-4 antibody obtained by (i) performing an aligned sandwich-ELISA with human or cynomolgus plasma and ~1:3 dilution series of binding protein and reference anti-PF-4 antibody from about 10 ng/ml to about 10000 ng/ml (final concentration) (e.g. as described in examples 3.3 and 3.4), (ii) plotting detected signal (y-axis) against log-transformed concentrations of binding protein or reference anti-PF-4 antibody (x-axis), and (iii) determining the area under the curve (AUC, or total peak area) from these non-curve fitted data in the measured range (concentrations of binding protein or reference antibody from about 10 ng/ml to about 10000 ng/ml). According to a particular embodiment of the invention, determining the cross-reaction to PF-4 by aligned sandwich-ELISA comprises the following: the wells of a protein adsorbing microtiter plate are coated with a certain amount of an aligning antibody suitable to capture the binding protein under investigation and the reference anti-PF-4 antibody, for example 100 µl/well of 50 µg/ml Fc specific anti-mouse IgG, Sigma cat. no.: M3534, in 100 mM sodium hydrogen carbonate, pH 9.6); the plate is then washed, blocked, and washed again; then contacted with a ~1:3 dilution series of the binding protein under investigation or of the reference anti-PF-4 antibody from about 10 ng/ml to about 10000 ng/ml (final concentration); after another washing step the plate is contacted with, e.g. 1:10 diluted, human or cynomolgus plasma, e.g. human plasma spiked with human PF-4, followed by detection of the PF-4 bound to the plate, e.g. by means of a primary PF-4 specific antibody, an enzyme-conjugated secondary antibody and a colorimetric reaction.

According to one aspect of the invention, the cross-reaction of Aβ binding protein of the present invention to PF-4, when analyzed via sandwich-ELISA with cynomolgus plasma as described herein, is smaller than the corresponding cross-reaction of a reference anti-PF-4 antibody, for example at least 2 times, at least 5 times, at least 10 times, at least 20 times, or at least 30 times smaller; and/or, when analyzed via sandwich-ELISA with human plasma as described herein, is smaller than the corresponding cross-reaction of a reference anti-PF-4 antibody, for example or at least 2 times, at least 5 times, at least 10 times, at least 15 times, or at least 20 times smaller.

According to another aspect of the invention, the cross-reaction of Aβ binding protein of the present invention to PF-4, when analyzed via aligned sandwich-ELISA with cynomolgus plasma as described herein, is smaller than the corresponding cross-reaction of a reference anti-PF-4 antibody, for example at least 2 times, at least 5 times, at least 10 times, at least 20 times, at least 30 times, at least 50 times, at least 80 times or at least 115 times smaller; and/or, when analyzed via aligned sandwich-ELISA with human plasma as described herein, is smaller than the corresponding cross-reaction of a reference anti-PF-4 antibody, for example at least 2 times, at least 5 times, at least 10 times, at least 15 times, at least 20 times, at least 25 times smaller.

According to another aspect of the invention, the cross-reaction of Aβ binding protein of the present invention to PF-4, when analyzed via sandwich-ELISA and aligned sandwich-ELISA with cynomolgus plasma as described herein, is smaller than the corresponding cross-reaction of a reference anti-PF-4 antibody, for example at least 2 times, at least 5 times, at least 10 times, at least 20 times, or at least 30 times smaller.

According to another aspect of the invention, the cross-reaction of Aβ binding protein of the present invention to PF-4, when analyzed via sandwich-ELISA and aligned sandwich-ELISA with human plasma as described herein, is smaller than the corresponding cross-reaction of a reference anti-PF-4 antibody, for example at least 2 times, at least 5 times, at least 10 times, at least 20 times, or at least 30 times smaller.

According to another aspect of the invention, the cross-reaction of Aβ binding protein of the present invention to PF-4, when analyzed via sandwich-ELISA and aligned sandwich-ELISA with cynomolgus and human plasma as described herein, is smaller than the corresponding cross-reaction of a reference anti-PF-4 antibody, for example at least 2 times, at least 5 times, at least 10 times, at least 20 times, or at least 30 times smaller.

The term "polypeptide" as used herein, refers to any polymeric chain of amino acids. The terms "peptide" and "protein" are used interchangeably with the term polypeptide and also refer to a polymeric chain of amino acids. The term "polypeptide" encompasses native or artificial proteins, protein fragments and polypeptide analogs of a protein sequence. A polypeptide may be monomeric or polymeric.

The term "isolated protein" or "isolated polypeptide" is a protein or polypeptide that by virtue of its origin or source of derivation is not associated with naturally associated components that accompany it in its native state; is substantially free of other proteins from the same species; is expressed by a cell from a different species; or does not occur in nature. Thus, a polypeptide that is chemically synthesized or synthesized in a cellular system different from the cell from which it naturally originates will be "isolated" from its naturally associated components. A protein may also be rendered substantially free of naturally associated components by isolation, using protein purification techniques well known in the art.

The term "recovering", as used herein, refers to the process of rendering a chemical species such as a polypeptide substantially free of naturally associated components by isolation, e.g., using protein purification techniques well known in the art.

The terms "specific binding" or "specifically binding", as used herein, in reference to the interaction of an antibody, a protein, or a peptide with a second chemical species, mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

The term "antibody", as used herein, broadly refers to any immunoglobulin (Ig) molecule comprised of four polypeptide chains, two heavy (H) chains and two light (L) chains, or any functional fragment, mutant, variant, or derivation thereof, which retains the essential epitope binding features of an Ig molecule. Such functional fragment, mutant, variant, or derivative antibody formats are known in the art. Nonlimiting embodiments of which are discussed below. A "full-length antibody", as used herein, refers to an Ig molecule comprising four polypeptide chains, two heavy chains and two light chains. The chains are usually linked to one another via disulfide bonds. Each heavy chain is comprised of a heavy chain variable region (also referred to herein as "variable heavy chain", or abbreviated herein as HCVR or VH) and a heavy chain constant region. The heavy chain constant region is comprised of three domains, CH1, CH2 and CH3. Each light chain is comprised of a light chain variable region (also referred to herein as "variable light chain", or abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. Immunoglobulin molecules can be of any type (e.g., IgG, IgE, IgM, IgD, IgA and IgY), class (e.g., IgG1, IgG2, IgG3, IgG4, IgA1 and IgA2) or subclass.

The terms "antigen-binding portion" of an antibody (or simply "antibody portion"), "antigen-binding moiety" of an antibody (or simply "antibody moiety"), as used herein, refers to one or more fragments of an antibody that retain the ability to specifically bind to an antigen (e.g., Aβ(20-42) globulomer), i.e. are functional fragments of an antibody. It has been shown that the antigen-binding function of an antibody can be performed by one or more fragments of a full-length antibody. Such antibody embodiments may also be bispecific, dual specific, or multi-specific, specifically binding to two or more different antigens. Examples of binding fragments encompassed within the term "antigen-binding portion" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., Nature 341: 544-546, 1989; Winter et al., WO 90/05144 A1, herein incorporated by reference), which comprises a single variable domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al., Science 242: 423-426, 1988; and Huston et al., Proc. Natl. Acad. Sci. USA 85: 5879-5883, 1988). Such single chain antibodies are also encompassed within the term "antigen-binding portion" of an antibody. Other forms of single chain antibodies, such as diabodies, are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger et al., Proc. Natl. Acad. Sci. USA 90: 6444-6448, 1993; Poljak et al., Structure 2: 1121-1123, 1994). Such antibody binding portions are known in the art (Kontermann and Dubel eds., Antibody Engineering, Springer-Verlag. New York. 790 pp., 2001, ISBN 3-540-41354-5).

The term "antibody", as used herein, also comprises antibody constructs. The term "antibody construct" as used herein refers to a polypeptide comprising one or more of the antigen-binding portions of the invention linked to a linker polypeptide or an immunoglobulin constant domain. Linker polypeptides comprise two or more amino acid residues joined by peptide bonds and are used to link one or more antigen binding portions. Such linker polypeptides are well known in the art (see e.g., Holliger et al., Proc. Natl. Acad. Sci. USA 90: 6444-6448, 1993; Poljak et al., Structure 2: 1121-1123, 1994).

An immunoglobulin constant domain refers to a heavy or light chain constant domain. Human IgG heavy chain and light chain constant domain amino acid sequences are known in the art and represented in Table 1.

TABLE 1

SEQUENCE OF HUMAN IgG HEAVY CHAIN CONSTANT DOMAIN AND LIGHT CHAIN CONSTANT DOMAIN

| Protein | Sequence Identifier | Sequence 123456789012345678901234567890 |
|---|---|---|
| Ig gamma-1 constant region | SEQ ID NO: 25 | ASTKGPSVFFLAPSSKSTSGGTAALGCLVK DYFPEPVTVSWNSGALTSGVHTFPAVLQSS GLYSLSSVVTVPSSSLGTQTYICNVNHKPS NTKVDKKVEPKSCDKTHTCPPCPAPELLGG PSVFLFPPKPKDTLMISRTPEVTCVVVDVS HEDPEVKFNWYVDGVEVHNAKTKPREEQYN STYRVVSVLTVLHQDWLNGKEYKCKVSNKA LPAPIEKTISKAKGQPREPQVYTLPPSREE MTKNQVSLTCLVKGFYPSDIAVEWESNGQP ENNYKTTPPVLDSDGSFFLYSKLTVDKSRW QQGNVFSCSVMHEALHNHYTQKSLSLSPGK |
| Ig gamma-1 constant region mutant | SEQ ID NO: 26 | ASTKGPSVFPLAPSSKSTSGGTAALGCLVK DYFPEPVTVSWNSGALTSGVHTFPAVLQSS GLYSLSSVVTVPSSSLGTQTYICNVNHKPS NTKVDKKVEPKSCDKTHTCPPCPAPELLGG PSVFLFPPKPKDTLMISRTPEVTCVVVDVS HEDPEVKFNWYVDGVEVHNAKTKPREEQYN STYRVVSVLTVLHQDWLNGKEYKCKVSNKA LPAPIEKTISKAKGQPREPQVYTLPPSREE MTKNQVSLTCLVKGFYPSDIAVEWESNGQP ENNYKTTPPVLDSDGSFFLYSKLTVDKSRW QQGNVFSCSVMHEALHNHYTQKSLSLSPGK |
| Ig Kappa constant region | SEQ ID NO: 27 | TVAAPSVFIFPPSDEQLKSGTASVVCLLNN FYPREAKVQWKVDNALQSGNSQESVTEQDS KDSTYSLSSTLTLSKADYEKHKVYACEVTH QGLSSPVTKSFNRGEC |
| Ig Lambda constant region | SEQ ID NO: 28 | QPKAAPSVTLFPPSSEELQANKATLVCLIS DFYPGAVTVAWKADSSPVKAGVETTTPSKQ SNNKYAASSYLSLTPEQWKSHRSYSCQVTH EGSTVEKTVAPTECS |

Still further, a binding protein of the present invention (e.g. an antibody) may be part of a larger immunoadhesion molecule, formed by covalent or noncovalent association of the binding protein of the invention with one or more other proteins or peptides. Examples of such immunoadhesion molecules include the use of the streptavidin core region to make a tetrameric scFv molecule (Kipriyanov et al., Human Antibodies and Hybridomas 6: 93-101, 1995) and use of a cysteine residue, a marker peptide and a C-terminal polyhistidine tag to make bivalent and biotinylated scFv molecules (Kipriyanov et al., Mol. Immunol. 31: 1047-1058, 1994). Antibody portions, such as Fab and F(ab')$_2$ fragments, can be prepared from whole antibodies using conventional techniques, such as papain or pepsin digestion, respectively, of whole antibodies. Moreover, antibodies, antibody portions and immunoadhesion molecules can be obtained using standard recombinant DNA techniques, as described herein.

An "isolated antibody", as used herein, is intended to refer to an antibody that is substantially free of other antibodies having different antigenic specificities. An isolated antibody that specifically binds Aβ(20-42) globulomer may, however, have cross-reactivity to other antigens, such as Aβ globulomers, e.g. Aβ(12-42) globulomer or other Aβ forms. Moreover, an isolated antibody may be substantially free of other cellular material and/or chemicals and/or any other targeted Aβ form.

The term "human antibody", as used herein, is intended to include antibodies having variable and constant regions derived from human germline immunoglobulin sequences. The human antibodies of the invention may include amino acid residues not encoded by human germline immunoglobulin sequences (e.g. mutations introduced by random or site-specific mutagenesis in vitro or by somatic mutation in vivo), for example in the CDRs and in particular in CDR3. However, the term "human antibody", as used herein, is not intended to include antibodies in which CDR sequences derived from the germline of another mammalian species, such as a mouse, have been grafted onto human framework sequences.

The term "recombinant human antibody", as used herein, is intended to include all human antibodies that are prepared, expressed, created or isolated by recombinant means, such as antibodies expressed using a recombinant expression vector transfected into a host cell (described further in Section B, below), antibodies isolated from a recombinant, combinatorial human antibody library (Hoogenboom, TIB Tech. 15: 62-70, 1997; Azzazy and Highsmith, Clin. Biochem. 35: 425-445, 2002; Gavilondo J. V., and Larrick J. W. (2002) BioTechniques 29:128-145; Hoogenboom H., and Chames P. (2000) Immunology Today 21:371-378), antibodies isolated from an animal (e.g. a mouse) that is transgenic for human immunoglobulin genes (see e.g. Taylor, L. D., et al. (1992) Nucl. Acids Res. 20:6287-6295; Kellermann S-A., and Green L. L. (2002) Current Opinion in Biotechnology 13:593-597; Little M. et at (2000) Immunology Today 21:364-370) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

The term "chimeric antibody" refers to antibodies which comprise heavy and light chain variable region sequences from one species and constant region sequences from another species, such as antibodies having murine heavy and light chain variable regions linked to human constant regions.

The term "CDR-grafted antibody" refers to antibodies which comprise heavy and light chain variable region sequences from one species but in which the sequences of one or more of the CDR regions of VH and/or VL are replaced with CDR sequences of another species, such as antibodies having murine CDRs (e.g., CDR3) in which one or more of the murine variable heavy and light chain regions has been replaced with human variable heavy and light chain sequences.

The terms "Kabat numbering", "Kabat definitions and "Kabat labeling" are used interchangeably herein. These terms, which are recognized in the art, refer to a system of numbering amino acid residues which are more variable (i.e. hypervariable) than other amino acid residues in the heavy and light chain variable regions of an antibody, or an antigen binding portion thereof (Kabat et al. (1971) Ann. NY Acad, Sci. 190:382-391 and, Kabat, E. A., et al. (1991) Sequences of Proteins of Immunological Interest, Fifth Edition, U.S. Department of Health and Human Services, NIH Publication No. 91-3242). For the heavy chain variable region, the hypervariable region ranges from amino acid positions 31 to 35 for CDR1, amino acid positions 50 to 65 for CDR2, and amino acid positions 95 to 102 for CDR3. For the light chain variable region, the hypervariable region ranges from amino acid positions 24 to 34 for CDR1, amino acid positions 50 to 56 for CDR2, and amino acid positions 89 to 97 for CDR3.

As used herein, the terms "acceptor" and "acceptor antibody" refer to the antibody or nucleic acid sequence providing or encoding at least 80%, at least 85%, at least 90%, at least 95%, at least 98% or 100% of the amino acid sequences of one or more of the framework regions. In some embodiments, the term "acceptor" refers to the antibody amino acid or nucleic acid sequence providing or encoding the constant region(s). In yet another embodiment, the term "acceptor" refers to the antibody amino acid or nucleic acid sequence providing or encoding one or more of the framework regions and the constant region(s). In a specific embodiment, the term "acceptor" refers to a human antibody amino acid or nucleic acid sequence that provides or encodes at least 80%, for example at least 85%, at least 90%, at least 95%, at least 98%, or 100% of the amino acid sequences of one or more of the framework regions. In accordance with this embodiment, an acceptor may contain at least 1, at least 2, at least 3, least 4, at least 5, or at least 10 amino acid residues that does (do) not occur at one or more specific positions of a human antibody. An acceptor framework region and/or acceptor constant region(s) may be, e.g., derived or obtained from a germline antibody gene, a mature antibody gene, a functional antibody (e.g., antibodies well-known in the art, antibodies in development, or antibodies commercially available).

As used herein, the term "CDR" refers to the complementarity determining region within antibody variable sequences. There are three CDRs in each of the variable regions of the heavy chain and the light chain, which are designated CDR1, CDR2 and CDR3, for each of the variable regions. The term "CDR set" as used herein refers to a group of three CDRs that occur in a single variable region capable of binding the antigen. The exact boundaries of these CDRs have been defined differently according to different systems. The system described by Kabat (Kabat et al., Sequences of Proteins of Immunological Interest (National Institutes of Health, Bethesda, Md. (1987) and (1991)) not only provides an unambiguous residue numbering system applicable to any variable region of an antibody, but also provides precise residue boundaries defining the three CDRs. These CDRs may be referred to as Kabat CDRs. Chothia and coworkers (Chothia & Lesk, J. Mol. Biol. 196:901-917 (1987) and Chothia et al., Nature 342:877-883 (1989)) found that certain sub-portions within Kabat CDRs adopt nearly identical peptide backbone conformations, despite having great diversity at the level of amino acid sequence. These sub-portions were designated as L1, L2 and L3 or H1, H2 and H3 where the "L" and the "H" designates the light chain and the heavy chains regions, respectively. These regions may be referred to as Chothia CDRs, which have boundaries that overlap with Kabat CDRs. Other boundaries defining CDRs overlapping with the Kabat CDRs have been described by Padlan (FASEB J. 9:133-139 (1995)) and MacCallum (J Mol Biol 262(5):732-45 (1996)). Still other CDR boundary definitions may not strictly follow one of the above systems, but will nonetheless overlap with the Kabat CDRs, although they may be shortened or lengthened in light of prediction or experimental findings that particular residues or groups of residues or even entire CDRs do not significantly impact antigen binding. The methods used herein may utilize CDRs defined according to any of these systems, particular embodiments use Kabat or Chothia defined CDRs.

As used herein, the term "canonical" residue refers to a residue in a CDR or framework that defines a particular canonical CDR structure as defined by Chothia et al. (J. Mol. Biol. 196:901-907 (1987); Chothia et al., J. Mol. Biol. 227: 799 (1992), both are incorporated herein by reference). According to Chothia et al., critical portions of the CDRs of many antibodies have nearly identical peptide backbone confirmations despite great diversity at the level of amino acid sequence. Each canonical structure specifies primarily a set of peptide backbone torsion angles for a contiguous segment of amino acid residues forming a loop.

As used herein, the terms "donor" and "donor antibody" refer to an antibody providing one or more CDRs. In one embodiment, the donor antibody is an antibody from a species different from the antibody from which the framework regions are obtained or derived. In the context of a humanized antibody, the term "donor antibody" refers to a non-human antibody providing one or more CDRs.

As used herein, the term "framework" or "framework sequence" refers to the remaining sequences of a variable region minus the CDRs. Because the exact definition of a CDR sequence can be determined by different systems, the meaning of a framework sequence is subject to correspondingly different interpretations. The six CDRs (CDR-L1, -L2, and -L3 of light chain and CDR-H1, -H2, and -H3 of heavy chain) also divide the framework regions on the light chain and the heavy chain into four sub-regions (FR1, FR2, FR3 and FR4) on each chain, in which CDR1 is positioned between FR1 and FR2, CDR2 between FR2 and FR3, and CDR3 between FR3 and FR4. Without specifying the particular sub-regions as FR1, FR2, FR3 or FR4, a framework region, as referred by others, represents the combined FR's within the variable region of a single, naturally occurring immunoglobulin chain. As used herein, a FR represents one of the four sub-regions, and FRs represents two or more of the four sub-regions constituting a framework region.

Human heavy chain and light chain acceptor sequences are known in the art. In one embodiment of the invention, the human heavy chain and light chain acceptor sequences are selected from the sequences described in Table 2 and Table 3. In another embodiment, the human heavy chain and light chain acceptor sequences are selected from sequences which are at least 90%, at least 91%, at least 92%, at least 93%, at least 94%, at least 95%, at least 96%, at least 97%, at least 98%, or at least 99% identical to the sequences described in Table 2 and Table 3.

TABLE 2

HEAVY CHAIN ACCEPTOR SEQUENCES

| SEQ ID NO | Protein region | Sequence 1234567890123456789012345678 90 |
|---|---|---|
| 34 | VH3_53/JH6 FR1 | EVQLVESGGGLIQPGGSLRLSCAASGFTVS |
| 35 | VH3_53/JH6 FR2 | WVRQAPGKGLEWVS |
| 36 | VH3_53/JH6 FR3 | RFTISRDNSKNTLYLQMNSLRAEDTAVYYC AR |
| 37 | VH3_53/JH6 FR4 | WGQGTTVTVSS |
| 38 | VH4_59/JH6 FR1 | QVQLQESGPGLVKPSETLSLTCTVSGGSIS |
| 39 | VH4_59/JH6 FR2 | WIRQPPGKGLEWIG |

TABLE 2-continued

HEAVY CHAIN ACCEPTOR SEQUENCES

| SEQ ID NO | Protein region | Sequence 1234567890123456789012345678 90 |
|---|---|---|
| 40 | VH4_59/JH6 FR3 | RVTISVDTSKNQFSLKLSSVTAADTAVYYC AR |
| 41 | VH4_59/JH6 FR4 | WGQGTTVTVSS |

TABLE 3

LIGHT CHAIN ACCEPTOR SEQUENCES

| SEQ ID NO | Protein region | Sequence 1234567890123456789012345678 90 |
|---|---|---|
| 42 | A1/2-30/Jκ2 FR1 | DVVMTQSPLSLPVTLGQPASISC |
| 43 | A1/2-30/Jκ2 FR2 | WFQQRPGQSPRRLIY |
| 44 | A1/2-30/Jκ2 FR3 | GVPDRFSGSGSGTDFTLKISRVEAEDVGVY YC |
| 45 | A1/2-30/Jκ2 FR4 | FGQGTKLEIKR |

As used herein, the term "germline antibody gene" or "gene fragment" refers to an immunoglobulin sequence encoded by non-lymphoid cells that have not undergone the maturation process that leads to genetic rearrangement and mutation for expression of a particular immunoglobulin. (See, e.g., Shapiro et al., Crit. Rev. Immunol. 22(3): 183-200 (2002); Marchalonis et al., Adv Exp Med Biol. 484:13-30 (2001)). One of the advantages provided by various embodiments of the present invention stems from the recognition that germline antibody genes are more likely than mature antibody genes to conserve essential amino acid sequence structures characteristic of individuals in the species, hence less likely to be recognized as from a foreign source when used therapeutically in that species.

As used herein, the term "key" residues refer to certain residues within the variable region that have more impact on the binding specificity and/or affinity of an antibody, in particular a humanized antibody. A key residue includes, but is not limited to, one or more of the following: a residue that is adjacent to a CDR, a potential glycosylation site (can be either N- or O-glycosylation site), a rare residue, a residue capable of interacting with the antigen, a residue capable of interacting with a CDR, a canonical residue, a contact residue between heavy chain variable region and light chain variable region, a residue within the Vernier zone, and a residue in the region that overlaps between the Chothia definition of a variable heavy chain CDR1 and the Kabat definition of the first heavy chain framework.

As used herein, the term "humanized antibody" is an antibody or a variant, derivative, analog or portion thereof which immunospecifically binds to an antigen of interest and which comprises a framework (FR) region having substantially the amino acid sequence of a human antibody and a complementary determining region (CDR) having substantially the amino acid sequence of a non-human antibody. As used herein, the term "substantially" in the context of a CDR refers to a CDR having an amino acid sequence at least 90%, at least 95%, at least 98% or at least 99% identical to the amino acid sequence of a non-human antibody CDR. A humanized antibody comprises substantially all of at least one, and typically two, variable domains (Fab, Fab', F(ab')$_2$, FabC, Fv) in which all or substantially all of the CDR regions correspond to those of a non-human immunoglobulin (i.e., donor antibody) and all or substantially all of the framework regions are those of a human immunoglobulin consensus sequence. According to one aspect, a humanized antibody also comprises at least a portion of an immunoglobulin constant region (Fc), typically that of a human immunoglobulin. In some embodiments, a humanized antibody contains both the light chain as well as at least the variable domain of a heavy chain. The antibody also may include the CH1, hinge, CH2, CH3, and CH4 regions of the heavy chain. In some embodiments, a humanized antibody only contains a humanized light chain. In some embodiments, a humanized antibody only contains a humanized heavy chain. In specific embodiments, a humanized antibody only contains a humanized variable domain of a light chain and/or of a heavy chain.

The humanized antibody can be selected from any class of immunoglobulins, including IgM, IgG, IgD, IgA and IgE, and any isotype, including without limitation IgG1, IgG2, IgG3 and IgG4. The humanized antibody may comprise sequences from more than one class or isotype, and particular constant domains may be selected to optimize desired effector functions using techniques well-known in the art.

The framework and CDR regions of a humanized antibody need not correspond precisely to the parental sequences, e.g., the donor antibody CDR or the consensus framework may be mutagenized by substitution, insertion and/or deletion of at least one amino acid residue so that the CDR or framework residue at that site does not correspond to either the donor antibody or the consensus framework. In one embodiment, such mutations, however, will not be extensive. Usually, at least 90%, at least 95%, at least 98%, or at least 99% of the humanized antibody residues will correspond to those of the parental FR and CDR sequences. As used herein, the term "consensus framework" refers to the framework region in the consensus immunoglobulin sequence. As used herein, the term "consensus immunoglobulin sequence" refers to the sequence formed from the most frequently occurring amino acids (or nucleotides) in a family of related immunoglobulin sequences (See e.g., Winnaker, From Genes to Clones (Verlagsgesellschaft, Weinheim, Germany 1987)). In a family of immunoglobulins, each position in the consensus sequence is occupied by the amino acid occurring most frequently at that position in the family. If two amino acids occur equally frequently, either can be included in the consensus sequence.

As used herein, "Vernier" zone refers to a subset of framework residues that may adjust CDR structure and fine-tune the fit to antigen as described by Foote and Winter (1992, J. Mol. Biol. 224:487-499, which is incorporated herein by reference). Vernier zone residues form a layer underlying the CDRs and may impact on the structure of CDRs and the affinity of the antibody.

The term "antibody", as used herein, also comprises multivalent binding proteins. The term "multivalent binding protein" is used in this specification to denote a binding protein comprising two or more antigen binding sites. The multivalent binding protein is engineered to have the three or more antigen binding sites, and is generally not a naturally occurring antibody. The term "multispecific binding protein" refers to a binding protein capable of binding two or more related or unrelated targets. Dual variable domain (DVD) binding proteins as used herein, are binding proteins that comprise two or more antigen binding sites and are tetravalent or multivalent binding proteins. Such DVDs may be monospecific, i.e. capable of binding one antigen or multispecific, i.e. capable of binding two or more antigens. DVD binding proteins comprising two heavy chain DVD polypeptides and two light chain DVD polypeptides are referred to a DVD Ig. Each half of a DVD Ig comprises a heavy chain DVD polypeptide, and a light chain DVD polypeptide, and two antigen binding sites. Each binding site comprises a heavy chain variable domain and a light chain variable domain with a total of 6 CDRs involved in antigen binding per antigen binding site. DVD binding proteins and methods of making DVD binding proteins are disclosed in U.S. patent application Ser. No. 11/507,050 and incorporated herein by reference.

The term "epitope" includes any polypeptide determinant capable of specific binding to an immunoglobulin or T-cell receptor. In certain embodiments, epitope determinants include chemically active surface groupings of molecules such as amino acids, sugar side chains, phosphoryl, or sulfonyl, and, in certain embodiments, may have specific three dimensional structural characteristics, and/or specific charge characteristics. An epitope is a region of an antigen that is bound by a binding protein, in particular by an antibody. In certain embodiments, a binding protein or an antibody is said to specifically bind an antigen when it preferentially recognizes its target antigen in a complex mixture of proteins and/or macromolecules.

The binding affinities of the antibodies of the invention may be evaluated by using standardized in-vitro immunoassays such as ELISA, dot blot or BIAcore analyses (Pharmacia Biosensor AB, Uppsala, Sweden and Piscataway, N.J.). For further descriptions, see Jönsson, U., et al. (1993) Ann. Biol. Clin. 51:19-26; Jönsson, U., et al. (1991) Biotechniques 11:620-627; Johnsson, B., et al. (1995) J. Mol. Recognit. 8:125-131; and Johnsson, B., et al. (1991) Anal. Biochem. 198:268-277.

According to a particular embodiment, the affinities defined herein refer to the values obtained by performing a dot blot and evaluating it by densitometry. According to a particular embodiment of the invention, determining the binding affinity by dot blot comprises the following: a certain amount of the antigen (e.g. the Aβ(X-Y) globulomer, Aβ(X-Y) monomer or Aβ(X-Y) fibrils, as defined above) or, expediently, an appropriate dilution thereof, for instance in 20 mM $NaH_2PO_4$, 140 mM NaCl, pH 7.4, 0.2 mg/ml BSA to an antigen concentration of, for example, 100 pmol/μl, 10 pmol/μl, 1 pmol/μl, 0.1 pmol/μl and 0.01 pmol/μl, is dotted onto a nitrocellulose membrane, the membrane is then blocked with milk to prevent unspecific binding and washed, then contacted with the antibody of interest followed by detection of the latter by means of an enzyme-conjugated secondary antibody and a colorimetric reaction; at defined antibody concentrations, the amount of antibody bound allows affinity determination. Thus the relative affinity of two different antibodies to one target, or of one antibody to two different targets, is here defined as the relation of the respective amounts of target-bound antibody observed with the two antibody-target combinations under otherwise identical dot blot conditions. Unlike a similar approach based on Western blotting, the dot blot approach will determine an antibody's affinity to a given target in the latter's natural conformation; unlike the ELISA approach, the dot blot approach does not suffer from differences in the affinities between different targets and the matrix, thereby allowing for more precise comparisons between different targets.

The term "surface plasmon resonance", as used herein, refers to an optical phenomenon that allows for the analysis of real-time biospecific interactions by detection of alterations in protein concentrations within a biosensor matrix, for example using the BIAcore system (Pharmacia Biosensor AB, Uppsala, Sweden and Piscataway, N.J.). For further descriptions, see Jönsson, U., et al. (1993) Ann. Biol. Clin., 51: 19-26; Jönsson et al., (1991) BioTechniques, 11: 620-627; Johnsson et al., (1995) J. Mol. Recognit., 8: 125-131; and Johnnson et al. (1991) Anal. Biochem., 198: 268-277.

The term "$k_{on}$" (also "Kon", "kon", "$K_{on}$"), as used herein, is intended to refer to the on-rate constant for association of a binding protein (e.g., an antibody) to an antigen to form an association complex, e.g., antibody/antigen complex, as is known in the art. The "$k_{on}$" also is known by the terms "association rate constant", or "ka", as used interchangeably herein. This value indicates the binding rate of a binding protein (e.g., an antibody) to its target antigen or the rate of complex formation between a binding protein (e.g., an antibody) and antigen as is shown by the equation below:

Antibody("Ab")+Antigen("Ag")→Ab-Ag.

The term "$k_{off}$" (also "Koff", "koff", "$K_{off}$"), as used herein, is intended to refer to the off rate constant for dissociation, or "dissociation rate constant", of a binding protein (e.g., an antibody) from an association complex (e.g., an antibody/antigen complex) as is known in the art. This value indicates the dissociation rate of a binding protein (e.g., an antibody) from its target antigen, or separation of the Ab–Ag complex over time into free antibody and antigen as shown by the equation below:

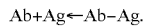

Ab+Ag←Ab–Ag.

The term "$K_D$" (also "$K_d$" or "KD"), as used herein, is intended to refer to the "equilibrium dissociation constant", and refers to the value obtained in a titration measurement at equilibrium, or by dividing the dissociation rate constant ($k_{off}$) by the association rate constant ($k_{on}$). The association rate constant ($k_{on}$), the dissociation rate constant ($k_{off}$), and the equilibrium dissociation constant ($K_D$) are used to represent the binding affinity of a binding protein (e.g., an antibody) to an antigen. Methods for determining association and dissociation rate constants are well known in the art. Using fluorescence-based techniques offers high sensitivity and the ability to examine samples in physiological buffers at equilibrium. Other experimental approaches and instruments such as a BIAcore® (biomolecular interaction analysis) assay can be used (e.g., instrument available from BIAcore International AB, a GE Healthcare company, Uppsala, Sweden). Additionally, a KinExA® (Kinetic Exclusion Assay) assay, available from Sapidyne Instruments (Boise, Id.) can also be used.

The term "labeled binding protein", as used herein, refers to a binding protein with a label incorporated that provides for the identification of the binding protein. Likewise, the term "labeled antibody" as used herein, refers to an antibody with a label incorporated that provides for the identification of the antibody. In one aspect, the label is a detectable marker, e.g., incorporation of a radiolabeled amino acid or attachment to a polypeptide of biotinyl moieties that can be detected by marked avidin (e.g., streptavidin containing a fluorescent marker or enzymatic activity that can be detected by optical or colorimetric methods). Examples of labels for polypeptides include, but are not limited to, the following: radioisotopes or radionuclides (e.g., $^3H$, $^{14}C$, $^{35}S$, $^{90}Y$, $^{99}Tc$, $^{111}In$, $^{125}I$, $^{131}I$, $^{177}Lu$, $^{166}Ho$, or $^{153}Sm$); fluorescent labels (e.g., FITC, rhodamine, lanthanide phosphors), enzymatic labels (e.g., horseradish peroxidase, luciferase, alkaline phosphatase); chemiluminescent markers; biotinyl groups; predetermined polypeptide epitopes recognized by a secondary reporter (e.g., leucine zipper pair sequences, binding sites for secondary antibodies, metal binding domains, epitope tags); and magnetic agents, such as gadolinium chelates.

The term "antibody", as used herein, also comprises antibody conjugates. The term "antibody conjugate" refers to a binding protein, such as an antibody, chemically linked to a second chemical moiety, such as a therapeutic agent.

The term "therapeutic agent" is used herein to denote a chemical compound, a mixture of chemical compounds, a biological macromolecule, or an extract made from biological materials that is a "cognitive enhancing drug," which is a drug that improves impaired human cognitive abilities of the brain (namely, thinking, learning, and memory). Cognitive enhancing drugs work by altering the availability of neurochemicals (e.g., neurotransmitters, enzymes, and hormones), by improving oxygen supply, by stimulating nerve growth, or by inhibiting nerve damage. Examples of cognitive enhancing drugs include a compound that increases the activity of acetylcholine such as, but not limited to, an acetylcholine receptor agonist (e.g., a nicotinic α-7 receptor agonist or allosteric modulator, an α4β2 nicotinic receptor agonist or allosteric modulators), an acetylcholinesterase inhibitor (e.g., donepezil, rivastigmine, and galantamine), a butyrylcholinesterase inhibitor, an N-methyl-D-aspartate (NMDA) receptor antagonist (e.g., memantine), an activity-dependent neuroprotective protein (ADNP) agonist, a serotonin 5-HT1A receptor agonist (e.g., xaliproden), a 5-HT$_4$ receptor agonist, a 5-HT$_6$ receptor antagonist, a serotonin 1A receptor antagonist, a histamine H$_3$ receptor antagonist, a calpain inhibitor, a vascular endothelial growth factor (VEGF) protein or agonist, a trophic growth factor, an anti-apoptotic compound, an AMPA-type glutamate receptor activator, a L-type or N-type calcium channel blocker or modulator, a potassium channel blocker, a hypoxia inducible factor (HIF) activator, a HIF prolyl 4-hydroxylase inhibitor, an anti-inflammatory agent, an inhibitor of amyloid Aβ peptide or amyloid plaque, an inhibitor of tau hyperphosphorylation, a phosphodiesterase 5 inhibitor (e.g., tadalafil, sildenafil), a phosphodiesterase 4 inhibitor, a monoamine oxidase inhibitor, or pharmaceutically acceptable salt thereof. Specific examples of such cognitive enhancing drugs include, but are not limited to, cholinesterase inhibitors such as donepezil (Aricept®), rivastigmine (Exelon®), galanthamine (Reminyl®), N-methyl-D-aspartate antagonists such as memantine (Namenda®).

The terms "crystal" and "crystallized", as used herein, refer to a binding protein (e.g., an antibody, or antigen binding portion thereof), that exists in the form of a crystal. Crystals are one form of the solid state of matter, which is distinct from other forms such as the amorphous solid state or the liquid crystalline state. Crystals are composed of regular, repeating, three-dimensional arrays of atoms, ions, molecules (e.g., proteins such as antibodies), or molecular assemblies (e.g., antigen/antibody complexes). These three-dimensional arrays are arranged according to specific mathematical relationships that are well-understood in the field. The fundamental unit, or building block, that is repeated in a crystal is called the asymmetric unit. Repetition of the asymmetric unit in an arrangement that conforms to a given, well-defined crystallographic symmetry provides the "unit cell" of the crystal. Repetition of the unit cell by regular translations in all three dimensions provides the crystal. See Giege, R. and Ducruix, A. Barrett, Crystallization of Nucleic Acids and Proteins, a Practical Approach, 2$^{nd}$ ed., pp. 20 1-16, Oxford University Press, New York, N.Y., (1999)."

As used herein, the term "neutralizing" refers to neutralization of biological activity of a targeted Aβ form when a binding protein specifically binds said Aβ form. For example, a neutralizing binding protein is a neutralizing antibody whose binding to the Aβ(20-42) amino acid region of the globulomer (and/or any other targeted Aβ form) results in inhibition of a biological activity of the globulomer. According to one aspect of the invention, the neutralizing binding protein binds to the Aβ(20-42) region of the globulomer (and/or any other targeted Aβ form), and reduces a biologically activity of the targeted Aβ form by at least about 20%, 40%, 60%, 80%, 85% or more. Inhibition of a biological activity of the targeted Aβ form by a neutralizing binding protein can be assessed by measuring one or more indicators of the targeted Aβ form biological activity well known in the art, for example interaction (e.g. binding) of the targeted Aβ form to a P/Q type voltage-gated presynaptic calcium channel, inhibition of P/Q type voltage-gated presynaptic calcium channel activity, $Ca^{++}$ flux through P/Q type voltage-gated presynaptic calcium channel, local (e.g. intracellular) $Ca^{++}$ concentration, synaptic activity.

The term "activity" includes activities such as the binding specificity/affinity of a binding protein, in particular of an antibody, for an antigen, for example an Aβ(20-42) globulomer (and any other targeted Aβ form); and/or the neutralizing potency of an antibody, for example an antibody whose binding to a targeted Aβ form inhibits the biological activity of the targeted Aβ form. Said biological activity of the targeted Aβ form comprises interaction of the Aβ form to P/Q type voltage-gated presynaptic calcium channels, which results in inhibition of the activity of said calcium channels.

The subject invention also provides isolated nucleotide sequences encoding the binding proteins of the present invention. The present invention also provides those nucleotide sequences (or fragments thereof) having sequences comprising, corresponding to, identical to, hybridizable to, or complementary to, at least about 70% (e.g., 70% 71%, 72%, 73%, 74%, 75%, 76%, 77%, 78% or 79%), at least about 80% (e.g., 80%, 81%, 82%, 83%, 84%, 85%, 86%, 87%, 88% or 89%), or at least about 90% (e.g., 91%, 92%, 93%, 94%, 95%, 96%, 97%, 98%, 99% or 100%) identity to these encoding nucleotide sequences. (All integers (and portions thereof) between and including 70% and 100% are considered to be within the scope of the present invention with respect to percent identity.) Such sequences may be derived from any source (e.g., either isolated from a natural source, produced via a semi-synthetic route, or synthesized de novo). In particular, such sequences may be isolated or derived from sources other than described in the examples (e.g., bacteria, fungus, algae, mouse or human).

For purposes of the present invention, a "fragment" of a nucleotide sequence is defined as a contiguous sequence of approximately at least 6, e.g. at least about 8, at least about 10 nucleotides, or at least about 15 nucleotides, corresponding to a region of the specified nucleotide sequence.

The term "identity" refers to the relatedness of two sequences on a nucleotide-by-nucleotide basis over a particular comparison window or segment. Thus, identity is defined as the degree of sameness, correspondence or equivalence between the same strands (either sense or antisense) of two DNA segments (or two amino acid sequences). "Percentage of sequence identity" is calculated by comparing two optimally aligned sequences over a particular region, determining the number of positions at which the identical base or amino acid occurs in both sequences in order to yield the number of matched positions, dividing the number of such positions by the total number of positions in the segment being compared and multiplying the result by 100. Optimal alignment of sequences may be conducted by the algorithm of Smith & Waterman, Appl. Math. 2: 482, 1981, by the algorithm of Needleman & Wunsch, J. Mol. Biol. 48: 443, 1970, by the method of Pearson & Lipman, Proc. Natl. Acad. Sci. (USA) 85: 2444, 1988, and by computer programs which implement the relevant algorithms (e.g., Clustal Macaw Pileup (Higgins et al., CABIOS. 5L151-153, 1989), FASTDB (Intelligenetics), BLAST (National Center for Biomedical Information; Altschul et al., Nucleic Acids Research 25: 3389-3402, 1997), PILEUP (Genetics Computer Group, Madison, Wis.) or GAP, BESTFIT, FASTA and TFASTA (Wisconsin Genetics Software Package Release 7.0, Genetics Computer Group, Madison, Wis.)). (See U.S. Pat. No. 5,912,120.)

For purposes of the present invention, "complementarity" is defined as the degree of relatedness between two DNA segments. It is determined by measuring the ability of the sense strand of one DNA segment to hybridize with the antisense strand of the other DNA segment, under appropriate conditions, to form a double helix. A "complement" is defined as a sequence which pairs to a given sequence based upon the canonic base-pairing rules. For example, a sequence A-G-T in one nucleotide strand is "complementary" to T-C-A in the other strand. In the double helix, adenine appears in one strand, thymine appears in the other strand. Similarly, wherever guanine is found in one strand, cytosine is found in the other. The greater the relatedness between the nucleotide sequences of two DNA segments, the greater the ability to form hybrid duplexes between the strands of the two DNA segments.

"Similarity" between two amino acid sequences is defined as the presence of a series of identical as well as conserved amino acid residues in both sequences. The higher the degree of similarity between two amino acid sequences, the higher the correspondence, sameness or equivalence of the two sequences. ("Identity between two amino acid sequences is defined as the presence of a series of exactly alike or invariant amino acid residues in both sequences.) The definitions of "complementarity", "identity" and "similarity" are well known to those of ordinary skill in the art.

"Encoded by" refers to a nucleic acid sequence which codes for a polypeptide sequence, wherein the polypeptide sequence or a portion thereof contains an amino acid sequence of at least 3 amino acids, e.g. at least 8 amino acids, or at least 15 amino acids, from a polypeptide encoded by the nucleic acid sequence.

The term "polynucleotide" as referred to herein, means a polymeric form of two or more nucleotides, either ribonucleotides or deoxynucleotides or a modified form of either type of nucleotide. The term includes single and double stranded forms of DNA, but preferably is double-stranded DNA.

The term "isolated polynucleotide" as used herein shall mean a polynucleotide (e.g., of genomic, cDNA, or synthetic origin, or some combination thereof) that, by virtue of its origin, the "isolated polynucleotide": is not associated with all or a portion of a polynucleotide with which the "isolated polynucleotide" is found in nature; is operably linked to a polynucleotide that it is not linked to in nature; or does not occur in nature as part of a larger sequence.

The term "vector", as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The term "operably linked" refers to a juxtaposition wherein the components described are in a relationship permitting them to function in their intended manner. A control sequence "operably linked" to a coding sequence is ligated in such a way that expression of the coding sequence is achieved under conditions compatible with the control sequences. "Operably linked" sequences include both expression control sequences that are contiguous with the gene of interest and expression control sequences that act in trans or at a distance to control the gene of interest. The term "expression control sequence" as used herein refers to polynucleotide sequences which are necessary to effect the expression and processing of coding sequences to which they are ligated. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion. The nature of such control sequences differs depending upon the host organism; in prokaryotes, such control sequences generally include promoter, ribosomal binding site, and transcription termination sequence; in eukaryotes, generally, such control sequences include promoters and transcription termination sequence. The term "control sequences" is intended to include components whose presence is essential for expression and processing, and can also include additional components whose presence is advantageous, for example, leader sequences and fusion partner sequences.

"Transformation", as defined herein, refers to any process by which exogenous DNA enters a host cell. Transformation may occur under natural or artificial conditions using various methods well known in the art. Transformation may rely on any known method for the insertion of foreign nucleic acid sequences into a prokaryotic or eukaryotic host cell. The method is selected based on the host cell being transformed and may include, but is not limited to, viral infection, electroporation, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

The term "recombinant host cell" (or simply "host cell"), as used herein, is intended to refer to a cell into which exogenous DNA has been introduced. It should be understood that such terms are intended to refer not only to the particular subject cell, but, to the progeny of such a cell. Because certain modifications may occur in succeeding generations due to either mutation or environmental influences, such progeny may not, in fact, be identical to the parent cell, but are still included within the scope of the term "host cell" as used herein. In one aspect, host cells include prokaryotic and eukaryotic cells selected from any of the kingdoms of life. Eukaryotic cells include protist, fungal, plant and animal cells. In another aspect host cells include, but are not limited to, the prokaryotic cell line *E. coli*; mammalian cell lines CHO, HEK 293 and COS; the insect cell line Sf9; and the fungal cell *Saccharomyces cerevisiae*.

Standard techniques may be used for recombinant DNA, oligonucleotide synthesis, and tissue culture and transformation (e.g., electroporation, lipofection). Enzymatic reactions and purification techniques may be performed according to manufacturer's specifications or as commonly accomplished in the art or as described herein. The foregoing techniques and procedures may be generally performed according to conventional methods well known in the art and as described in various general and more specific references that are cited and discussed throughout the present specification. See e.g., Sambrook et al. Molecular Cloning: A Laboratory Manual ($2^{nd}$ ed., Cold Spring Harbor Laboratory Press, Cold Spring Harbor, N.Y. (1989)), which is incorporated herein by reference for any purpose.

"Transgenic organism", as known in the art and as used herein, refers to an organism having cells that contain a transgene, wherein the transgene introduced into the organism (or an ancestor of the organism) expresses a polypeptide not naturally expressed in the organism. A "transgene" is a DNA construct, which is stably and operably integrated into the genome of a cell from which a transgenic organism develops, directing the expression of an encoded gene product in one or more cell types or tissues of the transgenic organism.

The terms "regulate" and "modulate" are used interchangeably, and, as used herein, refer to a change or an alteration in the activity of a molecule of interest (e.g., the biological activity of a targeted Aβ form). Modulation may be an increase or a decrease in the magnitude of a certain activity or function of the molecule of interest. Exemplary activities and functions of a molecule include, but are not limited to, binding characteristics, enzymatic activity, cell receptor activation, and signal transduction.

Correspondingly, the term "modulator," as used herein, is a compound capable of changing or altering an activity or function of a molecule of interest (e.g., the biological activity of a targeted Aβ form). For example, a modulator may cause an increase or decrease in the magnitude of a certain activity or function of a molecule compared to the magnitude of the activity or function observed in the absence of the modulator. In certain embodiments, a modulator is an inhibitor, which decreases the magnitude of at least one activity or function of a molecule.

The term "agonist", as used herein, refers to a modulator that, when contacted with a molecule of interest, causes an increase in the magnitude of a certain activity or function of the molecule compared to the magnitude of the activity or function observed in the absence of the agonist.

The term "antagonist" or "inhibitor", as used herein, refer to a modulator that, when contacted with a molecule of interest causes a decrease in the magnitude of a certain activity or function of the molecule compared to the magnitude of the activity or function observed in the absence of the antagonist. Particular antagonists of interest include those that block or modulate the biological activity of a targeted Aβ form. Antagonists and inhibitors of a targeted Aβ form may include, but are not limited to, the binding proteins of the invention, which bind to Aβ(20-42) globulomer and any other targeted Aβ form. An antagonist or inhibitor of a targeted Aβ form may, for example, reduce the inhibitory effect of said Aβ form on the activity of a P/Q type voltage-gated presynaptic calcium channel.

As used herein, the term "effective amount" refers to the amount of a therapy which is sufficient to reduce or ameliorate the severity and/or duration of a disorder or one or more symptoms thereof, prevent the advancement of a disorder, cause regression of a disorder, prevent the recurrence, development, onset or progression of one or more symptoms associated with a disorder, detect a disorder, or enhance or improve the prophylactic or therapeutic effect(s) of another therapy (e.g., prophylactic or therapeutic agent).

The term "sample", as used herein, is used in its broadest sense. A "biological sample", as used herein, includes, but is not limited to, any quantity of a substance from a living thing or formerly living thing. Such living things include, but are not limited to, humans, mice, rats, monkeys, dogs, rabbits and other animals. Such substances include, but are not limited to, blood, serum, urine, synovial fluid, cells, organs, tissues, bone marrow, lymph nodes and spleen.

I. Antibodies of the Invention

A first particular aspect of the invention provides CDR grafted antibodies, or antigen-binding portions thereof, that bind Aβ(20-42) globulomer and/or any other targeted Aβ form. A second particular aspect of the invention provides humanized antibodies, or antigen-binding portions thereof, that bind Aβ(20-42) globulomer and/or any other targeted Aβ form. According to one particular aspect, the antibodies, or portions thereof, are isolated antibodies. According to a further particular aspect, the antibodies of the invention neutralize an activity of Aβ(20-42) globulomer and/or of any other targeted Aβ form.

A. Method of Making Anti-Aβ(20-42) Globulomer Antibodies

Antibodies of the present invention may be made by any of a number of techniques known in the art.

1. Anti-Aβ(20-42) Globulomer Monoclonal Antibodies Using Hybridome Technology

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, (Cold Spring Harbor Laboratory Press, 2nd ed. 1988); Hammerling, et al., in: Monoclonal Antibodies and T-Cell Hybridomas 563-681 (Elsevier, N.Y., 1981) (said references incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well known in the art. In one embodiment, the present invention provides methods of generating monoclonal antibodies as well as antibodies produced by the method comprising culturing a hybridoma cell secreting an antibody of the invention wherein, e.g., the hybridoma is generated by fusing splenocytes isolated from a mouse immunized with an antigen of the invention with myeloma cells and then screening the hybridomas resulting from the fusion for hybridoma clones that secrete an antibody able to bind a polypeptide of the invention. Briefly, mice can be immunized with an Aβ(20-42) globulomer antigen. In a particular embodiment, the antigen is administered with a adjuvant to stimulate the immune response. Such adjuvants include complete or incomplete Freund's adjuvant, RIBI (muramyl dipeptides) or ISCOM (immunostimulating complexes). Such adjuvants may protect the polypeptide from rapid dispersal by sequestering it in a local deposit, or they may contain substances that stimulate the host to secrete factors that are chemotactic for macrophages and other components of the immune system. Preferably, if a polypeptide is being administered, the immunization schedule will involve two or more administrations of the polypeptide, spread out over several weeks.

After immunization of an animal with an Aβ(20-42) globulomer antigen, antibodies and/or antibody-producing cells may be obtained from the animal. An anti-Aβ(20-42) globulomer antibody-containing serum is obtained from the animal by bleeding or sacrificing the animal. The serum may be used as it is obtained from the animal, an immunoglobulin fraction may be obtained from the serum, or the anti-Aβ(20-42) globulomer antibodies may be purified from the serum. Serum or immunoglobulins obtained in this manner are polyclonal, thus having a heterogeneous array of properties.

Once an immune response is detected, e.g., antibodies specific for the antigen Aβ(20-42) globulomer are detected in the mouse serum, the mouse spleen is harvested and splenocytes isolated. The splenocytes are then fused by well-known techniques to any suitable myeloma cells, for example cells from cell line SP20 available from the ATCC. Hybridomas are selected and cloned by limited dilution. The hybridoma clones are then assayed by methods known in the art for cells that secrete antibodies capable of binding Aβ(20-42) globulomer. Ascites fluid, which generally contains high levels of antibodies, can be generated by immunizing mice with positive hybridoma clones.

In another embodiment, antibody-producing immortalized hybridomas may be prepared from the immunized animal. After immunization, the animal is sacrificed and the splenic B cells are fused to immortalized myeloma cells as is well known in the art (See, e.g., Harlow and Lane, supra). In a particular embodiment, the myeloma cells do not secrete immunoglobulin polypeptides (a non-secretory cell line). After fusion and antibiotic selection, the hybridomas are screened using Aβ(20-42) globulomer, or a portion thereof, or a cell expressing Aβ(20-42) globulomer. In a particular embodiment, the initial screening is performed using an enzyme-linked immunoassay (ELISA) or a radioimmunoassay (RIA). An example of ELISA screening is provided in WO 00/37504, herein incorporated by reference.

Anti-Aβ(20-42) globulomer antibody-producing hybridomas are selected, cloned and further screened for desirable characteristics, including robust hybridoma growth, high antibody production and desirable antibody characteristics, as discussed further below. Hybridomas may be cultured and expanded in vivo in syngeneic animals, in animals that lack an immune system, e.g., nude mice, or in cell culture in vitro. Methods of selecting, cloning and expanding hybridomas are well known to those of ordinary skill in the art.

In a particular embodiment, the hybridomas are mouse hybridomas, as described above. In another particular embodiment, the hybridomas are produced in a non-human, non-mouse species such as rats, sheep, pigs, goats, cattle or horses. In another embodiment, the hybridomas are human hybridomas, in which a human non-secretory myeloma is fused with a human cell expressing an anti-Aβ(20-42) globulomer antibody.

Antibody fragments that recognize specific epitopes may be generated by known techniques. For example, Fab and F(ab')2 fragments of the invention may be produced by proteolytic cleavage of immunoglobulin molecules, using enzymes such as papain (to produce Fab fragments) or pepsin (to produce F(ab')2 fragments). F(ab')2 fragments contain the variable region, the light chain constant region and the CH1 domain of the heavy chain.

2. Anti-Aβ(20-42) Globulomer Monoclonal Antibodies Using SLAM

In another aspect of the invention, recombinant antibodies are generated from single, isolated lymphocytes using a procedure referred to in the art as the selected lymphocyte antibody method (SLAM), as described in U.S. Pat. No. 5,627,052, PCT Publication WO92/02551 and Babcock, J. S. et al. (1996) Proc. Natl. Acad. Sci. USA 93:7843-7848. In this method, single cells secreting antibodies of interest, e.g., lymphocytes derived from any one of the immunized animals described in Section 1, are screened using an antigen-specific hemolytic plaque assay, wherein the antigen Aβ(20-42) globulomer, or a subunit thereof, is coupled to sheep red blood cells using a linker, such as biotin, and used to identify single cells that secrete antibodies with specificity for Aβ(20-42) globulomer. Following identification of antibody-secreting cells of interest, heavy- and light-chain variable region cDNAs are rescued from the cells by reverse transcriptase-PCR and these variable regions can then be expressed, in the context of appropriate immunoglobulin constant regions (e.g., human constant regions), in mammalian host cells, such as COS or CHO cells. The host cells transfected with the amplified immunoglobulin sequences, derived from in vivo selected lymphocytes, can then undergo further analysis and selection in vitro, for example by panning the transfected cells to isolate cells expressing antibodies to Aβ(20-42) globulomer. The amplified immunoglobulin sequences further can be manipulated in vitro, such as by in vitro affinity maturation methods such as those described in PCT Publication WO 97/29131 and PCT Publication WO 00/56772.

3. Anti-Aβ(20-42) Globulomer Monoclonal Antibodies Using Transgenic Animals

In another embodiment of the instant invention, antibodies are produced by immunizing a non-human animal comprising some, or all, of the human immunoglobulin locus with an Aβ(20-42) globulomer antigen. In a particular embodiment, the non-human animal is a XENOMOUSE transgenic mouse, an engineered mouse strain that comprises large fragments of the human immunoglobulin loci and is deficient in mouse antibody production. See, e.g., Green et al. Nature Genetics 7:13-21 (1994) and U.S. Pat. Nos. 5,916,771, 5,939,598, 5,985,615, 5,998,209, 6,075,181, 6,091,001, 6,114,598 and 6,130,364. See also WO 91/10741, published Jul. 25, 1991, WO 94/02602, published Feb. 3, 1994, WO 96/34096 and WO 96/33735, both published Oct. 31, 1996, WO 98/16654, published Apr. 23, 1998, WO 98/24893, published Jun. 11, 1998, WO 98/50433, published Nov. 12, 1998, WO 99/45031, published Sep. 10, 1999, WO 99/53049, published Oct. 21, 1999, WO 00 09560, published Feb. 24, 2000 and WO 00/037504, published Jun. 29, 2000. The XENOMOUSE transgenic mouse produces an adult-like human repertoire of fully human antibodies, and generates antigen-specific human monoclonal antibodies. The XENOMOUSE transgenic mouse contains approximately 80% of the human antibody repertoire through introduction of megabase sized, germline configuration YAC fragments of the human heavy chain loci and x light chain loci. See Mendez et al., Nature Genetics 15:146-156 (1997), Green and Jakobovits J. Exp. Med. 188:483-495 (1998), the disclosures of which are hereby incorporated by reference.

4. Anti-Aβ(20-42) Globulomer Monoclonal Antibodies Using Recombinant Antibody Libraries In vitro methods also can be used to make the antibodies of the invention, wherein an antibody library is screened to identify an antibody having the desired binding specificity. Methods for such screening of recombinant antibody libraries are well known in the art and include methods described in, for example, Ladner et al. U.S. Pat. No. 5,223,409; Kang et al. PCT Publication No. WO92/18619; Dower et al. PCT Publication No. WO91/17271; Winter et al. PCT Publication No. WO92/20791; Markland et al. PCT Publication No. WO92/15679; Breitling et al. PCT Publication No. WO93/01288; McCafferty et al. PCT Publication No. WO92/01047; Garrard et al. PCT Publication No. WO92/09690; Fuchs et al. (1991) Bio/Technology 9:1370-1372; Hay et al. (1992) Hum Antibod Hybridomas 3:81-85; Huse et al. (1989) Science 246:1275-1281; McCafferty et al., Nature (1990) 348:552-554; Griffiths et al. (1993) EMBO J 12:725-734; Hawkins et al. (1992) J Mol Biol 226:889-896; Clackson et al. (1991) Nature 352:624-628; Gram et al. (1992) PNAS 89:3576-3580; Garrad et al. (1991) Bio/Technology 9:1373-1377; Hoogenboom et al. (1991) Nuc Acid Res 19:4133-4137; and Barbas et al. (1991) PNAS 88:7978-7982, US patent application publication 20030186374, and PCT Publication No. WO97/29131, the contents of each of which are incorporated herein by reference.

The recombinant antibody library may be from a subject immunized with Aβ(20-42) globulomer, or a portion of Aβ(20-42) globulomer. Alternatively, the recombinant antibody library may be from a naïve subject, i.e., one who has not been immunized with Aβ(20-42) globulomer, such as a human antibody library from a human subject who has not been immunized with human Aβ(20-42) globulomer. Antibodies of the invention are selected by screening the recombinant antibody library with the peptide comprising human Aβ(20-42) globulomer to thereby select those antibodies that recognize Aβ(20-42) globulomer and discriminate Aβ(1-42) globulomer, Aβ(1-40) and Aβ(1-42) monomer, Aβ-fibrils and sAPPα. Methods for conducting such screening and selection are well known in the art, such as described in the references in the preceding paragraph. To select antibodies of the invention having particular binding affinities for Aβ(20-42) globulomer and discriminate Aβ(1-42) globulomer, Aβ(1-40) and Aβ(1-42) monomer, Aβ-fibrils and sAPPα, such as those that dissociate from human Aβ(20-42) globulomer with a particular koff rate constant, the art-known method of dot blot can be used to select antibodies having the desired koff rate constant. To select antibodies of the invention having a particular neutralizing activity for Aβ(20-42) globulomer and discriminate Aβ(1-42) globulomer, Aβ(1-40) and Aβ(1-42) monomer, Aβ-fibrils and sAPPα, such as those with a particular an IC50 standard methods known in the art for assessing the inhibition of Aβ(20-42) globulomer activity may be used.

In one aspect, the invention pertains to an isolated antibody, or an antigen-binding portion thereof, that binds human Aβ(20-42) globulomer and discriminates Aβ(1-42) globulomer, Aβ(1-40) and Aβ(1-42) monomer, Aβ-fibrils and sAPPα. According to one aspect, the antibody is a neutralizing antibody. In various embodiments, the antibody is a recombinant antibody or a monoclonal antibody.

For example, the antibodies of the present invention can also be generated using various phage display methods known in the art. In phage display methods, functional antibody domains are displayed on the surface of phage particles which carry the polynucleotide sequences encoding them. In a particular, such phage can be utilized to display antigen-binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein. Examples of phage display methods that can be used to make the antibodies of the present invention include those disclosed in Brinkman et al., J. Immunol. Methods 182:41-50 (1995); Ames et al., J. Immunol. Methods 184:177-186 (1995); Kettleborough et al., Eur. J. Immunol. 24:952-958 (1994); Persic et al., Gene 187 9-18 (1997); Burton et al., Advances in Immunology 57:191-280 (1994); PCT application No. PCT/GB91/01134; PCT publications WO90/02809; WO91/10737; WO92/01047; WO92/18619; WO93/11236; WO95/15982; WO95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780, 225; 5,658,727; 5,733,743 and 5,969,108; each of which is incorporated herein by reference in its entirety.

As described in the above references, after phage selection, the antibody coding regions from the phage can be isolated and used to generate whole antibodies including human antibodies or any other desired antigen binding fragment, and expressed in any desired host, including mammalian cells, insect cells, plant cells, yeast, and bacteria, e.g., as described in detail below. For example, techniques to recombinantly produce Fab, Fab' and F(ab')2 fragments can also be employed using methods known in the art such as those disclosed in PCT publication WO92/22324; Mullinax et al., BioTechniques 12(6):864-869 (1992); and Sawai et al., AJRI 34:26-34 (1995); and Better et al., Science 240:1041-1043 (1988) (said references incorporated by reference in their entireties). Examples of techniques which can be used to produce single-chain Fvs and antibodies include those described in U.S. Pat. Nos. 4,946,778 and 5,258,498; Huston et al., Methods in Enzymology 203:46-88 (1991); Shu et al., PNAS 90:7995-7999 (1993); and Skerra et al., Science 240:1038-1040 (1988).

Alternative to screening of recombinant antibody libraries by phage display, other methodologies known in the art for screening large combinatorial libraries can be applied to the identification of dual specificity antibodies of the invention. One type of alternative expression system is one in which the recombinant antibody library is expressed as RNA-protein fusions, as described in PCT Publication No. WO 98/31700 by Szostak and Roberts, and in Roberts, R. W. and Szostak, J. W. (1997) Proc. Natl. Acad. Sci. USA 94:12297-12302. In this system, a covalent fusion is created between an mRNA and the peptide or protein that it encodes by in vitro translation of synthetic mRNAs that carry puromycin, a peptidyl acceptor antibiotic, at their 3' end. Thus, a specific mRNA can be enriched from a complex mixture of mRNAs (e.g., a combinatorial library) based on the properties of the encoded peptide or protein, e.g., antibody, or portion thereof, such as binding of the antibody, or portion thereof, to the dual specificity antigen. Nucleic acid sequences encoding antibodies, or portions thereof, recovered from screening of such libraries can be expressed by recombinant means as described above (e.g., in mammalian host cells) and, moreover, can be subjected to further affinity maturation by either additional rounds of screening of mRNA-peptide fusions in which mutations have been introduced into the originally selected sequence(s), or by other methods for affinity maturation in vitro of recombinant antibodies, as described above.

In another approach the antibodies of the present invention can also be generated using yeast display methods known in the art. In yeast display methods, genetic methods are used to tether antibody domains to the yeast cell wall and display them on the surface of yeast. In particular, such yeast can be utilized to display antigen-binding domains expressed from a repertoire or combinatorial antibody library (e.g., human or murine). Examples of yeast display methods that can be used to make the antibodies of the present invention include those disclosed Wittrup, et al. U.S. Pat. No. 6,699,658 incorporated herein by reference.

B. Production of Recombinant Aβ(20-42) Globulomer Antibodies

Antibodies of the present invention may be produced by any of a number of techniques known in the art. For example, expression from host cells, wherein expression vector(s) encoding the heavy and light chains is (are) transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. It is possible to express the antibodies of the invention in either prokaryotic or eukaryotic host cells. According to a particular aspect of the invention, expression of antibodies is performed using eukaryotic cells, for example mammalian host cells, because such eukaryotic cells (and in particular mammalian cells) are more likely than prokaryotic cells to assemble and secrete a properly folded and immunologically active antibody.

According to one aspect, mammalian host cells for expressing the recombinant antibodies of the invention include Chinese Hamster Ovary (CHO cells) (including dhfr-CHO cells, described in Urlaub and Chasin, (1980) Proc. Natl. Acad. Sci. USA 77:4216-4220, used with a DHFR selectable marker, e.g., as described in R. J. Kaufman and P. A. Sharp (1982) Mol. Biol. 159:601-621), NS0 myeloma cells, COS cells and SP2 cells. When recombinant expression vectors encoding antibodies genes are introduced into mammalian host cells, the antibodies are produced by culturing the host cells for a period of time sufficient to allow for expression of the antibodies in the host cells or secretion of the antibodies into the culture medium in which the host cells are grown. Antibodies can be recovered from the culture medium using standard protein purification methods.

Host cells can also be used to produce functional antibody fragments, such as Fab fragments or scFv molecules. It will be understood that variations on the above procedure are within the scope of the present invention. For example, it may be desirable to transfect a host cell with DNA encoding functional fragments of either the light chain and/or the heavy chain of an antibody of this invention. Recombinant DNA technology may also be used to remove some, or all, of the DNA encoding either or both of the light and heavy chains that is not necessary for binding to the antigens of interest. The molecules expressed from such truncated DNA molecules are also encompassed by the antibodies of the invention. In addition, bifunctional antibodies may be produced in which one heavy and one light chain are an antibody of the invention and the other heavy and light chain are specific for an antigen other than the antigens of interest by crosslinking an antibody of the invention to a second antibody by standard chemical crosslinking methods.

In a particular system for recombinant expression of an antibody, or antigen-binding portion thereof, of the invention, a recombinant expression vector encoding both the antibody heavy chain and the antibody light chain is introduced into dhfr-CHO cells by calcium phosphate-mediated transfection. Within the recombinant expression vector, the antibody heavy and light chain genes are each operatively linked to CMV enhancer/AdMLP promoter regulatory elements to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy and light chains and intact antibody is recovered from the culture medium. Standard molecular biology techniques are used to prepare the recombinant expression vector, transfect the host cells, select for transformants, culture the host cells and recover the antibody from the culture medium. Still further the invention provides a method of synthesizing a recombinant antibody of the invention by culturing a host cell of the invention in a suitable culture medium until a recombinant antibody of the invention is synthesized. The method can further comprise isolating the recombinant antibody from the culture medium.

1. Anti-Aβ(20-42) Globulomer Murine Antibodies

Table 4 is a list of amino acid sequences of VH and VL regions of murine 4D10.

TABLE 4

LIST OF AMINO ACID SEQUENCES
OF VH AND VL REGIONS

| SEQ ID NO | PROTEIN REGION | SEQUENCE<br>12345678901234567890123456 7890 |
|---|---|---|
| 23 | m4D10_VH | QVQLKQSGPSLIQPSQSLSITCTVSGFSLT<br>SYGVHWVRQSPGKGLEWLGVIWRGGRIDYN<br>AAFMSRLSITKDNSKSQVFFKMNSLQADDT<br>AIYYCARNSDVWGTGTTVTVSS |
| 24 | m4D10_VL | DVVMTQTPLTLSVTIGQPASISCKSSQSLL<br>DIDGKTYLNWLLQRPGQSPKRLIYLVSKLD<br>SGVPDRFTGSGSGTDFTLKISRVEAEDLGV<br>YYCWQGTHFPYTFGGGTKLEIKR |

*CDRs are underlined in murine light and heavy chains.

2. Anti-Aβ(20-42) Globulomer Chimeric Antibodies

A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art and discussed in detail herein. See e.g., Morrison, Science 229:1202 (1985); Oi et al., BioTechniques 4:214 (1986); Gillies et al., (1989) J. Immunol. Methods 125:191-202; U.S. Pat. Nos. 5,807,715; 4,816,567; and 4,816,397, which are incorporated herein by reference in their entireties. In addition, techniques developed for the production of "chimeric antibodies" (Morrison et al., 1984, Proc. Natl. Acad. Sci. 81:851-855; Neuberger et al., 1984, Nature 312:604-608; Takeda et al., 1985, Nature 314:452-454 which are incorporated herein by reference in their entireties) by splicing genes from a mouse antibody molecule of appropriate antigen specificity together with genes from a human antibody molecule of appropriate biological activity can be used.

In one embodiment, the chimeric antibodies of the invention are produced by replacing the heavy chain constant region of the murine monoclonal anti-Aβ(20-42) globulomer antibody 4D10 described in WO2007/062852 with a human IgG1 constant region.

3. Anti-Aβ(20-42) Globulomer CDR Grafted Antibodies

CDR-grafted antibodies of the invention comprise heavy and light chain variable region sequences from a human antibody wherein one or more of the CDR regions of VH and/or VL are replaced with CDR sequences of the murine antibodies of the invention. A framework sequence from any human antibody may serve as the template for CDR grafting. However, straight chain replacement onto such a framework often leads to some loss of binding affinity to the antigen. The more homologous a human antibody is to the original murine antibody, the less likely the possibility that combining the murine CDRs with the human framework will introduce distortions in the CDRs that could reduce affinity. Therefore, the human variable framework chosen to replace the murine variable framework apart from the CDRs have for example at least a 65% sequence identity with the murine antibody variable region framework. The human and murine variable regions apart from the CDRs have for example at least 70%, least 75% sequence identity, or at least 80% sequence identity. Methods for producing chimeric antibodies are known in the art and discussed in detail herein. (also see EP 239,400; PCT publication WO 91/09967; U.S. Pat. Nos. 5,225,539; 5,530,101; and 5,585,089), veneering or resurfacing (EP 592,106; EP 519,596; Padlan, Molecular Immunology 28(4/5):489-498 (1991); Studnicka et al., Protein Engineering 7(6):805-814 (1994); Roguska et al., PNAS 91:969-973 (1994)), and chain shuffling (U.S. Pat. No. 5,565,352).

Table 5 below illustrates the sequences of CDR grafted antibodies of the present invention (4D10hum antibodies) and the CDRs contained therein.

TABLE 5

LIST OF AMINO ACID SEQUENCES OF VH
AND VL REGIONS OF CDR GRAFTED ANTIBODIES

| SEQ ID NO | PROTEIN REGION | | SEQUENCE<br>12345678901234567890123456 7890 |
|---|---|---|---|
| 4 | 4D10hum_VH.1z | | EVQLVESGGGLIQPGGSLRLSCAASGFTVS<br>WYGVHWVRQAPGKGLEWVSVIWRGGRIDYN<br>AAFMSRFTISRDNSKNTLYLQMNSLRAEDT<br>AVYYCARNSDVWGQGTTVTVSS |
| 8 | 4D10hum_VH.2z | | QVQLQESGPGLVKPSETLSLTCTVSGGSIS<br>SYGVHWIRQPPGKGLEWIGVIWRGGRIDYN<br>AAFMSRVTISVDTSKNQFSLKLSSVTAADT<br>AVYYCARNSDVWGQGTTVTVSS |
| 17 | VH 4D10hum CDR-H1 | Residues 31-35 of SEQ ID NOs: 4, 8 | SYGVH |
| 18 | VH 4D10hum CDR-H2 | Residues 50-65 of SEQ ID NOs: 4, 8 | VIWRGGRIDYNAAFMS |

TABLE 5-continued

LIST OF AMINO ACID SEQUENCES OF VH
AND VL REGIONS OF CDR GRAFTED ANTIBODIES

| SEQ ID NO | PROTEIN REGION | | SEQUENCE<br>123456789012345678901234567890 |
|---|---|---|---|
| 19 | VH 4D10hum<br>CDR-H3 | Residues 98-101 of<br>SEQ ID NOs: 4, 8 | NSDV |
| 12 | 4D10hum_Vκ.1z | | DVVMTQSPLSLPVTLGQPASISCKSSQSLL<br>DIDGKTYLNWFQQRPGQSPRRLIYLVSKLD<br>SGVPDRFSGSGSGTDFTLKISRVEAEDVGV<br>YYCWQGTHFPYTFGQGTKLEIKR |
| 20 | VL 4D10hum<br>CDR-L1 | Residues 24-39 of<br>SEQ ID NO: 12 | KSSQSLLDIDGKTYLN |
| 21 | VL 4D10hum<br>CDR-L2 | Residues 55-61 of<br>SEQ ID NO: 12 | LVSKLDS |
| 22 | VL 4D10hum<br>CDR-L3 | Residues 94-102 of<br>SEQ ID NO: 12 | WQGTHFPYT |

*CDRs are underlined in humanized light and heavy chains.

4. Anti-Aβ(20-42) Globulomer Humanized Antibodies

Humanized antibodies are antibody molecules from non-human species antibody that binds the desired antigen having one or more complementarity determining regions (CDRs) from the non-human species and framework regions from a human immunoglobulin molecule.

Known human Ig sequences are disclosed, e.g., Kabat et al., Sequences of Proteins of Immunological Interest, U.S. Dept. Health (1983), each entirely incorporated herein by reference. Such imported sequences can be used to reduce immunogenicity or reduce, enhance or modify binding, affinity, on-rate, off-rate, avidity, specificity, half-life, or any other suitable characteristic, as known in the art.

Framework residues in the human framework regions may be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., Nature 332:323 (1988), which are incorporated herein by reference in their entireties.) Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequences so that the desired antibody characteristic, such as increased affinity for the target antigen(s), is achieved. In general, the CDR residues are directly and most substantially involved in influencing antigen binding. Antibodies can be humanized using a variety of techniques known in the art, such as but not limited to those described in Jones et al., Nature 321:522 (1986); Verhoeyen et al., Science 239:1534 (1988), Sims et al., J. Immunol. 151: 2296 (1993); Chothia and Lesk, J. Mol. Biol. 196:901 (1987), Carter et al., Proc. Natl. Acad. Sci. U.S.A. 89:4285 (1992); Presta et al., J. Immunol. 151:2623 (1993), Padlan, Molecular Immunology 28(4/5):489-498 (1991); Studnicka et al., Protein Engineering 7(6):805-814 (1994); Roguska. et al., PNAS 91:969-973 (1994); PCT publication WO 91/09967, PCT/: U.S. Ser. No. 98/16280, U.S. Ser. No. 96/18978, U.S. Ser. No. 91/09630, U.S. Ser. No. 91/05939, U.S. Ser. No. 94/01234, GB89/01334, GB91/01134, GB92/01755; WO90/14443, WO90/14424, WO90/14430, EP 229246, EP 592,106; EP 519,596, EP 239,400, U.S. Pat. Nos. 5,565,332, 5,723,323, 5,976,862, 5,824,514, 5,817,483, 5,814,476, 5,763,192, 5,723,323, 5,766,886, 5,714,352, 6,204,023, 6,180,370, 5,693,762, 5,530,101, 5,585,089, 5,225,539; 4,816,567, each entirely incorporated herein by reference, included references cited therein.

Table 6 below illustrates the sequences of humanized antibodies of the present invention (4D10hum antibodies) and the CDRs contained therein.

TABLE 6

LIST OF AMINO ACID SEQUENCES OF VH AND VL
REGIONS OF HUMANIZED ANTIBODIES

| SEQ ID NO | PROTEIN REGION | SEQUENCE<br>123456789012345678901234567890 |
|---|---|---|
| 5 | 4D10hum_VH.1 | EVQLVESGGGLVQPGGSLRLSCAASGFTVS<br>SYGVHWVRQAPGKGLEWVSVIWRGGRIDYN<br>AAFMSRFTISRDNSKNTLYLQMNSLRAEDT<br>AVYYCARNSDVWGQGTTVTSS |

TABLE 6-continued

LIST OF AMINO ACID SEQUENCES OF VH AND VL
REGIONS OF HUMANIZED ANTIBODIES

| SEQ ID NO | PROTEIN REGION | | SEQUENCE<br>123456789012345678901234567890 |
|---|---|---|---|
| 6 | 4D10hum_VH.1a | | EVQLVESGGGLVQPGGSLRLSCAVSGFTLS<br>SYGVHWVRQAPGKGLEWLGVIWRGGRIDYN<br>AAFMSRLTISKDNSKSTVYLQMNSLRAEDT<br>AVYYCARNSDVWGQGTTVTVSS |
| 7 | 4D10hum_VH.1b | | EVQLVESGGGLIQPGGSLRLSCAASGFTLS<br>SYGVHWVRQAPGKGLEWVSVIWRGGRIDYN<br>AAFMSRFTISKDNSKNTLYLQMNSLRAEDT<br>AVYYCARNSDVWGQGTTVTVSS |
| 9 | 4D10hum_VH.2 | | EVQLQESGPGLVKPSETLSLTCTVSGGSIS<br>SYGVHWIRQPPGKGLEWIGVIWRGGRIDYN<br>AAFMSRVTISVDTSKNQFSLKLSSVTAADT<br>AVYYCARNSDVWGQGTTVTVSS |
| 10 | 4D10hum_VH.2a | | EVQLQESGPGLVKPSETLSLTCTVSGFSLS<br>SYGVHWVRQPPGKGLEWLGVIWRGGRIDYN<br>AAFMSRLTISKDTSKQVSLKLSSVTAADT<br>AVYYCARNSDVWGQGTTVTVSS |
| 11 | 4D10hum_VH.2b | | EVQLQESGPGLVKPSETLSLTCTVSGFSLS<br>SYGVHWIRQPPGKGLEWIGVIWRGGRIDYN<br>AAFMSRVTISKDTSKNQFSLKLSSVTAADT<br>AVYYCARNSDVWGQGTTVTVSS |
| 17 | VH 4D10hum<br>CDR-H1 | Residues 31-35 of<br>SEQ ID NOs: 5, 6, 7,<br>9, 10, 11 | SYGVH |
| 18 | VH 4D10hum<br>CDR-H2 | Residues 50-65 of<br>SEQ ID NOs: 5, 6, 7,<br>9, 10, 11 | VIWRGGRIDYNAAFMS |
| 19 | VH 4D10hum<br>CDR-H3 | Residues 98-101 of<br>SEQ ID NOs: 5, 6, 7,<br>9, 10, 11 | NSDV |
| 13 | 4D10hum_Vκ.1 | | DVVMTQTPLSLPVTPGQPASISCKSSQSLL<br>DIDGKTYLNWFLQKPGQSPQRLIYLVSKLD<br>SGVPDRFSGSGSGTDFTLKISRVEAEDVGV<br>YYCWQGTHFPYTFGQGTKLEIKR |
| 14 | 4D10hum_Vκ.1a | | DVVMTQTPLSLPVTPGQPASISCKSSQSLL<br>DIDGKTYLNWLLQKPGQSPQRLIYLVSKLD<br>SGVPDRFSGSGSGTDFTLKISRVEAEDVGV<br>YYCWQGTHFPYTFGQGTKLEIKR |
| 15 | 4D10hum_Vκ.1b | | DVVMTQTPLSLPVTLGQPASISCKSSQSLL<br>DIDGKTYLNWLLQRPGQSPRRLIYLVSKLD<br>SGVPDRFSGSGSGTDFTLKISRVEAEDVGV<br>YYCWQGTHFPYTFGQGTKLEIKR |
| 16 | 4D10hum_Vκ.1c | | DVVMTQTPLSLPVTLGQPASISCKSSQSLL<br>DIDGKTYLNWFLQKPGQSPRRLIYLVSKLD<br>SGVPDRFSGSGSGTDFTLKISRVEAEDVGV<br>YYCWQGTHFPYTFGQGTKLEIKR |
| 20 | VL-4D10hum<br>CDR-L1 | Residues 24-39 of<br>SEQ ID NOs: 13, 14,<br>15, 16 | KSSQSLLDIDGKTYLN |
| 21 | VL 4D10hum<br>CDR-L2 | Residues 55-61 of<br>SEQ ID NOs: 13, 14,<br>15, 16 | LVSKLDS |
| 22 | VL 4D10hum<br>CDR-L3 | Residues 94-102 of<br>SEQ ID NOs: 13, 14,<br>15, 16 | WQGTHFPYT |

*CDRs are underlined in humanized light and heavy chains.

C. Antibodies and Antibody-Producing Cell Lines

According to one aspect, anti-Aβ(20-42) globulomer antibodies of the present invention or antibodies against any other targeted Aβ form exhibit a high capacity to reduce or to neutralize activity of Aβ(20-42) globulomer (and/or any other targeted Aβ form).

In certain embodiments, the antibody comprises a heavy chain constant region, such as an IgG1, IgG2, IgG3, IgG4, IgA, IgE, IgM or IgD constant region. According to one aspect, the heavy chain constant region is an IgG1 heavy chain constant region or an IgG4 heavy chain constant region. According to a further aspect, the antibody comprises a light chain constant region, either a kappa light chain constant region or a lambda light chain constant region. According to one aspect, the antibody comprises a kappa light chain constant region. An antibody portion can be, for example, a Fab fragment or a single chain Fv fragment.

Replacements of amino acid residues in the Fc portion to alter antibody effector function are known in the art (Winter, et al. U.S. Pat. Nos. 5,648,260 and 5,624,821). The Fc portion of an antibody mediates several important effector functions e.g. cytokine induction, ADCC, phagocytosis, complement dependent cytotoxicity (CDC) and half-life/clearance rate of antibody and antigen-antibody complexes. In some cases these effector functions are desirable for therapeutic antibody but in other cases might be unnecessary or even deleterious, depending on the therapeutic objectives. Certain human IgG isotypes, particularly IgG1 and IgG3, mediate ADCC and CDC via binding to FcγRs and complement C1q, respectively. Neonatal Fc receptors (FcRn) are the critical components determining the circulating half-life of antibodies. In still another embodiment at least one amino acid residue is replaced in the constant region of the antibody, for example the Fc region of the antibody, such that effector functions of the antibody are altered.

One embodiment provides a labeled antibody wherein an antibody of the invention is derivatized or linked to another functional molecule (e.g., another peptide or protein). For example, a labeled antibody of the invention can be derived by functionally linking an antibody of the invention (by chemical coupling, genetic fusion, noncovalent association or otherwise) to one or more other molecular entities, such as another antibody (e.g., a bispecific antibody or a diabody), a detectable agent, a pharmaceutical agent, and/or a protein or peptide that can mediate association of the antibody with another molecule (such as a streptavidin core region or a polyhistidine tag).

Useful detectable agents with which an antibody of the invention may be derivatized include fluorescent compounds. Exemplary fluorescent detectable agents include fluorescein, fluorescein isothiocyanate, rhodamine, 5-dimethylamine-1-napthalenesulfonyl chloride, phycoerythrin and the like. An antibody may also be derivatized with detectable enzymes, such as alkaline phosphatase, horseradish peroxidase, glucose oxidase and the like. When an antibody is derivatized with a detectable enzyme, it is detected by adding additional reagents that the enzyme uses to produce a detectable reaction product. For example, when the detectable agent horseradish peroxidase is present, the addition of hydrogen peroxide and diaminobenzidine leads to a colored reaction product, which is detectable. An antibody may also be derivatized with biotin, and detected through indirect measurement of avidin or streptavidin binding.

Another embodiment of the invention provides a crystallized antibody. According to one aspect, the invention relates to crystals of whole anti-Aβ(20-42) globulomer antibodies and fragments thereof as disclosed herein, and formulations and compositions comprising such crystals. According to a further aspect, the crystallized antibody has a greater half-life in vivo than the soluble counterpart of the antibody. According to a further aspect, the antibody retains biological activity after crystallization.

Crystallized antibody of the invention may be produced according methods known in the art and as disclosed in WO02/072636, incorporated herein by reference.

Another embodiment of the invention provides a glycosylated antibody wherein the antibody comprises one or more carbohydrate residues. Nascent in vivo protein production may undergo further processing, known as post-translational modification. In particular, sugar (glycosyl) residues may be added enzymatically, a process known as glycosylation. The resulting proteins bearing covalently linked oligosaccharide side chains are known as glycosylated proteins or glycoproteins.

Antibodies are glycoproteins with one or more carbohydrate residues in the Fc domain, as well as the variable domain. Carbohydrate residues in the Fc domain have important effect on the effector function of the Fc domain, with minimal effect on antigen binding or half-life of the antibody (R. Jefferis, Biotechnol. Prog. 21 (2005), pp. 11-16). In contrast, glycosylation of the variable domain may have an effect on the antigen binding activity of the antibody. Glycosylation in the variable domain may have a negative effect on antibody binding affinity, likely due to steric hindrance (Co, M. S., et al., Mol. Immunol. (1993) 30:1361-1367), or result in increased affinity for the antigen (Wallick, S. C., et al., Exp. Med. (1988) 168:1099-1109; Wright, A., et al., EMBO J. (1991) 10:2717 2723).

One aspect of the present invention is directed to generating glycosylation site mutants in which the O- or N-linked glycosylation site of the antibody has been mutated. One skilled in the art can generate such mutants using standard well-known technologies. The creation of glycosylation site mutants that retain the biological activity but have increased or decreased binding activity is another object of the present invention.

In still another embodiment, the glycosylation of the antibody of the invention is modified. For example, an aglycosylated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region glycosylation sites to thereby eliminate glycosylation at that site. Such aglycosylation may increase the affinity of the antibody for antigen. Such an approach is described in further detail in International Appln. Publication No. WO03/016466A2, and U.S. Pat. Nos. 5,714,350 and 6,350,861, each of which is incorporated herein by reference in its entirety.

Additionally or alternatively, a modified antibody of the invention can be made that has an altered type of glycosylation, such as a hypofucosylated antibody having reduced amounts of fucosyl residues or an antibody having increased bisecting GlcNAc structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the invention to thereby produce an antibody with altered glycosylation. See, for example, Shields, R. L. et al.

(2002) J. Biol. Chem. 277:26733-26740; Umana et al. (1999) Nat. Biotech. 17:176-1, as well as, European Patent NO.: EP1,176,195; International Appln. Publication Nos. WO03/035835 and WO99/54342 80, each of which is incorporated herein by reference in its entirety.

Protein glycosylation depends on the amino acid sequence of the protein of interest, as well as the host cell in which the protein is expressed. Different organisms may produce different glycosylation enzymes (e.g., glycosyltransferases and glycosidases), and have different substrates (nucleotide sugars) available. Due to such factors, protein glycosylation pattern, and composition of glycosyl residues, may differ depending on the host system in which the particular protein is expressed. Glycosyl residues useful in the invention may include, but are not limited to, glucose, galactose, mannose, fucose, n-acetylglucosamine and sialic acid. According to one aspect, the glycosylated antibody comprises glycosyl residues such that the glycosylation pattern is human.

It is known to those skilled in the art that differing protein glycosylation may result in differing protein characteristics. For instance, the efficacy of a therapeutic protein produced in a microorganism host, such as yeast, and glycosylated utilizing the yeast endogenous pathway may be reduced compared to that of the same protein expressed in a mammalian cell, such as a CHO cell line. Such glycoproteins may also be immunogenic in humans and show reduced half-life in vivo after administration. Specific receptors in humans and other animals may recognize specific glycosyl residues and promote the rapid clearance of the protein from the bloodstream. Other adverse effects may include changes in protein folding, solubility, susceptibility to proteases, trafficking, transport, compartmentalization, secretion, recognition by other proteins or factors, antigenicity, or allergenicity. Accordingly, a practitioner may prefer a therapeutic protein with a specific composition and pattern of glycosylation, for example glycosylation composition and pattern identical, or at least similar, to that produced in human cells or in the species-specific cells of the intended subject animal.

Expressing glycosylated proteins different from that of a host cell may be achieved by genetically modifying the host cell to express heterologous glycosylation enzymes. Using techniques known in the art a practitioner may generate antibodies exhibiting human protein glycosylation. For example, yeast strains have been genetically modified to express non-naturally occurring glycosylation enzymes such that glycosylated proteins (glycoproteins) produced in these yeast strains exhibit protein glycosylation identical to that of animal cells, especially human cells (U.S. Patent Application Publication Nos. 20040018590 and 20020137134; and WO05/100584).

Another embodiment is directed to an anti-idiotypic (anti-Id) antibody specific for such antibodies of the invention. An anti-Id antibody is an antibody, which recognizes unique determinants generally associated with the antigen-binding region of another antibody. The anti-Id can be prepared by immunizing an animal with the antibody or a CDR containing region thereof. The immunized animal will recognize, and respond to the idiotypic determinants of the immunizing antibody and produce an anti-Id antibody. The anti-Id antibody may also be used as an "immunogen" to induce an immune response in yet another animal, producing a so-called anti-anti-Id antibody.

Further, it will be appreciated by one skilled in the art that a protein of interest may be expressed using a library of host cells genetically engineered to express various glycosylation enzymes, such that member host cells of the library produce the protein of interest with variant glycosylation patterns. A practitioner may then select and isolate the protein of interest with particular novel glycosylation patterns. According to a further aspect, the protein having a particularly selected novel glycosylation pattern exhibits improved or altered biological properties.

D. Uses of Anti-Aβ(20-42) Globulomer Antibodies

Given their ability to bind to Aβ(20-42) globulomer, the anti-Aβ(20-42) globulomer antibodies, or antibodies against any other targeted Aβ form, of the invention can be used to detect Aβ(20-42) globulomer and/or any other targeted Aβ form (e.g., in a biological sample such as serum, CSF, brain tissue or plasma), using a conventional immunoassay, such as an enzyme linked immunosorbent assays (ELISA), an radioimmunoassay (RIA) or tissue immunohistochemistry. The invention provides a method for detecting Aβ(20-42) globulomer and/or any other targeted Aβ form in a biological sample comprising contacting a biological sample with an antibody of the invention and detecting either the antibody bound to Aβ(20-42) globulomer (and/or any other targeted Aβ form) or unbound antibody, to thereby detect Aβ(20-42) globulomer, and/or any other targeted Aβ form in the biological sample. The antibody is directly or indirectly labeled with a detectable substance to facilitate detection of the bound or unbound antibody. Suitable detectable substances include various enzymes, prosthetic groups, fluorescent materials, luminescent materials and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include $^{3}H$, $^{14}C$, $^{35}S$, $^{90}Y$, $^{99}Tc$, $^{111}In$, $^{125}I$, $^{131}I$, $^{177}Lu$, $^{166}Ho$, or $^{153}Sm$.

Alternative to labeling the antibody, Aβ(20-42) globulomer and/or any other targeted Aβ form can be assayed in biological fluids by a competition immunoassay utilizing Aβ(20-42) globulomer standards labeled with a detectable substance and an unlabeled anti-Aβ(20-42) globulomer antibody. In this assay, the biological sample, the labeled Aβ(20-42) globulomer standards and the anti-Aβ(20-42) globulomer antibody are combined and the amount of labeled Aβ(20-42) globulomer standard bound to the unlabeled antibody is determined. The amount of Aβ(20-42) globulomer, and/or any other targeted Aβ form in the biological sample is inversely proportional to the amount of labeled Aβ(20-42) globulomer standard bound to the anti-Aβ(20-42) globulomer antibody.

According to one aspect of the invention, the antibodies of the invention are capable of neutralizing Aβ(20-42) globulomer activity, and/or activity of any other targeted Aβ form both in vitro and in vivo. Accordingly, such antibodies of the invention can be used to inhibit (i.e. reduce) Aβ(20-42) globulomer activity, and/or activity of any other targeted Aβ form, e.g., in a cell culture containing Aβ(20-42) globulomer, and/or any other targeted Aβ form in human subjects or in other mammalian subjects having Aβ(20-42) globulomer, and/or any other targeted Aβ form with which an antibody of the invention cross-reacts. In one embodiment, the invention provides a method for inhibiting (i.e. reducing) Aβ(20-42) globulomer activity, and/or activity of any other targeted Aβ form comprising contacting Aβ(20-42) globulomer, and/or any other targeted Aβ form with an antibody of the invention such that Aβ(20-42) globulomer activity, and/or activity of any other targeted Aβ form is inhibited (i.e. reduced). For example, in a cell culture containing, or suspected of containing Aβ(20-42) globulomer, and/or any other targeted Aβ form an antibody of the invention can be added to the culture medium to inhibit (i.e. reduce) Aβ(20-42) globulomer activity, and/or activity of any other targeted Aβ form in the culture.

In another embodiment, the invention provides a method for inhibiting (i.e. reducing) activity of a targeted Aβ form in a subject, advantageously in a subject suffering from a disease or disorder in which activity of said Aβ form is detrimental, or a disease or disorder or disorder which is selected from the group consisting of Alpha1-antitrypsin-deficiency, C1-inhibitor deficiency angioedema, Antithrombin deficiency thromboembolic disease, Kuru, Creutzfeld-Jacob disease/scrapie, Bovine spongiform encephalopathy, Gerstmann-Straussler-Scheinker disease, Fatal familial insomnia, Huntington's disease, Spinocerebellar ataxia, Machado-Joseph atrophy, Dentato-rubro-pallidoluysian atrophy, Frontotemporal dementia, Sickle cell anemia, Unstable hemoglobin inclusion-body hemolysis, Drug-induced inclusion body hemolysis, Parkinson's disease, Systemic AL amyloidosis, Nodular AL amyloidosis, Systemic AA amyloidosis, Prostatic amyloidosis, Hemodialysis amyloidosis, Hereditary (Icelandic) cerebral angiopathy, Huntington's disease, Familial visceral amyloidosis, Familial visceral polyneuropathy, Familial visceral amyloidosis, Senile systemic amyloidosis, Familial amyloid neurophathy, Familial cardiac amyloidosis, Alzheimer's disease, Down syndrome, Medullary carcinoma thyroid and Type 2 diabetes mellitus (T2DM).

The invention provides methods for inhibiting (i.e. reducing) the activity of a targeted Aβ form in a subject suffering from such a disease or disorder, which method comprises administering to the subject an antibody of the invention such that the activity of said Aβ form in the subject is inhibited (i.e. reduced). In one aspect of the invention, said targeted Aβ form is a human Aβ form, and the subject is a human subject. Alternatively, the subject can be a non-human mammal expressing APP or any Aβ-form resulting in the generation of a targeted Aβ form to which an antibody of the invention is capable of binding. Still further the subject can be a non-human mammal into which a targeted Aβ form has been introduced (e.g., by administration of the targeted Aβ form or by expression of APP or any other Aβ-form resulting in the generation of the targeted Aβ form. An antibody of the invention can be administered to a human subject for therapeutic purposes. Moreover, an antibody of the invention can be administered to a non-human mammal wherein expression of APP or any Aβ-form resulting in the generation of a targeted Aβ form with which the antibody is capable of binding for veterinary purposes or as an animal model of human disease. Regarding the latter, such animal models may be useful for evaluating the therapeutic efficacy of antibodies of the invention (e.g., testing of dosages and time courses of administration).

Another embodiment is a method for inhibiting (i.e. reducing) activity of a targeted Aβ form in a subject suffering from an amyloidosis, such as Alzheimer's disease or Down syndrome.

A disorder in which activity of a targeted Aβ form is detrimental includes diseases and other disorders in which the presence of a targeted Aβ form in a subject suffering from the disorder has been shown to be or is suspected of being either responsible for the pathophysiology of the disorder or a factor that contributes to a worsening of the disorder. Accordingly, a disorder in which activity of a targeted Aβ form is detrimental is a disorder in which inhibition (i.e. reduction) of the activity said Aβ form is expected to alleviate some or all of the symptoms and/or progression of the disorder. Such disorders may be evidenced, for example, by an increase in the concentration of a targeted Aβ form in a biological fluid of a subject suffering from the disorder (e.g., an increase in the concentration of the targeted Aβ form in serum, brain tissue, plasma, cerebrospinal fluid, etc. of the subject), which can be detected, for example, using an anti-Aβ(20-42) globulomer antibody and/or antibody against any other targeted Aβ form as described above or any antibody to any Aβ form that comprises the globulomer epitope with which the antibodies of the present invention are reactive. Non-limiting examples of disorders that can be treated with the antibodies of the invention include those disorders disclosed herein and those discussed in the section below pertaining to pharmaceutical compositions of the antibodies of the invention.

In still yet another embodiment, the present invention relates to a method for preventing the progression (e.g., worsening) of a disease condition described herein. The method comprises administering to the subject in need of treatment thereof (e.g., a mammal, such as a human) a therapeutically effective amount of any of the binding proteins or antibodies as described herein. Alternatively, the method comprises administering to the subject a therapeutically effective amount of any of the proteins as described herein, in combination with a therapeutically effective amount of at least one therapeutic agent.

In the above described methods for preventing the development or progression of a disorder described herein one or more biomarkers, diagnostic tests or combination of biomarkers and diagnostic tests known to those skilled the art can be used to determine whether or not (1) a subject is at risk of developing one or more of the disorders described herein; or (2) the disorders described herein in the subject previously diagnosed with one or more of the aforementioned disorders is progressing (e.g., worsening).

One or more biomarkers, diagnostic tests or combinations of biomarkers and diagnostic tests known in the art can be used to identify subjects who are at risk of developing a disorder described herein. Likewise, one or more biomarkers, diagnostic tests or combinations of biomarkers and diagnostic tests known in the art can be used to determine the progression of the disease or condition of subjects who have been identified as suffering from a disorder described herein. For example, one or more biological markers, neuroimaging markers or combination of biological or neuroimaging markers (e.g., MRI, etc.) can be used to identify subjects at risk of developing Alzheimer's disease or, for those subjects identified as suffering from Alzheimer's disease, the progression of the disease. Biological markers that can be examined include, but are not limited to, beta-amyloid$_{1-42}$, tau, phosphorylated tau (ptau), plasma Aβ antibodies, α-antichymotrypsin, amyloid precursor protein, APP isoform ratio in platelets, β-secretase (also known as BACE), CD59, 8-hydroxy-deoxyguanine, glutamine synthetase, glial fibrillary acidic protein (GFAP), antibodies to GFAP, interleukin-6-receptor complex, kallikrein, melanotransferrin, neurofilament proteins, nitrotyrosine, oxysterols, sulphatides, synaptic markers, S100β, NPS, plasma signaling proteins, etc., or any combinations thereof (See, Shaw, L., et al., *Nature Reviews* 2007, 6, 295-303. Borroni, B., et al., *Current Med. Chem.* 2007, 14, 1171-1178. Phillips, K., et al., *Nature Reviews* 2006, 5 463-469. Bouwman, F. H., et al., *Neurology* 2007, 69, 1006-1011; Ray, S., et al., *Nature Medicine* 2007, 13(11), 1359-1362. Cummings, J., et al., *Neurology* 2007, 69, 1622-1634.).

E. Pharmaceutical Compositions

The invention also provides pharmaceutical compositions comprising an antibody of the invention and a pharmaceutically acceptable carrier. The pharmaceutical compositions comprising antibodies of the invention are for use in, but not limited to, diagnosing, detecting, or monitoring a disorder, in preventing, treating, managing, or ameliorating of a disorder or one or more symptoms thereof, and/or in research. In a specific embodiment, a composition comprises one or more antibodies of the invention. In another embodiment, the pharmaceutical composition comprises one or more antibodies of the invention and one or more prophylactic or therapeutic agents other than antibodies of the invention for treating a disorder in which activity of a targeted Aβ form is detrimental. In a further embodiment, the prophylactic or therapeutic agents are known to be useful for, or have been, or are currently being used in the prevention, treatment, management, or amelioration of a disorder, or one or more symptoms thereof. In accordance with these embodiments, the composition may further comprise of a carrier, diluent or excipient.

The antibodies of the invention can be incorporated into pharmaceutical compositions suitable for administration to a subject. Typically, the pharmaceutical composition comprises an antibody of the invention and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the antibody.

In a further embodiment, the pharmaceutical composition comprises at least one additional therapeutic agent for treating a disorder as disclosed herein.

Various delivery systems are known and can be used to administer one or more antibodies of the invention or the combination of one or more antibodies of the invention and a prophylactic agent or therapeutic agent useful for preventing, managing, treating, or ameliorating a disorder or one or more symptoms thereof, e.g., encapsulation in liposomes, microparticles, microcapsules, recombinant cells capable of expressing the antibody or antibody fragment, receptor-mediated endocytosis (see, e.g., Wu and Wu, J. Biol. Chem. 262:4429-4432 (1987)), construction of a nucleic acid as part of a retroviral or other vector, etc. Methods of administering a prophylactic or therapeutic agent of the invention include, but are not limited to, parenteral administration (e.g., intradermal, intramuscular, intraperitoneal, intravenous and subcutaneous), epidurala administration, intratumoral administration, and mucosal administration (e.g., intranasal and oral routes). In addition, pulmonary administration can be employed, e.g., by use of an inhaler or nebulizer, and formulation with an aerosolizing agent. See, e.g., U.S. Pat. Nos. 6,019,968, 5,985,320, 5,985,309, 5,934,272, 5,874,064, 5,855,913, 5,290,540, and 4,880,078; and PCT Publication Nos. WO 92/19244, WO97/32572, WO97/44013, WO98/31346, and WO99/66903, each of which is incorporated herein by reference their entireties. In one embodiment, an antibody of the invention, combination therapy, or a composition of the invention is administered using Alkermes AIR® pulmonary drug delivery technology (Alkermes, Inc., Cambridge, Mass.). In a specific embodiment, prophylactic or therapeutic agents of the invention are administered intramuscularly, intravenously, intratumorally, orally, intranasally, pulmonary, or subcutaneously. The prophylactic or therapeutic agents may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

In a specific embodiment, it may be desirable to administer the antibodies of the invention locally to the area in need of treatment; this may be achieved by, for example, and not by way of limitation, local infusion, by injection, or by means of an implant, said implant being of a porous or non-porous material, including membranes and matrices, such as sialastic membranes, polymers, fibrous matrices (e.g., Tissuel®), or collagen matrices. In one embodiment, an effective amount of one or more antibodies of the invention is administered locally to the affected area to a subject to prevent, treat, manage, and/or ameliorate a disorder or a symptom thereof. In another embodiment, an effective amount of one or more antibodies of the invention is administered locally to the affected area in combination with an effective amount of one or more therapies (e.g., one or more prophylactic or therapeutic agents) other than an antibody of the invention of a subject to prevent, treat, manage, and/or ameliorate a disorder or one or more symptoms thereof.

In another embodiment, the antibody can be delivered in a controlled release or sustained release system. In one embodiment, a pump may be used to achieve controlled or sustained release (see Langer, supra; Sefton, 1987, CRC Crit. Ref. Biomed. Eng. 14:20; Buchwald et al., 1980, Surgery 88:507; Saudek et al., 1989, N. Engl. J. Med. 321:574). In another embodiment, polymeric materials can be used to achieve controlled or sustained release of the therapies of the invention (see e.g., Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, NY (1984); Ranger and Peppas, 1983, J., Macromol. Sci. Rev. Macromol. Chem. 23:61; see also Levy et al., 1985, Science 228:190; During et al., 1989, Ann. Neurol. 25:351; Howard et al., 1989, J. Neurosurg. 7 1:105); U.S. Pat. No. 5,679,377; U.S. Pat. No. 5,916,597; U. S. Pat. No. 5,912,015; U.S. Pat. No. 5,989,463; U.S. Pat. No. 5,128,326; PCT Publication No. WO99/15154; and PCT Publication No. WO99/20253. Examples of polymers used in sustained release formulations include, but are not limited to, poly(2-hydroxy ethyl methacrylate), poly(methyl methacrylate), poly(acrylic acid), poly(ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. In a particular embodiment, the polymer used in a sustained release formulation is inert, free of leachable impurities, stable on storage, sterile, and biodegradable. In yet another embodiment, a controlled or sustained release system can be placed in proximity of the prophylactic or therapeutic target, thus requiring only a fraction of the systemic dose (see, e.g., Goodson, in Medical Applications of Controlled Release, supra, vol. 2, pp. 115-138 (1984)).

Controlled release systems are discussed in the review by Langer (1990, Science 249:1527-1533). Any technique known to one of skill in the art can be used to produce sustained release formulations comprising one or more antibodies of the invention. See, e.g., U.S. Pat. No. 4,526,938, PCT publication WO91/05548, PCT publication WO96/20698, Ning et al., 1996, "Intratumoral Radioimmunotheraphy of a Human Colon Cancer Xenograft Using a Sustained-Release Gel," Radiotherapy & Oncology 39:179-189, Song et al., 1995, "Antibody Mediated Lung Targeting of Long-Circulating Emulsions," PDA Journal of Pharmaceutical Science & Technology 50:372-397, Cleek et al., 1997, "Biodegradable Polymeric Carriers for a bFGF Antibody for Cardiovascular Application," Pro. Int'l. Symp. Control. Rel. Bioact. Mater. 24:853-854, and Lam et al., 1997, "Microencapsulation of Recombinant Humanized Monoclonal Antibody for Local Delivery," Proc. Int'l. Symp. Control Rel. Bioact. Mater. 24:759-760, each of which is incorporated herein by reference in their entireties.

In a specific embodiment, where the composition of the invention is a nucleic acid encoding an antibody, the nucleic acid can be administered in vivo to promote expression of its encoded antibody, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see, e.g., Joliot et al., 1991, Proc. Natl. Acad. Sci. USA 88:1864-1868). Alternatively, a nucleic acid can be introduced intracellularly and incorporated within host cell DNA for expression by homologous recombination.

A pharmaceutical composition of the invention is formulated to be compatible with its intended route of administration. Examples of routes of administration include, but are not limited to, parenteral, e.g., intravenous, intradermal, subcutaneous, oral, intranasal (e.g., inhalation), transdermal (e.g., topical), transmucosal, and rectal administration. In a specific embodiment, the composition is formulated in accordance with routine procedures as a pharmaceutical composition adapted for intravenous, subcutaneous, intramuscular, oral, intranasal, or topical administration to human beings. Typically, compositions for intravenous administration are solutions in sterile isotonic aqueous buffer. Where necessary, the composition may also include a solubilizing agent and a local anesthetic such as lignocamne to ease pain at the site of the injection.

If the compositions of the invention are to be administered topically, the compositions can be formulated in the form of an ointment, cream, transdermal patch, lotion, gel, shampoo, spray, aerosol, solution, emulsion, or other form well-known to one of skill in the art. See, e.g., Remington's Pharmaceutical Sciences and Introduction to Pharmaceutical Dosage Forms, 19$^{th}$ ed., Mack Pub. Co., Easton, Pa. (1995). For non-sprayable topical dosage forms, viscous to semi-solid or solid forms comprising a carrier or one or more excipients compatible with topical application and having a dynamic viscosity greater than water are typically employed. Suitable formulations include, without limitation, solutions, suspensions, emulsions, creams, ointments, powders, liniments, salves, and the like, which are, if desired, sterilized or mixed with auxiliary agents (e.g., preservatives, stabilizers, wetting agents, buffers, or salts) for influencing various properties, such as, for example, osmotic pressure. Other suitable topical dosage forms include sprayable aerosol preparations wherein the active ingredient, for example in combination with a solid or liquid inert carrier, is packaged in a mixture with a pressurized volatile (e.g., a gaseous propellant, such as freon) or in a squeeze bottle. Moisturizers or humectants can also be added to pharmaceutical compositions and dosage forms if desired. Examples of such additional ingredients are well-known in the art.

If the method of the invention comprises intranasal administration of a composition, the composition can be formulated in an aerosol form, spray, mist or in the form of drops. In particular, prophylactic or therapeutic agents for use according to the present invention can be conveniently delivered in the form of an aerosol spray presentation from pressurized packs or a nebuliser, with the use of a suitable propellant (e.g., dichlorodifluoromethane, trichlorofluoromethane, dichlorotetrafluoroethane, carbon dioxide or other suitable gas). In the case of a pressurized aerosol the dosage unit may be determined by providing a valve to deliver a metered amount. Capsules and cartridges (composed of, e.g., gelatin) for use in an inhaler or insufflator may be formulated containing a powder mix of the compound and a suitable powder base such as lactose or starch.

If the method of the invention comprises oral administration, compositions can be formulated orally in the form of tablets, capsules, cachets, gelcaps, solutions, suspensions, and the like. Tablets or capsules can be prepared by conventional means with pharmaceutically acceptable excipients such as binding agents (e.g., pregelatinised maize starch, polyvinylpyrrolidone, or hydroxypropyl methylcellulose); fillers (e.g., lactose, microcrystalline cellulose, or calcium hydrogen phosphate); lubricants (e.g., magnesium stearate, talc, or silica); disintegrants (e.g., potato starch or sodium starch glycolate); or wetting agents (e.g., sodium lauryl sulphate). The tablets may be coated by methods well-known in the art. Liquid preparations for oral administration may take the form of, but not limited to, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives, or hydrogenated edible fats); emulsifying agents (e.g., lecithin or acacia); non-aqueous vehicles (e.g., almond oil, oily esters, ethyl alcohol, or fractionated vegetable oils); and preservatives (e.g., methyl or propyl-p-hydroxybenzoates or sorbic acid). The preparations may also contain buffer salts, flavoring, coloring, and sweetening agents as appropriate. Preparations for oral administration may be suitably formulated for slow release, controlled release, or sustained release of a prophylactic or therapeutic agent(s).

The method of the invention may comprise pulmonary administration, e.g., by use of an inhaler or nebulizer, of a composition formulated with an aerosolizing agent. See, e.g., U.S. Pat. Nos. 6,019,968, 5,985,320, 5,985,309, 5,934,272, 5,874,064, 5,855,913, 5,290,540, and 4,880,078; and PCT Publication Nos. WO 92/19244, WO 97/32572, WO 97/44013, WO 98/31346, and WO 99/66903, each of which is incorporated herein by reference their entireties. In a specific embodiment, an antibody of the invention, combination therapy, and/or composition of the invention is administered using Alkermes AIR® pulmonary drug delivery technology (Alkermes, Inc., Cambridge, Mass.).

The method of the invention may comprise administration of a composition formulated for parenteral administration by injection (e.g., by bolus injection or continuous infusion). Formulations for injection may be presented in unit dosage form (e.g., in ampoules or in multi-dose containers) with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle (e.g., sterile pyrogen-free water) before use. The methods of the invention may additionally comprise of administration of compositions formulated as depot preparations. Such long acting formulations may be administered by implantation (e.g., subcutaneously or intramuscularly) or by intramuscular injection. Thus, for example, the compositions may be formulated with suitable polymeric or hydrophobic materials (e.g., as an emulsion in an acceptable oil) or ion exchange resins, or as sparingly soluble derivatives (e.g., as a sparingly soluble salt).

The methods of the invention encompass administration of compositions formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

Generally, the ingredients of compositions are supplied either separately or mixed together in unit dosage form, for example, as a dry lyophilized powder or water free concentrate in a hermetically sealed container such as an ampoule or sachette indicating the quantity of active agent. Where the mode of administration is infusion, composition can be dispensed with an infusion bottle containing sterile pharmaceutical grade water or saline. Where the mode of administration is by injection, an ampoule of sterile water for injection or saline can be provided so that the ingredients may be mixed prior to administration.

In particular, the invention also provides that one or more of the antibodies, or pharmaceutical compositions, of the invention is packaged in a hermetically sealed container such as an ampoule or sachette indicating the quantity of the antibody. In one embodiment, one or more of the antibodies, or pharmaceutical compositions of the invention is supplied as a dry sterilized lyophilized powder or water free concentrate in a hermetically sealed container and can be reconstituted (e.g., with water or saline) to the appropriate concentration for administration to a subject. In one embodiment, one or more of the antibodies or pharmaceutical compositions of the invention is supplied as a dry sterile lyophilized powder in a hermetically sealed container at a unit dosage of at least 5 mg, for example at least 10 mg, at least 15 mg, at least 25 mg, at least 35 mg, at least 45 mg, at least 50 mg, at least 75 mg, or at least 100 mg. The lyophilized antibodies or pharmaceutical compositions of the invention should be stored at between 2° C. and 8° C. in its original container and the antibodies, or pharmaceutical compositions of the invention should be administered within 1 week, for example within 5 days, within 72 hours, within 48 hours, within 24 hours, within 12 hours, within 6 hours, within 5 hours, within 3 hours, or within 1 hour after being reconstituted. In an alternative embodiment, one or more of the antibodies or pharmaceutical compositions of the invention is supplied in liquid form in a hermetically sealed container indicating the quantity and concentration of the antibody. In a further embodiment, the liquid form of the administered composition is supplied in a hermetically sealed container at least 0.25 mg/ml, for example at least 0.5 mg/ml, at least 1 mg/ml, at least 2.5 mg/ml, at least 5 mg/ml, at least 8 mg/ml, at least 10 mg/ml, at least 15 mg/kg, at least 25 mg/ml, at least 50 mg/ml, at least 75 mg/ml or at least 100 mg/ml. The liquid form should be stored at between 2° C. and 8° C. in its original container.

The antibodies of the invention can be incorporated into a pharmaceutical composition suitable for parenteral administration. In one aspect, antibodies will be prepared as an injectable solution containing 0.1-250 mg/ml antibody. The injectable solution can be composed of either a liquid or lyophilized dosage form in a flint or amber vial, ampule or pre-filled syringe. The buffer can be L-histidine (1-50 mM), optimally 5-10 mM, at pH 5.0 to 7.0 (optimally pH 6.0). Other suitable buffers include but are not limited to, sodium succinate, sodium citrate, sodium phosphate or potassium phosphate. Sodium chloride can be used to modify the toxicity of the solution at a concentration of 0-300 mM (optimally 150 mM for a liquid dosage form). Cryoprotectants can be included for a lyophilized dosage form, principally 0-10% sucrose (optimally 0.5-1.0%). Other suitable cryoprotectants include trehalose and lactose. Bulking agents can be included for a lyophilized dosage form, principally 1-10% mannitol (optimally 2-4%). Stabilizers can be used in both liquid and lyophilized dosage forms, principally 1-50 mM L-Methionine (optimally 5-10 mM). Other suitable bulking agents include glycine, arginine, can be included as 0-0.05% polysorbate-80 (optimally 0.005-0.01%). Additional surfactants include but are not limited to polysorbate 20 and BRIJ surfactants. The pharmaceutical composition comprising the antibodies of the invention prepared as an injectable solution for parenteral administration, can further comprise an agent useful as an adjuvant, such as those used to increase the absorption, or dispersion of the antibody. A particularly useful adjuvant is hyaluronidase, such as Hylenex® (recombinant human hyaluronidase). Addition of hyaluronidase in the injectable solution improves human bioavailability following parenteral administration, particularly subcutaneous administration. It also allows for greater injection site volumes (i.e. greater than 1 ml) with less pain and discomfort, and minimum incidence of injection site reactions. (See International Appln. Publication No. WO 04/078140 and U.S. Patent Appln. Publication No. US2006104968, incorporated herein by reference.)

The compositions of this invention may be in a variety of forms. These include, for example, liquid, semi-solid and solid dosage forms, such as liquid solutions (e.g., injectable and infusible solutions), dispersions or suspensions, tablets, pills, powders, liposomes and suppositories. The preferred form depends on the intended mode of administration and therapeutic application. Compositions can be in the form of injectable or infusible solutions, such as compositions similar to those used for passive immunization of humans with other antibodies. In one embodiment, the antibody is administered by intravenous infusion or injection. In another embodiment, the antibody is administered by intramuscular or subcutaneous injection.

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the active compound (i.e., a binding protein, e.g. an antibody, of the present invention) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile, lyophilized powders for the preparation of sterile injectable solutions, methods of preparation comprise vacuum drying and spray-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including, in the composition, an agent that delays absorption, for example, monostearate salts and gelatin.

The antibodies of the present invention can be administered by a variety of methods known in the art. For many therapeutic applications, the route/mode of administration may be subcutaneous injection, intravenous injection or infusion. As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Sustained and Controlled Release Drug Delivery Systems, J. R. Robinson, ed., Marcel Dekker, Inc., New York, 1978.

In certain embodiments, an antibody of the invention may be orally administered, for example, with an inert diluent or an assimilable edible carrier. The antibody (and other ingredients, if desired) may also be enclosed in a hard or soft shell gelatin capsule, compressed into tablets, or incorporated directly into the subject's diet. For oral therapeutic administration, the antibody may be incorporated with excipients and used in the form of ingestible tablets, buccal tablets, troches, capsules, elixirs, suspensions, syrups, wafers, and the like. To administer an antibody of the invention by other than parenteral administration, it may be necessary to coat the antibody with, or co-administer the antibody with, a material to prevent its inactivation.

Supplementary active compounds can also be incorporated into the compositions. In certain embodiments, an antibody of the invention is coformulated with and/or coadministered with one or more additional therapeutic agents that are useful for treating disorders or diseases described herein. For example, an anti-Aβ(20-42) globulomer antibody of the invention may be coformulated and/or coadministered with one or more additional antibodies that bind other targets (e.g., antibodies that bind other soluble antigens or that bind cell surface molecules). Furthermore, one or more antibodies of the invention may be used in combination with two or more of the foregoing therapeutic agents. Such combination therapies may advantageously utilize lower dosages of the administered therapeutic agents, thus avoiding possible toxicities or complications associated with the various monotherapies.

In certain embodiments, an antibody of the invention is linked to a half-life extending vehicle known in the art. Such vehicles include, but are not limited to, the Fc domain, polyethylene glycol, and dextran. Such vehicles are described, e.g., in U.S. application Ser. No. 09/428,082 and published PCT Application No. WO 99/25044, which are hereby incorporated by reference for any purpose.

In a specific embodiment, nucleic acid sequences comprising nucleotide sequences encoding an antibody of the invention are administered to treat, prevent, manage, or ameliorate a disorder or one or more symptoms thereof by way of gene therapy. Gene therapy refers to therapy performed by the administration to a subject of an expressed or expressible nucleic acid. In this embodiment of the invention, the nucleic acids produce their encoded antibody of the invention that mediates a prophylactic or therapeutic effect.

Any of the methods for gene therapy available in the art can be used according to the present invention. For general reviews of the methods of gene therapy, see Goldspiel et al., 1993, Clinical Pharmacy 12:488-505; Wu and Wu, 1991, Biotherapy 3:87-95; Tolstoshev, 1993, Ann. Rev. Pharmacol. Toxicol. 32:573-596; Mulligan, Science 260:926-932 (1993); and Morgan and Anderson, 1993, Ann. Rev. Biochem. 62:191-217; May, 1993, TIBTECH 11(5):155-215. Methods commonly known in the art of recombinant DNA technology which can be used are described in Ausubel et al. (eds.), Current Protocols in Molecular Biology, John Wiley & Sons, NY (1993); and Kriegler, Gene Transfer and Expression, A Laboratory Manual, Stockton Press, NY (1990). Detailed description of various methods of gene therapy are disclosed in US20050042664 A1 which is incorporated herein by reference.

Antibodies of the invention can be used alone or in combination to treat diseases such as Alzheimer's disease, Down syndrome, dementia, Parkinson's disease, or any other disease or condition associated with a build up of amyloid beta protein within the brain. The antibodies of the present invention may be used to treat "conformational diseases". Such diseases arise from secondary to tertiary structural changes within constituent proteins with subsequent aggregation of the altered proteins (Hayden et al., JOP. J Pancreas 2005; 6(4):287-302). In particular, the antibodies of the present invention may be used to treat one or more of the following conformational diseases: Alpha1-antitrypsin-deficiency, C1-inhibitor deficiency angioedema, Antithrombin deficiency thromboembolic disease, Kuru, Creutzfeld-Jacob disease/scrapie, Bovine spongiform encephalopathy, Gerstmann-Straussler-Scheinker disease, Fatal familial insomnia, Huntington's disease, Spinocerebellar ataxia, Machado-Joseph atrophy, Dentato-rubro-pallidoluysian atrophy, Frontotemporal dementia, Sickle cell anemia, Unstable hemoglobin inclusion-body hemolysis, Drug-induced inclusion body hemolysis, Parkinson's disease, Systemic AL amyloidosis, Nodular AL amyloidosis, Systemic AA amyloidosis, Prostatic amyloidosis, Hemodialysis amyloidosis, Hereditary (Icelandic) cerebral angiopathy, Huntington's disease, Familial visceral amyloidosis, Familial visceral polyneuropathy, Familial visceral amyloidosis, Senile systemic amyloidosis, Familial amyloid neuropathy, Familial cardiac amyloidosis, Alzheimer's disease, Down syndrome, Medullary carcinoma thyroid and Type 2 diabetes mellitus (T2DM) Preferably, the antibodies of the present invention may be utilized to treat an amyloidosis, for example, Alzheimer's disease and Down syndrome.

It should be understood that the antibodies of the invention can be used alone or in combination with one or more additional agents, e.g., a therapeutic agent (for example, a small molecule or biologic), said additional agent being selected by the skilled artisan for its intended purpose. For example, the additional therapeutic agent can be a "cognitive enhancing drug," which is a drug that improves impaired human cognitive abilities of the brain (namely, thinking, learning, and memory). Cognitive enhancing drugs work by altering the availability of neurochemicals (e.g., neurotransmitters, enzymes, and hormones), by improving oxygen supply, by stimulating nerve growth, or by inhibiting nerve damage. Examples of cognitive enhancing drugs include a compound that increases the activity of acetylcholine such as, but not limited to, an acetylcholine receptor agonist (e.g., a nicotinic α-7 receptor agonist or allosteric modulator, an α4β2 nicotinic receptor agonist or allosteric modulators), an acetylcholinesterase inhibitor (e.g., donepezil, rivastigmine, and galantamine), a butyrylcholinesterase inhibitor, an N-methyl-D-aspartate (NMDA) receptor antagonist (e.g., memantine), an activity-dependent neuroprotective protein (ADNP) agonist, a serotonin 5-HT1A receptor agonist (e.g., xaliproden), a 5-HT$_4$ receptor agonist, a 5-HT$_6$ receptor antagonist, a serotonin 1A receptor antagonist, a histamine H$_3$ receptor antagonist, a calpain inhibitor, a vascular endothelial growth factor (VEGF) protein or agonist, a trophic growth factor, an anti-apoptotic compound, an AMPA-type glutamate receptor activator, a L-type or N-type calcium channel blocker or modulator, a potassium channel blocker, a hypoxia inducible factor (HIF) activator, a HIF prolyl 4-hydroxylase inhibitor, an anti-inflammatory agent, an inhibitor of amyloid Aβ peptide or amyloid plaque, an inhibitor of tau hyperphosphorylation, a phosphodiesterase 5 inhibitor (e.g., tadalafil, sildenafil), a phosphodiesterase 4 inhibitor, a monoamine oxidase inhibitor, or pharmaceutically acceptable salt thereof. Specific examples of such cognitive enhancing drugs include, but are not limited to, cholinesterase inhibitors such as donepezil (Aricept®), rivastigmine (Exelon®), galanthamine (Reminyl®), N-methyl-D-aspartate antagonists such as memantine (Namenda®). At least one cognitive enhancing drug can be administered simultaneously with the antibodies of the present invention or sequentially with the antibodies of the present invention (and in any order) including those agents currently recognized, or in the future being recognized, as useful to treat the disease or condition being treated by an antibody of the present invention). Additionally, it is believed that the combinations described herein may have additive or synergistic effects when used in the above-described treatment. The additional agent also can be an agent that imparts a beneficial attribute to the therapeutic composition, e.g., an agent that affects the viscosity of the composition.

It should further be understood that the combinations which are to be included within this invention are those combinations useful for their intended purpose. The agents set forth above are illustrative for purposes and not intended to be limited. The combinations, which are part of this invention, can comprise an antibody of the present invention and at least one additional agent selected from the lists below. The combination can also include more than one additional agent, e.g., two or three additional agents if the combination is such that the formed composition can perform its intended function.

The pharmaceutical compositions of the invention may include a "therapeutically effective amount" or a "prophylactically effective amount" of an antibody of the invention. A "therapeutically effective amount" refers to an amount effective, at dosages and for periods of time necessary, to achieve the desired therapeutic result. A therapeutically effective amount of the antibody may be determined by a person skilled in the art and may vary according to factors such as the disease state, age, sex, and weight of the individual, and the ability of the antibody to elicit a desired response in the individual. A therapeutically effective amount is also one in which any toxic or detrimental effects of the antibody are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic or prophylactic effect to be achieved, and (b) the limitations inherent in the art of compounding such an active compound for the treatment of sensitivity in individuals.

An exemplary, non-limiting range for a therapeutically or prophylactically effective amount of an antibody of the invention is 0.1-20 mg/kg, for example 1-10 mg/kg. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

It will be readily apparent to those skilled in the art that other suitable modifications and adaptations of the methods of the invention described herein are obvious and may be made using suitable equivalents without departing from the scope of the invention or the embodiments disclosed herein. Having now described the present invention in detail, the same will be more clearly understood by reference to the following examples, which are included for purposes of illustration only and are not intended to be limiting of the invention.

EXAMPLES

Example 1

Preparation of Globulomers a) Aβ(1-42) Globulomer:

The Aβ(1-42) synthetic peptide (H-1368, Bachem, Bubendorf, Switzerland) was suspended in 100% 1,1,1,3,3,3-hexafluoro-2-propanol (HFIP) at 6 mg/ml and incubated for complete solubilization under shaking at 37° C. for 1.5 h. The HFIP acts as a hydrogen-bond breaker and is used to eliminate pre-existing structural inhomogeneities in the Aβ peptide. HFIP was removed by evaporation in a SpeedVac and Aβ(1-42) resuspended at a concentration of 5 mM in dimethylsulfoxide and sonicated for 20 s. The HFIP-pre-treated Aβ(1-42) was diluted in phosphate-buffered saline (PBS) (20 mM NaH$_2$PO$_4$, 140 mM NaCl, pH 7.4) to 400 μM and ¹/₁₀ volume 2% sodium dodecyl sulfate (SDS) (in H$_2$O) added (final concentration of 0.2% SDS). An incubation for 6 h at 37° C. resulted in the 16/20-kDa Aβ(1-42) globulomer (short form for globular oligomer) intermediate. The 38/48-kDa Aβ(1-42) globulomer was generated by a further dilution with three volumes of H$_2$O and incubation for 18 h at 37° C. After centrifugation at 3000 g for 20 min the sample was concentrated by ultrafiltration (30-kDa cut-off), dialysed against 5 mM NaH$_2$PO$_4$, 35 mM NaCl, pH 7.4, centrifuged at 10,000 g for 10 min and the supernatant comprising the 38/48-kDa Aβ(1-42) globulomer withdrawn. As an alternative to dialysis the 38/48-kDa Aβ(1-42) globulomer could also be precipitated by a ninefold excess (v/v) of ice-cold methanol/acetic acid solution (33% methanol, 4% acetic acid) for 1 h at 4° C. The 38/48-kDa Aβ(1-42) globulomer is then pelleted (10 min at 16200 g), resuspended in 5 mM NaH$_2$PO$_4$, 35 mM NaCl, pH 7.4, and the pH adjusted to 7.4.

b) Aβ(20-42) Globulomer:

1.59 ml of Aβ(1-42) globulomer preparation prepared according to Example 1a were admixed with 38 ml of buffer (50 mM MES/NaOH, pH 7.4) and 200 µl of a 1 mg/ml thermolysin solution (Roche) in water. The reaction mixture was stirred at RT for 20 h. Then, 80 µl of a 100 mM EDTA solution, pH 7.4, in water were added and the mixture was furthermore adjusted to an SDS content of 0.01% with 400 µl of a 1% strength SDS solution. The reaction mixture was concentrated to approximately 1 ml via a 15 ml 30 kDa Centriprep tube. The concentrate was admixed with 9 ml of buffer (50 mM MES/NaOH, 0.02% SDS, pH 7.4) and again concentrated to 1 ml. The concentrate was dialyzed at 6° C. against 1 l of buffer (5 mM sodium phosphate, 35 mM NaCl) in a dialysis tube for 16 h. The dialysate was adjusted to an SDS content of 0.1% with a 2% strength SDS solution in water. The sample was centrifuged at 10,000 g for 10 min and the Aβ(20-42) globulomer supernatant was withdrawn.

c) Aβ(12-42) Globulomer:

2 ml of an Aβ(1-42) globulomer preparation prepared according to Example 1a were admixed with 38 ml buffer (5 mM sodium phosphate, 35 mM sodium chloride, pH 7.4) and 150 µl of a 1 mg/ml GluC endoproteinase (Roche) in water. The reaction mixture was stirred for 6 h at RT, and a further 150 µl of a 1 mg/ml GluC endoproteinase (Roche) in water were subsequently added. The reaction mixture was stirred at RT for another 16 h, followed by addition of 8 µl of a 5 M DIFP solution. The reaction mixture was concentrated to approximately 1 ml via a 15 ml 30 kDa Centriprep tube. The concentrate was admixed with 9 ml of buffer (5 mM sodium phosphate, 35 mM sodium chloride, pH 7.4) and again concentrated to 1 ml. The concentrate was dialyzed at 6° C. against 1 l of buffer (5 mM sodium phosphate, 35 mM NaCl) in a dialysis tube for 16 h. The dialysate was adjusted to an SDS content of 0.1% with a 1% strength SDS solution in water. The sample was centrifuged at 10,000 g for 10 min and the Aβ(12-42) globulomer supernatant was withdrawn.

d) Cross-Linked Aβ(1-42) Globulomer:

The Aβ(1-42) synthetic peptide (H-1368, Bachem, Bubendorf, Switzerland) was suspeneded in 100% 1,1,1,3,3,3-hexafluoro-2-propanol (HFIP) at 6 mg/ml and incubated for complete solubilization under shaking at 37° C. for 1.5 h. The HFIP acts as a hydrogen-bond breaker and was used to eliminate pre-existing structural inhomogeneities in the Aβ peptide. HFIP was removed by evaporation by a SpeedVac and Aβ(12-42) globulomer Aβ(1-42) resuspended at a concentration of 5 mM in dimethylsulfoxide and sonicated for 20 s. The HFIP-pre-treated Aβ(1-42) was diluted in PBS (20 mM NaH$_2$PO$_4$, 140 mM NaCl, pH 7.4) to 400 µM and 1/10 vol. 2% SDS (in water) added (final conc. Of 0.2% SDS). An incubation for 6 h at 37° C. resulted in the 16/20-kDa Aβ(1-42) globulomer (short form for globulomer oligomer) intermediate. The 38/48-kDa Aβ(1-42) globulomer was generated by a further dilution with 3 volumes of water and incubation for 18 h at 37° C. Cross-linking of the 38/48-kDa Aβ(1-42) globulomer was now performed by incubation with 1 mM glutaraldehyde for 2 h at 21° C. room temperature followed by ethanolamine (5 mM) treatment for 30 min at room temperature.

Example 2

Generation, Isolation and Characterization of Humanized Anti-Aβ(20-42) Globulomer Antibodies Example 2.1

Selection of Human Antibody Frameworks

Selection of human antibody frameworks was based on similarity of canonical structures and amino acid sequence homology of human antibodies. Further, the retention of amino acid residues which support loop structures and VH/VL interface as well as the retention of amino acid residues of the Vernier zone was taken into account when identifying suitable acceptor VL and VH framework sequences based on amino acid sequence homology of human VH and Vκ germline sequences. Moreover, immunogenicity of VH and VL sequences resulting from grafting 4D10 CDRs into potentially suitable acceptor VL and VH framework sequences was evaluated in silico based on the predicted affinity of overlapping peptides to a variety of MHC class I and/or MHC class II alleles. VH and VL were adapted to the consensus of the respective VH or VL family to further minimize potential immunogenicity. Selected backmutations to murine amino acid residues were performed to retain amino acids which support loop structures and VH/VL interface. The frequencies of these backmutations in corresponding pools of naturally occuring human VH or VL sequences having the respective VH or VL germline gene were determined by amino acid sequence alignments. The VH and VL sequences resulting from the considerations described above were checked for potential N-linked glycosylation sites (NXS or NXT, wherein X is any amino acid except P).

Example 2.2

Humanized of Murine Anti-Aβ(20-42) Globulomer Antibody

4D10hum_VH.1z (SEQ ID NO:4): The heavy chain CDR sequences from the murine anti-Aβ(20-42) globulomer antibody 4D10 described in Table 4 were grafted into an acceptor framework of human VH3-53 and JH6 sequences.

4D10hum_VH.1 (SEQ ID NO:5): The heavy chain CDR sequences from the murine anti-Aβ(20-42) globulomer antibody 4D10 described in Table 4 were grafted into an acceptor framework of human VH3-53 and JH6 sequences comprising VH3 consensus change I12V.

4D10hum_VH.1a (SEQ ID NO:6): The heavy chain CDR sequences from the murine anti-Aβ(20-42) globulomer antibody 4D10 described in Table 4 were grafted into an acceptor framework of human VH3-53 and JH6 sequences comprising VH3 consensus change I12V and framework backmutations A24V, V29L, V48L, S49G, F67L, R71K, N76S and L78V.

4D10hum_VH.1b (SEQ ID NO:7): The heavy chain CDR sequences from the murine anti-Aβ(20-42) globulomer antibody 4D10 described in Table 4 were grafted into an acceptor framework of human VH3-53 and JH6 sequences comprising backmutations V29L and R71K.

4D10hum_VH.2z (SEQ ID NO:8): The heavy chain CDR sequences from the murine anti-Aβ(20-42) globulomer antibody 4D10 described in Table 4 were grafted into an acceptor framework of human VH4-59 and JH6 sequences.

4D10hum_VH.2 (SEQ ID NO:9): The heavy chain CDR sequences from the murine anti-Aβ(20-42) globulomer antibody 4D10 described in Table 4 were grafted into an acceptor framework of human VH4-59 and JH6 sequences comprising a Q1E change to prevent N-terminal pyroglutamate formation.

4D10hum_VH.2a (SEQ ID NO:10): The heavy chain CDR sequences from the murine anti-Aβ(20-42) globulomer antibody 4D10 described in Table 4 were grafted into an acceptor framework of human VH4-59 and JH6 sequences comprising a Q1E change to prevent N-terminal pyroglutamate formation, and framework backmutations G27F, I29L, I37V, I48L, V67L, V71K, N76S and F78V.

4D10hum_VH.2b (SEQ ID NO:11): The heavy chain CDR sequences from the murine anti-Aβ(20-42) globulomer antibody 4D10 described in Table 4 were grafted into an acceptor framework of human VH4-59 and JH6 sequences comprising a Q1E change to prevent N-terminal pyroglutamate formation, and framework backmutations G27F, I29L and V71K.

4D10hum_Vκ.1z (SEQ ID NO:12): The light chain CDR sequences from the murine anti-Aβ(20-42) globulomer antibody 4D10 described in Table 4 were grafted into an acceptor framework of human Vκ A17/2-30 and Jκ2 sequences.

4D10hum_Vκ.1 (SEQ ID NO:13): The light chain CDR sequences from the murine anti-Aβ(20-42) globulomer antibody 4D10 described in Table 4 were grafted into an acceptor framework of human Vκ A17/2-30 and Jκ2 sequences comprising Vκ2 consensus changes S7T, L15P, Q37L, R39K and R45Q.

4D10hum_Vκ.1a (SEQ ID NO:14): The light chain CDR sequences from the murine anti-Aβ(20-42) globulomer antibody 4D10 described in Table 4 were grafted into an acceptor framework of human Vκ A17/2-30 and Jκ2 sequences comprising Vκ2 consensus changes S7T, L15P, Q37L, R39K and R45Q, and framework backmutation F36L which affects the VL/VH interface.

4D10hum_Vκ.1b (SEQ ID NO:15): The light chain CDR sequences from the murine anti-Aβ(20-42) globulomer antibody 4D10 described in Table 4 were grafted into an acceptor framework of human Vκ A17/2-30 and Jκ2 sequences comprising Vκ2 consensus changes S7T and Q37L.

4D10hum_Vκ.1c (SEQ ID NO:16): The light chain CDR sequences from the murine anti-Aβ(20-42) globulomer antibody 4D10 described in Table 4 were grafted into an acceptor framework of human Vκ A17/2-30 and Jκ2 sequences comprising Vκ2 consensus changes S7T, Q37L and R39K.

Some of said VH and Vκ back-mutations, consensus changes or the Q1E mutation in 4D10hum_VH.2, 4D10hum_VH.2a or 4D10hum_VH.2b may be removed during a subsequent affinity maturation.

Example 2.3

Construction of Humanized Antibodies

In silico constructed humanized antibodies described above will be constructed de novo using oligonucleotides. For each variable region cDNA, 6 oligonucleotides of 60-80 nucleotides each will be designed to overlap each other by 20 nucleotides at the 5' and/or 3' end of each oligonucleotide. In an annealing reaction, all 6 oligos will be combined, boiled, and annealed in the presence of dNTPs. Then DNA polymerase I, Large (Klenow) fragment (New England Biolabs #M0210, Beverley, Mass.) will be added to fill-in the approximately 40 bp gaps between the overlapping oligonucleotides. PCR will then be performed to amplify the entire variable region gene using two outermost primers containing overhanging sequences complementary to the multiple cloning site in a modified pBOS vector (Mizushima, S. and Nagata, S., (1990) Nucleic acids Research Vol 18, No. 17)). The PCR products derived from each cDNA assembly will be separated on an agarose gel and the band corresponding to the predicted variable region cDNA size will be excised and purified. The variable heavy region will be inserted in-frame onto a cDNA fragment encoding the human IgG1 constant region containing 2 hinge-region amino acid mutations by homologous recombination in bacteria. These mutations are a leucine to alanine change at position 234 (EU numbering) and a leucine to alanine change at position 235 (Lund et al., 1991, J. Immunol., 147:2657). The variable light chain region will be inserted in-frame with the human kappa constant region by homologous recombination. Bacterial colonies will be isolated and plasmid DNA extracted; cDNA inserts will be sequenced in their entirety. Correct humanized heavy and light chains corresponding to each antibody will be co-transfected into COS cells to transiently produce full-length humanized anti-Aβ globulomer antibodies. Cell supernatants containing recombinant chimeric antibody will be purified by Protein A Sepharose chromatography and bound antibody will be eluted by addition of acid buffer. Antibodies will be neutralized and dialyzed into PBS. (Dieder Moechars et al J Biol Chem 274:6483-6492 (1999); Ausubel, F. M. et al. eds., Short Protocols In Molecular Biology (4th Ed. 1999) John Wiley & Sons, NY. (ISBN 0-471-32938-X); Lu and Weiner eds., Cloning and Expression Vectors for Gene Function Analysis (2001) BioTechniques Press. Westborough, Mass. 298 pp. (ISBN 1-881299-21-X); Kontermann and Dubel eds., Antibody Engineering (2001) Springer-Verlag. New York. 790 pp. (ISBN 3-540-41354-5); Old, R. W. & S. B. Primrose, Principles of Gene Manipulation: An Introduction To Genetic Engineering (3d Ed. 1985) Blackwell Scientific Publications, Boston. Studies in Microbiology; V.2:409 pp. (ISBN 0-632-01318-4); Sambrook, J. et al. eds., Molecular Cloning: A Laboratory Manual (2d Ed. 1989) Cold Spring Harbor Laboratory Press, NY. Vols. 1-3. (ISBN 0-87969-309-6); Winnacker, E. L. From Genes To Clones: Introduction To Gene Technology (1987) VCH Publishers, NY (translated by Horst Ibelgaufts). 634 pp. (ISBN 0-89573-614-4); all of which are incorporated by reference in their entirety).

Although a number of embodiments and features have been described above, it will be understood by those skilled in the art that modifications and variations of the described embodiments and features may be made without departing from the present disclosure or the invention as defined in the appended claims.

Example 2:4

Expression and Purification of Humanized Antibodies in HEK293 Cells

DNA constructs encoding an antibody heavy chain as set forth in SEQ ID NO:46; an antibody heavy chain as set forth in SET ID NO:47, and an antibody light chain construct encoding a polypeptide as set forth in SEQ ID NO:48 were prepared as described in example 2.3. After DNA confirmation by sequencing, all heavy chain and light chain DNA constructs were expanded in E. coli and DNA was purified using Qiagen Endo Free Plasmid Maxi Prep (cat #12362, QIAGEN) according to the manufacturer's protocol.

For expression of a monoclonal antibody 4D10hum #1, HEK293 (EBNA) cells were transiently cotransfected with plasmids encoding the heavy chain set forth in SEQ ID NO:46 and the light chain set forth in SEQ ID NO:48. For expression of a monoclonal antibody 4D10hum #2, HEK293 (EBNA) cells were transiently cotransfected with plasmids encoding the heavy chain set forth in SEQ ID NO:47 and the light chain set forth in SEQ ID NO:48. Before transfection, HEK293 (EBNA) cells were propagated in Freestyle 293 media (Invitrogen, Carlsbad Calif.) at a 0.5 l scale in culture flasks (2 L Corning Cat #431198) shaking in a $CO_2$ incubator (8% $CO_2$, 125 rpm, 37° C.). When the cell cultures reached a density of $1\times10^6$ cells/ml, cells were transfected by adding transfection complex. The transfection complex was prepared by first mixing 150 μg of the plasmid encoding the light chain, 100 μg of the plasmid encoding the heavy chain and 25 ml Freestyle medium, followed by the addition of 500 μl PEI solution (1 mg/ml (pH 7.0) linear 25 kDa polyethylenimine, Polysciences Cat #23966). The transfection complex was mixed by inversion and incubated at room temperature for 15 min prior to being added to the cell culture. After transfection, cultures continued to be grown in the $CO_2$ incubator (8% $CO_2$, 125 rpm, 37° C.). Twenty-four hours after transfection, the culture media were supplemented with 50 ml of a 5% Tryptone N1 solution (Organo Technie, La Courneuve France Cat #19553). Six days after transfection, the cells were pelleted by centrifugation (16,000 g, 30 min), the supernatant containing the expressed antibodies was sterile filtered (0.2 μm PES filter) and placed at 4° C. until initiation of the purification step. The expressed antibodies were purified from the supernatants by Protein A sepharose affinity chromatography using Pierce Thermo Scientific reagents and protocol according to manufacturer's instructions. The protein eluates were dialyzed against PBS (pH 7). The purified 4D10hum antibodies were spectrophotometrically quantified at 280 nm, and analyzed by mass spectrometry and size exclusion chromatography (SEC).

Example 2:5

Affinity Analysis of Humanized Antibodies

Interaction of the purified humanized antibodies 4D10hum #1 and 4D10hum #2 to Aβ(20-42) globulomer was evaluated by surface plasmon resonance (SPR) analysis using a BIAcore device. Goat anti-human IgG Fc (10,000 RU) was directly immobilized on a CM5 sensor chip by an amine coupling procedure according to the manufacturer's instructions (BIAcore). The respective 4D10hum antibody was captured on the goat anti-human IgG Fc coated surface of the chip by injecting 5.0 μl of a 1 μg/ml 4D10hum antibody solution at a flow rate of 10-15 μl/min. Interaction of soluble Aβ(20-42) globulomer with the 4D10hum antibody on the sensor chip was examined by injecting globulomer solutions (concentration range: 20-0.3125 nM) at a flow rate of 50 μl/min. The association rate was monitored for 5.0 min and the dissociation rate was monitored for 10 min. From the resulting sensorgrams the association rate constant ($k_{on}$), dissociation rate constant ($k_{off}$) and equilibrium dissociation constant ($K_D$) were determined using to the manufacturer's software and instructions. The kinetic and equilibrium constants determined for three different preparations of 4D10hum #1 and two different preparations of 4D10hum #2 are summarized in table 7. Table 7 also shows affinity data of antibodies #3, #4 and #5 having chimeric and humanized chains. The heavy chains of antibodies #4 and #5 are as in 4D10hum #1 or #2, and the light chains are chimeras of m4D10 VL (SEQ ID NO:24) and the human Ig kappa constant region (SEQ ID NO:27). The light chains of antibody #3 are as in 4D10hum #1 and #2, and the heavy chains are chimeras of m4D10 VH (SEQ ID NO23) and the human Ig gamma-1 constant region (SEQ ID NO:25).

TABLE 7

AFFINITY OF 4D10HUM ANTIBODIES FOR Aβ(20-42) GLOBULOMER

| Antibody | Antibody Lot | Experiment | $k_{on}$ [$M^{-1}s^{-1}$] | $k_{off}$ [$s^{-1}$] | $K_D$ [M] |
|---|---|---|---|---|---|
| 4D10hum#1 | #1759115 | 1 | $5.22 \times 10^5$ | $3.02 \times 10^{-4}$ | $5.78 \times 10^{-10}$ |
| | | 2 | $5.39 \times 10^5$ | $3.61 \times 10^{-4}$ | $6.71 \times 10^{-10}$ |
| | | average | $5.31 \times 10^5$ | $3.32 \times 10^{-4}$ | $6.25 \times 10^{-10}$ |
| | #1763976 | 1 | $4.86 \times 10^5$ | $2.81 \times 10^{-4}$ | $5.78 \times 10^{-10}$ |
| | | 2 | $5.13 \times 10^5$ | $3.04 \times 10^{-4}$ | $5.93 \times 10^{-10}$ |
| | | average | $5.00 \times 10^5$ | $2.93 \times 10^{-4}$ | $5.86 \times 10^{-10}$ |
| | #1773662 | 1 | $4.66 \times 10^5$ | $2.49 \times 10^{-4}$ | $5.35 \times 10^{-10}$ |
| | | 2 | $5.18 \times 10^5$ | $2.87 \times 10^{-4}$ | $5.53 \times 10^{-10}$ |
| | | average | $4.92 \times 10^5$ | $2.68 \times 10^{-4}$ | $5.44 \times 10^{-10}$ |
| 4D10hum#2 | #1759119 | 1 | $5.93 \times 10^5$ | $2.70 \times 10^{-4}$ | $4.54 \times 10^{-10}$ |
| | | 2 | $5.46 \times 10^5$ | $3.32 \times 10^{-4}$ | $6.09 \times 10^{-10}$ |
| | | average | $5.70 \times 10^5$ | $3.01 \times 10^{-4}$ | $5.32 \times 10^{-10}$ |
| | #1773659 | 1 | $5.07 \times 10^5$ | $2.68 \times 10^{-4}$ | $5.29 \times 10^{-10}$ |
| | | 2 | $6.86 \times 10^5$ | $2.98 \times 10^{-4}$ | $4.35 \times 10^{-10}$ |
| | | average | $5.97 \times 10^5$ | $2.83 \times 10^{-4}$ | $4.82 \times 10^{-10}$ |

| Antibody | Experiment | $k_{on}$ [$M^{-1}s^{-1}$] | $k_{off}$ [$s^{-1}$] | $K_D$ [M] |
|---|---|---|---|---|
| 4D10#3 | 1 | $6.03 \times 10^5$ | $3.17 \times 10^{-4}$ | $5.25 \times 10^{-10}$ |
| (chimeric heavy chain; light | 2 | $5.22 \times 10^5$ | $3.49 \times 10^{-4}$ | $6.69 \times 10^{-10}$ |
| chain as 4D10hum#1 and #2) | average | $5.63 \times 10^5$ | $3.33 \times 10^{-4}$ | $5.97 \times 10^{-10}$ |
| 4D10#4 | 1 | $4.62 \times 10^5$ | $2.94 \times 10^{-4}$ | $6.35 \times 10^{-10}$ |
| (heavy chain as 4D10hum#1; | 2 | $5.06 \times 10^5$ | $3.32 \times 10^{-4}$ | $6.57 \times 10^{-10}$ |
| chimeric light chain) | average | $4.84 \times 10^5$ | $3.13 \times 10^{-4}$ | $6.46 \times 10^{-10}$ |
| 4D10#5 | 1 | $4.94 \times 10^5$ | $2.62 \times 10^{-4}$ | $5.30 \times 10^{-10}$ |
| (heavy chain as 4D10hum#2; | 2 | $4.72 \times 10^5$ | $2.92 \times 10^{-4}$ | $6.19 \times 10^{-10}$ |
| chimeric light chain) | average | $4.83 \times 10^5$ | $2.77 \times 10^{-4}$ | $5.75 \times 10^{-10}$ |

Example 2.6

Analysis of Antibody Selectivity Via Dot Blot

In order to characterize the selectivity of monoclonal anti Aβ(20-42) globulomer antibodies, they were tested for binding to different Aβ-forms. To this end, serial dilutions of the individual Aβ(1-42) forms ranging from 100 pmol/μl to 0.00001 pmol/μl in PBS supplemented with 0.2 mg/ml BSA were prepared. 1 μl of each dilution was blotted onto a nitrocellulose membrane. Detection was performed by incubating with the corresponding antibody (0.2 μg/ml) followed by immunostaining using Peroxidase conjugated anti-human-IgG and the staining reagent BM Blue POD Substrate (Roche).

Aβ-Standards for Dot-Blot:

1. Aβ(1-42) Globulomer

Aβ(1-42) globulomer was prepared as described in Example 1a (buffer exchange by dialysis).

2. Aβ(20-42) Globulomer

Aβ(20-42) globulomer was prepared as described in Example 1b.

3. Aβ(1-40) Monomer, 0.1% NaOH 2.5 mg Aβ(1-40) (Bachem Inc., cat. no. H-1368) was dissolved in 0.5 ml 0.1% NaOH in $H_2O$ (freshly prepared) (=5 mg/ml) and immediately shaken for 30 sec. at room temperature to obtain a clear solution. The sample was stored at −20° C. until use.

4. Aβ(1-42) Monomer, 0.1% NaOH 2.5 mg Aβ(1-42) (Bachem Inc., cat. no. H-1368) was dissolved in 0.5 ml 0.1% NaOH in $H_2O$ (freshly prepared) (=5 mg/ml) and immediately shaken for 30 sec. at room temperature to obtain a clear solution. The sample was stored at −20° C. until use.

5. Aβ(1-42) Fibrils 1 mg Aβ(1-42) (Bachem Inc. cat. no.: H-1368) was dissolved in 500 μl aqueous 0.1% $NH_4OH$ (Eppendorf tube) and stirred for 1 min at room temperature. 100 μl of this freshly prepared Aβ(1-42) solution were neutralized with 300 μl 20 mM $NaH_2PO_4$; 140 mM NaCl, pH 7.4. The pH was adjusted to pH 7.4 with 1% HCl. The sample was incubated for 24 h at 37° C. and centrifuged (10 min at 10000 g). The supernatant was discarded and the fibril pellet resuspended with 400 μl 20 mM $NaH_2PO_4$; 140 mM NaCl, pH 7.4 by vortexing for 1 min.

6. sAPPα

Supplied by Sigma (cat. no. 59564; 25 μg in 20 mM $NaH_2PO_4$; 140 mM NaCl; pH 7.4). The sAPPα was diluted to 0.1 mg/ml (=1 pmol/μl) with 20 mM $NaH_2PO_4$, 140 mM NaCl, pH 7.4, 0.2 mg/ml BSA.

7. Aβ(12-42) Globulomer

Aβ(12-42) globulomer was prepared as described in Example 1c.

Materials for Dot Blot:

Serial dilution of Aβ-standards (see above 1. to 7.) in 20 mM $NaH_2PO_4$, 140 mM NaCl, pH 7.4+0.2 mg/ml BSA to obtain concentrations of: 100 pmol/μl, 10 pmol/μl, 1 pmol/μl, 0.1 pmol/μl, 0.01 pmol/μl, 0.001 pmol/μl, 0.0001 pmol/μl, and 0.00001 pmol/μl.

Nitrocellulose: Trans-Blot Transfer medium, Pure Nitrocellulose Membrane (0.2 μm); BIO-RAD Anti-human-POD: cat no: 109-035-003 (Jackson Immuno Research)

Detection reagent: BM Blue POD Substrate, precipitating, cat no: 11442066001 (Roche)

Bovine serum albumin, (BSA): Cat no: 11926 (Serva)

Blocking reagent: 5% low fat milk in TBS

Buffer Solutions:

TBS: 25 mM Tris/HCl buffer pH 7.5+150 mM NaCl

TTBS: 25 mM Tris/HCl-buffer pH 7.5+150 mM NaCl+0.05% Tween 20

PBS+0.2 mg/ml BSA: 20 mM $NaH_2PO_4$ buffer pH 7.4+140 mM NaCl+0.2 mg/ml BSA

Antibody solution I: 0.2 μg/ml antibody in 20 ml 1% low fat milk in TBS

Antibody: humanized monoclonal anti-Aβ antibody 4D10hum #1; 4.7 mg/ml OD 280 nm; stored at −80° C.

Antibody solution II: 1:5000 dilution of anti-human-POD in 1% low fat milk in TBS Dot Blot Procedure:

1) 1 μl of each of the 8 concentrations of the different Aβ-standards (obtained by serial dilution) was dotted onto the nitrocellulose membrane in a distance of approximately 1 cm from each other.

2) The dots of Aβ-standards were allowed to dry on the nitrocellulose membrane on air for at least 10 min at room temperature (RT). (=dot blot)

3) Blocking:

The dot blot was incubated with 30 ml 5% low fat milk in TBS for 1.5 h at RT.

4) Washing:

The blocking solution was discarded and the dot blot was incubated under shaking with 20 ml TTBS for 10 min at RT.

5) Antibody solution I:

The washing buffer was discarded and the dot blot was incubated with antibody solution I for 2 h at RT 6) Washing:

The antibody solution I was discarded and the dot blot was incubated under shaking with 20 ml TTBS for 10 min at RT. The washing solution was discarded and the dot blot was incubated under shaking with 20 ml TTBS for 10 min at RT. The washing solution was discarded and the dot blot was incubated under shaking with 20 ml TBS for 10 min at RT.

7) Antibody solution II:

The washing buffer was discarded and the dot blot was incubated with antibody solution II for 1 h at RT 8) Washing:

The antibody solution II was discarded and the dot blot was incubated under shaking with 20 ml TTBS for 10 min at RT. The washing solution was discarded and the dot blot was incubated under shaking with 20 ml TTBS for 10 min at RT. The washing solution was discarded and the dot blot was incubated under shaking with 20 ml TBS for 10 min at RT.

9) Development:

The washing solution was discarded. The dot blot was developed with 7.5 ml BM Blue POD Substrate for 10 min. The development was stopped by intense washing of the dot blot with $H_2O$. Quantitative evaluation was done based on a densitometric analysis (GS800 densitometer (BioRad) and software package Quantity one, Version 4.5.0 (BioRad)) of the dot intensity. Only dots were evaluated that had a relative density of greater than 20% of the relative density of the last optically unambiguously identified dot of the Aβ(20-42) globulomer. This threshold value was determined for every dot blot independently. The calculated value indicates the relation between recognition of Aβ(20-42) globulomer and the respective Aβ form for the given antibody.

Dot blot analysis was performed with humanized monoclonal anti-Aβ antibody 4D10hum #1. The individual Aβ forms were applied in serial dilutions and incubated with the respective antibodies for immune reaction (1=Aβ(1-42) globulomer; 2=Aβ(20-42) globulomer; 3=Aβ(1-40) monomer, 0.1% NaOH; 4=Aβ(1-42) monomer, 0.1% NaOH; 5=Aβ (1-42) fibril preparation; 6=sAPPα (Sigma); (first dot: 1 pmol)). Results are summarized in Table 8.

TABLE 8

DOT BLOT QUANTIFICATION DATA

| ANTIGEN | ANTIBODY: 4D10hum#1 |
|---|---|
| Aβ(1-42) globulomer | >10000 |
| Aβ(20-42) globulomer | 1 |
| Aβ(1-40) monomer in 0.1% NaOH | 72000 |
| Aβ(1-42) monomer in 0.1% NaOH | 72000 |
| Aβ(1-42) fibril | >10000 |
| sAPPα | >100 |
| Aβ(12-42) globulomer | 11 |

Example 3

Determination of Platelet Factor 4 Cross-Reaction

Example 3.1

Determination of Cross-Reaction with Platelet Factor 4 in Cynomolgus Monkey Plasma Via Sandwich-ELISA Reagent List:
F96 Cert. Maxisorp NUNC-Immuno Plate cat. no. 439454
Binding Antibodies in Experiment E1:
Humanized monoclonal anti-Aβ antibody 4D10hum #1; 2.36 mg/ml OD 280 nm; stored at −80° C.
Humanized monoclonal anti-Aβ antibody 4D10hum #2; 1.74 mg/ml OD 280 nm; stored at −80° C.
Human/mouse chimeric anti-Aβ monoclonal antibody clone h1G5 wild type Fc-frame (chim h1G5 wt); 0.99 mg/ml OD 280 nm; stored at −80° C. (used as a positive control)
Affinity purified human polyclonal antibody hIgG1 (Chemicon (Millipore), Cat #AG502); 1.00 mg/ml OD 280 nm; stored at −80° C. (used as a negative control)
Binding Antibodies in Reference Experiment R1:
Anti-HPF4 monoclonal antibody; 4.2 mg/ml OD 280 nm; Abcam cat. no. ab49735; stored at −30° C. (used as a positive control)
Anti-Aβ monoclonal antibody clone m1G5; 1.70 mg/ml OD 280 nm; stored at −80° C.
Anti-Aβ monoclonal antibody clone m4D10; 8.60 mg/ml OD 280 nm; stored at −80° C.
Monoclonal antibody clone mIgG2a; 7.89 mg/ml OD 280 nm; stored at −80° C. (used as a negative control)
Coating buffer: 100 mM sodium hydrogen carbonate; pH 9.6
Blocking reagent for ELISA; Roche Diagnostics GmbH cat. no.: 1112589
PBST buffer: 20 mM $NaH_2PO_4$; 140 mM NaCl; 0.05% Tween 20; pH 7.4
PBST+0.5% BSA buffer: 20 mM $NaH_2PO_4$; 140 mM NaCl; 0.05% Tween 20; pH 7.4+0.5% BSA; Serva cat. no. 11926
Cynomolgus plasma: Cynomolgus EDTA plasma pool from 13 different donors; stored at −30° C.
Trypsin inhibitor: Sigma cat. no. T7902
Primary antibody: pRAb-HPF4; 0.5 mg/ml; Abcam cat. no. ab9561

Label reagent: anti-rabbit-POD conjugate; Jackson ImmunoResearch Ltd. cat. no.: 111-036-045
Staining Solution: 42 mM TMB (Roche Diagnostics GmbH cat. no.: 92817060) in DMSO; 3% $H_2O_2$ in water; 100 mM sodium acetate, pH 4.9
Stop solution: 2 M sulfonic acid
Method used in Preparation of Reagents:
Binding Antibody:
The binding antibodies were diluted to 10 μg/ml in coating buffer.
Blocking Solution:
Blocking reagent was dissolved in 100 ml water to prepare the blocking stock solution and aliquots of 10 ml were stored at −20° C. 3 ml blocking stock solution was diluted with 27 ml water for each plate to block.
Preparation of Cynomolgus (*Macaca fascicularis*) Plasma Stock Solution:
2 ml Cynomolgus plasma pool were centrifuged for 10 min at 10,000 g. 1.58 ml of the supernatant was removed and diluted with 3.42 ml PBST+0.5% BSA buffer (=1:3.16 dilution). Then 50 μl 10 mg/ml trypsin inhibitor in $H_2O$ were added. After incubation for 10 min at room temperature the sample was filtrated through a 0.22 μm filter (Millipore cat. no. SLGS0250S).
Dilution Series of Cynomolgus Plasma Stock Solution:

| No | Volume of cynomolgus plasma dilution | Volume of PBST + 0.5% BSA buffer | Final dilution of cynomolgus plasma |
|---|---|---|---|
| 1 | 250 μl stock solution | 0 ml | 1:3.16 |
| 2 | 79 μl (1) | 171 μl | 1:10 |
| 3 | 79 μl (2) | 171 μl | 1:31.6 |
| 4 | 79 μl (3) | 171 μl | 1:100 |
| 5 | 79 μl (4) | 171 μl | 1:316 |
| 6 | 79 μl (5) | 171 μl | 1:1000 |
| 7 | 79 μl (6) | 171 μl | 1:3160 |
| 8 | 0 μl | 250 μl | buffer only |

Primary Antibody Solution:
The primary antibody was diluted to 1 μg/ml in PBST+ 0.5% BSA buffer. The dilution factor was 1:500. The antibody solution was used immediately.
Label Reagent:
Anti-rabbit-POD conjugate lyophilizate was reconstituted in 0.5 ml water. 500 μl glycerol was added and aliquots of 100 μl were stored at −20° C. for further use. The concentrated label reagent was diluted in PBST buffer. The dilution factor was 1:10000. The reagent was used immediately.
TMB Solution:
20 ml 100 mM of sodium acetate, pH 4.9, was mixed with 200 μl of the TMB stock solution and 29.5 μl 3% peroxide solution. The solution was used immediately.
Standard Plate Setup for Experiment E1. Dilutions of cynomolgus plasma. Note that each sample was run in duplicate.

|   | 1 | 2 | 3 | 4 | 5 | 6 | 7 | 8 | 9 | 10 | 11 | 12 |
|---|---|---|---|---|---|---|---|---|---|---|---|---|
|   | Positive control chim h1G5 wt | | 4D10hum#1 | | 4D10hum#2 | | Negative control hIgG1 | | | | | |
| A | 1:3.16 | 1:3.16 | 1:3.16 | 1:3.16 | 1:3.16 | 1:3.16 | 1:3.16 | 1:3.16 | none | none | none | none |
| B | 1:10 | 1:10 | 1:10 | 1:10 | 1:10 | 1:10 | 1:10 | 1:10 | none | none | none | none |
| C | 1:31.6 | 1:31.6 | 1:31.6 | 1:31.6 | 1:31.6 | 1:31.6 | 1:31.6 | 1:31.6 | none | none | none | none |
| D | 1:100 | 1:100 | 1:100 | 1:100 | 1:100 | 1:100 | 1:100 | 1:100 | none | none | none | none |
| E | 1:316 | 1:316 | 1:316 | 1:316 | 1:316 | 1:316 | 1:316 | 1:316 | none | none | none | none |
| F | 1:1000 | 1:1000 | 1:1000 | 1:1000 | 1:1000 | 1:1000 | 1:1000 | 1:1000 | none | none | none | none |
| G | 1:3160 | 1:3160 | 1:3160 | 1:3160 | 1:3160 | 1:3160 | 1:3160 | 1:3160 | none | none | none | none |
| H | 0.0 | 0.0 | 0.0 | 0.0 | 0.0 | 0.0 | 0.0 | 0.0 | none | none | none | none |

Standard Plate Setup for Reference Experiment R1. Dilutions of cynomolgus plasma. Note that each sample was run in duplicate.

|   | 1 | 2 | 3 | 4 | 5 | 6 | 7 | 8 | 9 | 10 | 11 | 12 |
|---|---|---|---|---|---|---|---|---|---|---|---|---|
|   | Positive control anti-HPF4 | | mAb m1G5 | | mAb m4D10 | | Negative control mIgG2a | | | | | |
| A | 1:3.16 | 1:3.16 | 1:3.16 | 1:3.16 | 1:3.16 | 1:3.16 | 1:3.16 | 1:3.16 | none | none | none | none |
| B | 1:10 | 1:10 | 1:10 | 1:10 | 1:10 | 1:10 | 1:10 | 1:10 | none | none | none | none |
| C | 1:31.6 | 1:31.6 | 1:31.6 | 1:31.6 | 1:31.6 | 1:31.6 | 1:31.6 | 1:31.6 | none | none | none | none |
| D | 1:100 | 1:100 | 1:100 | 1:100 | 1:100 | 1:100 | 1:100 | 1:100 | none | none | none | none |
| E | 1:316 | 1:316 | 1:316 | 1:316 | 1:316 | 1:316 | 1:316 | 1:316 | none | none | none | none |
| F | 1:1000 | 1:1000 | 1:1000 | 1:1000 | 1:1000 | 1:1000 | 1:1000 | 1:1000 | none | none | none | none |
| G | 1:3160 | 1:3160 | 1:3160 | 1:3160 | 1:3160 | 1:3160 | 1:3160 | 1:3160 | none | none | none | none |
| H | 0.0 | 0.0 | 0.0 | 0.0 | 0.0 | 0.0 | 0.0 | 0.0 | none | none | none | none |

Procedure Used:
1. 100 µl binding antibody solution per well were applied and incubated overnight at 4° C.
2. The antibody solution was discarded and the wells were washed three times with 250 µl PBST buffer.
3. 265 µl blocking solution per well were added and incubated 1.5 h at room temperature.
4. The blocking solution was discarded and the wells were washed three times with 250 µl PBST buffer.
5. After preparation of the cynomolgus plasma dilution series, 100 µl per well of these dilutions were applied to the plate. The plate was incubated 2 h at room temperature.
6. The cynomolgus plasma dilutions were discarded and the wells were washed three times with 250 µl PBST buffer.
7. 100 µl of primary antibody solution per well were added and incubated 1 h at room temperature.
8. The primary antibody solution was discarded and the wells were washed three times with 250 µl PBST buffer.
9. 200 µl label solution per well were added and incubated 1 h at room temperature.
10. The label solution was discarded and the wells were washed three times with 250 µl PBST buffer.
11. 100 µl of TMB solution were added to each well.
12. Plate colour was monitored during development (5-15 min at ambient temperature) and the reaction was terminated by adding 50 µl/well of stop solution when an appropriate colour had developed.
13. The absorbance was read at 450 nm.

Data Analysis:

Plasma dilution factors (X-values) were log-transformed using the equation: $X=\log(X)$. Data were plotted using the log-transformed X-values on the X-axis expressed as dilution of plasma (1:X). The $OD_{450\,nm}$ value of the respective PBST blank in row H was subtracted from the values of the plasma dilution series of each column in row A-G. The resulting background corrected $OD_{450\,nm}$ values were plotted on the Y-axis. The dilution effect curves were calculated from these data points by curve fitting using a non-linear regression "four parameter logistic equation" with a "least squares (ordinary) fit" fitting method (that equals the fitting method "sigmoidal dose-response (variable slope)") using the Data analysis software package GraphPadPrism (Version 5.03; GraphPad Software Inc.). Curve fitting was performed for the sole purpose of data visualization but not as basis for any further calculations i.e. the area under the curve calculation. The area under the curve (AUC, or total peak area) was determined based on non-curve fitted data, the log-transformed X-values and the $OD_{450\,nm}$ values in the measured range (final plasma dilutions from 1:3.16 to 1:3160). The following calculation settings were used within the Data analysis software package GraphPadPrism (Version 5.03; GraphPad Software Inc.):

The baseline was set to Y=0.0.

Minimum peak height: Ignore peaks that are less than 10% of the distance from minimum to maximum Y.

Peak direction: By definition, all peaks must go above the baseline

For each individual antibody a PF4 discrimination factor was calculated using the commercially available anti-HPF4 antibody (Abcam cat. no.: ab49735) as a reference antibody for PF4 recognition, wherein $$[\text{PF4 discrimination factor}] = \frac{[\text{total peak area of anti-HPF4 antibody ab49735}]}{[\text{total peak area of antibody to be determined}]}$$

Note: The PF4 discrimination factor was calculated based on the anti-HPF4 antibody AUCs obtained in the reference experiment as no human version of an anti-HPF4 exists.

Results of experiment E1 and reference experiment R1 are shown in FIGS. 20A and 22A as well as in Tables 9A and 9B.

Example 3.2

Determination of Cross-Reaction with Platelet Factor 4 in Human Plasma Via Sandwich-ELISA The same reagents and procedures for reagent preparation were used as for Example 3.1 except from:

Human plasma (Human EDTA plasma pool from 4 different donors; stored at −30° C.) spiked with human PF4 (7.3 mg/ml; Molecular Innovation cat. no. HPF4; stored at −30° C.) was used instead of cynomolgus plasma. HPF4-spiked human plasma stock solution was prepared as follows.

A) Preparation of Human Plasma Dilution:

2 ml human plasma pool were centrifuged for 10 min at 10000 g. 1.58 ml of the supernatant was removed and diluted with 3.42 ml PBST+0.5% BSA (=1:3.16 dilution). Then 50 μl 10 mg/ml trypsin inhibitor in H$_2$O were added. After incubation for 10 min at room temperature the sample was filtrated through a 0.22 μm filter (Millipore cat. no. SLGS0250S).

B) Preparation of HPF4 Stock Solution:

1 μl HPF4 was added to 99 μl PBST+0.5% BSA buffer=73 μg/ml.

C) Preparation of Human Plasma Stock Solution Spiked with 10 ng/ml HPF4:

0.69 μl of 73 μg/ml HPF4 stock solution were added to 5 ml 1:3.16 diluted human plasma resulting in 10 ng/ml HPF4 spiking of the human plasma stock dilution.

The preparation of a dilution series, the standard plate setup, the experimental procedure and the data analysis for sandwich-ELISA with HPF4-spiked human plasma were analogous to those described for sandwich-ELISA with cynomolgus plasma in Example 3.1.

Binding antibodies in experiment E2: same as used in experiment E1 in Example 3.1 Binding antibodies in reference experiment R2: same as used in reference experiment R1 in Example 3.1.

Results of experiment E2 and reference experiment R2 are shown in FIGS. 20B and 22B as well as in Tables 9A and 9B.

TABLE 9A

AUC (OR TOTAL PEAK AREA) CALCULATED FROM LOG-TRANSFORMED DATA OF EXPERIMENTS E1 and E2 DEPICTED IN FIGS. 20A AND 20B

| | | Positive control chim h1G5 wt[1] | mAb 4D10hum#1 | mAb 4D10hum#2 | Negative control hIgG1 |
|---|---|---|---|---|---|
| Cynomolgus plasma (data from FIG. 20A) | Area Under Curve[2] | 1.255 | 0.042 | 0.075 | 0.075 |
| | Ratio HPF4/aAβ antibody | 2 | 64 | 36 | 27 |
| Human plasma (data from FIG. 20B) | Area Under Curve[2] | 0.949 | 0.067 | 0.116 | 0.113 |
| | Ratio HPF4/aAβ antibody | 2 | 30 | 17 | 18 |

[1]chim h1G5 wt is an antibody as described in WO 2007/062853, i.e. a monoclonal antibody having a binding affinity to the Aβ(20-42) globulomer that is greater than its binding affinity to the Aβ(1-42) globulomer.
[2]Area under curve was calculated as described in example 3.1.

TABLE 9B

AUC (OR TOTAL PEAK AREA) CALCULATED FROM LOG-TRANSFORMED DATA OF REFERENCE EXPERIMENTS R1 and R2 DEPICTED IN FIGS. 22A AND 22B

| | | Positive control anti-HPF4 | mAb m1G5[1] | mAb m4D10 | Negative control mIgG2a |
|---|---|---|---|---|---|
| Cynomolgus plasma (data from FIG. 22A) | Area Under Curve[2] | 2.681 | 0.861 | 0.086 | 0.005 |
| | Ratio HPF4/aAβ antibody | 1 | 3 | 31 | 517 |
| Human plasma (data from FIG. 22B) | Area Under Curve[2] | 1.986 | 0.311 | 0.093 | 0.006 |
| | Ratio HPF4/aAβ antibody | 1 | 6 | 21 | 331 |

[1]m1G5 is an antibody as described in WO 2007/062853, i.e. a monoclonal antibody having a binding affinity to the Aβ(20-42) globulomer that is greater than its binding affinity the Aβ(1-42) globulomer.
[2]Area under curve was calculated as described in example 3.1.

Example 3.3

Determination of Cross-Reaction with Platelet Factor 4 in Cynomolus Monkey Plasma Via Aligned Sandwich-ELISA The reagents described in Example 3.1 and aligning antibodies anti-mouse IgG (Fc specific; produced in goat; Sigma cat. no.: M3534; 2.3 mg/ml; stored at −20° C. for murine binding antibodies in reference experiment R3) and anti-human IgG (Fc specific; produced in goat; Sigma cat. no.: 12136; 2.2 mg/ml; stored at −20° C., for human, humanized and human/mouse chimeric binding antibodies in experiment E3) were used.

Methods used in Preparation of Reagents:

Blocking solution, primary antibody and TMB solution were prepared as described in Example 3.1.

Each aligning antibody was diluted to 10 μg/ml in coating buffer.

Binding antibodies in experiment E3: same as used in experiment E1 in Example 3.1 Binding antibodies in reference experiment R3: same as used in reference experiment R1 in Example 3.1.

Each binding antibody was diluted with PBST+0.5% BSA buffer to 10 µg/ml (stock solution), and dilution series were prepared as follows:

| No | Volume of antibody dilution | Volume of PBST + 0.5% BSA buffer | Final antibody concentration |
|---|---|---|---|
| 1 | 250 µl stock solution | 0 ml | 10000 ng/ml |
| 2 | 79 µl (1) | 171 µl | 3160 ng/ml |
| 3 | 79 µl (2) | 171 µl | 1000 ng/ml |
| 4 | 79 µl (3) | 171 µl | 316 ng/ml |
| 5 | 79 µl (4) | 171 µl | 100 ng/ml |
| 6 | 79 µl (5) | 171 µl | 31.6 ng/ml |
| 7 | 79 µl (6) | 171 µl | 10 ng/ml |
| 8 | 0 µl | 250 µl | buffer only |

Cynomolgus Plasma:

400 µl Cynomolgus plasma pool were centrifuged for 10 min at 10000 g. 158 µl of the supernatant was removed and diluted with 684 µl PBST+0.5% BSA (=1:3.16 dilution). Then 10 µl 10 mg/ml trypsin inhibitor in $H_2O$ were added. After incubation for 10 min at room temperature the sample was filtrated through a 0.22 µm filter (Millipore cat. no. SLGS0250S). Afterwards 500 µl of this 1:3.16 diluted plasma sample was again diluted 1:31.6 with 15.3 ml PBST+0.5% BSA buffer resulting in a total dilution of 1:100.

Label Reagent:

Anti-rabbit-POD conjugate lyophilised was reconstituted in 0.5 ml water. 500 µl glycerol was added and aliquots of 100 µl were stored at −20° C. for further use. The concentrated label reagent was diluted in PBST buffer. The dilution factor was 1:5000. The reagent was used immediately.

Binding Antibody Plate Setup for Experiment E2. Dilutions of binding antibodies. Note that each concentration of each binding antibody was run in duplicate.

Procedure used:
1. 100 µl of the respective aligning antibody solution (anti-human IgG for experiment E3; anti-murine IgG for reference experiment R3) per well were applied and incubated overnight at 4° C.
2. The antibody solution was discarded and the wells were washed three times with 250 µl PBST-buffer.
3. 265 µl blocking solution per well were added and incubated 2 h at room temperature.
4. The blocking solution was discarded and the wells were washed three times with 250 µl PBST buffer.
5. After preparation of the dilution series of each binding antibody, 100 µl per well of these antibody dilutions were applied to the plate. The plate was incubated 2 h at room temperature.
6. The antibody solutions were discarded and the wells were washed three times with 250 µl PBST buffer.
7. 100 µl 1:100 dilution of cynomolgus plasma per well were added and incubated 2 h at room temperature.
8. The plasma solution was discarded and the wells were washed three times with 250 µl PBST buffer.
9. 100 µl primary antibody solution per well were added and incubated 1 h at room temperature.
10. The primary antibody solution was discarded and the wells were washed three times with 250 µl PBST buffer.
11. 200 µl label reagent per well were added and incubated 1 h at room temperature.
12. The label reagent was discarded and the wells were washed three times with 250 µl PBST buffer.
13. 100 µl of TMB solution were added to each well.
14. Plate colour was monitored during development (5-15 min at ambient temperature) and the reaction was terminated by adding 50 µl/well of stop solution when an appropriate colour had developed.
15. The absorbance was read at 450 nm.

|   | 1 | 2 | 3 | 4 | 5 | 6 | 7 | 8 | 9 | 10 | 11 | 12 |
|---|---|---|---|---|---|---|---|---|---|---|---|---|
|   | Positive control chim h1G5 wt | | 4D10hum#1 | | 4D10hum#2 | | Negative control hIgG1 | | | | | |
| A | 10000 | 10000 | 10000 | 10000 | 10000 | 10000 | 10000 | 10000 | none | none | none | none |
| B | 3160 | 3160 | 3160 | 3160 | 3160 | 3160 | 3160 | 3160 | none | none | none | none |
| C | 1000 | 1000 | 1000 | 1000 | 1000 | 1000 | 1000 | 1000 | none | none | none | none |
| D | 316 | 316 | 316 | 316 | 316 | 316 | 316 | 316 | none | none | none | none |
| E | 100 | 100 | 100 | 100 | 100 | 100 | 100 | 100 | none | none | none | none |
| F | 31.6 | 31.6 | 31.6 | 31.6 | 31.6 | 31.6 | 31.6 | 31.6 | none | none | none | none |
| G | 10 | 10 | 10 | 10 | 10 | 10 | 10 | 10 | none | none | none | none |
| H | 0.0 | 0.0 | 0.0 | 0.0 | 0.0 | 0.0 | 0.0 | 0.0 | none | none | none | none |

Binding Antibody Plate Setup for Reference Experiment R3. Dilutions of binding antibodies. Note that each concentration of each binding antibody was run in duplicate.

Data analysis was performed as described for sandwich-ELISA with cynomolgus plasma in Example 3.1, except that not plasma dilution factors but the amounts of antibody (ex-

|   | 1 | 2 | 3 | 4 | 5 | 6 | 7 | 8 | 9 | 10 | 11 | 12 |
|---|---|---|---|---|---|---|---|---|---|---|---|---|
|   | Positive control anti-HPF4 | | mAb m1G5 | | mAb m4D10 | | Negative control mIgG2a | | | | | |
| A | 10000 | 10000 | 10000 | 10000 | 10000 | 10000 | 10000 | 10000 | none | none | none | none |
| B | 3160 | 3160 | 3160 | 3160 | 3160 | 3160 | 3160 | 3160 | none | none | none | none |
| C | 1000 | 1000 | 1000 | 1000 | 1000 | 1000 | 1000 | 1000 | none | none | none | none |
| D | 316 | 316 | 316 | 316 | 316 | 316 | 316 | 316 | none | none | none | none |
| E | 100 | 100 | 100 | 100 | 100 | 100 | 100 | 100 | none | none | none | none |
| F | 31.6 | 31.6 | 31.6 | 31.6 | 31.6 | 31.6 | 31.6 | 31.6 | none | none | none | none |
| G | 10 | 10 | 10 | 10 | 10 | 10 | 10 | 10 | none | none | none | none |
| H | 0.0 | 0.0 | 0.0 | 0.0 | 0.0 | 0.0 | 0.0 | 0.0 | none | none | none | none | pressed in ng/ml) were used as X-values and thus concentration effect curves were calculated. Accordingly, area under curve was determined based on non-curve fitted data, the log-transformed X-values and the $OD_{450\ nm}$ values in the measured range (final antibody concentrations from 10 ng/ml to 10000 ng/ml).

Results of experiment E3 and reference experiment R3 are shown in FIGS. 21A and 23A as well as in Tables 10A and 10B.

Example 3.4

Determination of Cross-Reaction with Platelet Factor 4 in Human Plasma Via Aligned Sandwich-ELISA The same reagents and procedures for reagent preparation were used as for Example 3.3 except from:

Each aligning antibody used for experiment E4 was diluted to 10 µg/ml in coating buffer, and each aligning antibody used for experiment R4 was diluted to 50 µg/ml in coating Human plasma (Human EDTA plasma pool from 4 different donors; stored at −30° C.) spiked with human PF4 (7.3 mg/ml; Molecular Innovation cat. no. HPF4; stored at −30° C.) was used instead of cynomolgus plasma. HPF4-spiked human plasma stock solution was prepared as follows.

A) Preparation of Human Plasma Dilution:

4 ml human plasma pool were centrifuged for 10 min at 10000 g. 3.16 ml of the supernatant was removed and diluted with 6.84 ml PBST+0.5% BSA (=1:3.16 dilution). Then 100 µl 10 mg/ml trypsin inhibitor in $H_2O$ were added. After incubation for 10 min at room temperature the sample was filtrated through a 0.22 µm filter (Millipore cat. no. SLGS0250S). Afterwards 5 ml of this 1:3.16 diluted plasma sample was again diluted 1:3.16 with 10.8 ml PBST+0.5% BSA buffer resulting in a total dilution of 1:10.

B) Preparation of HPF4 Stock Solution:

1 µl HPF4 was added to 99 µl PBST+0.5% BSA buffer=73 µg/ml.

C) Preparation of Human Plasma Stock Solution Spiked with 10 ng/ml HPF4:

1.64 µl of 73 µg/ml HPF4 stock solution were added to 12 ml 1:10 diluted human plasma resulting in 10 ng/ml HPF4 spiking of the human plasma stock dilution.

The preparation of dilution series of the binding antibodies; the binding antibody plate setup; the preparation of blocking solution, primary antibody, reagent and TMB solution were the same as in Example 3.3.

Aligning antibody and binding antibodies in experiment E4: same as used in experiment E3 in Example 3.3

Aligning antibody and binding antibodies in reference experiment R4: same as used in reference experiment R4 in Example 3.3.

The experimental procedure (but using 1:10 diluted human plasma in step 7) and data analysis for aligned sandwich-ELISA with HPF4-spiked human plasma were analogous to that described for aligned sandwich-ELISA with cynomolgus plasma in Example 3.3.

Results of experiment E4 and reference experiment R4 are shown in FIGS. 21B and 23B as well as in Tables 10A and 10B.

TABLE 10A

AUC (OR TOTAL PEAK AREA) CALCULATED FROM LOG-TRANSFORMED DATA OF EXPERIMENTS E3 and E4 DEPICTED IN FIGS. 21A AND 21B

| | | Positive control chim h1G5 wt[1] | mAb 4D10 hum#1 | mAb 4D10 hum#2 | Negative control hIgG1 |
|---|---|---|---|---|---|
| Cynomolgus plasma (data from FIG. 21A) | Area Under Curve[2] | 0.290 | 0.030 | 0 | 0 |
| | Ratio HPF4/aAβ antibody | 16 | 158 | >158[3] | >158[3] |
| Human plasma (data from FIG. 21B) | Area Under Curve[2] | 0.106 | 0.168 | 0.051 | 0.024 |
| | Ratio HPF4/aAβ antibody | 36 | 23 | 75 | 157 |

[1]chim h1G5 wt is an antibody as described in WO 2007/062853, i.e. a monoclonal antibody having a binding affinity to the Aβ(20-42) globulomer that is greater than its binding affinity to the Aβ(1-42) globulomer.
[2]Area under curve was calculated as described in example 3.3.
[3]For antibodies 4D10hum#2 and hIgG1 the HPF4 binding activity was so low that the AUC was calculated to be 0. Therefore the ratio HPF4/aAβ antibody could not be calculated and was indicated to be >158 (the highest ratio achieved by another antibody (4D10hum#1) in this assay).

TABLE 10B

AUC (OR TOTAL PEAK AREA) CALCULATED FROM LOG-TRANSFORMED DATA OF REFERENCE EXPERIMENTS R3 and R4 DEPICTED IN FIGS. 21A AND 21B

| | | Positive control anti-HPF4 | mAb m1G5[1] | mAb m4D10 | Negative control mIgG2a |
|---|---|---|---|---|---|
| Cynomolgus plasma (data from FIG. 23A) | Area Under Curve[2] | 4.781 | 0.2768 | 0.04066 | 0.01473 |
| | Ratio HPF4/aAβ antibody | 1 | 17 | 118 | 325 |
| Human plasma (data from FIG. 23B) | Area Under Curve[2] | 3.844 | 0.165 | 0.141 | 0.033 |
| | Ratio HPF4/aAβ antibody | 1 | 23 | 27 | 118 |

[1]m1G5 is an antibody as described in WO 2007/062853, i.e. a monoclonal antibody having a binding affinity to the Aβ(20-42) globulomer that is greater than its binding affinity to both the Aβ(1-42) globulomer.
[2]Area under curve was calculated as described in example 3.3.

What is claimed is:

1. An isolated antibody or antigen-binding portion thereof comprising:
   a first amino acid sequence which is at least 90% identical to SEQ ID NO:2 or SEQ ID NO:3; and a second amino acid sequence which is at least 90% identical to SEQ ID NO:1,
   wherein the first amino acid sequence comprises at least three complementarity determining regions consisting of amino acids 31-35, 50-65, and 98-101 respectively of SEQ ID NO:2 or SEQ ID NO:3;
   wherein the second amino acid sequence comprises at least three complementarity determining regions consisting of amino acids 24-39, 55-61, and 94-102 respectively of SEQ ID NO:1; and
   wherein the antibody or antigen-binding portion thereof has a binding affinity to an Aβ(20-42) globulomer that is greater than the binding affinity of the antibody or antigen-binding portion thereof to an Aβ(1-42) globulomer.

2. The isolated antibody or antigen-binding portion thereof according to claim 1, wherein the first amino acid sequence is at least 90% identical to an amino acid sequence selected from the group consisting of SEQ ID NO:4, SEQ ID NO:5, SEQ ID NO:6, SEQ ID NO:7, SEQ ID NO:8, SEQ ID NO:9, SEQ ID NO:10, and SEQ ID NO:11.

3. The isolated antibody or antigen-binding portion thereof according to claim 1, wherein the second amino acid sequence is at least 90% identical to an amino acid sequence selected from the group consisting of SEQ ID NO:12, SEQ ID NO:13, SEQ ID NO:14, SEQ ID NO:15, and SEQ ID NO:16.

4. An isolated antibody or antigen-binding portion thereof according to any one of claims 1 to 3 comprising:
   a first amino acid sequence which is at least 90% identical to an amino acid sequence selected from the group consisting of SEQ ID NO:4, SEQ ID NO:5, SEQ ID NO:6, SEQ ID NO:7, SEQ ID NO:8, SEQ ID NO:9, SEQ ID NO:10, and SEQ ID NO:11; and a second amino acid sequence which is at least 90% identical to an amino acid sequence selected from the group consisting of SEQ ID NO:12, SEQ ID NO:13, SEQ ID NO:14, SEQ ID NO:15, and SEQ ID NO:16.

5. The isolated antibody or antigen-binding portion thereof of claim 1, wherein said antibody or antigen-binding portion thereof is selected from the group consisting of: a disulfide linked Fv, a monoclonal antibody, a scFv, a chimeric antibody, a CDR-grafted antibody, a diabody, a humanized antibody, a multispecific antibody, a Fab, a Fab', a bispecific antibody, a F(ab')$_2$, and a Fv.

6. The isolated antibody or antigen-binding portion thereof of claim 1 further comprising an immunoglobulin light chain constant region having an amino acid sequence selected from the group consisting of SEQ ID NO:27 and SEQ ID NO:28.

7. The isolated antibody or antigen-binding portion thereof of claim 1, wherein said antibody or antigen-binding portion thereof further comprises an agent selected from the group consisting of: an immunoadhesion molecule, an imaging agent, and a therapeutic agent.

8. The isolated antibody or antigen-binding portion thereof of claim 1, wherein said antibody or antigen-binding portion thereof possesses a human glycosylation pattern.

9. An isolated antibody or antigen-binding portion thereof produced according to a method comprising culturing a host cell comprising a vector comprising an isolated nucleic acid encoding the isolated antibody or antigen-binding portion thereof of claim 1.

10. A pharmaceutical composition comprising the isolated antibody or antigen-binding portion thereof of claim 1, and a pharmaceutically acceptable carrier.

11. The pharmaceutical composition of claim 10 further comprising at least one additional therapeutic agent.

* * * * *

SEQUENCE LISTING

<160> NUMBER OF SEQ ID NOS: 48

<210> SEQ ID NO 1
<211> LENGTH: 113
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (7)..(7)
<223> OTHER INFORMATION: Xaa can be Ser or Thr
<220> FEATURE:
<221> NAME/KEY: misc_feature
<222> LOCATION: (15)..(15)
<223> OTHER INFORMATION: Xaa can be Leu or Pro
<220> FEATURE:
<221> NAME/KEY: misc_feature
<222> LOCATION: (41)..(41)
<223> OTHER INFORMATION: Xaa can be Phe or Leu
<220> FEATURE:
<221> NAME/KEY: misc_feature
<222> LOCATION: (42)..(42)
<223> OTHER INFORMATION: Xaa can be Gln or Leu
<220> FEATURE:
<221> NAME/KEY: misc_feature
<222> LOCATION: (44)..(44)
<223> OTHER INFORMATION: Xaa can be Arg or Lys
<220> FEATURE:
<221> NAME/KEY: misc_feature
<222> LOCATION: (50)..(50)
<223> OTHER INFORMATION: Xaa can be Arg or Gln

<400> SEQUENCE: 1

Asp Val Val Met Thr Gln Xaa Pro Leu Ser Leu Pro Val Thr Xaa Gly
1               5                   10                  15

Gln Pro Ala Ser Ile Ser Cys Lys Ser Ser Gln Ser Leu Leu Asp Ile
            20                  25                  30

Asp Gly Lys Thr Tyr Leu Asn Trp Xaa Xaa Gln Xaa Pro Gly Gln Ser
        35                  40                  45

Pro Xaa Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Tyr Thr Phe Gly Gln Gly Thr Lys Leu Glu Ile Lys
            100                 105                 110

Arg

<210> SEQ ID NO 2
<211> LENGTH: 112
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (12)..(12)
<223> OTHER INFORMATION: Xaa can be Ile or Val
<220> FEATURE:
<221> NAME/KEY: misc_feature
<222> LOCATION: (24)..(24)
<223> OTHER INFORMATION: Xaa can be Ala or Val
<220> FEATURE:
<221> NAME/KEY: misc_feature
<222> LOCATION: (29)..(29)
<223> OTHER INFORMATION: Xaa can be Val or Leu
<220> FEATURE:

```
<221> NAME/KEY: misc_feature
<222> LOCATION: (48)..(48)
<223> OTHER INFORMATION: Xaa can be Val or Leu
<220> FEATURE:
<221> NAME/KEY: misc_feature
<222> LOCATION: (49)..(49)
<223> OTHER INFORMATION: Xaa can be Ser or Gly
<220> FEATURE:
<221> NAME/KEY: misc_feature
<222> LOCATION: (67)..(67)
<223> OTHER INFORMATION: Xaa can be Phe or Leu
<220> FEATURE:
<221> NAME/KEY: misc_feature
<222> LOCATION: (71)..(71)
<223> OTHER INFORMATION: Xaa can be Arg or Lys
<220> FEATURE:
<221> NAME/KEY: misc_feature
<222> LOCATION: (76)..(76)
<223> OTHER INFORMATION: Xaa can be Asn or Ser
<220> FEATURE:
<221> NAME/KEY: misc_feature
<222> LOCATION: (78)..(78)
<223> OTHER INFORMATION: Xaa can be Leu or Val

<400> SEQUENCE: 2

Glu Val Gln Leu Val Glu Ser Gly Gly Gly Leu Xaa Gln Pro Gly Gly
1               5                   10                  15

Ser Leu Arg Leu Ser Cys Ala Xaa Ser Gly Phe Thr Xaa Ser Ser Tyr
            20                  25                  30

Gly Val His Trp Val Arg Gln Ala Pro Gly Lys Gly Leu Glu Trp Xaa
        35                  40                  45

Xaa Val Ile Trp Arg Gly Gly Arg Ile Asp Tyr Asn Ala Ala Phe Met
    50                  55                  60

Ser Arg Xaa Thr Ile Ser Xaa Asp Asn Ser Lys Xaa Thr Xaa Tyr Leu
65                  70                  75                  80

Gln Met Asn Ser Leu Arg Ala Glu Asp Thr Ala Val Tyr Tyr Cys Ala
            85                  90                  95

Arg Asn Ser Asp Val Trp Gly Gln Gly Thr Thr Val Thr Val Ser Ser
        100                 105                 110

<210> SEQ ID NO 3
<211> LENGTH: 112
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(1)
<223> OTHER INFORMATION: Xaa can be Gln or Glu
<220> FEATURE:
<221> NAME/KEY: misc_feature
<222> LOCATION: (27)..(27)
<223> OTHER INFORMATION: Xaa can be Gly or Phe
<220> FEATURE:
<221> NAME/KEY: misc_feature
<222> LOCATION: (29)..(29)
<223> OTHER INFORMATION: Xaa can be Ile or Leu
<220> FEATURE:
<221> NAME/KEY: misc_feature
<222> LOCATION: (37)..(37)
<223> OTHER INFORMATION: Xaa can be Ile or Val
<220> FEATURE:
<221> NAME/KEY: misc_feature
<222> LOCATION: (48)..(48)
<223> OTHER INFORMATION: Xaa can be Ile or Leu
<220> FEATURE:
<221> NAME/KEY: misc_feature
<222> LOCATION: (67)..(67)
<223> OTHER INFORMATION: Xaa can be Val or Leu
<220> FEATURE:
```

```
<221> NAME/KEY: misc_feature
<222> LOCATION: (71)..(71)
<223> OTHER INFORMATION: Xaa can be Val or Lys
<220> FEATURE:
<221> NAME/KEY: misc_feature
<222> LOCATION: (76)..(76)
<223> OTHER INFORMATION: Xaa can be Asn or Ser
<220> FEATURE:
<221> NAME/KEY: misc_feature
<222> LOCATION: (78)..(78)
<223> OTHER INFORMATION: Xaa can be Phe or Val

<400> SEQUENCE: 3

Xaa Val Gln Leu Gln Glu Ser Gly Pro Gly Leu Val Lys Pro Ser Glu
1               5                   10                  15

Thr Leu Ser Leu Thr Cys Thr Val Ser Gly Xaa Ser Xaa Ser Ser Tyr
            20                  25                  30

Gly Val His Trp Xaa Arg Gln Pro Pro Gly Lys Gly Leu Glu Trp Xaa
        35                  40                  45

Gly Val Ile Trp Arg Gly Gly Arg Ile Asp Tyr Asn Ala Ala Phe Met
    50                  55                  60

Ser Arg Xaa Thr Ile Ser Xaa Asp Thr Ser Lys Xaa Gln Xaa Ser Leu
65                  70                  75                  80

Lys Leu Ser Ser Val Thr Ala Ala Asp Thr Ala Val Tyr Tyr Cys Ala
                85                  90                  95

Arg Asn Ser Asp Val Trp Gly Gln Gly Thr Thr Val Thr Val Ser Ser
            100                 105                 110

<210> SEQ ID NO 4
<211> LENGTH: 112
<212> TYPE: PRT
<213> ORGANISM: Artificial Sequence
<220> FEATURE:
<223> OTHER INFORMATION: synthetic

<400> SEQUENCE: 4

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Tyr
            20                  25                  30

Gly Val His Trp Val Arg Gln Ala Pro Gly Lys Gly Leu Glu Trp Val
        35                  40                  45

Ser Val Ile Trp Arg Gly Gly Arg Ile Asp Tyr Asn Ala Ala Phe Met
    50                  55                  60

Ser Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asn Ser Asp Val Trp Gly Gln Gly Thr Thr Val Thr Val Ser Ser
            100                 105                 110

<210> SEQ ID NO 5
<211> LENGTH: 112
<212> TYPE: PRT
<213> ORGANISM: Artificial Sequence
<220> FEATURE:
<223> OTHER INFORMATION: synthetic

<400> SEQUENCE: 5

Glu Val Gln Leu Val Glu Ser Gly Gly Gly Leu Val Gln Pro Gly Gly
1               5                   10                  15
```

```
Ser Leu Arg Leu Ser Cys Ala Ala Ser Gly Phe Thr Val Ser Ser Tyr
            20                  25                  30

Gly Val His Trp Val Arg Gln Ala Pro Gly Lys Gly Leu Glu Trp Val
        35                  40                  45

Ser Val Ile Trp Arg Gly Gly Arg Ile Asp Tyr Asn Ala Ala Phe Met
    50                  55                  60

Ser Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asn Ser Asp Val Trp Gly Gln Gly Thr Thr Val Thr Val Ser Ser
            100                 105                 110
```

<210> SEQ ID NO 6
<211> LENGTH: 112
<212> TYPE: PRT
<213> ORGANISM: Artificial Sequence
<220> FEATURE:
<223> OTHER INFORMATION: synthetic

<400> SEQUENCE: 6

```
Glu Val Gln Leu Val Glu Ser Gly Gly Gly Leu Val Gln Pro Gly Gly
1               5                   10                  15

Ser Leu Arg Leu Ser Cys Ala Val Ser Gly Phe Thr Leu Ser Ser Tyr
            20                  25                  30

Gly Val His Trp Val Arg Gln Ala Pro Gly Lys Gly Leu Glu Trp Leu
        35                  40                  45

Gly Val Ile Trp Arg Gly Gly Arg Ile Asp Tyr Asn Ala Ala Phe Met
    50                  55                  60

Ser Arg Leu Thr Ile Ser Lys Asp Asn Ser Lys Ser Thr Val Tyr Leu
65                  70                  75                  80

Gln Met Asn Ser Leu Arg Ala Glu Asp Thr Ala Val Tyr Tyr Cys Ala
                85                  90                  95

Arg Asn Ser Asp Val Trp Gly Gln Gly Thr Thr Val Thr Val Ser Ser
            100                 105                 110
```

<210> SEQ ID NO 7
<211> LENGTH: 112
<212> TYPE: PRT
<213> ORGANISM: Artificial Sequence
<220> FEATURE:
<223> OTHER INFORMATION: synthetic

<400> SEQUENCE: 7

```
Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Leu Ser Ser Tyr
            20                  25                  30

Gly Val His Trp Val Arg Gln Ala Pro Gly Lys Gly Leu Glu Trp Val
        35                  40                  45

Ser Val Ile Trp Arg Gly Gly Arg Ile Asp Tyr Asn Ala Ala Phe Met
    50                  55                  60

Ser Arg Phe Thr Ile Ser Lys Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asn Ser Asp Val Trp Gly Gln Gly Thr Thr Val Thr Val Ser Ser
            100                 105                 110
```

```
<210> SEQ ID NO 8
<211> LENGTH: 112
<212> TYPE: PRT
<213> ORGANISM: Artificial Sequence
<220> FEATURE:
<223> OTHER INFORMATION: synthetic

<400> SEQUENCE: 8
```

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Gly Val His Trp Ile Arg Gln Pro Pro Gly Lys Gly Leu Glu Trp Ile
        35                  40                  45

Gly Val Ile Trp Arg Gly Gly Arg Ile Asp Tyr Asn Ala Ala Phe Met
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asn Ser Asp Val Trp Gly Gln Gly Thr Thr Val Thr Val Ser Ser
            100                 105                 110

```
<210> SEQ ID NO 9
<211> LENGTH: 112
<212> TYPE: PRT
<213> ORGANISM: Artificial Sequence
<220> FEATURE:
<223> OTHER INFORMATION: synthetic

<400> SEQUENCE: 9
```

Glu Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Gly Val His Trp Ile Arg Gln Pro Pro Gly Lys Gly Leu Glu Trp Ile
        35                  40                  45

Gly Val Ile Trp Arg Gly Gly Arg Ile Asp Tyr Asn Ala Ala Phe Met
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asn Ser Asp Val Trp Gly Gln Gly Thr Thr Val Thr Val Ser Ser
            100                 105                 110

```
<210> SEQ ID NO 10
<211> LENGTH: 112
<212> TYPE: PRT
<213> ORGANISM: Artificial Sequence
<220> FEATURE:
<223> OTHER INFORMATION: synthetic

<400> SEQUENCE: 10
```

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Ser Tyr
            20                  25                  30

Gly Val His Trp Val Arg Gln Pro Gly Lys Gly Leu Glu Trp Leu
         35                  40                  45

Gly Val Ile Trp Arg Gly Gly Arg Ile Asp Tyr Asn Ala Ala Phe Met
         50                  55                  60

Ser Arg Leu Thr Ile Ser Lys Asp Thr Ser Lys Ser Gln Val Ser Leu
65                  70                  75                  80

Lys Leu Ser Ser Val Thr Ala Ala Asp Thr Ala Val Tyr Tyr Cys Ala
                 85                  90                  95

Arg Asn Ser Asp Val Trp Gly Gln Gly Thr Thr Val Thr Val Ser Ser
                100                 105                 110

<210> SEQ ID NO 11
<211> LENGTH: 112
<212> TYPE: PRT
<213> ORGANISM: Artificial Sequence
<220> FEATURE:
<223> OTHER INFORMATION: synthetic

<400> SEQUENCE: 11

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Ser Tyr
                 20                  25                  30

Gly Val His Trp Ile Arg Gln Pro Pro Gly Lys Gly Leu Glu Trp Ile
         35                  40                  45

Gly Val Ile Trp Arg Gly Gly Arg Ile Asp Tyr Asn Ala Ala Phe Met
         50                  55                  60

Ser Arg Val Thr Ile Ser Lys Asp Thr Ser Lys Asn Gln Phe Ser Leu
65                  70                  75                  80

Lys Leu Ser Ser Val Thr Ala Ala Asp Thr Ala Val Tyr Tyr Cys Ala
                 85                  90                  95

Arg Asn Ser Asp Val Trp Gly Gln Gly Thr Thr Val Thr Val Ser Ser
                100                 105                 110

<210> SEQ ID NO 12
<211> LENGTH: 113
<212> TYPE: PRT
<213> ORGANISM: Artificial Sequence
<220> FEATURE:
<223> OTHER INFORMATION: synthetic

<400> SEQUENCE: 12

Asp Val Val Met Thr Gln Ser Pro Leu Ser Leu Pro Val Thr Leu Gly
1               5                   10                  15

Gln Pro Ala Ser Ile Ser Cys Lys Ser Ser Gln Ser Leu Leu Asp Ile
                 20                  25                  30

Asp Gly Lys Thr Tyr Leu Asn Trp Phe Gln Gln Arg Pro Gly Gln Ser
         35                  40                  45

Pro Arg Arg Leu Ile Tyr Leu Val Ser Lys Leu Asp Ser Gly Val Pro
         50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                 85                  90                  95

Thr His Phe Pro Tyr Thr Phe Gly Gln Gly Thr Lys Leu Glu Ile Lys
                100                 105                 110

Arg

```
<210> SEQ ID NO 13
<211> LENGTH: 113
<212> TYPE: PRT
<213> ORGANISM: Artificial Sequence
<220> FEATURE:
<223> OTHER INFORMATION: synthetic

<400> SEQUENCE: 13

Asp Val Val Met Thr Gln Thr Pro Leu Ser Leu Pro Val Thr Pro Gly
1               5                   10                  15

Gln Pro Ala Ser Ile Ser Cys Lys Ser Ser Gln Ser Leu Leu Asp Ile
            20                  25                  30

Asp Gly Lys Thr Tyr Leu Asn Trp Phe Leu Gln Lys Pro Gly Gln Ser
        35                  40                  45

Pro Gln Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Tyr Thr Phe Gly Gln Gly Thr Lys Leu Glu Ile Lys
            100                 105                 110

Arg

<210> SEQ ID NO 14
<211> LENGTH: 113
<212> TYPE: PRT
<213> ORGANISM: Artificial Sequence
<220> FEATURE:
<223> OTHER INFORMATION: synthetic

<400> SEQUENCE: 14

Asp Val Val Met Thr Gln Thr Pro Leu Ser Leu Pro Val Thr Pro Gly
1               5                   10                  15

Gln Pro Ala Ser Ile Ser Cys Lys Ser Ser Gln Ser Leu Leu Asp Ile
            20                  25                  30

Asp Gly Lys Thr Tyr Leu Asn Trp Leu Leu Gln Lys Pro Gly Gln Ser
        35                  40                  45

Pro Gln Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Tyr Thr Phe Gly Gln Gly Thr Lys Leu Glu Ile Lys
            100                 105                 110

Arg

<210> SEQ ID NO 15
<211> LENGTH: 113
<212> TYPE: PRT
<213> ORGANISM: Artificial Sequence
<220> FEATURE:
<223> OTHER INFORMATION: synthetic

<400> SEQUENCE: 15

Asp Val Val Met Thr Gln Thr Pro Leu Ser Leu Pro Val Thr Leu Gly
1               5                   10                  15
```

Gln Pro Ala Ser Ile Ser Cys Lys Ser Ser Gln Ser Leu Leu Asp Ile
            20                  25                  30

Asp Gly Lys Thr Tyr Leu Asn Trp Leu Leu Gln Arg Pro Gly Gln Ser
        35                  40                  45

Pro Arg Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Tyr Thr Phe Gly Gln Gly Thr Lys Leu Glu Ile Lys
            100                 105                 110

Arg

<210> SEQ ID NO 16
<211> LENGTH: 113
<212> TYPE: PRT
<213> ORGANISM: Artificial Sequence
<220> FEATURE:
<223> OTHER INFORMATION: synthetic

<400> SEQUENCE: 16

Asp Val Val Met Thr Gln Thr Pro Leu Ser Leu Pro Val Thr Leu Gly
1               5                   10                  15

Gln Pro Ala Ser Ile Ser Cys Lys Ser Ser Gln Ser Leu Leu Asp Ile
            20                  25                  30

Asp Gly Lys Thr Tyr Leu Asn Trp Phe Leu Gln Lys Pro Gly Gln Ser
        35                  40                  45

Pro Arg Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Tyr Thr Phe Gly Gln Gly Thr Lys Leu Glu Ile Lys
            100                 105                 110

Arg

<210> SEQ ID NO 17
<211> LENGTH: 5
<212> TYPE: PRT
<213> ORGANISM: Artificial Sequence
<220> FEATURE:
<223> OTHER INFORMATION: synthetic

<400> SEQUENCE: 17

Ser Tyr Gly Val His
1               5

<210> SEQ ID NO 18
<211> LENGTH: 16
<212> TYPE: PRT
<213> ORGANISM: Artificial Sequence
<220> FEATURE:
<223> OTHER INFORMATION: synthetic

<400> SEQUENCE: 18

Val Ile Trp Arg Gly Gly Arg Ile Asp Tyr Asn Ala Ala Phe Met Ser
1               5                   10                  15

<210> SEQ ID NO 19
<211> LENGTH: 4
<212> TYPE: PRT
<213> ORGANISM: Artificial Sequence
<220> FEATURE:
<223> OTHER INFORMATION: synthetic

<400> SEQUENCE: 19

Asn Ser Asp Val
1

<210> SEQ ID NO 20
<211> LENGTH: 16
<212> TYPE: PRT
<213> ORGANISM: Artificial Sequence
<220> FEATURE:
<223> OTHER INFORMATION: synthetic

<400> SEQUENCE: 20

Lys Ser Ser Gln Ser Leu Leu Asp Ile Asp Gly Lys Thr Tyr Leu Asn
1               5                   10                  15

<210> SEQ ID NO 21
<211> LENGTH: 7
<212> TYPE: PRT
<213> ORGANISM: Artificial Sequence
<220> FEATURE:
<223> OTHER INFORMATION: synthetic

<400> SEQUENCE: 21

Leu Val Ser Lys Leu Asp Ser
1               5

<210> SEQ ID NO 22
<211> LENGTH: 9
<212> TYPE: PRT
<213> ORGANISM: Artificial Sequence
<220> FEATURE:
<223> OTHER INFORMATION: synthetic

<400> SEQUENCE: 22

Trp Gln Gly Thr His Phe Pro Tyr Thr
1               5

<210> SEQ ID NO 23
<211> LENGTH: 112
<212> TYPE: PRT
<213> ORGANISM: Artificial Sequence
<220> FEATURE:
<223> OTHER INFORMATION: synthetic

<400> SEQUENCE: 23

Gln Val Gln Leu Lys Gln Ser Gly Pro Ser Leu Ile Gln Pro Ser Gln
1               5                   10                  15

Ser Leu Ser Ile Thr Cys Thr Val Ser Gly Phe Ser Leu Thr Ser Tyr
                20                  25                  30

Gly Val His Trp Val Arg Gln Ser Pro Gly Lys Gly Leu Glu Trp Leu
            35                  40                  45

Gly Val Ile Trp Arg Gly Gly Arg Ile Asp Tyr Asn Ala Ala Phe Met
        50                  55                  60

Ser Arg Leu Ser Ile Thr Lys Asp Asn Ser Lys Ser Gln Val Phe Phe
65                  70                  75                  80

Lys Met Asn Ser Leu Gln Ala Asp Asp Thr Ala Ile Tyr Tyr Cys Ala
                85                  90                  95

```
Arg Asn Ser Asp Val Trp Gly Thr Gly Thr Thr Val Thr Val Ser Ser
                100                 105                 110
```

<210> SEQ ID NO 24
<211> LENGTH: 113
<212> TYPE: PRT
<213> ORGANISM: Artificial Sequence
<220> FEATURE:
<223> OTHER INFORMATION: synthetic

<400> SEQUENCE: 24

```
Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asp Ile
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Phe Pro Tyr Thr Phe Gly Gly Gly Thr Lys Leu Glu Ile Lys
            100                 105                 110

Arg
```

<210> SEQ ID NO 25
<211> LENGTH: 330
<212> TYPE: PRT
<213> ORGANISM: Artificial Sequence
<220> FEATURE:
<223> OTHER INFORMATION: synthetic

<400> SEQUENCE: 25

```
Ala Ser Thr Lys Gly Pro Ser Val Phe Phe Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175
```

```
Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 26
<211> LENGTH: 330
<212> TYPE: PRT
<213> ORGANISM: Artificial Sequence
<220> FEATURE:
<223> OTHER INFORMATION: synthetic

<400> SEQUENCE: 26

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205
```

```
Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 27
<211> LENGTH: 106
<212> TYPE: PRT
<213> ORGANISM: Artificial Sequence
<220> FEATURE:
<223> OTHER INFORMATION: synthetic

<400> SEQUENCE: 27

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 28
<211> LENGTH: 105
<212> TYPE: PRT
<213> ORGANISM: Artificial Sequence
<220> FEATURE:
<223> OTHER INFORMATION: synthetic

<400> SEQUENCE: 28

Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Ser Ser Pro Val
        35                  40                  45

Lys Ala Gly Val Glu Thr Thr Thr Pro Ser Lys Gln Ser Asn Asn Lys
    50                  55                  60

Tyr Ala Ala Ser Ser Tyr Leu Ser Leu Thr Pro Glu Gln Trp Lys Ser
```

```
            65                  70                  75                  80
His Arg Ser Tyr Ser Cys Gln Val Thr His Glu Gly Ser Thr Val Glu
                85                  90                  95

Lys Thr Val Ala Pro Thr Glu Cys Ser
            100                 105

<210> SEQ ID NO 29
<211> LENGTH: 43
<212> TYPE: PRT
<213> ORGANISM: Artificial Sequence
<220> FEATURE:
<223> OTHER INFORMATION: synthetic

<400> SEQUENCE: 29

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala Thr
            35                  40

<210> SEQ ID NO 30
<211> LENGTH: 42
<212> TYPE: PRT
<213> ORGANISM: Artificial Sequence
<220> FEATURE:
<223> OTHER INFORMATION: synthetic

<400> SEQUENCE: 30

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
            35                  40

<210> SEQ ID NO 31
<211> LENGTH: 42
<212> TYPE: PRT
<213> ORGANISM: Artificial Sequence
<220> FEATURE:
<223> OTHER INFORMATION: synthetic

<400> SEQUENCE: 31

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
            35                  40

<210> SEQ ID NO 32
<211> LENGTH: 31
<212> TYPE: PRT
<213> ORGANISM: Artificial Sequence
<220> FEATURE:
<223> OTHER INFORMATION: synthetic

<400> SEQUENCE: 32

Val His His Gln Lys Leu Val Phe Phe Ala Glu Asp Val Gly Ser Asn
1               5                   10                  15

Lys Gly Ala Ile Ile Gly Leu Met Val Gly Gly Val Val Ile Ala
```

-continued

```
                 20                  25                  30

<210> SEQ ID NO 33
<211> LENGTH: 23
<212> TYPE: PRT
<213> ORGANISM: Artificial Sequence
<220> FEATURE:
<223> OTHER INFORMATION: synthetic

<400> SEQUENCE: 33

Phe Ala Glu Asp Val Gly Ser Asn Lys Gly Ala Ile Ile Gly Leu Met
1               5                   10                  15

Val Gly Gly Val Val Ile Ala
            20

<210> SEQ ID NO 34
<211> LENGTH: 30
<212> TYPE: PRT
<213> ORGANISM: Artificial Sequence
<220> FEATURE:
<223> OTHER INFORMATION: synthetic

<400> SEQUENCE: 34

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser
            20                  25                  30

<210> SEQ ID NO 35
<211> LENGTH: 14
<212> TYPE: PRT
<213> ORGANISM: Artificial Sequence
<220> FEATURE:
<223> OTHER INFORMATION: synthetic

<400> SEQUENCE: 35

Trp Val Arg Gln Ala Pro Gly Lys Gly Leu Glu Trp Val Ser
1               5                   10

<210> SEQ ID NO 36
<211> LENGTH: 32
<212> TYPE: PRT
<213> ORGANISM: Artificial Sequence
<220> FEATURE:
<223> OTHER INFORMATION: synthetic

<400> SEQUENCE: 36

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 37
<211> LENGTH: 11
<212> TYPE: PRT
<213> ORGANISM: Artificial Sequence
<220> FEATURE:
<223> OTHER INFORMATION: synthetic

<400> SEQUENCE: 37

Trp Gly Gln Gly Thr Thr Val Thr Val Ser Ser
1               5                   10

<210> SEQ ID NO 38
<211> LENGTH: 30
```

<212> TYPE: PRT
<213> ORGANISM: Artificial Sequence
<220> FEATURE:
<223> OTHER INFORMATION: synthetic

<400> SEQUENCE: 38

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser
            20                  25                  30

<210> SEQ ID NO 39
<211> LENGTH: 14
<212> TYPE: PRT
<213> ORGANISM: Artificial Sequence
<220> FEATURE:
<223> OTHER INFORMATION: synthetic

<400> SEQUENCE: 39

Trp Ile Arg Gln Pro Pro Gly Lys Gly Leu Glu Trp Ile Gly
1               5                   10

<210> SEQ ID NO 40
<211> LENGTH: 32
<212> TYPE: PRT
<213> ORGANISM: Artificial Sequence
<220> FEATURE:
<223> OTHER INFORMATION: synthetic

<400> SEQUENCE: 40

Arg Val Thr Ile Ser Val Asp Thr Ser Lys Asn Gln Phe Ser Leu Lys
1               5                   10                  15

Leu Ser Ser Val Thr Ala Ala Asp Thr Ala Val Tyr Tyr Cys Ala Arg
            20                  25                  30

<210> SEQ ID NO 41
<211> LENGTH: 11
<212> TYPE: PRT
<213> ORGANISM: Artificial Sequence
<220> FEATURE:
<223> OTHER INFORMATION: synthetic

<400> SEQUENCE: 41

Trp Gly Gln Gly Thr Thr Val Thr Val Ser Ser
1               5                   10

<210> SEQ ID NO 42
<211> LENGTH: 23
<212> TYPE: PRT
<213> ORGANISM: Artificial Sequence
<220> FEATURE:
<223> OTHER INFORMATION: synthetic

<400> SEQUENCE: 42

Asp Val Val Met Thr Gln Ser Pro Leu Ser Leu Pro Val Thr Leu Gly
1               5                   10                  15

Gln Pro Ala Ser Ile Ser Cys
            20

<210> SEQ ID NO 43
<211> LENGTH: 15
<212> TYPE: PRT
<213> ORGANISM: Artificial Sequence
<220> FEATURE:
<223> OTHER INFORMATION: synthetic

<400> SEQUENCE: 43

Trp Phe Gln Gln Arg Pro Gly Gln Ser Pro Arg Arg Leu Ile Tyr
1               5                   10                  15

<210> SEQ ID NO 44
<211> LENGTH: 32
<212> TYPE: PRT
<213> ORGANISM: Artificial Sequence
<220> FEATURE:
<223> OTHER INFORMATION: synthetic

<400> SEQUENCE: 44

Gly Val Pro Asp Arg Phe Ser Gly Ser Gly Ser Gly Thr Asp Phe Thr
1               5                   10                  15

Leu Lys Ile Ser Arg Val Glu Ala Glu Asp Val Gly Val Tyr Tyr Cys
            20                  25                  30

<210> SEQ ID NO 45
<211> LENGTH: 11
<212> TYPE: PRT
<213> ORGANISM: Artificial Sequence
<220> FEATURE:
<223> OTHER INFORMATION: synthetic

<400> SEQUENCE: 45

Phe Gly Gln Gly Thr Lys Leu Glu Ile Lys Arg
1               5                   10

<210> SEQ ID NO 46
<211> LENGTH: 442
<212> TYPE: PRT
<213> ORGANISM: Artificial Sequence
<220> FEATURE:
<223> OTHER INFORMATION: synthetic

<400> SEQUENCE: 46

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Thr Leu Ser Ser Tyr
            20                  25                  30

Gly Val His Trp Val Arg Gln Ala Pro Gly Lys Gly Leu Glu Trp Leu
        35                  40                  45

Gly Val Ile Trp Arg Gly Gly Arg Ile Asp Tyr Asn Ala Ala Phe Met
    50                  55                  60

Ser Arg Leu Thr Ile Ser Lys Asp Asn Ser Lys Ser Thr Val Tyr Leu
65                  70                  75                  80

Gln Met Asn Ser Leu Arg Ala Glu Asp Thr Ala Val Tyr Tyr Cys Ala
                85                  90                  95

Arg Asn Ser Asp Val Trp Gly Gln Gly Thr Thr Val Thr Val Ser Ser
            100                 105                 110

Ala Ser Thr Lys Gly Pro Ser Val Phe Pro Leu Ala Pro Ser Ser Lys
        115                 120                 125

Ser Thr Ser Gly Gly Thr Ala Ala Leu Gly Cys Leu Val Lys Asp Tyr
    130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Ser Leu Gly Thr Gln Thr
            180                 185                 190

```
Tyr Ile Cys Asn Val Asn His Lys Pro Ser Asn Thr Lys Val Asp Lys
            195                 200                 205

Lys Val Glu Pro Lys Ser Cys Asp Lys Thr His Thr Cys Pro Pro Cys
    210                 215                 220

Pro Ala Pro Glu Leu Leu Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser His Glu Asp Pro Glu Val Lys Phe Asn Trp
            260                 265                 270

Tyr Val Asp Gly Val Glu Val His Asn Ala Lys Thr Lys Pro Arg Glu
        275                 280                 285

Glu Gln Tyr Asn Ser Thr Tyr Arg Val Val Ser Val Leu Thr Val Leu
    290                 295                 300

His Gln Asp Trp Leu Asn Gly Lys Glu Tyr Lys Cys Lys Val Ser Asn
305                 310                 315                 320

Lys Ala Leu Pro Ala Pro Ile Glu Lys Thr Ile Ser Lys Ala Lys Gly
                325                 330                 335

Gln Pro Arg Glu Pro Gln Val Tyr Thr Leu Pro Pro Ser Arg Glu Glu
            340                 345                 350

Met Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
    370                 375                 380

Asn Tyr Lys Thr Thr Pro Pro Val Leu Asp Ser Asp Gly Ser Phe Phe
385                 390                 395                 400

Leu Tyr Ser Lys Leu Thr Val Asp Lys Ser Arg Trp Gln Gln Gly Asn
                405                 410                 415

Val Phe Ser Cys Ser Val Met His Glu Ala Leu His Asn His Tyr Thr
            420                 425                 430

Gln Lys Ser Leu Ser Leu Ser Pro Gly Lys
        435                 440

<210> SEQ ID NO 47
<211> LENGTH: 442
<212> TYPE: PRT
<213> ORGANISM: Artificial Sequence
<220> FEATURE:
<223> OTHER INFORMATION: synthetic

<400> SEQUENCE: 47

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Ser Tyr
            20                  25                  30

Gly Val His Trp Val Arg Gln Pro Pro Gly Lys Gly Leu Glu Trp Leu
        35                  40                  45

Gly Val Ile Trp Arg Gly Gly Arg Ile Asp Tyr Asn Ala Ala Phe Met
    50                  55                  60

Ser Arg Leu Thr Ile Ser Lys Asp Thr Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Arg Asn Ser Asp Val Trp Gly Gln Gly Thr Thr Val Thr Val Ser Ser
            100                 105                 110
```

```
Ala Ser Thr Lys Gly Pro Ser Val Phe Pro Leu Ala Pro Ser Ser Lys
            115                 120                 125

Ser Thr Ser Gly Gly Thr Ala Ala Leu Gly Cys Leu Val Lys Asp Tyr
        130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Ser Leu Gly Thr Gln Thr
            180                 185                 190

Tyr Ile Cys Asn Val Asn His Lys Pro Ser Asn Thr Lys Val Asp Lys
        195                 200                 205

Lys Val Glu Pro Lys Ser Cys Asp Lys Thr His Thr Cys Pro Pro Cys
210                 215                 220

Pro Ala Pro Glu Leu Leu Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser His Glu Asp Pro Glu Val Lys Phe Asn Trp
            260                 265                 270

Tyr Val Asp Gly Val Glu Val His Asn Ala Lys Thr Lys Pro Arg Glu
        275                 280                 285

Glu Gln Tyr Asn Ser Thr Tyr Arg Val Val Ser Val Leu Thr Val Leu
290                 295                 300

His Gln Asp Trp Leu Asn Gly Lys Glu Tyr Lys Cys Lys Val Ser Asn
305                 310                 315                 320

Lys Ala Leu Pro Ala Pro Ile Glu Lys Thr Ile Ser Lys Ala Lys Gly
                325                 330                 335

Gln Pro Arg Glu Pro Gln Val Tyr Thr Leu Pro Pro Ser Arg Glu Glu
            340                 345                 350

Met Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
370                 375                 380

Asn Tyr Lys Thr Thr Pro Pro Val Leu Asp Ser Asp Gly Ser Phe Phe
385                 390                 395                 400

Leu Tyr Ser Lys Leu Thr Val Asp Lys Ser Arg Trp Gln Gln Gly Asn
                405                 410                 415

Val Phe Ser Cys Ser Val Met His Glu Ala Leu His Asn His Tyr Thr
            420                 425                 430

Gln Lys Ser Leu Ser Leu Ser Pro Gly Lys
        435                 440

<210> SEQ ID NO 48
<211> LENGTH: 219
<212> TYPE: PRT
<213> ORGANISM: Artificial Sequence
<220> FEATURE:
<223> OTHER INFORMATION: synthetic

<400> SEQUENCE: 48
```

-continued

```
Asp Val Val Met Thr Gln Thr Pro Leu Ser Leu Pro Val Thr Pro Gly
 1               5                  10                  15
Gln Pro Ala Ser Ile Ser Cys Lys Ser Ser Gln Ser Leu Leu Asp Ile
             20                  25                  30
Asp Gly Lys Thr Tyr Leu Asn Trp Leu Leu Gln Lys Pro Gly Gln Ser
         35                  40                  45
Pro Gln Arg Leu Ile Tyr Leu Val Ser Lys Leu Asp Ser Gly Val Pro
     50                  55                  60
Asp Arg Phe Ser Gly Ser Gly Ser Gly Thr Asp Phe Thr Leu Lys Ile
 65                  70                  75                  80
Ser Arg Val Glu Ala Glu Asp Val Gly Val Tyr Tyr Cys Trp Gln Gly
                 85                  90                  95
Thr His Phe Pro Tyr Thr Phe Gly Gln Gly Thr Lys Leu Glu Ile Lys
             100                 105                 110
Arg Thr Val Ala Ala Pro Ser Val Phe Ile Phe Pro Pro Ser Asp Glu
         115                 120                 125
Gln Leu Lys Ser Gly Thr Ala Ser Val Val Cys Leu Leu Asn Asn Phe
     130                 135                 140
Tyr Pro Arg Glu Ala Lys Val Gln Trp Lys Val Asp Asn Ala Leu Gln
145                 150                 155                 160
Ser Gly Asn Ser Gln Glu Ser Val Thr Glu Gln Asp Ser Lys Asp Ser
                 165                 170                 175
Thr Tyr Ser Leu Ser Ser Thr Leu Thr Leu Ser Lys Ala Asp Tyr Glu
             180                 185                 190
Lys His Lys Val Tyr Ala Cys Glu Val Thr His Gln Gly Leu Ser Ser
         195                 200                 205
Pro Val Thr Lys Ser Phe Asn Arg Gly Glu Cys
     210                 215
```